United States Patent
Felding et al.

(10) Patent No.: US 11,292,788 B2
(45) Date of Patent: Apr. 5, 2022

(54) IL-17 AND IFN-GAMMA INHIBITION FOR THE TREATMENT OF AUTOIMMUNE DISEASES AND CHRONIC INFLAMMATION

(71) Applicant: Immunic AG, Gräfelfing (DE)

(72) Inventors: Jakob Felding, Charlottenlund (DK); Hella Kohlhof, Munich (DE); Manfred Groppel, Munich (DE); Rolf Andreas Muhler, Munich (DE); Daniel Vitt, Germering (DE); Carine Chevrier, Munich (DE); Mirko Zaja, Augsburg (DE); Stefan Tasler, Seefeld (DE)

(73) Assignee: Immunic AG, Planegg-Martinsried (DE)

( * ) Notice: Subject to any disclaimer, the term of this patent is extended or adjusted under 35 U.S.C. 154(b) by 26 days.

(21) Appl. No.: 16/644,581

(22) PCT Filed: Sep. 6, 2018

(86) PCT No.: PCT/EP2018/073993
§ 371 (c)(1),
(2) Date: Mar. 5, 2020

(87) PCT Pub. No.: WO2019/048541
PCT Pub. Date: Mar. 14, 2019

(65) Prior Publication Data
US 2021/0061796 A1    Mar. 4, 2021

(30) Foreign Application Priority Data
Sep. 6, 2017   (EP) .................................... 17189652

(51) Int. Cl.
*C07D 413/04*    (2006.01)
*C07D 417/14*    (2006.01)

(52) U.S. Cl.
CPC ......... *C07D 413/04* (2013.01); *C07D 417/14* (2013.01); *C07B 2200/13* (2013.01)

(58) Field of Classification Search
CPC .......................... C07D 413/04; C07D 417/14
USPC ....................................................... 514/364
See application file for complete search history.

(56) References Cited

U.S. PATENT DOCUMENTS

| 8,354,436 B2 | 1/2013 | Leban et al. |
| 8,592,456 B2 | 11/2013 | Leban et al. |
| 2012/0196861 A1 | 8/2012 | Leban et al. |
| 2012/0196862 A1 | 8/2012 | Leban et al. |

FOREIGN PATENT DOCUMENTS

| WO | 2012/101261 A1 | 8/2012 | |
| WO | 2012/101263 A1 | 8/2012 | |
| WO | WO-2012101261 A1 * | 8/2012 | ............. A61P 17/10 |

OTHER PUBLICATIONS

International Search Report dated Nov. 19, 2018 issued in corresponding PCT/EP2018/073993 application (3 pages).

* cited by examiner

*Primary Examiner* — Kahsay Habte
(74) *Attorney, Agent, or Firm* — Millen White Zelano and Branigan, PC; Richard J. Traverso

(57) ABSTRACT

The present invention relates to compounds of the general formula (I), and the pharmaceutically acceptable salts and solvates thereof, wherein Ar, Z and Y are as described herein and R1 is a group of the structure

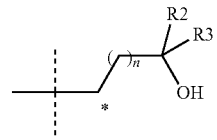

wherein n is 0 or 1; R2 is H, deuterium or methyl; R3 is methyl, trifluoromethyl, ethyl, or taken with R2 together forms a cyclopropyl group, or R3 forms a methylene bridge to the carbon atom marked *, which are suitable for the treatment of autoimmune diseases and chronic inflammation.

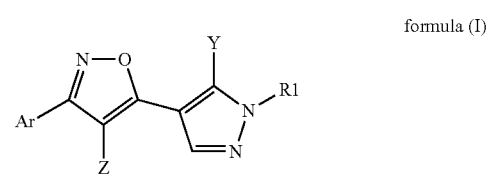

formula (I)

11 Claims, No Drawings

IL-17 AND IFN-GAMMA INHIBITION FOR THE TREATMENT OF AUTOIMMUNE DISEASES AND CHRONIC INFLAMMATION

INTRODUCTION

The IL-17 family of cytokines has been associated with the pathogenesis of autoimmune diseases and is generally blamed for the pathogenic symptoms of autoimmune and chronic inflammation. Overexpression of IL-17 is a hallmark of autoimmune and chronic inflammatory diseases like rheumatoid arthritis, psoriasis and psoriatic arthritis, ankylosing spondylitis, inflammatory bowel disease, multiple sclerosis, vasculitis and atherosclerosis, systemic lupus erythematosus, as well as lung disorders, asthma and chronic obstructive pulmonary diseases. (review in Miossec and Kolls, Nature Reviews Drug Discovery, 2012[1]).

The IL-17 cytokine family comprises six members, out of which IL-17A and IL-17F are the best characterized. IL-17A and IL-17F exist as homo—as well as heterodimers (IL-17AA, IL-17AF, IL-17FF). IL-17A and IL-17F are clearly associated with inflammation, whereas the role of the other IL-17 family members is less explored (summarized in Reynold et al., Cytokine Growth Factor Rev., 2010[2]).

Secretion of IL-17 is mainly caused by a specific subtype of T helper cells termed Th17 cells. Differentiation of naïve CD4+ T cells into Th17 cells is induced in the presence of the cytokines IL-1β, TGFβ and IL-6, whereas IL-23 maintains TH17 cell survival. Important transcription factors for the transcription and secretion of IL-17 from Th17 cells are RORγt and STAT3. IL-17 itself induces production of effector molecules in IL17R expressing cells like endothelial cells, epithelial cells or fibroblasts, macrophages and dendritic cells, chondrocytes and osteoblasts. Those effector molecules are pro-inflammatory cytokines (IL-6, TNF-α and IL-1b), chemokines (like CXCL1, CXCL2, CXCL5, CCL2, CCL7 and CCL20), growth factors (G-CSF, GM-CSF) and nitric oxide, prostaglandin E2 and matrix-metalloproteases. Initiated by these effector molecules, neutrophil infiltration, tissue damage and chronic inflammation occurs (summarized in Miossec and Kolls, Nature Reviews Drug Discovery, 2012[1]).

Before the recognition of the importance of IL-17 in autoimmune inflammation, IFN-gamma derived from Th1 cells was believed to be the important cytokine that drives autoimmune disorders. IFN-gamma transcription and secretion from Th1 effector cells is regulated by the transcription factors T-bet and STAT4. As an effector cytokine of Th1 immunity, IFN-gamma is the key regulator of macrophage activation. In parallel, INF-gamma signaling generates other cytokines and inflammatory factors to sustain inflammation, maintain Th1 responses and inhibit differentiation of regulatory T cells, Th2 cells and Th17 cells (summarized in Pollard et al., Discov. Med., 2014[3] and Green et al., J. Biol. Chem., 2017[4]).

Recently, the existence of hybrid Th1/Th17 cells was described. These cells can be induced in vitro by IL-23 and IL-6 in concert with IL-1 and secrete IL-17 and IFN-gamma. It was demonstrated that these double producing cells harbor pronounced pro-inflammatory properties and are involved in the pathogenesis of IBD, EAE and Type 1 Diabetes (Buonocore et al., Nature, 2010[5]; Ghoreschi et al., Nature, 2010[6]; Marwaha et al., Clin Immunol, 2014[7]; Ramesh et al., J. Exp. Med. 2014[8]).

Compounds which target and suppress both IL-17 and IFN-gamma are therefore predestined for the treatment of autoimmune disorders.

The effectiveness of blocking IL-17 signaling alone as therapeutic treatment in autoimmune diseases has already been proven in clinical trials with e.g. monoclonal antibodies against IL-17A (sekukinumab, ixekizumab, ABT-122, CNTO 6785, CJM112, COVA322, ALX-0761, bimekizumab, SCH-900117) and/or the IL-17 receptor IL-17RA (AMG827, brodalumab). Further antibodies in clinical development targeting IL-17-Th17 pathway by addressing the p19 subunit of IL-23 are tildrakizumab, guselkumab, AMG139, BI655066 and LY3074828 (summarized in Bartlett and Million, Nature Reviews Drug Discovery 2015).[9] Positive results have been reported for the treatment of rheumatoid arthritis, psoriasis, psoriatic arthritic, uveitis, ankylosing spondylitis and spondyloarthritis. Other autoimmune diseases under investigation are Crohn's disease, asthma and multiple sclerosis.

On the other hand, blocking the IFN-gamma signaling alone in autoimmune diseases with IFN-gamma-specific monoclonal antibody AMG811 was investigated in clinical trials for systemic and discoid lupus erythematosus without significant clinical benefit so far (Werth et al., Arthritis 2017[10]).

1. Miossec, P. & Kolls, J. K. Targeting IL-17 and TH17 cells in chronic inflammation. Nat. Rev. Drug Discov. 11, 763-776 (2012).
2. Reynolds, J. M., Angkasekwinai, P. & Dong, C. IL-17 family member cytokines: regulation, and function in innate immunity. Cytokine Growth Factor Rev. 21, 413-423 (2010).
3. Pollard, K. M., Cauvi, D. M., Toomey, C., Morris, K. V. & Kono, D. H. Interferon-γ and Systemic Autoimmunity. Discov. Med. 16, 123-131 (2013).
4. Green, D. S., Young, H. A. & Valencia, J. C. Current prospects of type II interferon gamma signaling and autoimmunity. J. Biol. Chem. jbc.R116.774745 (2017). doi:10.1074/jbc.R116.774745
5. Buonocore, S. et al. Innate lymphoid cells drive IL-23 dependent innate intestinal pathology. Nature 464, 1371-1375 (2010).
6. Ghoreschi, K. et al. Generation of Pathogenic Th17 Cells in the Absence of TGF-β Signaling. Nature 467, 967-971 (2010).
7. Marwaha, A. K., Tan, S. & Dutz, J. P. Targeting the IL-17/IFN-γ axis as a potential new clinical therapy for type 1 diabetes. Clin. Immunol. Orlando Fla. 154, 84-89 (2014).
8. Ramesh, R. et al. Pro-inflammatory human Th17 cells selectively express P-glycoprotein and are refractory to glucocorticoids. J. Exp. Med. 211, 89-104 (2014).
9. Bartlett, H. S. & Million, R. P. Targeting the IL-17-TH17 pathway. Nat. Rev. Drug Discov. 14, 11-12 (2015).
10. Werth, V. P. et al. Brief Report: Pharmacodynamics, Safety, and Clinical Efficacy of AMG 811, a Human Anti-Interferon-γ Antibody, in Patients With Discoid Lupus Erythematosus. Arthritis Rheumatol. Hoboken N.J. 69, 1028-1034 (2017).

WO 2012/101261 A1 and WO 2012/101263 A1 describe compounds having the core structure of the compounds of the present invention, but different substitution patterns, in particular with regard to group R1.

DETAILED DESCRIPTION OF THE INVENTION

In certain embodiments the present invention relates to a compound of formula (I) as described in the following items:

1. A compound of formula (I) or a pharmaceutically acceptable salt or solvate thereof,

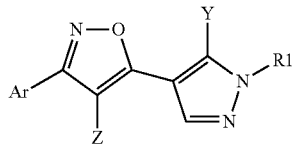

formula (I)

wherein
Ar is selected from the group consisting of phenyl and heteroaryl, each of which is optionally substituted by one or more independently selected substituents $R^{Ar}$;
$R^{Ar}$ is selected from the group consisting of halogen, —OH, —CN, alkoxy, haloalkoxy, alkyl, haloalkyl, mono- or dialkylamino-alkyl, mono- or di-alkylamino-alkoxy, —COOR', —CONHR', —CO—R', —SO$_2$NHR', —NH—CO—R', —NO$_2$, —NH—SO$_2$—R', —SO$_2$—R', benzyloxy, —CO-heterocyclyl, —CO-cycloalkyl, —CONH-cycloalkyl, —CONH-heterocyclyl, —O-alkyl-heterocyclyl, —O-alkyl-cycloalkyl, (2-oxa-6-azaspiro[3.3]hept-6-yl)-C$_{1-4}$-alkoxy, amino, aralkyl, cycloalkyl, heterocyclyl, phenyl and heteroaryl, wherein each of said alkoxy, aralkyl, alkyl, cycloalkyl, heterocyclyl, phenyl and heteroaryl groups is optionally substituted be one or more substituents independently selected from alkyl, haloalkyl, halogen and OH, and wherein R' is independently selected from the group consisting of independently represents H, OH, alkyl and haloalkyl;
Z is selected from the group consisting of H, halogen, —CO—R$^Z$, —CH$_2$—O—R$^Z$, —CO—CH$_2$—R$^Z$, —CO—CH$_2$—O—R$^Z$, —COOR$^Z$, —NHCO—R$^Z$, —CO—NHR$^Z$, —N(R$^Z$)$_2$, —CN, —NHCOOR$^Z$, —SO$_2$—R$^Z$, —SO$_2$NHR$^Z$, -alkyl-O—R$^Z$, -alkyl-O-alkyl-O—R$^Z$, amino, alkyl, phenyl, heteroaryl, heterocyclyl and cycloalkyl, wherein each of said alkyl, phenyl, heteroaryl, heterocyclyl and cycloalkyl groups is optionally substituted be one or more substituents independently selected from the group consisting of halogen, alkyl, alkoxy, haloalkyl, —COO-alkyl, OH and cycloalkyl;
$R^Z$ is selected from the group consisting of H, halogen, —OH, alkyl, haloalkyl, cycloalkyl, heterocyclyl, heteroaryl, phenyl and heteroaryl,
Y is H, halogen, haloalkyl, alkyl or an alkylester;
R1 is a group of the structure

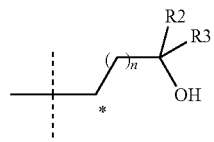

wherein
n is 0 or 1;
R2 is H, deuterium or methyl;
R3 is methyl, trifluoromethyl, ethyl, or taken with R2 together forms a cyclopropyl group, or R3 forms a methylene bridge to the carbon atom marked *.

2. The compound of formula (I) according to item 1 or a pharmaceutically acceptable salt or solvate thereof, wherein Ar is selected from the group consisting of phenyl, cycloalkyl, heterocyclyl and heteroaryl, each of which is optionally substituted by one or more independently selected substituents $R^{Ar}$;
$R^{Ar}$ is selected from the group consisting of halogen, —OH, —CN, alkoxy, haloalkoxy, alkyl, haloalkyl, mono- or dialkylamino-alkyl, mono- or di-alkylamino-alkoxy, —COOR', —CONHR', —CO—R', —SO$_2$NHR', —NH—CO—R', —NO$_2$, —NH—SO$_2$—R', —SO$_2$—R', benzyloxy, —CO-heterocyclyl, —CO-cycloalkyl, —CONH-cycloalkyl, —CONH-heterocyclyl, —O-alkyl-heterocyclyl, —O-alkyl-cycloalkyl, (2-oxa-6-azaspiro[3.3]hept-6-yl)-C$_{1-4}$-alkoxy, amino, aralkyl, cycloalkyl, heterocyclyl, phenyl and heteroaryl, wherein each of said alkoxy, aralkyl, alkyl, cycloalkyl, heterocyclyl, phenyl and heteroaryl groups is optionally substituted be one or more substituents independently selected from alkyl, haloalkyl, halogen and OH, and wherein R' is independently selected from the group consisting of independently represents H, OH, alkyl and haloalkyl;
Z is selected from the group consisting of H, halogen, —CO—R$^Z$, —CH$_2$—O—R$^Z$, —CO—CH$_2$—R$^Z$, —CO—CH$_2$—O—R$^Z$, —COOR$^Z$, —NHCO—R$^Z$, —CO—NHR$^Z$, —N(R$^Z$)$_2$, —CN, —NHCO$_2$R$^Z$, —SO$_2$—R$^Z$, —SO$_2$NHR$^Z$, -alkyl-O—R$^Z$, -alkyl-O-alkyl-O—R$^Z$, amino, alkyl, phenyl, heteroaryl, heterocyclyl and cycloalkyl, wherein each of said alkyl, phenyl, heteroaryl, heterocyclyl and cycloalkyl groups is optionally substituted be one or more substituents independently selected from the group consisting of halogen, alkyl, alkoxy, haloalkyl, —COO-alkyl, OH and cycloalkyl;
$R^Z$ is selected from the group consisting of H, halogen, —OH, alkyl, haloalkyl, cycloalkyl, heterocyclyl, heterocyclyl, phenyl and heteroaryl,
Y is H, halogen, haloalkyl, alkyl or an alkylester;
R1 is a group of the structure

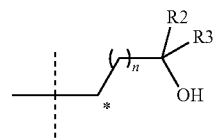

wherein
n is 0 or 1;
R2 is H, deuterium or methyl;
R3 is methyl, trifluoromethyl, ethyl, or taken with R2 together forms a cyclopropyl group;
or
n is 1, R2 is H, deuterium or methyl and R3 forms a methylene bridge to the carbon atom marked *.

3. The compound of formula (I) according to item 1 or 2 or a pharmaceutically acceptable salt or solvate thereof, wherein
Ar is selected from the group consisting of phenyl and 5- or 6-membered heteroaryl, each of which is optionally substituted by one or more substituents $R^{Ar}$;
$R^{Ar}$ is selected from the group consisting of halogen, OH, CN, C$_{1-4}$-alkyl, C$_{1-4}$-haloalkyl, —NH$_2$, acetamido, —COO—C$_{1-4}$-alkyl, C$_{1-4}$-alkoxy, and (mono- or di-C$_{1-4}$-alkyl-amino)-C$_{1-4}$-alkoxy, more particularly halogen, C$_{1-4}$-alkoxy, and (mono- or di-C$_{1-4}$-alkyl-amino)-C$_{1-4}$-alkoxy, benzyloxy, —CO—N(R$^N$)$_2$ wherein one $R^N$ is H and the other is $C_{1-3}$-alkyl, $C_{3-4}$cycloalkyl or both $R^N$ taken together with the N to which they are attached form an azetane, pyrrolidine or morpholine ring, —CONR$^N$ wherein one $R^N$ is H and the other is isopropyl or cyclobutyl or both $R^N$ taken together with the N to which they are attached form a pyrrolidine, morpholine, 1,1-dioxothiomorpholine, 4-methyl-piperazin, or 2-oxa-6-azaspiro[3.3]heptane ring;

Z is selected from the group consisting of H, halogen, —CO—$C_{1-4}$-alkyl, —CO—$CH_2$—$C_{1-4}$-alkoxy, —CO—$CH_2$—O—$C_{3-5}$-cycloalkyl, —CO-heterocyclyl, —$CH_2$—OH, —$CH_2$—O—$C_{1-4}$-alkyl, —$CH_2$—O—$C_{3-5}$-cycloalkyl, —$NH_2$, —NH—COO—$C_{1-4}$alkyl, —CN, —COO—$C_{1-4}$alkyl, —CONH—$C_{1-4}$alkyl, —CONH-arylalkyl, —CONH-cycloalkyl, —CON($C_{1-4}$alkyl)$_2$, —CON($C_{1-4}$alkyl)-O—$C_{1-4}$alkyl, —CO—$CH_2$-cycloalkyl, COO-heterocyclyl, —COO-cycloalkyl, cycloalkylmethyl, alken-1-one, alkyloxyalkyl, —$C_{1-2}$-alkyl-O—$C_{1-2}$-alkyl-O—$C_{1-4}$-alkyl, cycloalkylmethyl-alken-1-ol, heteroaryl, phenyl, or heterocyclyl, wherein said phenyl, and heterocyclyl is optionally substituted by one or more substituents independently selected from the group comprising halogen, alkyl, alkoxy, haloalkyl, —COO-alkyl, OH and cycloalkyl;

Y is selected from the group consisting of H, alkyl, haloalkyl, and alkylester;

R1 is a group of the structure

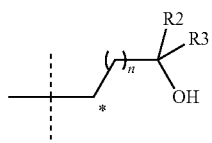

wherein
n is 0;
R2 is H, deuterium or methyl;
R3 is methyl, trifluoromethyl, ethyl, or taken with R2 together forms a cyclopropyl group;
or
n is 1;
R2 is H, deuterium or methyl;
R3 is methyl or trifluoromethyl or forms a methylene bridge to the carbon atom marked *.

4. The compound according to any of items 1 to 3 or a pharmaceutically acceptable salt or solvate thereof, wherein Ar is selected from the group consisting of phenyl and pyridyl, each of which is optionally substituted by one or more substituents $R^{Ar}$;

$R^{Ar}$ is selected from the group consisting of halogen, OH, —O—$C_{1-3}$-alkyl, —O—$C_{1-3}$-haloalkyl, $C_{1-4}$alkyl, $C_{1-4}$-haloalkyl, (mono- or dimethylamino)-$C_{1-3}$-alkyl and (mono- or dimethylamino)-$C_{1-2}$-alkoxy;

Z is selected from the group consisting of H, —COO—$C_{1-3}$-alkyl, —CO—$C_{1-2}$-alkyl, —CO—$CH_2$—$C_{1-3}$-alkoxy, —CO—$CH_2$—O—$C_{3-4}$-cycloalkyl, 5- or 6-membered heteroaryl, phenyl, —COO—$C_{3-6}$-cycloalkyl, —COO—$C_{3-6}$-heterocyclyl, —CON—$C_{3-6}$-cycloalkyl, —CON—$C_{3-6}$-heterocyclyl, —CO—$CH_2$—$C_{3-6}$-cycloalkyl, —$CH_2$—O—$C_{3-6}$-cycloalkyl, —CO—$C_{1-4}$-alkyl, —$C_{1-2}$-alkyl-O—$C_{1-2}$-alkyl, —$CH_2$—OH, —$CH_2$—O—$C_{1-3}$-alkyl, —$CH_2$—O-cyclobutyl, —$C_{1-2}$-alkyl-O—$C_{1-2}$-alkyl-O—$C_{1-2}$-alkyl and —C(OH)($C_{1-4}$-alkyl)($CH_2$—$C_{3-6}$-cycloalkyl), wherein said heteroaryl, phenyl, heterocyclyl, cycloalkyl and alkyl is optionally substituted with one or more substituents independently selected from the group consisting of methyl, halogen, $CF_3$, OMe and OH;

Y is selected from the group consisting of $CF_3$ and Me;
R1 is selected from the group consisting of 3-hydroxy-3-methylbutyl, 2-hydroxy-2-methylpropyl, 3-hydroxy-3-methyl-cyclobutyl, 2-hydroxypropyl, 2-hydroxybutyl, 3-hydroxy-cyclobutyl, 2-hydroxy-3,3,3-trifluoropropyl, 2-hydroxy-2-deutero-propyl, and 1-hydroxy-cyclopropylmethyl.

5. The compound according to any of items 1 to 4 or a pharmaceutically acceptable salt or solvate thereof, wherein Ar is selected from the group consisting of phenyl optionally substituted by one or more substituents $R^{Ar}$;

$R^{Ar}$ is selected from the group consisting of halogen, —O—$C_{1-3}$-alkyl, —O—$C_{1-3}$-haloalkyl, $C_{1-4}$-alkyl, $C_{1-4}$-haloalkyl and (dimethylamino)-$C_{1-2}$-alkoxy;

Z is selected from the group consisting of H, COO—$C_{1-3}$-alkyl, pyrimidyl, pyrazinyl, thiazolyl, oxazolyl, isoxazolyl, isothiazolyl imidazolyl, oxadiazolyl, thiadiazolyl, thiophenyl, furan, tetrahydrofuran, cyclopropoxymethyl, cyclohexoxymethyl, cyclopentoxymethyl, —COO-cyclopropyl, —COO-cyclobutyl, —COO-cyclopentyl, —COO-cyclohexyl, pent-4-en-1-one, hydroxymethyl, methoxymethyl, ethoxymethyl, isopropoxymethyl, cyclobutoxymethyl, methoxyethyl, acetyl, methoxyacetyl, —CO—$CH_2$-cyclobutyl, —CO—$CH_2$-cyclopropyl, —CO—$CH_2$-cyclopentyl, —CO—$CH_2$-cyclohexyl, —COO-oxetan, 1-cyclopropylmethyl-pent-4-en-1-ol, -methoxy-ethoxy-methyl, —CONH-cyclopropyl, —CONH-cyclobutyl, —CONH-cyclopentyl, and —CONH-cyclohexyl, wherein said pyrimidyl, pyrazinyl, thiazolyl, oxazolyl, isoxazolyl, isothiazolyl imidazolyl, oxadiazolyl, thiadiazolyl, thiophenyl, tetrahydrofuran and furan is optionally substituted with one or more substituents independently selected from the group consisting of methyl, halogen, $CF_3$, OMe and OH;

Y is selected from the group consisting of $CF_3$ and Me;
R1 is selected from the group consisting of 3-hydroxy-3-methylbutyl, 2-hydroxy-2-methylpropyl, 3-hydroxy-3-methyl-cyclobutyl, 2-hydroxypropyl, 2-hydroxybutyl, 3-hydroxy-cyclobutyl, 2-hydroxy-3,3,3-trifluoropropyl, 2-hydroxy-2-deutero-propyl, and 1-hydroxy-cyclopropylmethyl.

6. The compound according to any of items 1 to 5 or a pharmaceutically acceptable salt or solvate thereof, wherein Ar is phenyl which is optionally substituted by one or more substituents $R^{Ar}$;

$R^{Ar}$ is selected from the group consisting of Cl, —OMe, F and 2-(dimethylamino)-ethoxy;

Z is selected from the group consisting of H, -acetyl, —COOMe, —COOEt, —CO—$CH_2$—OMe, pyrimidin-2-yl, pyrazin-2-yl, thiazol-2-yl, cyclopropoxymethyl, —COO-cyclopropyl, —COO-cyclobutyl, pent-4-en-1-one, pyrimidin-4-yl, 2-tetrahydrofuryl, methoxymethyl, ethoxymethyl, isopropoxymethyl, cyclobutoxymethyl, 3-oxetanyloxymethyl, hydroxymethyl, pyrazin-2-yl, —CO—$CH_2$-cyclobutyl, —COO-oxetan, 5-methyl-isoxazol-2-yl, 1-cyclopropylmethyl-pent-4-en-1-ol, 2-methoxy-ethoxymethyl, —CONH-cyclopropyl, —CONH-cyclobutyl and —CONH-cyclopentyl;

Y is selected from the group consisting of $CF_3$ and Me;
R1 is selected from the group consisting of 3-hydroxy-3-methylbutyl, 3-hydroxy-3-methyl-cyclobutyl, 2-hydroxypropyl, 2-hydroxybutyl, 3-hydroxy-cyclobutyl, 2-hydroxy-3,3,3-trifluoropropyl, 2-hydroxy-2-deuteropropyl, and 1-hydroxy-cyclopropylmethyl.

7. The compound according to any of items 1 to 6, wherein the compound is selected from the group consisting of the examples as listed herein in the example section.
8. The compound according to any of items 1 to 7 for use as a medicament.
9. The compound according to any of items 1 to 7 for use in the treatment of a disease or medical condition is selected from the group consisting of psoriasis, psoriatric arthritis, autoimmune thyroiditis, Grave's disease, rheumatoid arthritis, vitiligo, Crohn's disease, ulcerative colitis, inflammatory bowel disease, ankylosing spondylitis, diabetes type I, multiple sclerosis, celiac disease, systemic lupus erythematosus, uveitis, Behcet disease, atopic dermatitis, Lichen planus, Sjögren's syndrome, spinal disc herniation, acne, Graft-versus-Host-Reaction, Host-versus-Graft-Reaction, AIH (Autoimmunhepatitis), PBC (peripheral biliary cholangitis), PSC (primary scleroting cholangitis), obesity, Lupus nephritis, Autoimmune Thyroid Disorders including Graves Disease and Hashimoto's Disease, Autoimmune Uveitis, Colitis, IMQ Psoriasis, Juvenile Idiopathic Arthritis, Myasthenia Gravis, Systemic Sclerosis, diabetis melitus and osteoarthritis.
10. Use of a compound of the formula (I) as defined in any of items 1 to 7, or a pharmaceutically acceptable salt or solvate thereof in the manufacture of a medicament for the treatment of a disease or medical condition in which the inhibition of interleukin-17 (IL-17) and/or Interferon-γ (INF-γ) is beneficial.
11. The use of item 10 wherein the disease or medical condition is selected from the group consisting of psoriasis, psoriatric arthritis, autoimmune thyroiditis, Grave's disease, rheumatoid arthritis, vitiligo, Crohn's disease, ulcerative colitis, inflammatory bowel disease, ankylosing spondylitis, diabetes type I, multiple sclerosis, celiac disease, systemic lupus erythematosus, uveitis, Behcet disease, atopic dermatitis, Lichen planus, Sjögren's syndrome, spinal disc herniation, acne, Graft-versus-Host-Reaction, Host-versus-Graft-Reaction, AIH (Autoimmunhepatitis), PBC (peripheral biliary cholangitis), PSC (primary scleroting cholangitis), obesity, Lupus nephritis, Autoimmune Thyroid Disorders including Graves Disease and Hashimoto's Disease, Autoimmune Uveitis, Colitis, IMQ Psoriasis, Juvenile Idiopathic Arthritis, Myasthenia Gravis, Systemic Sclerosis, diabetes mellitus and osteoarthritis.

In particular embodiments, as used herein a heteroaryl group denotes a 5- or 6-membered heterocyclic group containing at least one heteroatom independently selected from O, N or S. This heterocyclic group is optionally fused to another aromatic or heteroaromatic 5- or 6-membered ring containing at least one heteroatom independently selected from O, N or S. For example, this group can be selected from a thiadiazole, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-oxadiazol-3-yl, 1,2,4-oxadiazol-5-yl, 1,2,5-oxadiazol-3-yl, benzooxazol-2-yl, benzooxazol-4-yl, benzooxazol-5-yl, benzoisooxazol-3-yl, benzoisooxazol-4-yl, benzoisooxazol-5-yl, 1,2,5-oxadiazol-4-yl, 1,3,4-oxadiazol-2-yl, 1,2,4-thiadiazol-3-yl, 1,2,4-thiadiazol-5-yl, 1,3,4-thiadiazol-2-yl, isothiazol-3-yl, isothiazol-4-yl, isothiazol-5-yl, benzoisothiazol-3-yl, benzoisothiazol-4-yl, benzoisothiazol-5-yl, 1,2,5-thiadiazol-3-yl, 1-imidazolyl, 2-imidazolyl, 1,2,5-thiadiazol-4-yl, 4-imidazolyl, benzoimidazol-4-yl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-2-yl, pyrid-3-yl, pyrid-4-yl, pyrid-5-yl, pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3-yl, tetrazolyl, acridyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-4-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, or tetrahydroisoquinolinyl, purine, phthalazine, pteridine, thiatetraazaindene, thiatriazaindene, isothiazolopyrazine, 6-pyrimidinyl, 2,4-dimethoxy-6-pyrimidinyl, benzimidazol-2-yl, 1H-benzimidazolyl, benzimidazol-4-yl, benz-imidazol-5-yl, benzimidazol-6-yl, benzimidazol-7-yl, tetrazole, tetrahydrothieno[3,4-d]imidazol-2-one, pyrazolo[5,1-c][1,2,4]triazine, is othiazolopyrimidine, pyrazolotriazine, pyrazolopyrimidine, imidazopyridazine, imidazopyrimidine, imidazopyridine, imidazolotriazine, triazolotriazine, triazolopyridine, triazolopyrazine, triazolopyrimidine, or triazolopyridazine group. Particular heteroaryl groups are pyrimidin-4-yl, pyrimidin-2-yl, thiazol-2-yl, pyrazin-2-yl and isoxazol-2-yl.

In particular embodiments, as used herein a heterocyclyl group denotes a 3- to 8-membered, more particularly a 3 to 6-membered heterocyclic non-aromatic group containing at least one heteroatom independently selected from the group consisting of O, N, and S, wherein the heterocyclyl group is optionally fused to another non-aromatic cylcoalkyl or heterocyclyl ring; the heterocyclyl residue is in particular selected from the group consisting of oxetanyl, morpholine-4-yl, piperazinyl, isoxazolidine-2-yl, 1-alkylpiperazine-4-yl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl. Particular heterocyclyl groups are tetrahydropyran and oxetan.

To keep the definitions as short as possible, as used herein "alkyl", and "alk" (as e.g. in alkoxy) is to be understood to encompass linear and branched alkanyl, alkenyl and alkynyl, more particularly alkyl and alkenyl, even more particularly alkanyl. If not stated otherwise, these are in particular embodiments $C_1$-$C_6$-alkanyl, $C_2$-$C_6$-alkenyl or $C_2$-$C_6$-alkynyl, more particularly $C_1$-$C_5$-alkanyl, $C_2$-$C_5$-alkenyl or $C_2$-$C_5$ alkynyl, even more particularly $C_1$-$C_4$-alkanyl, $C_2$-$C_4$-alkenyl or $C_2$-$C_4$ alkynyl. The alkyl group may for instance be selected from the group consisting of —$CH_3$, —$C_2H_5$, —CH=$CH_2$, —C≡CH, —$C_3H_7$, —CH($CH_3$)$_2$, —$CH_2$—CH=$CH_2$, —C($CH_3$)=$CH_2$, —CH=CH—$CH_3$, —C≡C—$CH_3$, —$CH_2$—C≡CH, —$C_4H_9$, —$CH_2$—CH($CH_3$)$_2$, —CH($CH_3$)—$C_2H_5$, —C($CH_3$)$_3$, —$C_5H_{11}$, —$C_6H_{13}$, —$C_2H_4$—CH=$CH_2$, —CH=CH—$C_2H_5$, —CH=C($CH_3$)$_2$, —$CH_2$—CH=CH—$CH_3$, —CH=CH—CH=$CH_2$, —$C_2H_4$—C≡CH, —C≡C—$C_2H_5$, —$CH_2$—C≡C—$CH_3$, —C≡C—CH=$CH_2$, —CH=CH—C≡CH, —C≡C—C≡CH, —$C_2H_4$—CH($CH_3$)$_2$, —CH($CH_3$)—

$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$C_3H_6$—$CH$=$CH_2$, —$CH$=$CH$—$C_3H_7$, —$C_2H_4$—$CH$=$CH$—$CH_3$, —$CH_2$—$CH$=$CH$—$C_2H_5$, —$CH_2$—$CH$=$CH$—$CH$=$CH_2$, —$CH$=$CH$—$CH$=$CH$—$CH_3$, —$CH$=$CH$—$CH_2$—$CH$=$CH_2$, —$C(CH_3)$=$CH$—$CH$=$CH_2$, —$CH$=$C(CH_3)$—$CH$=$CH_2$, —$CH$=$CH$—$C(CH_3)$=$CH_2$, —$CH_2$—$CH$=$C(CH_3)_2$, $C(CH_3)$=$C(CH_3)_2$, —$C_3H_6$—$C$≡$CH$, —$C$≡$C$—$C_3H_7$, —$C_2H_4$—$C$≡$C$—$CH_3$, —$CH_2$—$C$≡$C$—$C_2H_5$, —$CH_2$—$C$≡$C$—$CH$=$CH_2$, —$CH_2$—$CH$=$CH$—$C$≡$CH$, —$CH_2$—$C$≡$C$—$C$≡$CH$, —$C$≡$C$—$CH$=$CH$—$CH_3$, —$CH$=$CH$—$C$≡$C$—$CH_3$, —$C$≡$C$—$C$≡$C$—$CH_3$, —$C$≡$C$—$CH_2$—$CH$=$CH_2$, —$CH$=$CH$—$CH_2$—$C$≡$CH$, —$C$≡$C$—$CH_2$—$C$≡$CH$, —$C(CH_3)$=$CH$—$CH$=$CH_2$, —$CH$=$C(CH_3)$—$CH$=$CH_2$, —$CH$=$CH$—$C(CH_3)$=$CH_2$, —$C(CH_3)$=$CH$—$C$≡$CH$, —$CH$=$C(CH_3)$—$C$≡$CH$, —$C$≡$C$—$C(CH_3)$=$CH_2$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$C_4H_8$—$CH$=$CH_2$, —$CH$=$CH$—$C_4H_9$, —$C_3H_6$—$CH$=$CH$—$CH_3$, —$CH_2$—$CH$=$CH$—$C_3H_7$, —$C_2H_4$—$CH$=$CH$—$C_2H_5$, —$CH_2$—$C(CH_3)$=$C(CH_3)_2$, —$C_2H_4$—$CH$=$CH(CH_3)_2$, —$C_4H_8$—$C$≡$CH$, —$C$≡$C$—$C_4H_9$, —$C_3H_6$—$C$≡$C$—$CH_3$, —$CH_2$—$C$≡$C$—$C_3H_7$, and —$C_2H_4$—$C$≡$C$—$C_2H_5$. Particular alkyl groups are methyl, ethyl, propyl, butyl, pentyl, butenyl and pentenyl.

In particular embodiments, as used herein an arylalkyl group denotes a linear or branched $C_1$-$C_6$-alkyl substituted with at least one aryl group as defined herein. Exemplary arylalkyl groups include benzyl, phenylethyl, 4-hydroxybenzyl, 3-fluorobenzyl, 2-fluorophenylethyl, and the like.

In particular embodiments, as used herein a cycloalkyl group denotes a non-aromatic ring system containing three to eight carbon atoms, particularly four to eight carbon atoms, more particularly three to six carbon atoms, even more particularly three to five carbon atoms.

In particular embodiments, as used herein an alkoxy group denotes an O-alkyl group, the alkyl group being as defined above. More particularly the alkoxy group is a methoxy, ethoxy, isopropoxy, t-butoxy or pentoxy group, even more particularly methoxy.

In particular embodiments, as used herein a haloalkyl group denotes an alkyl group wherein one or more, particularly more than half, more particularly all, of the hydrogen atoms are replaced by halogen atoms. The haloalkyl group is for instance —$C(R^{10})_3$, —$CR^{10}(R^{10'})_2$, —$CR^{10}(R^{10'})R^{10''}$, —$C_2(R^{10})_5$, —$CH_2$—$C(R^{10})_3$, —$C(R^{10'})_2$—$CH(R^{10'})_2$, —$CH_2$—$CR^{10}(R^{10'})_2$, —$CH_2$—$CR^{10}(R^{10'})R^{10''}$, —$C_3(R^{10})_7$, or —$C_2H_4$—$C(R^{10})_3$, wherein $R^{10}$, $R^{10'}$, $R^{10''}$ particularly independently represent F, Cl, Br or I, more particularly F. More particularly, haloalkyl is $CF_3$.

In particular embodiments, as used herein a haloalkoxy group denotes an —O-haloalkyl group.

In particular embodiments, as used herein a halo or halogen group denotes fluorine, chlorine, bromine, or iodine; particularly chlorine or fluorine;

Unless stated otherwise, the terms "included", "including", "include" and the like are to be understood as meaning including but non-limiting.

Constituents which are optionally substituted as stated herein may be substituted, unless otherwise noted, at any chemically possible position.

In particular embodiments of the present invention, Ar is selected from the group consisting of phenyl and 5- or 6-membered heteroaryl, more particularly pyridyl, which are optionally substituted by one or more substituents $R^{Ar}$ independently selected from the group consisting of halogen, $C_{1-4}$-alkyl, $C_{1-4}$-haloalkyl, —$NH_2$, acetamido, —COO—$C_{1-4}$-alkyl, $C_{1-4}$-alkoxy, and (mono- or di-$C_{1-4}$-alkyl-amino)-$C_{1-4}$-alkoxy, more particularly halogen, $C_{1-4}$-alkoxy, benzyloxy, hydroxyl, 4-6-membered heterocyclylcarbonyl, $C_{1-4}$-alkylaminocarbonyl, $C_{3-4}$-cycloalkylaminocarbonyl, 5-6-membered heterocyclyl-$C_{1-4}$-alkoxy, (2-oxa-6-azaspiro[3.3]hept-6-yl)-$C_{1-4}$-alkoxy and (mono- or di-$C_{1-4}$-alkyl-amino)-$C_{1-4}$-alkoxy;

in other particular embodiments Ar is selected from the group consisting of phenyl and pyridyl, which are optionally substituted by one or more substituents $R^{Ar}$ independently selected from the group consisting of halogen, $C_{1-4}$-alkoxy, and (mono- or di-$C_{1-4}$-alkyl-amino)-$C_{1-4}$-alkoxy;

in other particular embodiments Ar is phenyl, which is optionally substituted by one or more substituents $R^{Ar}$ independently selected from the group consisting of halogen, $C_{1-4}$-alkoxy, and (mono- or di-$C_{1-4}$-alkyl-amino)-$C_{1-4}$-alkoxy;

in other particular embodiments Ar is selected from the group consisting of phenyl, 2,6-difluorophenyl, 2-chloro-6-fluorophenyl, 2-chloro-6-methoxyphenyl, 2-fluorophenyl, 3-fluorophenyl, 2-chlorophenyl, 4-chlorophenyl, 4-methoxyphenyl, 2,6-dichlorophenyl, 3,4-dichlorophenyl, 2,4-dichlorophenyl, 3-fluoropyridin-4-yl, 3,5-dichloropyridin-4-yl, 3-chloro-5-fluoropyridin-4-yl, 2-methoxyphenyl, 2-methoxypyridin-3-yl, 2-chloro-3-(N-morpholinocarbonyl)phenyl, 2-chloro-3-(N-azetanylcarbonyl)phenyl, 2-chloro-3-(N-azetanylcarbonyl)phenyl, 2-chloro-3-(N-pyrrolidinylcarbonyl)phenyl, 2-chloro-3-(ethylamino)carbonyl-phenyl, 2-chloro-3-(isopropylamino)carbonyl-phenyl, 2-chloro-3-(cyclopropylamino)carbonyl-phenyl, 2-chloro-3-(cyclbutylamino)carbonyl-phenyl, 2-methoxy-3-(ethylamino)carbonyl-phenyl, 2-methoxy-3-(isopropylamino)carbonyl-phenyl, 2-methoxy-3-(cyclopropylamino)carbonyl-phenyl, 2-methoxy-3-(N-azetanylcarbonyl)-phenyl, 3-(cyclobutylamino)carbonyl-phenyl, 3-(isopropylamino)carbonyl-phenyl, 2-chloro-3-methoxyphenyl, 2-chloro-3-hydroxyphenyl, 2-chloro-3-benzyloxyphenyl, 2-chloro-3-(2-(N-morpholinyl)ethoxy)phenyl, 2-chloro-3-(2-(N-1,1-dioxothiomorpholinyl)ethoxy)phenyl, 2-chloro-3-(2-(2-oxa-6-azaspiro[3.3]hept-6-yl)ethoxy)phenyl, 2-chloro-3-(2-(N-pyrrolidinyl)ethoxy)phenyl, 2-chloro-3-(2-(N-4-methylpiperazinyl)ethoxy)phenyl, 2-chloro-3-(2-(diethylamino)-ethoxy)phenyl and 2-chloro-3-(2-(dimethylamino)-ethoxy)-phenyl;

in other particular embodiments Ar is selected from the group consisting of 2-chloro-6-fluorophenyl, 2-chlorophenyl, 2-chloro-3-methoxyphenyl, and 2-chloro-3-(2-(dimethylamino)-ethoxy)-phenyl;

in other particular embodiments Ar is selected from the group consisting of phenyl, 2,6-difluorophenyl, 2-chloro-6-fluorophenyl, 2-chloro-6-methoxyphenyl, 2-fluorophenyl, 2-chlorophenyl, 2,6-dichlorophenyl, 2,4-dichlorophenyl, 3-fluoropyridin-4-yl, 3,5-dichloropyridin-4-yl, 3-chloro-5-fluoropyridin-4-yl, and 2-chloro-3-(2-(dimethylamino)-ethoxy)-phenyl;

in other particular embodiments Ar is selected from the group consisting of phenyl, 2,6-difluorophenyl, 2-chloro-6-fluorophenyl, 2-chloro-6-methoxyphenyl, 2-fluorophenyl, 2-chlorophenyl, 2,6-dichlorophenyl, 2,4-dichlorophenyl, 3-fluoropyridin-4-yl, 3,5-dichloropyridin-4-yl, 3-chloro-5-fluoropyridin-4-yl, and 2-chloro-3-methoxy-phenyl;

in other particular embodiments Ar is selected from the group consisting of phenyl, 2-chloro-6-fluorophenyl, 2-fluorophenyl, 2-chlorophenyl, 2,6-dichlorophenyl, 2,4-dichlorophenyl, 3-fluoropyridin-4-yl, 3,5-dichloropyridin-4-yl, 3-chloro-5-fluoropyridin-4-yl and 2-chloro-3-methoxy-phenyl;

in other particular embodiments Ar is selected from the group consisting of 2-chloro-6-fluorophenyl, 2-chlorophenyl, and 2-chloro-3-methoxy-phenyl.

In particular embodiments of the present invention, Z is selected from the group consisting of H, halogen, —CO-heterocyclyl, —CO-alkyl, —CO-alkoxyalkyl, —NH$_2$, —NH—COO—C$_{1-4}$alkyl, —CN, —COO—C$_{1-4}$alkyl, —CONH—C$_{1-4}$alkyl, —CONH-arylalkyl, —CONH-cycloalkyl, —CON(C$_{1-4}$alkyl)$_2$, —CON(C$_{1-4}$alkyl)-O—C$_{1-4}$alkyl, —CO—CH$_2$-cycloalkyl, COO-heterocyclyl, —COO-cycloalkyl, cycloalkylmethyl, hydroxymethyl, -alkyl-O-alkoxyalkyl, alken-1-one, alkyloxyalkyl, cycloalkylmethyl-alken-1-ol, heteroaryl, phenyl, or heterocyclyl, wherein said phenyl, and heterocyclyl is optionally substituted by one or more substituents independently selected from the group comprising halogen, alkyl, alkoxy, haloalkyl, —COO-alkyl, OH and cycloalkyl;

in other particular embodiments of the present invention Z is selected from the group consisting of hydrogen, bromine, —COMe, —CO—CH$_2$—OMe, ethoxymethyl, isopropoxymethyl, cyclobutoxymethyl, 2-methoxy-ethoxymethyl, hydroxymethyl, tetrahydrofuryl, —CONH-cyclopropyl, —CONH-cyclobutyl, —CO-morpholin-4-yl, —CO-piperidin-4-yl, —COOH, —CONH$_2$, —CONHNH$_2$, —CONHNH—CO-methyl, —CONH-(2,4,6-trimethoxyphenyl)methyl, —CONHN=isopropyl, —NH—CO-methyl, —NH—CO-trifluoromethyl, —NH—COH, —CO—(N-methyl-piperazin-4-yl), —CO-(4-[chlorobenzyl]-piperazin-1-yl), —CO-pyrrolidinyl, —CO-isoxazolidinyl, —NH$_2$, —NH—COO-methyl, —CN, —COO—C$_{1-3}$alkyl, —CONH-methyl, —CONH-(trifluoromethyl-substituted benzyl), —CONH-cyclohexyl, —CON(methyl)$_2$, —CON(methyl)-O-methyl, —COOMe, —COOEt, cyclopropoxymethyl, —COO-cyclopropyl, —COO-cyclobutyl, pent-4-en-1-one, methoxymethyl, —CO—CH$_2$-cyclobutyl, COO-oxetan, -methyl-isoxazol-2-yl, 1-cyclopropylmethyl-pent-4-en-1-ol, —CONH-cyclopentyl, phenyl, tetrazolyl, thiazolyl, pyrimidyl, oxadiazolyl, oxazolyl, thiadiazolyl, pyrazinyl, furanyl, and thiophenyl, wherein said phenyl, tetrazolyl, thiazolyl, pyrimidyl, oxadiazolyl, oxazolyl, thiadiazolyl, pyrazinyl, furanyl, or thiophenyl is optionally substituted by one or more substituents independently selected from the group comprising halogen, methyl, OMe, CF$_3$, —COOMe, and —COOEt;

in other particular embodiments of the present invention Z is selected from the group consisting of H, —COO—C$_{1-3}$-alkyl, —CO—C$_{1-2}$-alkyl, —CO—C$_{1-2}$-alkoxy-C$_{1-2}$-alkyl, 5- or 6-membered heteroaryl comprising one or two heteroatoms independently selected from N, S and O, —CH$_2$—O—V, wherein V is selected from the group consisting of H, C$_{1-4}$-alkyl, C$_{3-5}$-cycloalkyl and C$_{1-2}$alkoxy-C$_{1-2}$-alkyl, —COO—C$_{3-6}$-cycloalkyl, C$_{3-6}$-alken-1-one, pyrazinyl, —CO—CH$_2$—C$_{3-5}$-cycloalkyl, COO-(3- to 5-membered heterocyclyl), methyl-isoxazolyl, 1-cyclopropylmethyl-C$_{3-6}$-alken-1-ol, —CONH—C$_{5-6}$-heterocyclyl and —CONH—C$_{3-6}$-cycloalkyl;

in other particular embodiments of the present invention Z is selected from the group consisting of H, —COOMe, —COOEt, —COMe, —CO—CH$_2$—OMe, pyrimidin-2-yl, thiazol-2-yl, cyclopropoxymethyl, —COO-cyclopropyl, —COO-cyclobutyl, pent-4-en-1-one, pyrimidin-4-yl, methoxymethyl, ethoxymethyl, isopropoxymethyl, cyclobutoxymethyl, 2-methoxy-ethoxymethyl, hydroxymethyl, pyrazin-2-yl, —CO—CH$_2$-cyclobutyl, —COO-oxetan, 5-methyl-isoxazol-2-yl, tetrahydrofuryl, 1-cyclopropylmethyl-pent-4-en-1-ol, —CONH-cyclopropyl, —CONH-cyclobutyl, and —CONH-cyclopentyl;

in other particular embodiments of the present invention Z is selected from the group consisting of —COOMe, —COOEt, pyrimidin-2-yl, thiazol-2-yl, pyrimidin-4-yl, methoxymethyl, and 5-methyl-isoxazol-2-yl.

In particular embodiments of the present invention, Y is selected from the group consisting of H, alkyl, haloalkyl, and alkylester;

in other particular embodiments Y is selected from the group consisting of H, pentafluoroethyl, trifluoromethyl, methyl and methoxycarbonyl;

in other particular embodiments Y is selected from the group consisting of H, trifluoromethyl, methyl and methoxycarbonyl;

in other particular embodiments Y is selected from the group consisting of trifluoromethyl and methyl.

In particular embodiments of the present invention, R' is independently selected from the group consisting of H, OH, Me, Et, iPr, iBu, and CF$_3$, more particularly H, OH, Me, Et, and CF$_3$.

In particular embodiments of the present invention, R1 is a group of the structure

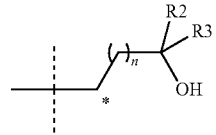

wherein
n is 0 or 1;
R2 is H, deuterium or methyl;
R3 is methyl, trifluoromethyl, ethyl, or taken with R2 together forms a cyclopropyl group;
or
n is 1, R2 is H, deuterium or methyl and R3 forms a methylene bridge to the carbon atom marked *;

in other particular embodiments of the present invention, R1 is a group of the structure

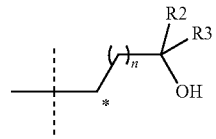

wherein
n is 0;
R2 is H, deuterium or methyl;
R3 is methyl, trifluoromethyl, ethyl, or taken with R2 together forms a cyclopropyl group;
or
n is 1;
R2 is H, deuterium or methyl;
R3 is methyl or trifluoromethyl or forms a methylene bridge to the carbon atom marked *;

in other particular embodiments of the present invention, R1 is selected from the group consisting of 3-hydroxy-3-methylbutyl, 2-hydroxy-2-methylpropyl, 3-hydroxy-3-methyl-cyclobutyl, 2-hydroxypropyl, 2-hydroxybutyl, 3-hydroxy-cyclobutyl, 2-hydroxy-3,3,3-trifluoropropyl, 2-hydroxy-2-deutero-propyl, and 1-hydroxy-cyclopropylmethyl;

in other particular embodiments of the present invention, R1 is selected from the group consisting of 3-hydroxy-3-methylbutyl, 2-hydroxy-2-methylpropyl, 2-hydroxypropyl, 3-hydroxy-3-methyl-cyclobutyl, 3-hydroxy-cyclobutyl, and 1-hydroxy-cyclopropylmethyl;

in other particular embodiments of the present invention, R1 is selected from the group consisting of 3-hydroxy-3-methylbutyl, 2-hydroxy-2-methylpropyl, 2-hydroxypropyl and 1-hydroxy-cyclopropylmethyl;

in other particular embodiments of the present invention, R1 is selected from the group consisting of 3-hydroxy-3-methylbutyl, 2-hydroxy-2-methylpropyl, and 2-hydroxypropyl;

in other particular embodiments of the present invention, R1 is 3-hydroxy-3-methyl-cyclobutyl or 3-hydroxy-cyclobutyl;

in other particular embodiments of the present invention, R1 is selected from the group consisting of 3-hydroxy-3-methylbutyl, 2-hydroxy-2-methylpropyl, and 3-hydroxy-3-methyl-cyclobutyl;

in other more particular embodiments of the present invention, R1 is 3-hydroxy-3-methyl-cyclobutyl.

in other more particular embodiments of the present invention, R1 is 3-hydroxy-3-methylbutyl.

Particular compounds of the present invention are the compounds of the below examples of the present invention, more particularly the compounds of below examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 43, 44, 45, 46, 47, 48, 49, 50, 51, 52, 53, 54, 55, 56, 57, 58, 59, 60, 61, 62, 64, 65, 66, 67, 68, 69, 70, 71, 72, 73, 74, 75, 76, 77, 78, 79, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, and 167, more particularly the compounds of below examples 1, 2, 3, 4, 5, 6, 7, 8, 9, 10, 11, 12, 13, 14, 15, 16, 18, 19, 20, 22, 23, 24, 25, 27, 29, 30, 31, 32, 33, 35, 36, 37, 44, 46, 47, 49, 50, 51, 52, 53, 54, 55, 56, 57, 58, 59, 60, 61, 62, 66, 67, 68, 69, 72, 74, 76, 77, 78, 79, 81, 82, 83, 84, 85, 86, 87, 89, 90, 91, 92, 93, 95, 96, 97, 98, 99, 100, 102, 103, 104, 105, 106, 107, 108, 109, 110, 111, 112, 113, 115, 117, 118, 119, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 154, 155, 157, 158, 159, 160, and 162, even more particularly the compounds of below examples 1, 2, 3, 4, 5, 6, 7, 8, 9, 10, 11, 12, 13, 14, 15, 16, 18, 19, 20, 22, 23, 25, 27, 31, 32, 33, 49, 50, 51, 53, 55, 56, 58, 59, 61, 62, 66, 67, 69, 72, 76, 77, 78, 79, 82, 83, 85, 86, 87, 89, 90, 91, 92, 97, 98, 99, 100, 102, 103, 104, 106, 107, 111, 112, 118, 121, 122, 123, 124, 125, 127, 128, 130, 131, 132, 133, 134, 135, 138, 139, 141, 143, 148, 150 and 160, yet even more particularly the compounds of below examples 3, 4, 6, 7, 10, 11, 12, 14, 15, 16, 27, 32, 49, 61, 82, 89, 92, 97, 98, 102, 103, 112, 121, 123, 128, 130 and 132.

It is apparent that the respective embodiments regarding the residues Ar, $R^{Ar}$, Z, $R^{Z}$, Y, R1 and R' described herein may be combined with one another to yield further more particular embodiments. Some examples of such combinations are, without limiting the invention to the particular combinations, described herein.

According to expert's knowledge the compounds of the invention as well as their salts may contain, e.g. when isolated in crystalline form, varying amounts of solvents. Included within the scope of the invention are therefore all solvates and in particular all hydrates of the compounds of formula (I) as well as all solvates and in particular all hydrates of the salts of the compounds of formula (I).

The present invention further relates to methods of treatment of the diseases or medical conditions which are described herein, particularly a disease or medical condition in which the inhibition of interleukin-17 (IL-17A), interleukin 17F (IL-17F), interleukin-22 (IL-22) and/or Interferon-γ (INF-γ) is beneficial, more particularly a disease or medical condition selected from the group consisting of psoriasis, psoriatric arthritis, autoimmune thyroiditis, Grave's disease, rheumatoid arthritis, vitiligo, Crohn's disease, ulcerative colitis, inflammatory bowel disease, ankylosing spondylitis, diabetes type I, multiple sclerosis, celiac disease, systemic lupus erythematosus, uveitis, Behcet disease, atopic dermatitis, Lichen planus, Sjögren's syndrome, spinal disc herniation, acne, Graft-versus-Host-Reaction, Host-versus-Graft-Reaction, AIH (Autoimmunhepatitis), PBC (peripheral biliary cholangitis), PSC (primary sclerotising cholangitis), obesity, Lupus nephritis, diabetes mellitus and osteoarthritis, said method comprising administering to a subject in need thereof an effective amount of a compound of formula (I) as described herein. Analogously, the present invention further relates to methods as the one described above, which encompass the further embodiments described herein, in particular the medical uses and compounds for use in medical treatments as described herein.

The present invention further relates to pharmaceutical compositions, kits and kits-of parts comprising the compounds according to the present invention.

The present invention further relates to the use of the compounds according to the present invention for the production of pharmaceutical compositions which are employed for the treatment and/or prophylaxis of the diseases, disorders, illnesses and/or conditions as mentioned herein.

The present invention further relates to the methods and medical uses described herein, encompassing the pharmaceutical compositions as described herein.

The pharmaceutical compositions as described herein comprise one or more of the compounds according to this invention and a pharmaceutically acceptable carrier or diluent.

Additionally, the invention relates to an article of manufacture, which comprises packaging material and a pharmaceutical agent contained within said packaging material, wherein the pharmaceutical agent is therapeutically effective against the medical conditions as described herein, and wherein the packaging material comprises a label or package insert which indicates that the pharmaceutical agent is useful for preventing or treating said medical conditions, and wherein said pharmaceutical agent comprises one or more compounds of formula (I) according to the invention. The packaging material, label and package insert otherwise parallel or resemble what is generally regarded as standard packaging material, labels and package inserts for pharmaceuticals having related utilities.

The pharmaceutical compositions according to this invention are prepared by processes which are known per se and familiar to the person skilled in the art. As pharmaceutical compositions, the compounds of the invention (=active compounds) are either employed as such, or particularly in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

Depending upon the particular disease, to be treated or prevented, additional therapeutic active agents, which are normally administered to treat or prevent that disease, may optionally be coadministered with the compounds according to the present invention. As used herein, additional therapeutic agents that are normally administered to treat or prevent a particular disease are known as appropriate for the disease being treated.

In a further aspect of the present invention, the compounds according to this invention or the salts or solvates of said compounds of formula (I) may be combined with standard therapeutic agents which are commonly used for the treatment of the medical conditions as described herein.

The person skilled in the art is aware on the base of his/her expert knowledge of the total daily dosage(s) and administration form(s) of the additional therapeutic agent(s) coadministered. Said total daily dosage(s) can vary within a wide range. In practicing the present invention and depending on the details, characteristics or purposes of their uses mentioned above, the compounds according to the present invention may be administered in combination therapy separately, sequentially, simultaneously or chronologically staggered (e.g. as combined unit dosage forms, as separate unit dosage forms or a adjacent discrete unit dosage forms, as fixed or nonfixed combinations, as kit-of-parts or as admixtures) with one or more standard therapeutics, in particular art-known chemotherapeutic or target specific anti-cancer agents, such as those mentioned above.

Thus, a further aspect of the present invention is a combination or pharmaceutical composition comprising a first active ingredient, which is a compound according to this invention or a pharmaceutically acceptable salt or solvate thereof, a second active ingredient, which is an art-known standard therapeutic for the medical conditions as described herein, and optionally a pharmacologically acceptable carrier, diluent and/or excipient for sequential, separate, simultaneous or chronologically staggered use in therapy in any order, e.g. to treat, prevent or ameliorate in a patient the medical conditions as described herein.

In this context, the present invention further relates to a combination comprising a first active ingredient, which is at least one compound according to this invention, and a second active ingredient, which is at least one art-known standard therapeutic for the medical conditions as described herein, for separate, sequential, simultaneous or chronologically staggered use in therapy, such as e.g. in therapy of those diseases mentioned herein.

The term "combination" according to this invention may be present as a fixed combination, a non-fixed combination or a kit-of-parts. A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously or chronologically staggered.

The first and second active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a medical condition as described herein A further aspect of the present invention is a method for treating cotherapeutically the medical conditions as described herein, in a patient in need of such treatment comprising administering separately, sequentially, simultaneously, fixed or non-fixed a therapeutically effective and tolerable amount of one or more of the compounds according to the present invention and a therapeutically effective and tolerable amount of one or more art-known therapeutic agents for the medical conditions as described herein, to said patient.

References and claims to the use of a compound of the formula (I) or a pharmaceutically acceptable salt or solvate thereof in the manufacture of a medicament for the treatment of a disease or medical condition in their general and specific forms likewise refer to the corresponding methods of treating said disease or medical condition, said method comprising administering a therapeutically effective and tolerable amount of a compound of the formula (I) or a pharmaceutically acceptable salt or solvate thereof to a subject in need thereof, compositions comprising a compound of the formula (I) or a pharmaceutically acceptable salt or solvate thereof for the treatment of said disease or medical condition, a compound of the formula (I) or a pharmaceutically acceptable salt or solvate thereof for use in the treatment of said disease or medical condition, and vice versa.

For the production of the pharmaceutical compositions, the compounds of the invention (=active compounds) are particularly mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions. The pharmaceutical compositions according to the invention are prepared by processes known per se.

The dosage of the active compounds is carried out in the customary order of magnitude. Topical application forms (such as ointments) thus contain the active compounds in a concentration of, for example, 0.1-99%. The customary dose in the case of systemic therapy (p.o.) is usually between 0.3 and 30 mg/kg per day, (i. v.) is usually between 0.3 and 30 mg/kg/h. The choice of the optimal dosage regime and duration of medication, particularly the optimal dose and manner of administration of the active compounds necessary in each case can be determined by a person skilled in the art on the basis of his/her expert knowledge.

The class of compounds of the present invention is useful for the development of medicaments suitable for the treatment of autoimmune diseases and chronic inflammation or, more generally, for the treatment of diseases where the inhibition of interleukin-17 (IL-17) and/or Interferon-γ (INF-γ) is beneficial.

The compounds of the present invention are also useful for the treatment of diseases which are related to or mediated by inflammatory cytokines, such as psoriasis, psoriatic arthritis, autoimmune thyroiditis, Grave's disease, rheumatoid arthritis, vitiligo, Crohn's disease, ulcerative colitis, inflammatory bowel disease, ankylosing spondylitis, diabetes type I, multiple sclerosis, celiac disease, systemic lupus erythematosus, uveitis, Behcet disease, atopic dermatitis, Lichen planus, Sjögren's syndrome, spinal disc herniation, acne, Graft-versus-Host-Reaction, Host-versus-Graft-Reaction, AIH (Autoimmunhepatitis), PBC (peripheral biliary cholangitis), PSC (primary scleroting cholangitis), obesity, Lupus nephritis, diabetes mellitus and osteoarthritis It has unexpectedly been found that compounds having the R1 groups as detailed herein show high cytokine induction while having favorable aqueous solubility and/or microsomal stability. The following example section shows further details.

EXAMPLES a) Synthesis

As used herein, the term "room temperature" or "r.t." usually refers to about 25° C.; "aq" refers to aqueous; "prep." refers to preparative; "TLC" refers to thin layer chromatography; "quant." refers to quantitative. Compounds with stereo centers where stereochemistry is not specifically indicated were obtained as mixtures of stereoisomers. For sake of completeness, residues "R" indicated in the following synthesis schemes in each case refer to a generic placeholder group, including in particular the specific groups as can be seen in the specific examples following each scheme and analogs thereof, and the meaning of "R" may vary between different synthesis schemes and positions within each scheme.

Analytical Devices Used

Analytical LC/ESI-MS: Waters 2700 Autosampler. Waters 1525 Multisolvent Delivery System. 5 uL sample loop. Column, Phenomenex Onyx Monolythic C18 50×2 mm, with stainless steel 2 μm prefilter. Eluent A, $H_2O+0.1\%$ HCOOH; eluent B, MeCN. Gradient, 5% B to 100% B within 3.80 min, then isocratic for 0.20 min, then back to 5% B within 0.07 min, then isocratic for 0.23 min; flow, 0.6 ml/min or 1.2 ml/min.

Waters Micromass ZQ 4000 single quadrupol mass spectrometer with electrospray source. MS method, MS4_15minPM-80-800-35V; positive/negative ion mode scanning, m/z 80-800 in 0.5 s; capillary voltage, 3.50 kV; cone voltage, 50 V; multiplier voltage, 650 V; source block and desolvation gas temperature, 120° C. and 300° C., respectively. Waters 2487 Dual λ Absorbance Detector, set to 254 nm. Software, Waters Masslynx V 4.0.

Waters Micromass LCZ Platform 4000 single quadrupol mass spectrometer with electrospray source. MS method, MS4_minPM-80-800-35V; positive/negative ion mode scanning, m/z 80-800 in 1 s; capillary voltage, 4.0 kV; cone voltage, 30 V; multiplier voltage, 900 V; source block and desolvation gas temperature, 120° C. and 300° C., respectively. Waters 996 Photodiode Array Detector, set 200 to 400 nm. Software, Waters Masslynx V4.0.

Values for $[M+H]^+$ given in the examples are those m/z found within the corresponding LC/MS chromatogram for the respective compound. These values were all found within tolerable margins of +/−0.3 units compared to calculated exact mass upon protonation of the compound.

Preparative thin layer chromatography (preparative TLC): Merck PLC plates, silica gel 60 $F_{254}$, 0.5 mm, 1.0 mm or 2.0 mm.

Column chromatography: Acros silica gel 60A, 0.035-0.070 mm.

Preparative HPLC-MS: I) Waters 2767 Autosampler, Waters 600 Multisolvent Delivery System with analytical pump heads (100 μL); Waters 600 Controller; Waters 2525 Binary Gradient Modul with preparative pump heads (500 μL). At-Column-Dilution: solvent1, $MeCN:H_2O$ 70:30 (v/v), solvent2, MeCN:MeOH:DMF 80:15:5 (v/v/v); flow rate, 5 mL/min. Autosampler 2767 with 10 mL syringe and 10 mL Sample loop. Column 6-position valve Flom 401 with Waters X-Terra RP18, 5 μm, 19×150 mm with X-Terra RP18 guard cartridge 5 μm, 19×10 mm, used at flow rate 20 mL/min; Waters SunFire Prep OBD 5 μm, 30×50 mm with SunFire RP18 guard cartridge 5 μm, 19×10 mm, used at flow rate 25 mL/min; Waters Atlantis Prep T3 OBD 5 μm, 30×50 mm with Atlantis guard cartridge, used at flow rate 50 mL/min; Waters X-Bridge Prep OBD 5 μm, 19×150 mm with X-Bridge RP18 guard cartridge 5 μm, 19×10 mm used at flow rate 20 mL/min; Waters Atlantis Prep T3 OBD 5 μm, 19×50 mm with Atlantis guard cartridge, used at flow rate 25 mL/min and YMC-Actus Hydrosphere C18 5 μm, 20×50 mm with Actus guard cartridge, used at flow rate 20 mL/min. Eluent A, $H_2O$ containing 0.1% (v/v) $HCO_2H$ or $H_2O$ containing 0.1% (v/v) $NEt_3$; eluent B, MeCN. Different linear gradients, individually adapted to sample. Injection volume 9 mL, depending on sample. Make-up solvent, $MeOH-MeCN—H_2O—HCO_2H$ 80:15:4.95:0.05 (v/v/v/v). Make-up pump, Waters Reagent Manager, flow rate 0.5 mL/min Waters ZQ single quadrupole mass spectrometer with electrospray source. Positive or negative ion mode scanning m/z 105-950 in 1 s; capillary, 3.6 kV; cone voltage, 45 V; multiplier voltage, 700 V; probe and desolvation gas temperature, 120° C. and 250° C., respectively. Waters Fraction Collector 2767 with mass or UV-triggered fraction collection. Waters 2487 Dual λ Absorbance Detector, set to 254 nm. Software, Waters Masslynx V 4.0 SP4.

[1] H NMR spectra were recorded at room temperature on a Bruker Supraleitendes Fourier NMR Spektrometer (superconducting Fourier NMR spectrometer), Avance™ 300 MHz. Chemical shifts δ are reported in ppm. Multiplicity of a certain signal (singlet, doublet, triplet, quartet, multiplet) is indicated by the respective abbreviation (s, d, t, q, m respectively). "br s" indicates a broad singlet, "$m_C$" a centered multiplet. The solvent residual signals were used as internal standards: δ(CDCl$_3$)=7.26, δ(d6-DMSO)=2.50, δ(CD$_3$OD)=3.31, δ(d6-acetone)=2.05.

General Procedure for the Preparation of alkyl 5-methylisoxazole-4-carboxylates

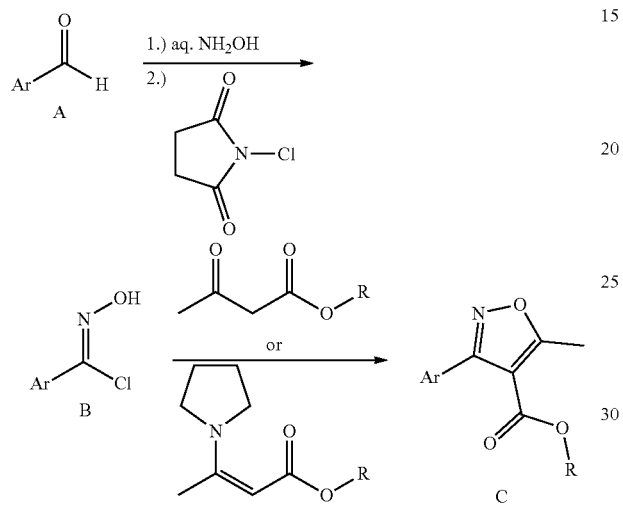

To a stirred mixture of aldehyde (scale: 60 mmol) A in ethanol (0.5 mL/mmol) and water (0.5 mL/mmol) was added hydroxylamine (1.3 eq., 50 wt % in water) at 0° C. The mixture was stirred at room temperature for 24 h, upon which all volatiles were removed under reduced pressure. Resulting crude oxime was taken up in DMF (1 mL/mmol) and treated with NCS (1.0 eq.) at room temperature for 24 h.

If required, reaction initiation can be better controlled by adding only 0.15 eq. NCS followed by dry hydrogen chloride being bubbled into the DMF solution until the reaction temperature rises up to 35° C.; afterwards NCS (0.85 eq.) can be added portionwise.

The reaction mixture was partitioned between DCM and water. Combined organic layers were dried over MgSO$_4$, filtrated and concentrated under reduced pressure to give crude hydroxamoyl chloride B.

The following hydroxamyl chlorides B were also synthesized for conversions within the "Cycloaddition reaction" section, being part of the syntheses of Examples 97 through 129 and related Building Blocks:

2-chloro-6-fluoro-N-hydroxybenzimidoyl chloride; Result of LC/MS [M+H]$^+$: 208.1;
2-chloro-N-hydroxybenzimidoyl chloride; Result of LC/MS [M+H]$^+$: 190.1;
2,6-dichloro-3-methoxy-N-hydroxybenzimidoyl chloride: this aromatic substitution pattern was generated from N-[(2-chloro-3-methoxyphenyl)methylidene]hydroxylamine when treated with 2.0 NCS instead of 1.0 eq. as used to generate 2-chloro-3-methoxy-N-hydroxybenzimidoyl chloride); Result of LC/MS [M+H]$^+$: 253.9;

$^1$H NMR (CDCl$_3$): δ3.92 (3H, s, CH$_3$), δ6.97 (1H, d, CH), 7.32 (1H, d, CH), 8.39 (1H, s, OH).
2-chloro-3-methoxy-N-hydroxybenzimidoyl chloride; Result of LC/MS [M+H]$^+$: 220.0;
2-methoxy-N-hydroxybenzimidoyl chloride
3-(benzyloxy)-2-chloro-N-hydroxybenzimidoyl chloride; Result of LC/MS [M+H]$^+$: 295.9;
methyl 2-chloro-3-(chloro(hydroxyimino)methyl)benzoate
methyl 3-(chloro(hydroxyimino)methyl)-2-methoxybenzoate
methyl 3-(chloro(hydroxyimino)methyl)benzoate According to this procedure, the following building blocks C were synthesized with an additional synthetic step as described below:

(Z)-ethyl 3-(pyrrolidin-1-yl)but-2-enoate: To pyrrolidine (6 mmol) was slowly added ethyl 3-oxobutanoate (1.0 eq.), (ATTENTION: highly exothermic!) to give a yellow suspension. Toluene was added (5 mL/mmol) to remove H$_2$O resulting from the condensation reaction using a Dean Stark trap. The mixture was heated under reflux for 5 h resulting in a solution, which was fractionated afterwards by distillation (8 mbar, 150° C.) to yield the product as a yellow oil (4.2 mmol, 70%).

$^1$H NMR (CDCl$_3$): δ1.24 (3H, t, CH$_3$), 1.92 (4H, m, CH$_2$), 2.45 (3H, s, CH$_3$), 3.28 (4H, m, CH$_2$), 4.08 (2H, q, CH$_2$), 4.46 (1H, s, CH).

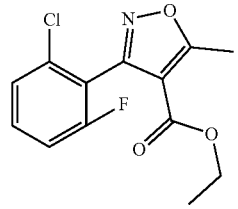 [SMILES: CCOC(=O)c1c(-c2c(F)cccc2Cl)noc1C]

Ethyl 3-(2-chloro-6-fluorophenyl)-5-methylisoxazole-4-carboxylate

To a solution of (Z)-2-chloro-6-fluoro-N-hydroxybenzimidoyl chloride (65 mmol) in DMF (2 mL/mmol) at 0° C. was added dropwise a solution of (Z)-ethyl 3-(pyrrolidin-1-yl)but-2-enoate (1.05 eq. in EtOH, 0.3 mL/mmol). After stirring at room temperature for 1 h, triethylamine (1.1 eq. in EtOH, 0.1 mL/mmol) was added dropwise over 2 h. The mixture was stirred at room temperature for 24 h. The resulting mixture was filtered and the filtrate was partitioned between CH$_2$Cl$_2$ and water. Combined organic layers were dried over MgSO$_4$ and concentrated under reduced pressure. The crude product was distilled at 10 mbar and 160° C. The product was obtained as an orange oil (80%).

$^1$H NMR (CDCl$_3$): δ1.07 (3H, t, CH$_3$), 2.79 (3H, s, CH$_3$), 4.14 (2H, q, CH$_2$), 7.09 (1H, td, CH-arom.), 7.29 (1H, d, CH-arom.), 7.39 (1H, m, CH-arom.).

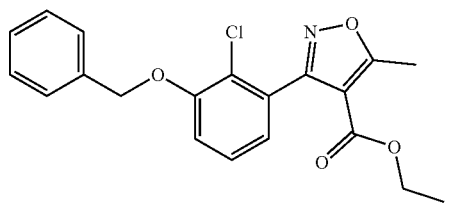 [SMILES: CCOC(=O)c1c(-c2cccc(OCc3ccccc3)c2Cl)noc1C]

Ethyl 3-(3-benzyloxy-2-chloro-phenyl)-5-methyl-isoxazole-4-carboxylate

To a solution of (Z)-3-(benzyloxy)-2-chloro-N-hydroxy-benzimidoyl chloride (60 mmol) in DMF (1 mL/mmol) at 0° C. was added dropwise a solution of (Z)-ethyl 3-(pyrrolidin-1-yl)but-2-enoate (1.05 eq. in EtOH, 0.3 mL/mmol). After stirring at room temperature for 1 h, triethylamine (1.1 eq. in EtOH, 0.1 mL/mmol) was added dropwise over 2 h. The mixture was stirred at room temperature for 24 h. All volatiles were removed under reduced pressure. The crude product was distilled at 2 mbar and 175-185° C. The product was obtained as an oily yellow solid (94%).

Result of LC/MS [M+H]$^+$: 372.0;

$^1$H NMR (CDCl$_3$): δ0.98 (3H, t, CH$_3$), 4.06 (2H, q, CH$_2$), 4.57 (3H, s, CH$_3$), 5.07 (2H, s, CH$_2$), 6.80 (1H, d, CH-arom.), 7.30 (7H, m, CH-arom.).

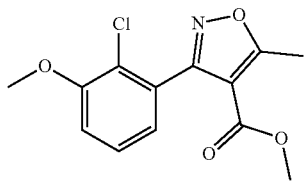

Methyl 3-(2-chloro-3-methoxy-phenyl)-5-methyl-isoxazole-4-carboxylate (Z)-2-Chloro-N-hydroxy-3-methoxybenzene-1-carbonimidoyl chloride (17 mmol) was dissolved in DMF (2 mL/mmol), and methyl acetoacetate (2.0 eq.) was added, followed by triethylamine (5.0 eq.). The mixture was stirred at room temperature for 24 h and then partitioned between CH$_2$Cl$_2$ and water. Combined organic layers were dried over MgSO$_4$, filtrated and concentrated under reduced pressure. Crude product was purified by column chromatography on silica gel (eluent: petroleum ether to petroleum ether/ethyl acetate 80:20) to yield a pale brownish solid (75%).

Result of LC/MS [M+H]$^+$: 282.00;

$^1$H NMR (CDCl$_3$): δ2.75 (3H, s, CH$_3$), 3.69 (3H, s, OCH$_3$), 3.94 (3H, s, OCH$_3$), 7.01 (1H, dd, CH-arom.), 7.05 (1H, dd, CH-arom.), 7.31 (1H, dd, CH-arom.).

Methyl 3-(2-chloro-6-fluorophenyl)-5-methylisoxazole-4-carboxylate was purchased from Apollo Scientific (PC9397). Methyl 3-(2-chlorophenyl)-5-methylisoxazole-4-carboxylate and ethyl 3-(2-chlorophenyl)-5-methylisoxazole-4-carboxylate were purchased from ABCR (AB158164 and AB334755, respectively).

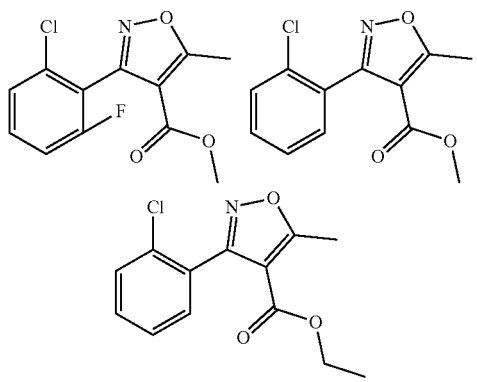

Preparation of 3-(2-chloro-6-fluorophenyl)-5-methyl-4-(thiazol-2-yl)isoxazole

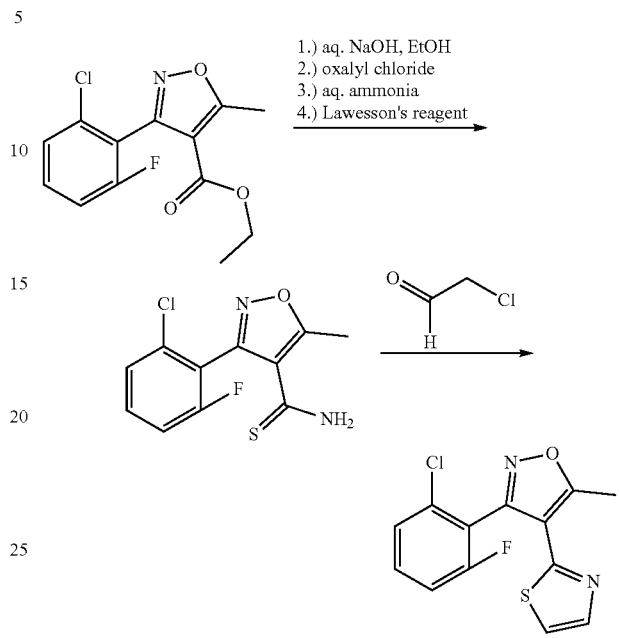

A solution of 28.4 g (100 mmol) of ethyl 3-(2-chloro-6-fluorophenyl)-5-methylisoxazole-4-carboxylate was dissolved in 40 mL ethanol, and 40 mL aq. NaOH (4.0 M) were added. The mixture was heated to 60° C. for 24 h. The ethanol was partially evaporated under reduced pressure and the remaining solution was acidified by addition of aq. HCl (4.0 M). A precipitate formed, which was filtered off, washed with H$_2$O and dried in vacuum to yield 25.2 g (99%) of crude 3-(2-chloro-6-fluorophenyl)-5-methylisoxazole-4-carboxylic acid as an off-white solid.

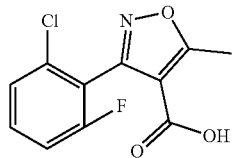 [SMILES: Cc1onc(-c2c(F)cccc2Cl)c1C(=O)O]

Result of LC/MS [M+H]$^+$: 255.9;

$^1$H NMR (CDCl$_3$): δ2.79 (3H, s, CH$_3$), 7.09 (1H, dt, CH-arom.), 7.30 (1H, dd, CH-arom.), 7.47-7.34 (1H, m, CH-arom.).

To a light beige suspension of 25.2 g (99 mmol) crude 3-(2-chloro-6-fluorophenyl)-5-methylisoxazole-4-carboxylic acid in CH$_2$Cl$_2$ (300 mL) a catalytic amount of DMF was added (ca. 0.1 mL), followed by dropwise addition of oxalyl chloride (5.0 eq.), resulting in an orange-red solution. The reaction mixture was refluxed for 1 h, upon which all volatiles were removed under reduced pressure. The crude material 3-(2-chloro-6-fluorophenyl)-5-methylisoxazole-4-carbonyl chloride was directly taken up in Et$_2$O (250 mL) and cooled to 0° C. 10% aq. Na$_2$CO$_3$ was added (250 mL), and the resulting two-phase mixture was vigorously stirred as aq ammonia solution was added slowly (50 mL; 35 wt % solution of NH$_3$ in water). The reaction mixture was stirred at 0° C. for 10 min and then at r.t. for 3 h. The two phases were separated, the organic phase was washed with H₂O and 5% aq. HCl, dried over MgSO₄ and concentrated under reduced pressure to yield crude 3-(2-chloro-6-fluorophenyl)-5-methylisoxazole-4-carboxamide as a beige solid (22.7 g, 90%).

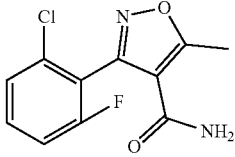 [SMILES: Cc1onc(-c2c(F)cccc2Cl)c1C(N)=O]

Result of LC/MS [M+H]⁺: 254.9;
¹H NMR (CDCl₃): δ2.79 (3H, s, CH₃), 5.40 (2H, br, NH₂), 7.18 (1H, t, CH-arom.), 7.38 (1H, d, CH-arom.), 7.55-7.42 (1H, m, CH-arom.).

To a solution of 12.7 g (50 mmol) crude 3-(2-chloro-6-fluorophenyl)-5-methylisoxazole-4-carboxamide in 150 mL dioxane (Sure/Seal), 1.0 eq. Lawesson's Reagent were added. The mixture was stirred for 4 h under reflux. Upon cooling to r.t., a precipitate was filtered off and the filtrate was concentrated under reduced pressure. The oily residue was purified by column chromatography (silica gel; eluent: 100% CH₂Cl₂) to yield 11.0 g (81%) of 3-(2-chloro-6-fluorophenyl)-5-methylisoxazole-4-carbothioamide as a yellow solid.

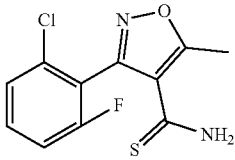 [SMILES: Cc1onc(-c2c(F)cccc2Cl)c1C(N)=S]

Result of LC/MS [M+H]⁺: 270.9;
¹H NMR (CDCl₃): δ2.84 (3H, s, CH₃), 6.50 (1H, br, NH), 7.17 (1H, td, CH-arom.), 7.30 (1H, br, NH), 7.36 (1H, dt, CH-arom.), 7.51-7.40 (1H, m, CH-arom.).

To a yellow suspension of 10.8 g (40 mmol) 3-(2-chloro-6-fluorophenyl)-5-methylisoxazole-4-carbothioamide in ethanol was added chloroacetaldehyde solution (10 eq.; 50 wt % in H₂O) and the reaction mixture was stirred at reflux for 24 h. All volatiles were removed under reduced pressure. The residue was dissolved in EtOAc and washed 3 times with water. The organic phase was dried over MgSO₄, filtered and concentrated under reduced pressure. The residue was purified by flash column chromatography on silica gel (eluent: 100% CH₂Cl₂). The title compound 3-(2-chloro-6-fluorophenyl)-5-methyl-4-(thiazol-2-yl)isoxazole was obtained as a yellow oil (8.37 g, 71%).

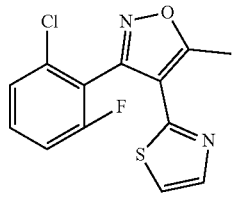 [SMILES: Cc1onc(-c2c(F)cccc2Cl)c1-c1nccs1]

Result of LC/MS [M+H]⁺: 294.9;
¹H NMR (CDCl₃): δ2.89 (3H, s, CH₃), 7.15 (1H, td, CH-arom.), 7.19 (1H, d, CH-arom), 7.35 (1H, dt, CH-arom.), 7.52-7.42 (1H, m, CH-arom.), 7.80 (1H, d CH-arom.).

General Procedure for the Preparation of 5-(1-(dimethylamino)-4,4,4-trifluoro-3-oxobut-1-en-2-yl)isoxazoles and 5-(1-(dimethylamino)-3-oxobut-1-en-2-yl)isoxazoles

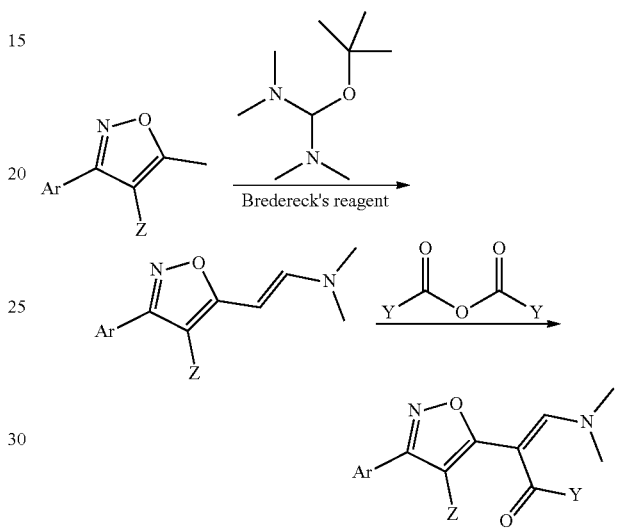

Step 1: To a solution of 3-aryl-5-methylisoxazole (10 mmol) in dry toluene (Sure/Seal; 2 mL/mmol) was added tert-butoxy-bis(dimethylamino)methane (Bredereck's reagent; 2.5 eq.). The reaction mixture was heated under reflux for 5 h, then cooled to room temperature, concentrated under reduced pressure and partitioned between CH₂Cl₂ and water. Combined organic layers were dried over MgSO₄, volatiles were removed under reduced pressure to give crude enamine intermediate.

Step 2a, Y=CF₃: Crude enamine intermediate out of step 1 (10 mmol) was dissolved in CH₂Cl₂ (3 mL/mmol) and cooled to 0° C. Trifluoroacetic anhydride (2.0 eq.) was added dropwise at this temperature, followed by triethylamine (1.0 eq.). The reaction mixture was allowed to warm to room temperature within 3 h, and was next partitioned between CH₂Cl₂ and water. Combined organic layers were washed with saturated aq. NaHCO₃ and dried over MgSO₄. Crude product was purified by flash chromatography on silica gel (eluent: CH₂Cl₂ to CH₂Cl₂/MeOH 95:5).

Step 2b, Y=Me: Crude enamine intermediate out of step 1 (10 mmol) was dissolved in THF (Sure/Seal; 3 mL/mmol) and acetyl chloride (2.5 eq.) and diisopropylethylamine (3.0 eq.) were added. The reaction mixture was heated under reflux for 18 h. Conversion was monitored by TLC, additional acetyl chloride might be required to drive conversion to completion. Upon cooling to room temperature, the mixture was partitioned between CH₂Cl₂ and water. Combined organic layers were washed with saturated aq. NaHCO₃ and dried over MgSO₄. Crude product was purified by flash chromatography on silica gel (eluent: CH₂Cl₂ to CH₂Cl₂/MeOH 95:5).

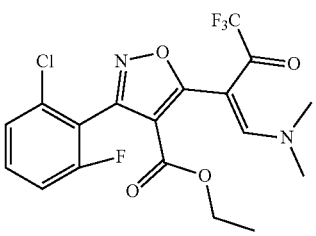 [SMILES: CCOC(=O)c1c(-c2c(F)cccc2Cl)noc1/C(=C/N(C)C)C(=O)C(F)(F)F]

ethyl (Z)-3-(2-chloro-6-fluorophenyl)-5-(1-(dimethylamino)-4,4,4-trifluoro-3-oxobut-1-en-2-yl)isoxazole-4-carboxylate (step 1+2a)

Off-white powder, 48% yield over two steps.

Result of LC/MS [M+H]$^+$: 434.8;

$^1$H NMR (DMSO): δ0.84 (3H, t, CH$_3$), 2.52 (3H, s, CH$_3$), 3.29 (H, s, CH$_3$), 3.92 (2H, q, CH$_2$), 7.32 (1H, t, CH-arom.), 7.42 (1H, d, CH-arom.), 7.54 (7H, m, CH-arom.), 8.00 (1H, s, CH).

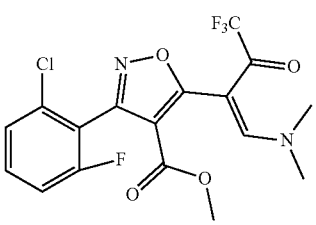 [SMILES: COC(=O)c1c(-c2c(F)cccc2Cl)noc1/C(=C/N(C)C)C(=O)C(F)(F)F]

methyl (Z)-3-(2-chloro-6-fluorophenyl)-5-(1-(dimethylamino)-4,4,4-trifluoro-3-oxobut-1-en-2-yl)isoxazole-4-carboxylate (step 1+2a)

Pale yellow powder, 53% yield over two steps.

Result of LC/MS [M+H]$^+$: 420.8;

$^1$H NMR (DMSO): δ3.63 (3H, s, CH$_3$), 3.40 (3H, s, CH$_3$), 3.57 (3H, s, CH$_3$), 7.44 (1H, t, CH-arom.), 7.53 (1H, d, CH-arom.), 7.65 (7H, m, CH-arom.), 8.12 (1H, s, CH).

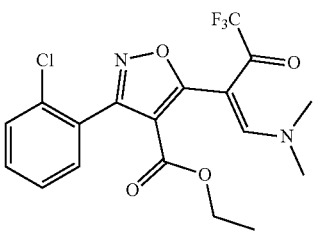 [SMILES: CCOC(=O)c1c(-c2ccccc2Cl)noc1/C(=C/N(C)C)C(=O)C(F)(F)F]

ethyl (Z)-3-(2-chlorophenyl)-5-(1-(dimethylamino)-4,4,4-trifluoro-3-oxobut-1-en-2-yl)isoxazole-4-carboxylate (step 1+2a)

Yellow solid, 46% yield over two steps.

Result of LC/MS [M+H]$^+$: 416.7;

$^1$H NMR (CDCl$_3$): δ0.38 (3H, t, CH$_3$), 2.75 (6H, s, 2x CH$_3$), 4.12 (2H, q, CH$_2$), 7.45 (5H, t, CH-arom.).

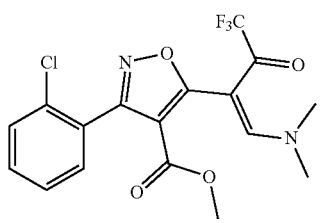 [SMILES: COC(=O)c1c(-c2ccccc2Cl)noc1/C(=C/N(C)C)C(=O)C(F)(F)F]

methyl (Z)-3-(2-chlorophenyl)-5-(1-(dimethylamino)-4,4,4-trifluoro-3-oxobut-1-en-2-yl)isoxazole-4-carboxylate (step 1+2a)

Pale yellow powder, 42% yield over two steps.

Result of LC/MS [M+H]$^+$: 403.1;

$^1$H NMR (CDCl$_3$): δ3.72 (3H, s, CH$_3$), 3.34 (3H, s, CH$_3$), 3.63 (3H, s, CH$_3$), 7.44 (4H, m, CH-arom.), 7.95 (1H, s, CH).

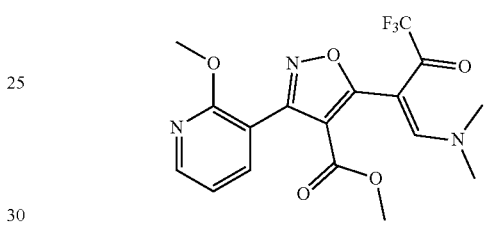

methyl (Z)-5-(1-(dimethylamino)-4,4,4-trifluoro-3-oxobut-1-en-2-yl)-3-(2-methoxypyridin-3-yl)isoxazole-4-carboxylate Starting with building block 2-methoxypyridine-3-carboxaldehyde (30 mmol), the general reaction procedures described above followed by step 1+2a yielded the title compound as pale yellow powder in 16% yield over 5 steps.

Result of LC/MS [M+H]$^+$: 399.9;

$^1$H NMR (DMSO): δ3.64 (3H, s, CH$_3$), 3.41 (3H, s, CH$_3$), 3.59 (3H, s, CH$_3$), 3.82 (3H, s, CH$_3$), 7.15 (1H, dd, CH-arom.), 7.92 (1H, dd, CH-arom.), 8.09 (1H, s, CH), 8.34 (1H, dd, CH-arom.).

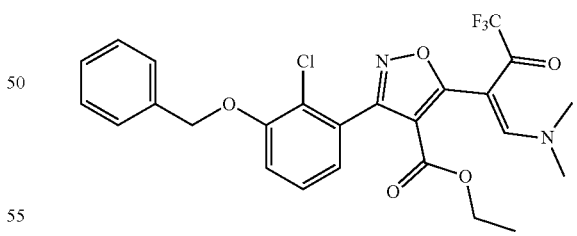

ethyl (Z)-3-(3-(benzyloxy)-2-chlorophenyl)-5-(1-(dimethylamino)-4,4,4-trifluoro-3-oxobut-1-en-2-yl)isoxazole-4-carboxylate (step 1+2a)

Brownish oil, 38% yield over two steps.

Result of LC/MS [M+H]$^+$: 523.1;

$^1$H NMR (DMSO): δ1.02 (3H, t, CH$_3$), 2.73 (3H, d, N—CH$_3$), 3.34 (3H, d, N—CH$_3$), 4.09 (2H, q, CH$_2$), 5.21 (2H, s, CH$_2$), 7.12 (2H, m, CH-arom.) 7.39 (6H, m, CH-arom.), 7.97 (1H, s, CH).

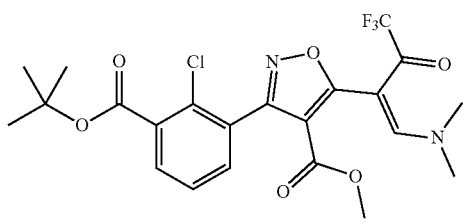 [SMILES: COC(=O)c1c(-c2cccc(C(=O)OC(C)(C)C)c2Cl)noc1/C(=C/N(C)C)C(=O)C(F)(F)F]

methyl (Z)-3-(3-(tert-butoxycarbonyl)-2-chlorophenyl)-5-(1-(dimethylamino)-4,4,4-trifluoro-3-oxobut-1-en-2-yl)isoxazole-4-carboxylate 2-Chloro-3-formylbenzoic acid (25 mmol) was dissolved in THF (75 mL) and di-tert-butyldicarbonate (2.0 eq.) and N,N-dimethylaminopyridine (0.2 eq.) were added. The mixture was stirred at room temperature for 18 h. The mixture was partitioned between ethyl acetate and water. Combined organic layers were washed with saturated aq. $NaHCO_3$ and brine, dried over $MgSO_4$ and concentrated under reduced pressure. Flash chromatography on silica gel (eluent: petroleum ether to petroleum ether/ethyl acetate 80:20) yielded tert-butyl 2-chloro-3-formylbenzoate (87%). Starting with this building block, the general reaction procedures described above followed by step 1+2a yielded the title compound as an off-white powder in 27% yield over 5 steps.

Result of LC/MS $[M+H]^+$: 523.1;

$^1$H NMR ($CDCl_3$): δ1.61 (9H, s, t-Bu), 3.73 (3H, s, $CH_3$), 3.35 (3H, s, $CH_3$), 3.63 (3H, s, $CH_3$), 7.43 (1H, t, CH-arom.), 7.59 (1H, dd, CH-arom.), 7.81 (1H, dd, CH-arom.), 7.96 (1H, s, CH).

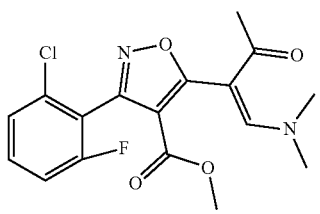 [SMILES: COC(=O)c1c(-c2c(F)cccc2Cl)noc1/C(=C/N(C)C)C(C)=O]

methyl (Z)-3-(2-chloro-6-fluorophenyl)-5-(1-(dimethylamino)-3-oxobut-1-en-2-yl)isoxazole-4-carboxylate (step 1+2b)

Orange solid, 52% yield over two steps.

Result of LC/MS $[M+H]^+$: 367.1;

$^1$H NMR ($CDCl_3$): δ2.04 (3H, s, $CH_3$), 2.63 (3H, d, N—$CH_3$), 3.21 (3H, d, N—$CH_3$), 3.64 (3H, s, $CH_3$), 7.13 (1H, t, CH-arom.), 7.31 (1H, d, CH-arom.), 7.41 (1H, m, CH-arom.), 7.87 (1H, s, CH).

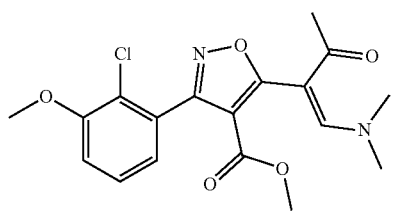

methyl (Z)-3-(2-chloro-3-methoxyphenyl)-5-(1-(dimethylamino)-3-oxobut-1-en-2-yl)isoxazole-4-carboxylate (step 1+2b)

Brownish oil, 63% yield over two steps.

Result of LC/MS $[M+H]^+$: 379.0;

$^1$H NMR ($CDCl_3$): δ2.45 (3H, s, $CH_3$), 2.67 (3H, d, N—$CH_3$), 3.17 (3H, d, N—$CH_3$), 3.63 (3H, s, $CH_3$), 3.94 (3H, s, $CH_3$), 7.09 (2H, m, CH-arom.), 7.35 (1H, t, CH-arom.), 7.41 (1H, m, CH-arom.), 7.85 (1H, s, CH).

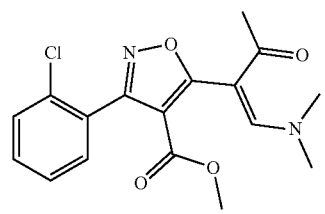 [SMILES: COC(=O)c1c(-c2ccccc2Cl)noc1/C(=C/N(C)C)C(C)=O]

methyl (Z)-3-(2-chlorophenyl)-5-(1-(dimethylamino)-3-oxobut-1-en-2-yl)isoxazole-4-carboxylate (step 1+2b)

Beige-brown solid, 40% yield over two steps.

Result of LC/MS $[M+H]^+$: 349.3;

$^1$H NMR ($CDCl_3$): δ2.05 (3H, s, $CH_3$), 2.70 (3H, d, N—$CH_3$), 3.17 (3H, d, N—$CH_3$), 3.63 (3H, s, $CH_3$), 7.44 (4H, m, CH-arom.), 7.87 (1H, s, CH).

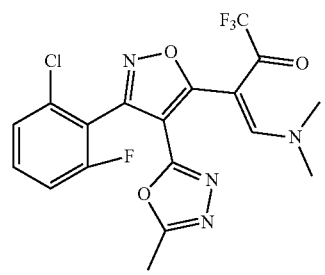 [SMILES: Cc1nnc(-c2c(-c3c(F)cccc3Cl)noc2/C(=C/N(C)C)C(=O)C(F)(F)F)o1]

(Z)-3-(3-(2-chloro-6-fluorophenyl)-4-(5-methyl-1,3,4-oxadiazol-2-yl)isoxazol-5-yl)-4-(dimethylamino)-1,1,1-trifluorobut-3-en-2-one A solution of methyl 3-(2-chloro-6-fluorophenyl)-5-methylisoxazole-4-carboxylate (50 mmol) was dissolved in 20 mL ethanol, and 20 mL aq. NaOH (4.0 M) were added. The mixture was heated to 60° C. for 24 h. The ethanol was partially evaporated under reduced pressure and the remaining solution was acidified by addition of aq. HCl (4.0 M). A precipitate formed, which was filtered off, washed with $H_2O$ and dried in vacuum to yield crude 3-(2-chloro-6-fluorophenyl)-5-methylisoxazole-4-carboxylic acid quantitatively as an off-white solid.

A solution of the carboxylic acid (10 mmol) in 30 mL $SOCl_2$ was refluxed for 3 h. Volatiles were thoroughly evaporated in vacuum. The residue was dissolved in dioxane (Sure/Seal; 100 mL) and added dropwise to a stirred mixture of $N_2H_4$*$H_2O$ (20 eq.) in 50 mL dioxane. The mixture was stirred at room temperature for 2 h, and was next partitioned between ethyl acetate and water. Combined organic layers were washed with water and brine, dried over $MgSO_4$. Evaporation to dryness yielded crude hydrazide, which was next heated in samples of ca. 1.85 mmol (ca. 500 mg) in the presence of 10 mL acetic anhydride under microwave irradiation at 140° C. for 6 h. The combined mixtures of multiple microwave reactions were diluted with dichloromethane and washed with water, dried over sodium sulfate, filtered and concentrated under reduced pressure. Column chromatography on silica gel (eluent: $CH_2Cl_2$ to $CH_2Cl_2$/MeOH 98:2) gave 2-[3-(2-chloro-6-fluorophenyl)-

5-methyl-1,2-oxazol-4-yl]-5-methyl-1,3,4-oxadiazole as a yellowish oil in 38% yield over three steps.

Starting with this building block (3 mmol), the general reaction steps 1+2a described above yielded the title compound as yellow powder in 44% yield over 2 steps.

Result of LC/MS [M+H]⁺: 349.3;

¹H NMR (CDCl₃): δ2.39 (3H, s, CH₃), 2.73 (3H, d, N—CH₃), 3.36 (3H, d, N—CH₃), 7.14 (1H, t, CH-arom.), 7.33 (1H, d, CH-arom.), 7.45 (1H, m, CH-arom.), 8.04 (1H, s, CH).

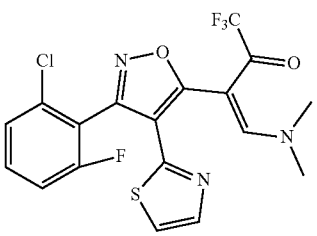 [SMILES: CN(C)/C=C(\C(=O)C(F)(F)F)c1onc(-c2c(F)cccc2Cl)c1-c1nccs1]

(Z)-3-(3-(2-chloro-6-fluorophenyl)-4-(thiazol-2-yl)isoxazol-5-yl)-4-(dimethyl amino)-1,1,1-trifluorobut-3-en-2-one (step 1+2a)

Orange powder, 25% yield over two steps.

Result of LC/MS [M+H]⁺: 445.7;

¹H NMR (CDCl₃): δ2.65 (3H, d, N—CH₃), 3.25 (3H, d, N—CH₃), 7.06 (1H, t, CH-arom.), 7.15 (1H, d, CH-arom.), 7.25 (1H, d, CH-arom.), 7.38 (1H, m, CH-arom.), 7.60 (1H, d, CH-arom.), 8.01 (1H, s, CH).

Synthesis of 3-hydrazinyl-cyclobutanols 3-hydrazinyl-1-methylcyclobutan-1-ol

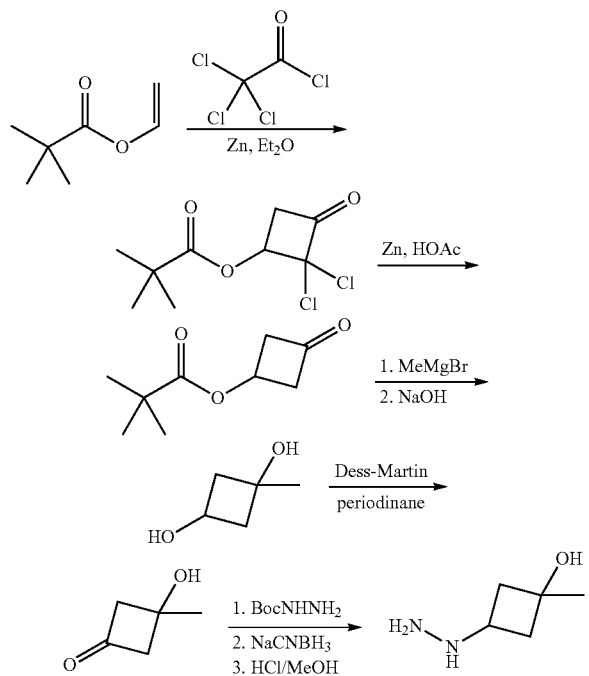

2,2-dichloro-3-oxocyclobutyl pivalate

To a stirred solution of vinyl pivalate (40.0 g, 0.321 mol) and Zn powder (41.2 g, 0.634 mol) in Et₂O (300 mL) cooled to 15° C. was added dropwise slowly (over 2 h) a solution of 2,2,2-trichloroacetyl chloride (73.2 g, 0.407 mol) in Et₂O (150 mL). The reaction mixture was stirred at room temperature for additional 4 h and then filtered through a pad of celite. The filtrate was washed with water (400 mL) and brine (400 mL), dried over anhydrous Na₂SO₄ and concentrated under reduced pressure. The residue was purified by column chromatography on silica gel (eluent: petroleum ether/ethyl acetate 30:1) to afford the desired compound (59.2 g, yield: 79%) as a colorless solid.

3-oxocyclobutyl pivalate

To a stirred suspension of Zn powder (80.8 g, 1.24 mol) in AcOH (300 mL) cooled to 15° C. was added dropwise slowly (over 0.5 h) a solution of 2,2-dichloro-3-oxocyclobutyl pivalate (59.0 g, 0.248 mol) in AcOH (100 mL). The reaction mixture was stirred at room temperature for additional 1 h and then filtered through a pad of celite. The filtrate was diluted with methyl tert-butyl ether (1.5 L), washed with brine (400 mL×4) and saturated aq. NaHCO₃ (400 mL×4) in turn until the pH was approximately 8, dried over anhydrous Na₂SO₄ and concentrated under reduced pressure. The residue was purified by column chromatography on silica gel (eluent: petroleum ether/ethyl acetate 25:1) to afford the desired compound (29.0 g, yield: 59%) as an oil.

3-hydroxy-3-methylcyclobutyl pivalate

To a stirred suspension of MeMgBr (118 mL, 0.353 mol, 3 M in Et₂O) in dry THF (80 mL) cooled to 0° C. was added dropwise slowly (over 0.5 h) a solution of 3-oxocyclobutyl pivalate (40.0 g, 0.235 mol) in THF (100 mL). The reaction mixture was stirred at room temperature for additional 1.5 h. The reaction mixture was poured into cold saturated aq. NH₄Cl (300 mL). The organic phase was washed with brine (200 mL), dried over anhydrous Na₂SO₄ and concentrated under reduced pressure. The residue was purified by column chromatography on silica gel (eluent: petroleum ether/ethyl acetate 2:1) to afford the desired compound (26.0 g, yield: 60%) as a sticky oil.

1-methylcyclobutane-1,3-diol

To a stirred solution of 3-hydroxy-3-methylcyclobutyl pivalate (3.30 g, 0.0177 mol) in MeOH (30 mL) at room temperature was added a solution of NaOH (3.18 g, 0.0775 mol) in water (30 mL). The reaction mixture was stirred at room temperature for 18 h and then concentrated under reduced pressure to remove most of MeOH. The residue was adjusted to pH=4 with 1 M aq. HCl and washed with CH₂Cl₂ (30 mL×2). The aqueous phase was concentrated under reduced pressure at 55° C. The residue was subjected to azeotropic distillation with EtOH (20 mL×2). A solution of CH₂Cl₂/EtOH 10:1 (30 mL) and NaHCO₃ solid (2 g) were added. The resulting mixture was filtered through a pad of celite. The filtrate was concentrated under reduced pressure to afford the desired compound (1.40 g, yield: 77%) as a light yellow oil.

3-hydroxy-3-methylcyclobutanone

To a stirred solution of 1-methylcyclobutane-1,3-diol (11.6 g, 0.114 mol) in CH₂Cl₂ (200 mL) and THF (30 mL)

at room temperature was added Dess-Martin periodinane (53.0 g, 0.125 mol). The reaction mixture was stirred at room temperature for 18 h and then filtered through a pad of celite. The filtrate was concentrated under reduced pressure to afford the crude desired compound (11.4 g) as a pale yellow oil. This crude product was used in the next step without further purification.

tert-butyl 2-(3-hydroxy-3-methylcyclobutyl)hydrazinecarboxylate

To a stirred solution of 3-hydroxy-3-methylcyclobutanone (11.4 g crude, 0.114 mol) in MeOH (200 mL) at room temperature was added BocNHNH₂ (18.1 g, 0.137 mol) and AcOH (0.5 mL). The reaction mixture was stirred at room temperature for 3 h and then NaBH₃CN (14.4 g, 0.228 mol) was added at room temperature The reaction mixture was stirred at room temperature for 2 h and then heated to 80° C. for 18 h. The reaction mixture was cooled to room temperature and concentrated under reduced pressure. The residue was diluted with EtOAc (200 mL), washed with water (200 mL) and brine (200 mL) in turn, dried over anhydrous Na₂SO₄ and concentrated under reduced pressure. The residue was purified by column chromatography on silica gel (eluent: CH₂Cl₂/MeOH 100:1 to 40:1) to afford the desired compound (12.0 g, yield: 40%) as a sticky oil.

3-hydrazinyl-1-methylcyclobutanol hydrochloride

A solution of tert-butyl 2-(3-hydroxy-3-methylcyclobutyl)hydrazinecarboxylate (350 mg, 1.62 mmol) in HCl/MeOH (3 M; 4 mL) was stirred at room temperature for 1 h. The reaction mixture was concentrated under reduced pressure to afford the desired compound (275 mg, yield: 100%) as a sticky oil.

Result of LC/MS [M+H]⁺: 116.9;

¹H NMR (CDCl₃): δ1.23 (3H, d, CH₃), 2.09 (4H, m, CH₂), 3.68 (1H, m, CH), 3.91 (2H, s, NH₂).

3-hydrazineyl-1-(methoxymethyl)cyclobutan-1-ol

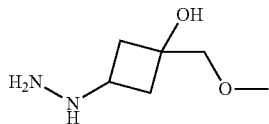

This hydrazinyl-cyclobutanol was synthesized in analogy to 3-hydrazinyl-1-methylcyclobutan-1-ol, only the reaction step using MeMgBr was substituted by using methoxymethyl magnesium chloride in THF (30° C., 18 h).

General Procedure for the Preparation of 3-aryl-5-(1,5-disubstituted-1H-pyrazol-4-yl)isoxazoles

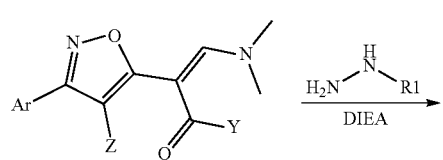

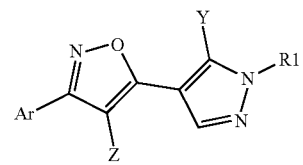

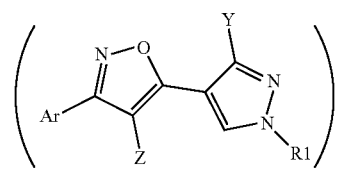

minor structural isomer

To a solution of 2-acyl-1-(dimethylamino)-ethylene in dried ethanol (4 mL/mmol), were added the respective hydrazine derivative (1.3 eq.) and N,N-diisopropylethylamine (1.3 eq. if hydrazine was used as a free base, 3.0 eq. if hydrazine was used as hydrochloride salt). The reaction mixture was heated at 60° C. for 2 to 18 h, depending on conversion as monitored by LCMS. In a few cases, heating up to 78° C. was necessary to drive conversion to completion. Mixtures were partitioned between CH₂Cl₂ and saturated. aq. NH₄Cl, organic layer was dried over MgSO₄ and concentrated under reduced pressure. Products were isolated by using preparative TLC (pTLC) on silica gel.

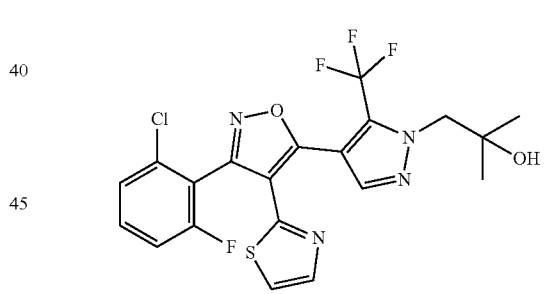

Example 1: 1-(4-(3-(2-chloro-6-fluorophenyl)-4-(thiazol-2-yl)isoxazol-5-yl)-5-(trifluoromethyl)-1H-pyrazol-1-yl)-2-methylpropan-2-ol Title compound was synthesized from (Z)-3-(3-(2-chloro-6-fluorophenyl)-4-(thiazol-2-yl)isoxazol-5-yl)-4-(dimethylamino)-1,1,1-trifluorobut-3-en-2-one (2.2 mmol) and 1-hydrazinyl-2-methylpropan-2-ol as yellowish solid (53%; pTLC, eluent: petroleum ether/ethyl acetate 1:1).

Result of LC/MS [M+H]⁺: 486.8;

¹H NMR (CDCl₃): δ1.26 (6H, s, 2xCH₃), 4.26 (1H, s, OH), 4.32 (2H, s, CH₂), 7.17 (1H, td, CH-arom.), 7.21 (1H, d, CH-arom.), 7.36 (1H, dt, CH-arom.), 7.54-7.44 (1H, m, CH-arom.), 7.69 (1H, d, CH-arom.), 8.11 (1H, s, CH-arom.).

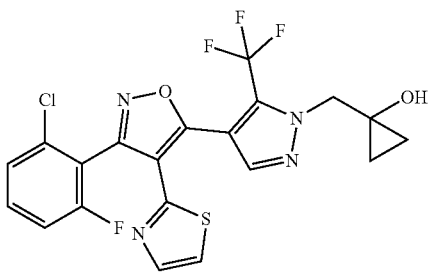 [SMILES: OC1(Cn2ncc(-c3onc(-c4c(F)cccc4Cl)c3-c3nccs3)c2C(F)(F)F)CC1]

Example 2: 1-((4-(3-(2-chloro-6-fluorophenyl)-4-(thiazol-2-yl)isoxazol-5-yl)-5-(trifluoromethyl)-1H-pyrazol-1-yl)methyl)cyclopropanol Title compound was synthesized from (Z)-3-(3-(2-chloro-6-fluorophenyl)-4-(thiazol-2-yl)isoxazol-5-yl)-4-(dimethylamino)-1,1,1-trifluorobut-3-en-2-one (0.22 mmol) and 1-(hydrazinylmethyl)cyclopropanol as orange oil (27%; pTLC, eluent: petroleum ether/ethyl acetate 1:1).

Result of LC/MS [M+H]$^+$: 484.6;

$^1$H NMR (CDCl$_3$): δ0.81-0.74 (2H, m, CH$_2$), 1.05-0.97 (2H, m, CH$_2$), 4.21-4.00 (1H, m, OH), 4.42 (2H, s, CH$_2$), 7.16 (1H, td, CH-arom.), 7.22 (1H, d, CH-arom.), 7.35 (1H, dt, CH-arom.), 7.53-7.43 (1H, m, CH-arom.), 7.71 (1H, d CH-arom.), 8.12 (1H, s, CH-arom.).

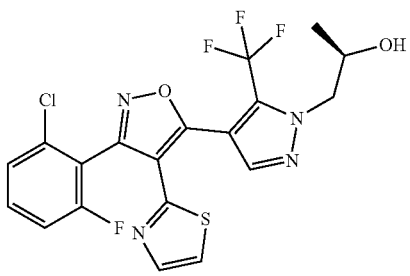

Example 4: (2R)-1-(4-(3-(2-chloro-6-fluorophenyl)-4-(thiazol-2-yl)isoxazol-5-yl)-5-(trifluoromethyl)-1H-pyrazol-1-yl)propan-2-ol Title compound was synthesized from (Z)-3-(3-(2-chloro-6-fluorophenyl)-4-(thiazol-2-yl)isoxazol-5-yl)-4-(dimethylamino)-1,1,1-trifluorobut-3-en-2-one (0.14 mmol) and (R)-1-hydrazinylpropan-2-ol as yellowish oil (23%; pTLC, eluent: CH$_2$Cl$_2$/MeOH 95:5 and pTLC, eluent: petroleum ether/ethyl acetate 1:1).

Result of LC/MS [M+H]$^+$: 472.8;

$^1$H NMR (CDCl$_3$): δ1.32 (3H, d, CH$_3$), 3.37 (1H, d, OH), 4.25 (1H, dd, CH), 4.48-4.32 (2H, m, 2xCH), 7.16 (1H, td, CH-arom.), 7.22 (1H, d, CH-arom.), 7.36 (1H, d, CH-arom.), 7.54-7.44 (1H, m, CH-arom.), 7.71 (1H, d, CH-arom.), 8.09 (1H, s, CH-arom.).

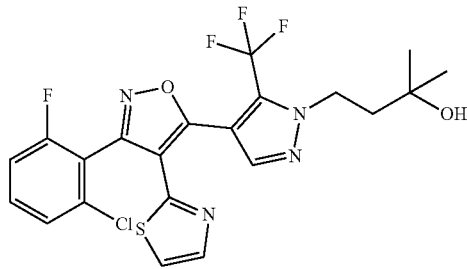 [SMILES: CC(C)(O)CCn1ncc(-c2onc(-c3c(F)cccc3Cl)c2-c2nccs2)c1C(F)(F)F]

Example 3: 4-(4-(3-(2-chloro-6-fluorophenyl)-4-(thiazol-2-yl)isoxazol-5-yl)-5-(trifluoromethyl)-1H-pyrazol-1-yl)-2-methylbutan-2-ol Title compound was synthesized from (2)-3-(3-(2-chloro-6-fluorophenyl)-4-(thiazol-2-yl)isoxazol-5-yl)-4-(dimethylamino)-1,1,1-trifluorobut-3-en-2-one (0.57 mmol) and 4-hydrazinyl-2-methylbutan-2-ol as yellowish oil (2%; pTLC, eluent: petroleum ether/ethyl acetate 1:1 and pTLC, eluent: CH$_2$Cl$_2$/MeOH 98:2).

Result of LC/MS [M+H]$^+$: 501.2;

$^1$H NMR (CDCl$_3$): δ1.33 (6H, s, 2xCH$_3$), 2.14 (2H, dt, CH$_2$), 4.54 (2H, dt, CH$_2$), 7.16 (1H, td, CH-arom.), 7.21 (1H, d, CH-arom.), 7.35 (1H, dt, CH-arom.), 7.52-7.43 (1H, m, CH-arom.), 7.71 (1H, d, CH-arom.), 8.03 (1H, s, CH-arom.).

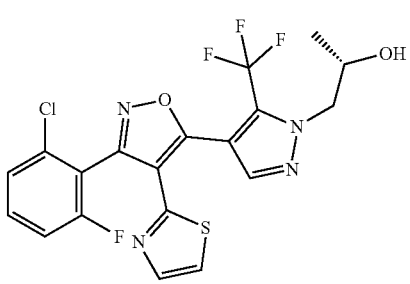 [SMILES: C[C@H](O)Cn1ncc(-c2onc(-c3c(F)cccc3Cl)c2-c2nccs2)c1C(F)(F)F]

Example 5: (2S)-1-(4-(3-(2-chloro-6-fluorophenyl)-4-(thiazol-2-yl)isoxazol-5-yl)-5-(trifluoromethyl)-1H-pyrazol-1-yl)propan-2-ol Title compound was synthesized from (Z)-3-(3-(2-chloro-6-fluorophenyl)-4-(thiazol-2-yl)isoxazol-5-yl)-4-(dimethylamino)-1,1,1-trifluorobut-3-en-2-one (0.14 mmol) and (S)-1-hydrazinylpropan-2-ol as yellowish oil (33%; pTLC, eluent: CH$_2$Cl$_2$/MeOH 95:5 and pTLC, eluent: petroleum ether/ethyl acetate 1:1).

Result of LC/MS [M+H]$^+$: 472.8;

$^1$H NMR (CDCl$_3$): δ1.32 (3H, d, CH$_3$), 3.37 (1H, d, OH), 4.25 (1H, dd, CH), 4.47-4.32 (2H, m, 2xCH), 7.17 (1H, td, CH-arom.), 7.22 (1H, d, CH-arom.), 7.36 (1H, d, CH-arom.), 7.54-7.44 (1H, m, CH-arom.), 7.71 (1H, d, CH-arom.), 8.09 (1H, s, CH-arom.).

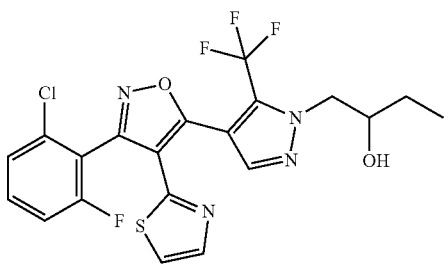 [SMILES: CCC(O)Cn1ncc(-c2onc(-c3c(F)cccc3Cl)c2-c2nccs2)c1C(F)(F)F]

Example 6: 1-{4-[3-(2-chloro-6-fluorophenyl)-4-(1,3-thiazol-2-yl)-1,2-oxazol-5-yl]-5-(trifluoromethyl)-1H-pyrazol-1-yl}butan-2-ol (Racemic)

Title compound was synthesized from (Z)-3-(3-(2-chloro-6-fluorophenyl)-4-(thiazol-2-yl)isoxazol-5-yl)-4-(dimethylamino)-1,1,1-trifluorobut-3-en-2-one (0.60 mmol) and 1-hydrazino-2-butanol as yellow solid (7%; pTLC, eluent: CH$_2$Cl$_2$/MeOH 95:5 and pTLC, eluent: petroleum ether/ethyl acetate 1:1).

Result of LC/MS [M+H]$^+$: 486.8;

$^1$H NMR (CDCl$_3$): δ1.06 (3H, t, CH$_3$), 1.69-1.55 (2H, m, CH$_2$), 3.32 (1H, br, OH), 4.18-4.07 (1H, m, CH), 4.25 (1H, dd, CH), 4.41 (1H, dd, CH), 7.16 (1H, td, CH-arom.), 7.22 (1H, d, CH-arom.), 7.35 (1H, dt, CH-arom.), 7.54-7.42 (1H, m, CH-arom.), 7.71 (1H, d, CH-arom.), 8.09 (1H, s, CH-arom.).

Example 8: ethyl 3-(2-chloro-6-fluorophenyl)-5-(1-(2-hydroxy-2-methylpropyl)-5-(trifluoromethyl)-1H-pyrazol-4-yl)isoxazole-4-carboxylate Title compound was synthesized from ethyl (Z)-3-(2-chloro-6-fluorophenyl)-5-(1-(dimethylamino)-4,4,4-trifluoro-3-oxobut-1-en-2-yl)isoxazole-4-carboxylate (1.1 mmol) and 1-hydrazinyl-2-methylpropan-2-ol as colorless powder (21%; pTLC, eluent: petroleum ether/ethyl acetate 1:1 and pTLC, eluent: petroleum ether/CH$_2$Cl$_2$/MeOH 9:4:1).

Result of LC/MS [M+H]$^+$: 475.70;

$^1$H NMR (CDCl$_3$): δ1.00 (3H, t, CH$_3$), 1.26 (6H, s, 2x CH$_3$), 4.10 (2H, q, CH$_2$), 4.31 (2H, s, CH$_2$), 7.11 (1H, td, CH-arom.), 7.33 (1H, d, CH-arom), 7.43 (1H, m, CH-arom.), 8.04 (1H, s, CH-arom).

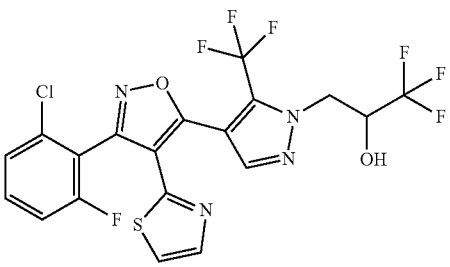 [SMILES: OC(Cn1ncc(-c2onc(-c3c(F)cccc3Cl)c2-c2nccs2)c1C(F)(F)F)C(F)(F)F]

Example 7: 3-{4-[3-(2-chloro-6-fluorophenyl)-4-(1,3-thiazol-2-yl)-1,2-oxazol-5-yl]-5-(trifluoromethyl)-1H-pyrazol-1-yl}-1,1,1-trifluoropropan-2-ol (Racemic)

Title compound was synthesized from (Z)-3-(3-(2-chloro-6-fluorophenyl)-4-(thiazol-2-yl)isoxazol-5-yl)-4-(dimethylamino)-1,1,1-trifluorobut-3-en-2-one (0.50 mmol) and 1,1,1-trifluoro-3-hydrazinylpropan-2-ol (racemic) as yellow solid (38%; pTLC, eluent: CH$_2$Cl$_2$/MeOH 95:5; mixture of structural isomers at pyrazol 60:40, cf. Scheme above).

Result of LC/MS [M+H]$^+$: 527.20;

$^1$H NMR (CDCl$_3$): δ4.15 (1H, br, OH), 4.39 (1H, dd, CH), 4.71-4.49 (2H, m, CH$_2$), 7.17 (1H, t, CH-arom.), 7.23 (1H, d, CH-arom.), 7.36 (1H, d, CH-arom.), 7.55-7.45 (1H, m, CH-arom.), 7.71 (1H, d, CH-arom.), 8.14 (1H, s, CH-arom.).

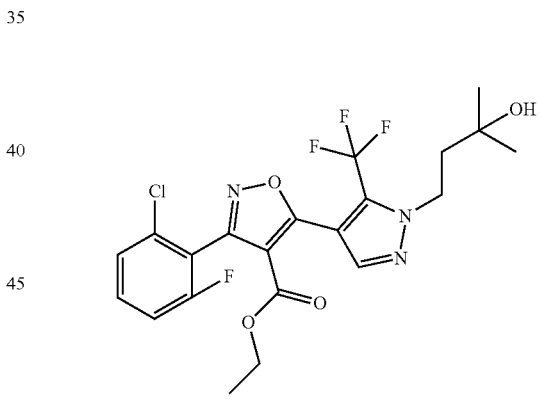

Example 9: ethyl 3-(2-chloro-6-fluorophenyl)-5-[1-(3-hydroxy-3-methylbutyl)-5-(trifluoromethyl)-1H-pyrazol-4-yl]-1,2-oxazole-4-carboxylate Title compound was synthesized from ethyl (Z)-3-(2-chloro-6-fluorophenyl)-5-(1-(dimethylamino)-4,4,4-trifluoro-3-oxobut-1-en-2-yl)isoxazole-4-carboxylate (2.3 mmol) and 4-hydrazinyl-2-methylbutan-2-ol as yellow oil (45%; pTLC, eluent: CH$_2$Cl$_2$/MeOH 95:5).

Result of LC/MS [M+H]$^+$: 490.30;

$^1$H NMR (CDCl$_3$): δ0.99 (3H, t, CH$_3$), 1.33 (3H, s, CH$_3$), 1.64 (1H, br, OH), 2.15 (2H, m, CH$_2$), 4.09 (2H, q, CH$_2$), 4.53 (2H, m, CH$_2$), 7.13 (1H, td, CH-arom.), 7.32 (1H, d, CH-arom), 7.41 (1H, m, CH-arom.), 7.97 (1H, s, CH-arom).

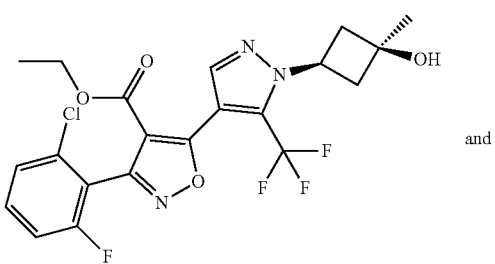

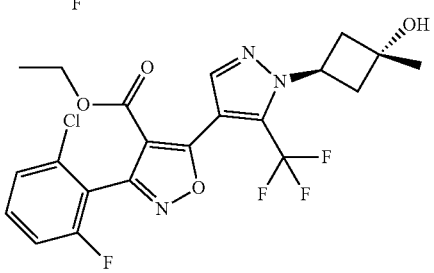

Examples 10 and 11: ethyl 3-(2-chloro-6-fluorophenyl)-5-[1-(3-hydroxy-3-methylcyclobutyl)-5-(trifluoromethyl)-1H-pyrazol-4-yl]-1,2-oxazole-4-carboxylate, Syn- and Anti-Configuration)

Title compounds were synthesized from ethyl (Z)-3-(2-chloro-6-fluorophenyl)-5-(1-(dimethylamino)-4,4,4-trifluoro-3-oxobut-1-en-2-yl)isoxazole-4-carboxylate (0.17 mmol) and 3-hydrazinyl-1-methylcyclobutan-1-ol (syn/anti mixture) (pTLC, eluent: CH$_2$Cl$_2$/MeOH 95:5 and pTLC, eluent: CH$_2$Cl$_2$/MeOH 98:2);

Example 10: syn-diastereomer (3%)
Result of LC/MS [M+H]$^+$: 488.20;
$^1$H NMR (CDCl$_3$): δ0.99 (3H, t, CH$_3$), 1.49 (3H, s, CH$_3$), 2.80 (4H, m, CH$_2$), 4.09 (2H, q, CH$_2$), 4.72 (1H, m, CH), 7.13 (1H, td, CH-arom.), 7.33 (1H, d, CH-arom.), 7.42 (1H, m, CH-arom.), 8.00 (1H, s, CH-arom).

Example 11: anti-diastereomer (5%)
Result of LC/MS [M+H]$^+$: 488.20;
$^1$H NMR (CDCl$_3$): δ0.99 (3H, t, CH$_3$), 1.49 (3H, s, CH$_3$), 2.65 (2H, m, CH$_2$), 2.83 (2H, m, CH$_2$), 4.09 (2H, q, CH$_2$), 5.26 (1H, m, CH), 7.13 (1H, td, CH-arom.), 7.32 (1H, d, CH-arom.), 7.42 (1H, m, CH-arom.), 7.96 (1H, s, CH-arom).

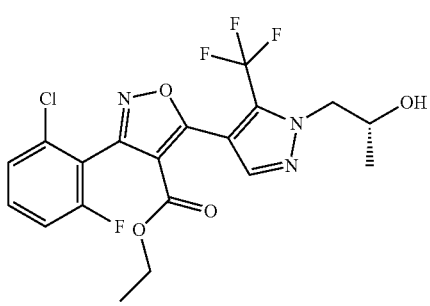 [SMILES: CCOC(=O)c1c(-c2c(F)cccc2Cl)noc1-c1cnn(C[C@@H](C)O)c1C(F)(F)F]

Example 12: ethyl 3-(2-chloro-6-fluorophenyl)-5-{1-[(2R)-2-hydroxypropyl]-5-(trifluoromethyl)-1H-pyrazol-4-yl}-1,2-oxazole-4-carboxylate Title compound was synthesized from ethyl (Z)-3-(2-chloro-6-fluorophenyl)-5-(1-(dimethylamino)-4,4,4-trifluoro-3-oxobut-1-en-2-yl)isoxazole-4-carboxylate (0.5 mmol) and (R)-1-hydrazinylpropan-2-ol as yellow oil (39%; pTLC, eluent: petroleum ether/ethyl acetate 1:1).

Result of LC/MS [M+H]$^+$: 461.70;
$^1$H NMR (CDCl$_3$): δ0.99 (3H, t, CH$_3$), 1.31 (3H, d, CH$_3$), 3.33 (1H, br, OH), 4.09 (2H, q, CH$_2$), 4.24 (1H, dd, CH), 4.36 (2H, dd, CH$_2$), 7.13 (1H, td, CH-arom.), 7.32 (1H, d, CH-arom), 7.42 (1H, m, CH-arom.), 8.01 (1H, s, CH-arom).

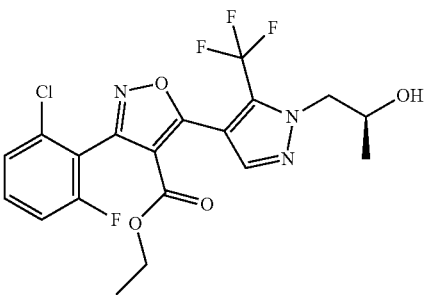 [SMILES: CCOC(=O)c1c(-c2c(F)cccc2Cl)noc1-c1cnn(C[C@H](C)O)c1C(F)(F)F]

Example 13: ethyl 3-(2-chloro-6-fluorophenyl)-5-(1-((2S)-2-hydroxypropyl)-5-(trifluoromethyl)-1H-pyrazol-4-yl)-1,2-oxazole-4-carboxylate Title compound was synthesized from ethyl (Z)-3-(2-chloro-6-fluorophenyl)-5-(1-(dimethylamino)-4,4,4-trifluoro-3-oxobut-1-en-2-yl)isoxazole-4-carboxylate (0.5 mmol) and (S)-1-hydrazinylpropan-2-ol as yellow oil (31%; pTLC, eluent: petroleum ether/ethyl acetate 1:1).

Result of LC/MS [M+H]$^+$: 461.70;
$^1$H NMR (CDCl$_3$): δ1.00 (3H, t, CH$_3$), 1.32 (3H, d, CH$_3$), 3.30 (1H, s, OH), 4.10 (2H, q, CH$_2$), 4.25 (1H, dd, CH), 4.37 (2H, dd, CH$_2$), 7.14 (1H, td, CH-arom.), 7.33 (1H, d, CH-arom), 7.43 (1H, m, CH-arom.), 8.02 (1H, s, CH-arom).

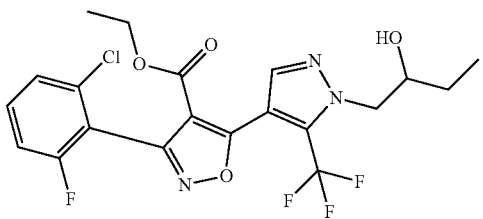 [SMILES: CCOC(=O)c1c(-c2c(F)cccc2Cl)noc1-c1cnn(CC(O)CC)c1C(F)(F)F]

Example 14: ethyl 3-(2-chloro-6-fluorophenyl)-5-[1-(2-hydroxybutyl)-5-(trifluoromethyl)-1H-pyrazol-4-yl]-1,2-oxazole-4-carboxylate (Racemic)

Title compound was synthesized from ethyl (Z)-3-(2-chloro-6-fluorophenyl)-5-(1-(dimethylamino)-4,4,4-trifluoro-3-oxobut-1-en-2-yl)isoxazole-4-carboxylate (0.23 mmol) and 1-hydrazino-2-butanol as yellow oil (26%; pTLC, eluent: CH$_2$Cl$_2$/MeOH 95:5 and again pTLC, eluent: CH$_2$Cl$_2$/MeOH 95:5).

Result of LC/MS [M+H]$^+$: 475.8;
$^1$H NMR (CDCl$_3$): δ0.99 (3H, t, CH$_3$), 1.06 (3H, t, CH$_3$), 1.61 (2H, quint., CH$_2$), 3.15 (1H, d, OH), 4.09 (2H, q, CH$_2$), 4.25 (1H, dd, CH$_2$), 4.40 (1H, dd, CH$_2$), 7.13 (1H, td, CH-arom.), 7.32 (1H, d, CH-arom.), 7.42 (1H, m, CH-arom.), 8.01 (1H, s, CH-arom).

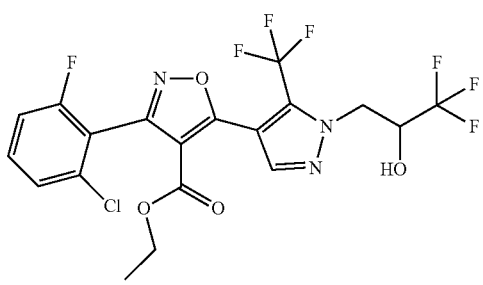 [SMILES: CCOC(=O)c1c(-c2c(F)cccc2Cl)noc1-c1cnn(CC(O)C(F)(F)F)c1C(F)(F)F]

Example 15: ethyl 3-(2-chloro-6-fluorophenyl)-5-[1-(3,3,3-trifluoro-2-hydroxypropyl)-5-(trifluoromethyl)-1H-pyrazol-4-yl]-1,2-oxazole-4-carboxylate (Racemic)

Title compound was synthesized from ethyl (Z)-3-(2-chloro-6-fluorophenyl)-5-(1-(dimethylamino)-4,4,4-trifluoro-3-oxobut-1-en-2-yl)isoxazole-4-carboxylate (0.52 mmol) and 1,1,1-trifluoro-3-hydrazinylpropan-2-ol (racemic) as colorless oil (35%; pTLC, eluent: $CH_2Cl_2$/MeOH 95:5 and pTLC, eluent: petroleum ether/ethyl acetate 3:2; mixture of structural isomers at pyrazol 95:5, cf. Scheme above).

Result of LC/MS [M+H]$^+$: 515.8;

$^1$H NMR (CDCl$_3$): δ0.99 (3H, t, CH$_3$), 4.08 (3H, m, CH$_2$, CH), 4.62 (2H, m, CH$_2$), 7.13 (1H, td, CH-arom.), 7.33 (1H, d, CH-arom), 7.43 (1H, m, CH-arom.), 8.05 (1H, s, CH-arom).

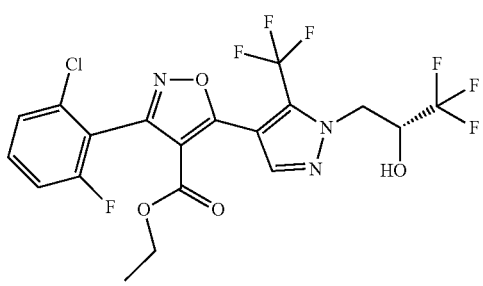 [SMILES: CCOC(=O)c1c(-c2c(F)cccc2Cl)noc1-c1cnn(C[C@@H](O)C(F)(F)F)c1C(F)(F)F]

Example 16: ethyl 3-(2-chloro-6-fluorophenyl)-5-{1-[(2R)-3,3,3-trifluoro-2-hydroxypropyl]-5-(trifluoromethyl)-1H-pyrazol-4-yl}-1,2-oxazole-4-carboxylate Title compound was synthesized from ethyl (Z)-3-(2-chloro-6-fluorophenyl)-5-(1-(dimethylamino)-4,4,4-trifluoro-3-oxobut-1-en-2-yl)isoxazole-4-carboxylate (0.14 mmol) and (R)-1,1,1-trifluoro-3-hydrazinylpropan-2-ol as colorless oil (15%; pTLC, eluent: $CH_2Cl_2$/MeOH 95:5).

Result of LC/MS [M+H]$^+$: 516.2;

$^1$H NMR (CDCl$_3$): δ0.99 (3H, t, CH$_3$), 3.96 (1H, d, OH), 4.09 (2H, q, CH$_2$), 4.62 (3H, m, CH$_2$, CH), 7.13 (1H, td, CH-arom.), 7.33 (1H, d, CH-arom), 7.43 (1H, m, CH-arom.), 8.06 (1H, s, CH-arom).

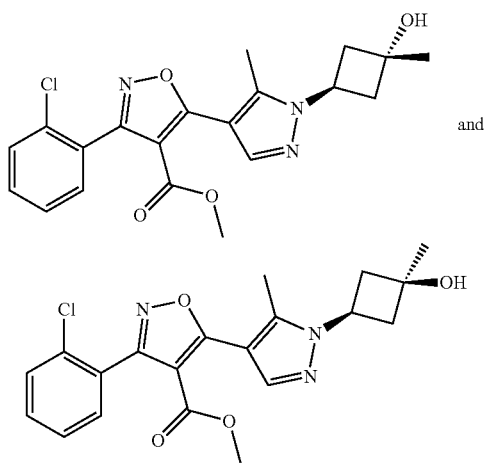

and

Example 17 and 18: methyl 3-(2-chlorophenyl)-5-(1-(3-hydroxy-3-methylcyclobutyl)-5-methyl-1H-pyrazol-4-yl)isoxazole-4-carboxylate (Anti- and Syn-Configuration)

Title compounds were synthesized from methyl (Z)-3-(2-chlorophenyl)-5-[1-(dimethylamino)-3-oxobut-1-en-2-yl]-1,2-oxazole-4-carboxylate (0.60 mmol) and 3-hydrazinyl-1-methylcyclobutan-1-ol (syn/anti mixture) as orange oils (pTLC, eluent: $CH_2Cl_2$/MeOH 95:5);

Example 17: anti-configuration within cyclobutanol system, 21% yield;

Result of LC/MS [M+H]$^+$: 402.30;

$^1$H NMR (CDCl$_3$): δ1.55 (3H, s, CH$_3$), 2.57 (3H, s, CH$_3$), 2.59 (2H, m, CH$_2$), 2.81 (2H, m, CH$_2$), 3.66 (3H, s, O—CH$_3$), 5.04 (1H, m, CH), 7.35 (4H, m, CH-arom.), 8.31 (1H, s, CH-arom).

Example 18: syn-configuration within cyclobutanol system, 11% yield;

Result of LC/MS [M+H]$^+$: 402.3;

$^1$H NMR (CDCl$_3$): δ1.47 (3H, s, CH$_3$), 2.57 (3H, s, CH$_3$), 2.82-2.70 (4H, m, 2xCH$_2$), 2.87 (1H, br, OH), 3.65 (3H, s, CH$_3$), 4.54 (1H, quint, CH), 7.53-7.33 (4H, m, 4xCH-arom.), 8.37 (1H, s, CH-arom.).

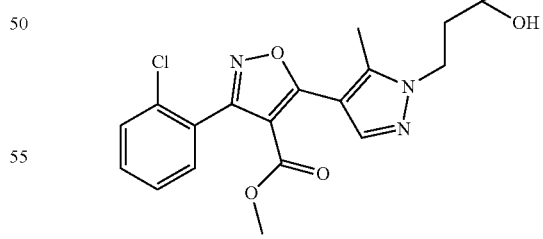

Example 19: methyl 3-(2-chlorophenyl)-5-[1-(3-hydroxy-3-methylbutyl)-5-methyl-1H-pyrazol-4-yl]-1,2-oxazole-4-carboxylate Title compound was synthesized from methyl (Z)-3-(2-chlorophenyl)-5-[1-(dimethylamino)-3-oxobut-1-en-2-yl]-1,2-oxazole-4-carboxylate (0.86 mmol) and 4-hydrazinyl-2- methylbutan-2-ol as yellow oil (31%; pTLC, eluent: CH$_2$Cl$_2$/MeOH 95:5 and again pTLC, eluent: CH$_2$Cl$_2$/MeOH 95:5).

Result of LC/MS [M+H]$^+$: 404.0;

$^1$H NMR (CDCl$_3$): δ1.30 (6H, s, 2x CH$_3$), 2.05 (2H, s, CH$_2$), 2.62 (3H, s, CH$_3$), 3.65 (3H, s, CH$_3$), 4.32 (2H, m, CH$_2$), 7.34 (4H, m, CH-arom.), 8.30 (1H, s, CH-arom).

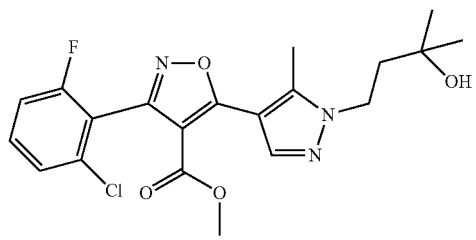 [SMILES: COC(=O)c1c(-c2c(F)cccc2Cl)noc1-c1cnn(CCC(C)(C)O)c1C]

Example 20: methyl 3-(2-chloro-6-fluorophenyl)-5-[1-(3-hydroxy-3-methylbutyl)-5-methyl-1H-pyrazol-4-yl]-1,2-oxazole-4-carboxylate Title compound was synthesized from methyl (Z)-3-(2-chloro-6-fluorophenyl)-5-(1-(dimethylamino)-3-oxobut-1-en-2-yl)isoxazole-4-carboxylate (0.79 mmol) and 4-hydrazinyl-2-methylbutan-2-ol as yellow oil (29%; pTLC, eluent: CH$_2$Cl$_2$/MeOH 98:2 and pTLC, eluent: CH$_2$Cl$_2$/MeOH 95:5).

Result of LC/MS [M+H]$^+$: 422.00;

$^1$H NMR (CDCl$_3$): δ1.31 (6H, s, 2x CH$_3$), 2.05 (2H, t, CH$_2$), 2.64 (3H, s, CH$_3$), 3.65 (3H, s, CH$_3$), 4.32 (2H, m, CH$_2$), 7.12 (1H, td, CH-arom.), 7.32 (1H, d, CH-arom), 7.41 (1H, m, CH-arom.), 8.33 (1H, s, CH-arom).

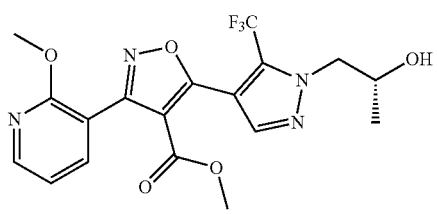 [SMILES: COC(=O)c1c(-c2cccnc2OC)noc1-c1cnn(C[C@@H](C)O)c1C(F)(F)F]

Example 21: methyl (R)-5-(1-(2-hydroxypropyl)-5-(trifluoromethyl)-1H-pyrazol-4-yl)-3-(2-methoxypyridin-3-yl)isoxazole-4-carboxylate Title compound was synthesized from methyl (Z)-5-(1-(dimethylamino)-4,4,4-trifluoro-3-oxobut-1-en-2-yl)-3-(2-methoxypyridin-3-yl)isoxazole-4-carboxylate (0.55 mmol) and (R)-1-hydrazinylpropan-2-ol (30%; pTLC, eluent: CH$_2$Cl$_2$/MeOH 95:5).

Result of LC/MS [M+H]$^+$: 426.8;

$^1$H NMR (CDCl$_3$): δ1.31 (3H, d, CH$_3$), 3.66 (3H, s, CH$_3$), 3.93 (3H, s, CH$_3$), 4.31 (3H, m, CH, CH$_2$), 7.01 (1H, dd, CH-arom.), 7.83 (1H, dd, CH-arom.), 8.01 (1H, s, CH-arom.), 8.30 (1H, dd, CH-arom).

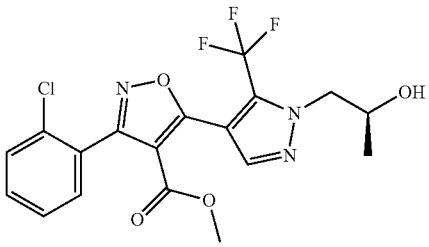 [SMILES: COC(=O)c1c(-c2ccccc2Cl)noc1-c1cnn(C[C@H](C)O)c1C(F)(F)F]

Example 22: methyl (S)-3-(2-chlorophenyl)-5-(1-(2-hydroxypropyl)-5-(trifluoromethyl)-1H-pyrazol-4-yl)isoxazole-4-carboxylate Title compound was synthesized from methyl (Z)-3-(2-chlorophenyl)-5-(1-(dimethylamino)-4,4,4-trifluoro-3-oxobut-1-en-2-yl)isoxazole-4-carboxylate (1.0 mmol) and (S)-1-hydrazinylpropan-2-ol (49%; pTLC, eluent: CH$_2$Cl$_2$/MeOH 95:5).

Result of LC/MS [M+H]$^+$: 429.8;

$^1$H NMR (CDCl$_3$): δ1.32 (3H, d, CH$_3$), 3.64 (3H, s, OCH$_3$), 4.24 (1H, dd, CH), 4.48-4.31 (2H, m, CH$_2$), 7.56-7.34 (4H, m, 4xCH-arom.), 8.00 (1H, s, CH-arom.).

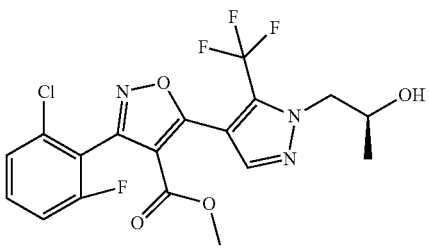 [SMILES: COC(=O)c1c(-c2c(F)cccc2Cl)noc1-c1cnn(C[C@H](C)O)c1C(F)(F)F]

Example 23: methyl (S)-3-(2-chloro-6-fluorophenyl)-5-(1-(2-hydroxypropyl)-5-(trifluoromethyl)-1H-pyrazol-4-yl)isoxazole-4-carboxylate Title compound was synthesized from methyl (Z)-3-(2-chloro-6-fluorophenyl)-5-(1-(dimethylamino)-4,4,4-trifluoro-3-oxobut-1-en-2-yl)isoxazole-4-carboxylate (0.83 mmol) and (S)-1-hydrazinylpropan-2-ol (27%; pTLC, eluent: CH$_2$Cl$_2$/MeOH 95:5 and pTLC, eluent: petroleum ether/ethyl acetate 3:2).

Result of LC/MS [M+H]$^+$: 448.2;

$^1$H NMR (CDCl$_3$): δ1.32 (3H, d, CH$_3$), 3.64 (3H, s, OCH$_3$), 4.25 (1H, dd, OCH$_2$), 4.48-4.32 (2H, m, CH$_2$), 7.14 (1H, td, CH-arom.), 7.33 (1H, dt, CH-arom.), 7.48-7.38 (1H, m, CH-arom.), 7.99 (1H, s, CH-arom.).

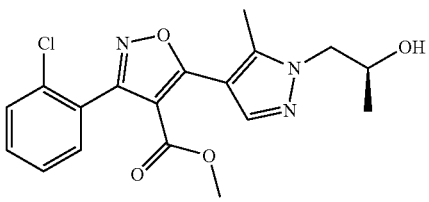 [SMILES: COC(=O)c1c(-c2ccccc2Cl)noc1-c1cnn(C[C@H](C)O)c1C]

Example 24: methyl (S)-3-(2-chlorophenyl)-5-(1-(2-hydroxypropyl)-5-methyl-1H-pyrazol-4-yl)isoxazole-4-carboxylate Title compound was synthesized from methyl (Z)-3-(2-chlorophenyl)-5-[1-(dimethylamino)-3-oxobut-1-en-2-yl]-1,2-oxazole-4-carboxylate (1.0 mmol) and (S)-1-hydrazinylpropan-2-ol (32%; pTLC, eluent: CH$_2$Cl$_2$/MeOH 95:5).

Result of LC/MS [M+H]$^+$: 376.3;

$^1$H NMR (CDCl$_3$): δ1.30 (3H, d, CH$_3$), 2.61 (3H, s, CH$_3$), 3.65 (3H, s, OCH$_3$), 4.58-3.82 (3H, m, CH and CH$_2$), 7.55-7.33 (4H, m, 4xCH-arom.), 8.38 (1H, s, CH-arom.).

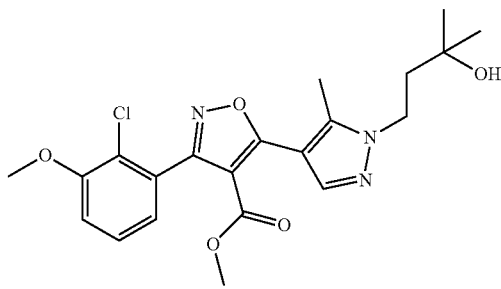 [SMILES: COC(=O)c1c(-c2cccc(OC)c2Cl)noc1-c1cnn(CCC(C)(C)O)c1C]

Example 25: methyl 3-(2-chloro-3-methoxyphenyl)-5-[1-(3-hydroxy-3-methylbutyl)-5-methyl-1H-pyrazol-4-yl]-1,2-oxazole-4-carboxylate Title compound was synthesized from methyl (Z)-3-(2-chloro-3-methoxyphenyl)-5-[1-(dimethylamino)-3-oxobut-1-en-2-yl]-1,2-oxazole-4-carboxylate (1.1 mmol) and 4-hydrazinyl-2-methylbutan-2-ol as orange oil (33%; pTLC, eluent: CH$_2$Cl$_2$/MeOH 95:5 and again pTLC, eluent: CH$_2$Cl$_2$/MeOH 95:5).

Result of LC/MS [M+H]$^+$: 434.0;

$^1$H NMR (CDCl$_3$): δ1.30 (6H, s, 2x CH$_3$), 2.04 (2H, m, CH$_2$), 2.62 (3H, s, CH$_3$), 3.65 (3H, s, CH$_3$), 3.95 (4H, s, OH, CH$_3$), 4.31 (2H, m, CH$_2$), 7.07 (2H, m, CH-arom.), 7.33 (1H, t, CH-arom.), 8.28 (1H, s, CH-arom.).

Examples 26 and 27: methyl 3-(2-chloro-6-fluorophenyl)-5-(1-(3-hydroxy-3-methylcyclobutyl)-5-(trifluoromethyl)-1H-pyrazol-4-yl)isoxazole-4-carboxylate (Anti- and Syn-Configuration)

Title compounds were synthesized from methyl (Z)-3-(2-chloro-6-fluorophenyl)-5-[1-(dimethylamino)-4,4,4-trifluoro-3-oxobut-1-en-2-yl]-1,2-oxazole-4-carboxylate (0.24 mmol) and 3-hydrazinyl-1-methylcyclobutan-1-ol (syn/anti mixture) (pTLC, eluent: CH$_2$Cl$_2$/MeOH 95:5).

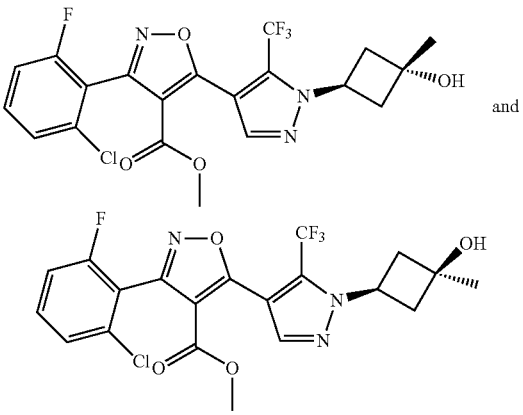

and

Example 26: anti-configuration within cyclobutanol system, 18% yield;

Result of LC/MS [M+H]$^+$: 473.80;

$^1$H NMR (CDCl$_3$): δ1.56 (3H, s, CH$_3$), 2.75-2.49 (2H, m, CH$_2$), 2.95-2.75 (2H, m, CH$_2$), 3.63 (3H, s, OCH$_3$), 5.26 (1H, quint, CH), 7.13 (1H, td, CH-arom.), 7.33 (1H, d, CH-arom.), 7.47-7.37 (1H, m, CH-arom.), 7.94 (1H, s, CH-arom.).

Example 27: syn-configuration within cyclobutanol system; 18% yield;

Result of LC/MS [M+H]$^+$: 473.8;

$^1$H NMR (CDCl$_3$): δ1.50 (3H, s, CH$_3$), 2.95-2.71 (4H, m, 2xCH$_2$), 3.63 (3H, s, OCH$_3$), 4.71 (1H, quint, CH), 7.14 (1H, td, CH-arom.), 7.33 (1H, d, CH-arom.), 7.48-7.38 (1H, m, CH-arom.), 7.99 (1H, s, CH-arom.).

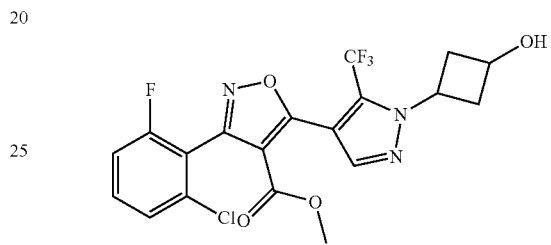

Example 28: methyl 3-(2-chloro-6-fluorophenyl)-5-(1-(3-hydroxycyclobutyl)-5-(trifluoromethyl)-1H-pyrazol-4-yl)isoxazole-4-carboxylate Title compound was synthesized from methyl (Z)-3-(2-chloro-6-fluorophenyl)-5-[1-(dimethylamino)-4,4,4-trifluoro-3-oxobut-1-en-2-yl]-1,2-oxazole-4-carboxylate (0.24 mmol) and 3-hydrazinylcyclobutan-1-ol (syn/anti mixture) (46% as mixture of syn- and anti-configuration within cyclobutanol system; pTLC, eluent: CH$_2$Cl$_2$/MeOH 95:5).

Result of LC/MS [M+H]$^+$: 459.8;

$^1$H NMR (CDCl$_3$): δ2.86-2.69 (2H, m, CH$_2$), 3.10-2.93 (2H, m, CH$_2$), 3.63 (3H, s, CH$_3$), 4.26 (1H, quint, CH), 4.62 (1H, quint, CH), 7.13 (1H, td, CH-arom.), 7.33 (1H, d, CH-arom.), 7.47-7.37 (1H, m, CH-arom.), 7.99 (1H, s, CH-arom.).

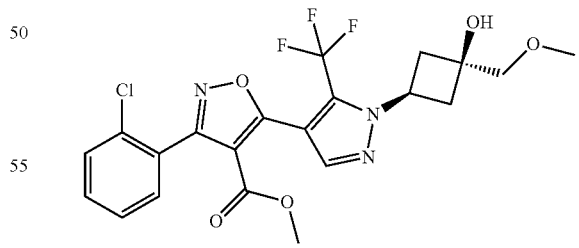

Example 29: methyl 3-(2-chlorophenyl)-5-(1-(3-hydroxy-3-(methoxymethyl)cyclobutyl)-5-(trifluoromethyl)-1H-pyrazol-4-yl)isoxazole-4-carboxylate (Syn-Configuration)

Title compound was synthesized from methyl (Z)-3-(2-chlorophenyl)-5-(1-(dimethylamino)-4,4,4-trifluoro-3- oxobut-1-en-2-yl)isoxazole-4-carboxylate (0.30 mmol) and 3-hydrazinyl-1-(methoxymethyl)cyclobutan-1-ol (mixture syn/anti) in 34% yield. Syn- and anti-configurations within the resulting product were not separable at this stage, therefore, the hydroxyl group was silylated using tert-butyldimethylsilyl triflate, N,N-diisopropylethylamine in CH$_2$Cl$_2$ (cf. general silylation procedures described below), upon which a separation of isomers succeeded by pTLC, eluent: petroleum ether/ethyl acetate 4:1 and pTLC, eluent: CH$_2$Cl$_2$/MeOH 95:5. Desilylation was achieved using HCl in MeOH (room temperature, 2 h) to give the title compound with syn-configuration in 50% yield from the mixture of isomers, along with 16% of the anti-isomer (the pH was adjusted to around 8 by adding aq. NaOH (1M), and the mixture was extracted with EtOAc. The organic layers were washed with brine, dried over anhydrous MgSO$_4$ and concentrated under reduced pressure. The residue was purified by preparative TLC (eluent: petroleum ether/ethyl acetate 1:5).

Result of LC/MS [M+H]$^+$: 486.20;
$^1$H NMR (CDCl$_3$): δ2.09 (1H, br, OH), 2.86 (4H, m, CH$_2$), 3.49 (5H, s, CH$_2$/CH$_3$), 3.63 (3H, s, O—CH$_3$), 4.67 (1H, m, CH), 7.44 (4H, m, CH-arom.), 8.00 (1H, s, CH-arom).

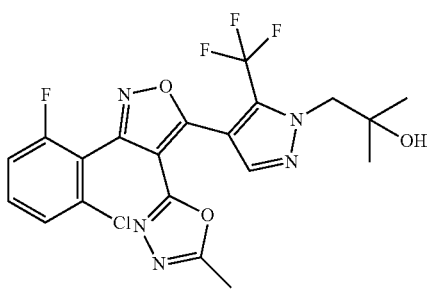 [SMILES: Cc1nnc(-c2c(-c3c(F)cccc3Cl)noc2-c2cnn(CC(C)(C)O)c2C(F)(F)F)o1]

Example 30: 1-(4-(3-(2-chloro-6-fluorophenyl)-4-(5-methyl-1,3,4-oxadiazol-2-yl)isoxazol-5-yl)-5-(trifluoromethyl)-1H-pyrazol-1-yl)-2-methylpropan-2-ol Title compound was synthesized from (Z)-3-(3-(2-chloro-6-fluorophenyl)-4-(5-methyl-1,3,4-oxadiazol-2-yl)isoxazol-5-yl)-4-(dimethylamino)-1,1,1-trifluorobut-3-en-2-one (0.18 mmol) and 1-hydrazinyl-2-methylpropan-2-ol as pale yellow oil (4%; pTLC, eluent: petroleum ether/ethyl acetate 4:1 and pTLC, eluent: CH$_2$Cl$_2$/MeOH 95:5).

Result of LC/MS [M+H]$^+$: 485.70;
$^1$H NMR (CDCl$_3$): δ1.27 (6H, s, 2x CH$_3$), 2.39 (3H, s, CH$_3$), 4.34 (2H, s, CH$_2$), 7.16 (1H, td, CH-arom.), 7.35 (1H, dt, CH-arom), 7.47 (1H, m, CH-arom.), 8.15 (1H, s, CH-arom).

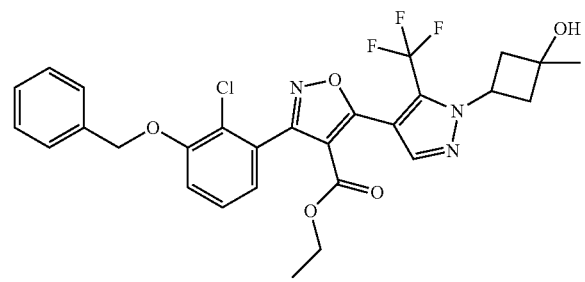 [SMILES: CCOC(=O)c1c(-c2cccc(OCc3ccccc3)c2Cl)noc1-c1cnn(C2CC(C)(O)C2)c1C(F)(F)F]

ethyl 3-(3-(benzyloxy)-2-chlorophenyl)-5-(1-(3-hydroxy-3-methylcyclobutyl)-5-(trifluoromethyl)-1H-pyrazol-4-yl)isoxazole-4-carboxylate Title compound was synthesized (syn/anti mixture) from ethyl (Z)-3-(3-(benzyloxy)-2-chlorophenyl)-5-(1-(dimethylamino)-4,4,4-trifluoro-3-oxobut-1-en-2-yl)isoxazole-4-carboxylate (3.3 mmol) and 3-hydrazinyl-1-methylcyclobutan-1-ol (syn/anti mixture) as yellow oil (34%; pTLC, eluent: petroleum ether/ethyl acetate 4:1 and pTLC, eluent: petroleum ether/ethyl acetate 1:1).

Result of LC/MS [M+H]$^+$: 576.3;
$^1$H NMR (CDCl$_3$): δ1.27 (3H, t, CH$_3$), 2.04 (3H, s, CH$_3$), 2.77 (4H, m, 2x CH$_2$), 4.08 (1H, m, CH), 4.13 (2H, q, CH$_2$), 5.23 (2H, s, CH$_2$), 7.10 (2H, d, CH-arom.), 7.35 (4H, m, CH-arom.), 7.47 (2H, d, CH-arom.), 7.98 (1H, s, CH-arom.).

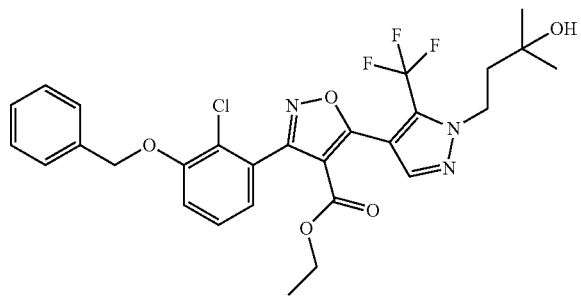 [SMILES: CCOC(=O)c1c(-c2cccc(OCc3ccccc3)c2Cl)noc1-c1cnn(CCC(C)(C)O)c1C(F)(F)F]

ethyl 3-(3-(benzyloxy)-2-chlorophenyl)-5-(1-(3-hydroxy-3-methylbutyl)-5-(trifluoromethyl)-1H-pyrazol-4-yl)isoxazole-4-carboxylate Title compound was synthesized from ethyl (Z)-3-(3-(benzyloxy)-2-chlorophenyl)-5-(1-(dimethylamino)-4,4,4-trifluoro-3-oxobut-1-en-2-yl)isoxazole-4-carboxylate (6.6 mmol) and 4-hydrazinyl-2-methylbutan-2-ol as yellow oil (84%; column chromatography on silica gel, eluent: CH$_2$Cl$_2$/MeOH 98:2).

Result of LC/MS [M+H]$^+$: 578.3;
$^1$H NMR (CDCl$_3$): δ0.99 (3H, t, CH$_3$), 1.33 (6H, s, 2x CH$_3$), 2.14 (2H, m, CH$_2$), 3.38 (2H, s, CH$_2$), 3.56 (1H, m, CH), 3.65 (1H, m, CH), 4.07 (2H, q, CH$_2$), 7.07 (2H, dd, CH-arom.), 7.40 (6H, m, CH-arom.), 7.98 (1H, s, CH-arom.).

Synthesis of Deuterated Alcohols

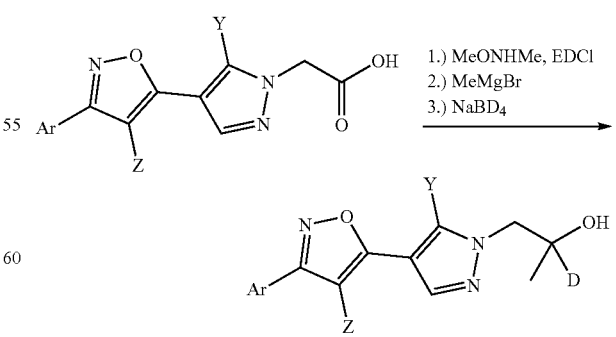

Respective acetic acid derivatives were synthesized according to the general procedure described above for pyrazole formation using 2-hydrazinylacetic acid. Reaction mixtures were only partitioned between CH$_2$Cl$_2$ and saturated. aq. NH$_4$Cl, organic layer was dried over MgSO$_4$ and concentrated under reduced pressure, and products were used as crude material for the following steps.

2-(4-(3-(2-chloro-6-fluorophenyl)-4-(thiazol-2-yl)isoxazol-5-yl)-5-(trifluoromethyl)-1H-pyrazol-1-yl)acetic acid from (Z)-3-(3-(2-chloro-6-fluorophenyl)-4-(thiazol-2-yl)isoxazol-5-yl)-4-(dimethylamino)-1,1,1-trifluorobut-3-en-2-one;
Result of LC/MS [M+H]$^+$: 472.7;
$^1$H NMR (CDCl$_3$): δ3.15 (1H, s, COOH), 5.15 (2H, s, CH$_2$), 7.16 (1H, t, CH-arom.), 7.24 (1H, d, CH-arom.), 7.35 (1H, d, CH-arom.), 7.48 (1H, m, CH-arom.), 7.75 7.48 (1H, d, CH-arom.), 8.13 (1H, s, CH-arom.).

2-{4-[3-(2-chloro-6-fluorophenyl)-4-(ethoxycarbonyl)-1,2-oxazol-5-yl]-5-(trifluoromethyl)-1H-pyrazol-1-yl}acetic acid from ethyl (Z)-3-(2-chloro-6-fluorophenyl)-5-(1-(dimethylamino)-4,4,4-trifluoro-3-oxobut-1-en-2-yl)isoxazole-4-carboxylate;
Result of LC/MS [M+H]$^+$: 461.7;
$^1$H NMR (CDCl$_3$): δ0.98 (3H, t, CH$_3$), 4.06 (2H, q, CH$_2$), 4.97 (2H, s, CH$_2$), 7.09 (1H, t, CH-arom.), 7.29 (1H, d, CH-arom.), 7.39 (1H, m, CH-arom.), 8.03 (1H, s, CH-arom.).

2-{4-[3-(2-chloro-6-fluorophenyl)-4-(methoxycarbonyl)-1,2-oxazol-5-yl]-5-(trifluoromethyl)-1H-pyrazol-1-yl}acetic acid from methyl (Z)-3-(2-chloro-6-fluorophenyl)-5-(1-(dimethylamino)-4,4,4-trifluoro-3-oxobut-1-en-2-yl)isoxazole-4-carboxylate;

Crude acetic acid derivative (1.0 mmol), N,O-dimethylhydroxylamine hydrochloride (1.0 eq.), 1-hydroxybenzotriazole (1.0 eq.) and 1-(3-dimethylaminopropyl)-3-ethylcarbodiimide hydrochloride (EDCI; 1.2 eq.) were dissolved in dry DMF (Sure/Seal, 4 mL/mmol). N-methylmorpholine (10 eq.) was added and the reaction was stirred at room temperature for 18 h.

DMF was removed under reduced pressure and an aq. 5% solution of citric acid was added. The mixture was extracted with CH$_2$Cl$_2$, the combined organic phases washed with water and dried over MgSO$_4$ and concentrated under reduced pressure:

2-{4-[3-(2-chloro-6-fluorophenyl)-4-(1,3-thiazol-2-yl)-1,2-oxazol-5-yl]-5-(trifluoromethyl)-1H-pyrazol-1-yl}-N-methoxy-N-methylacetamide; preparative TLC on silica gel (eluent: petroleum ether/ethyl acetate 7:3), orange oil, 14% yield over two steps;
Result of LC/MS [M+H]$^+$: 515.8;
$^1$H NMR (CDCl$_3$): δ3.26 (3H, s, CH$_3$), 3.81 (3H, s, CH$_3$), 5.34 (2H, s, CH$_2$), 7.14 (1H, m, CH-arom.), 7.23 (1H, dd, CH-arom.), 7.34 (1H, m, CH-arom.), 7.47 (1H, m, CH-arom.), 7.73 (1H, d, CH-arom.), 8.20 (1H, s, CH-arom.).

ethyl 3-(2-chloro-6-fluorophenyl)-5-(1-{[methoxy(methyl)carbamoyl]methyl}-5-(trifluoromethyl)-1H-pyrazol-4-yl)-1,2-oxazole-4-carboxylate; preparative TLC on silica gel (eluent: petroleum ether/ethyl acetate 7:3), orange oil, 38% yield over two steps;
Result of LC/MS [M+H]$^+$: 504.7;
$^1$H NMR (CDCl$_3$): δ1.04 (3H, t, CH$_3$), 3.24 (3H, s, CH$_3$), 3.79 (3H, s, CH$_3$), 4.10 (2H, q, CH$_2$), 5.33 (2H, s, CH$_2$), 7.12 (1H, t, CH-arom.), 7.31 (1H, d, CH-arom.), 7.41 (1H, m, CH-arom.), 8.13 (1H, s, CH-arom.).

methyl 3-(2-chloro-6-fluorophenyl)-5-(1-{[methoxy(methyl)carbamoyl]methyl}-5-(trifluoromethyl)-1H-pyrazol-4-yl)-1,2-oxazole-4-carboxylate; crude material was used as such for the next step The respective Weinreb amide was dissolved in THF (Sure/Seal; 4 mL/mmol) at 0° C. Methylmagnesium bromide (5.0 eq.; 3.2 M in 2-methyl-THF) was added slowly and the mixture was stirred at 0° C. for 1 h and then at room temperature for additional 5 h. The mixture was quenched with water and partitioned between CH$_2$Cl$_2$ and water. Combined organic layers were dried over MgSO$_4$, filtrated and concentrated under reduced pressure to give crude methyl ketone:

1-{4-[3-(2-chloro-6-fluorophenyl)-4-(1,3-thiazol-2-yl)-1,2-oxazol-5-yl]-5-(trifluoromethyl)-1H-pyrazol-1-yl}propan-2-one, 70% yield (crude);
Result of LC/MS [M+H]$^+$: 470.8.

ethyl 3-(2-chloro-6-fluorophenyl)-5-[1-(2-oxopropyl)-5-(trifluoromethyl)-1H-pyrazol-4-yl]-1,2-oxazole-4-carboxylate; preparative TLC on silica gel (eluent: petroleum ether/ethyl acetate 3:2 and pTLC, eluent: CH$_2$Cl$_2$/MeOH 95:5), 12% yield;
Result of LC/MS [M+H]$^+$: 459.70;
$^1$H NMR (CDCl$_3$): δ1.03 (3H, t, CH$_3$), 3.23 (3H, s, CH$_3$), 4.12 (2H, q, CH$_2$), 5.18 (2H, s, CH$_2$), 7.13 (1H, t, CH-arom.), 7.33 (1H, d, CH-arom.), 7.43 (1H, m, CH-arom.), 8.12 (1H, s, CH-arom.).

methyl 3-(2-chloro-6-fluorophenyl)-5-(1-(2-oxopropyl)-5-(trifluoromethyl)-1H-pyrazol-4-yl)-1,2-oxazole-4-carboxylate; preparative TLC on silica gel (eluent: petroleum ether/ethyl acetate 3:2), 8% yield over three steps;
Result of LC/MS [M+H]$^+$: 445.7;
$^1$H NMR (CDCl$_3$): δ1.23 (3H, s, CH$_3$), 3.65 (3H, s, CH$_3$), 5.18 (2H, s, CH$_2$), 7.14 (1H, td, CH-arom.), 7.33 (1H, d, CH-arom.), 7.43 (1H, m, CH-arom.), 8.07 (1H, s, CH-arom.).

The respective methyl ketone was dissolved in THF (10 mL/mmol) and cooled to 0° C. NaBD$_4$ (1.1 eq.) was added and the mixture was stirred at 0° C. for 1 h.

The mixture was quenched with water and partitioned between CH$_2$Cl$_2$ and water. Combined organic layers were dried over MgSO$_4$, filtrated and concentrated under reduced pressure. Alpha-deuterated alcohols were purified by preparative TLC on silica gel (eluent: CH$_2$Cl$_2$/MeOH 95:5):

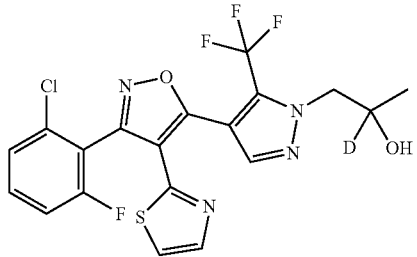 [SMILES: [2H]C(C)(O)Cn1ncc(-c2onc(-c3c(F)cccc3Cl)c2-c2nccs2)c1C(F)(F)F]

Example 31: 1-{4-[3-(2-chloro-6-fluorophenyl)-4-(1,3-thiazol-2-yl)-1,2-oxazol-5-yl]-5-(trifluoromethyl)-1H-pyrazol-1-yl}(2-$^2$H)propan-2-ol (Racemic) was Isolated in 28% Yield Result of LC/MS [M+H]$^+$: 473.8
$^1$H NMR (CDCl$_3$): δ1.31 (3H, s, CH$_3$), 4.25 (1H, s, CH), 4.38 (1H, d, CH), 7.17 (1H, t, CH-arom.), 7.22 (1H, d, CH-arom.), 7.36 (1H, d, CH-arom.), 7.54-7.44 (1H, m, CH-arom.), 7.71 (1H, d, CH-arom.), 8.09 (1H, s, CH-arom.).

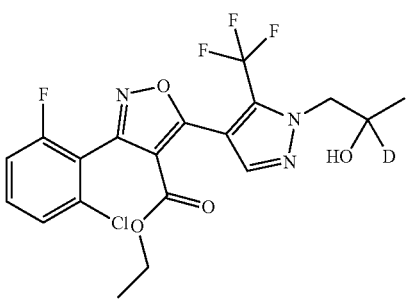 [SMILES: [2H]C(C)(O)Cn1ncc(-c2onc(-c3c(F)cccc3Cl)c2C(=O)OCC)c1C(F)(F)F]

Example 32: ethyl 3-(2-chloro-6-fluorophenyl)-5-
{1-[2-hydroxy(2-²H)propyl]-5-(trifluoromethyl)-1H-
pyrazol-4-yl}-1,2-oxazole-4-carboxylate (Racemic)
was Isolated as Pale Yellow Oil in 10% Yield Result of LC/MS [M+H]⁺: 462.7;
¹H NMR (CDCl₃): δ0.99 (3H, t, CH₃), 1.31 (3H, s, CH₃), 3.25 (1H, s, OH), 4.09 (2H, q, CH₂), 4.30 (2H, dd, CH₂), 7.13 (1H, td, CH-arom.), 7.33 (1H, d, CH-arom.), 7.43 (1H, m, CH-arom.), 8.01 (1H, s, CH-arom).

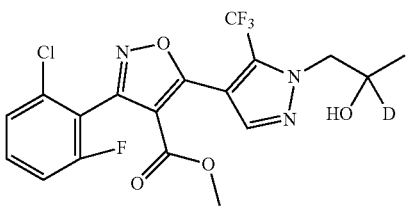 [SMILES: [2H]C(C)(O)Cn1ncc(-c2onc(-c3c(F)cccc3Cl)c2C(=O)OC)c1C(F)(F)F]

Example 33: methyl 3-(2-chloro-6-fluorophenyl)-5-
{1-[2-hydroxy(2-²H)propyl]-5-(trifluoromethyl)-1H-
pyrazol-4-yl}-1,2-oxazole-4-carboxylate (Racemic)
was Isolated in 24% Yield Result of LC/MS [M+H]⁺: 448.80;
¹H NMR (CDCl₃): δ1.31 (3H, s, CH₃), 3.64 (3H, s, OCH₃), 4.31 (2H, q, CH₂), 7.14 (1H, td, CH-arom.), 7.33 (1H, dt, CH-arom.), 7.48-7.38 (1H, m, CH-arom.), 7.99 (1H, s, CH-arom.).

Synthesis of 4-Acyl Isoxazoles

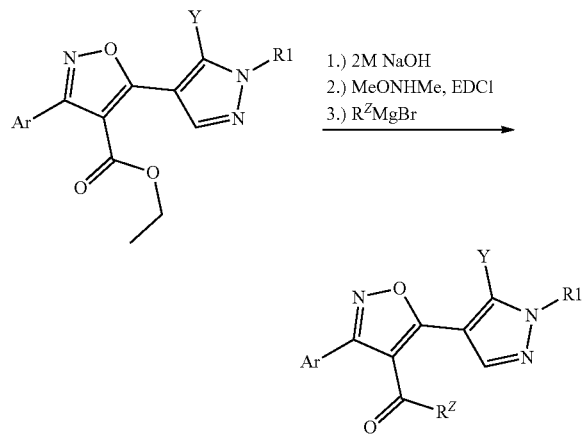

Esters Example 8 or Example 12 (0.25 mmol) were dissolved in 2 mL ethanol, and 2 mL aq. NaOH (2.0 M) were added. The mixture was heated to 60° C. for 1 h and then acidified by addition of aq. HCl (1.0 M). The resulting suspension was partitioned between CH₂Cl₂ and water, combined organic layers were dried over MgSO₄, and the solvent was removed under reduced pressure to give crude carboxylic acids:

3-(2-chloro-6-fluorophenyl)-5-(1-(2-hydroxy-2-methyl-propyl)-5-(trifluoromethyl)-1H-pyrazol-4-yl)-1,2-oxazole-4-carboxylic acid as off-white solid, 94% yield;

Result of LC/MS [M+H]⁺: 447.8;
¹H NMR (CDCl₃): δ1.22 (6H, s, 2xCH₃), 4.30 (2H, s, CH₂), 7.12 (1H, td, CH-arom.), 7.32 (1H, dt, CH-arom.), 7.47-7.37 (1H, m, CH-arom.), 8.00 (1H, s, CH-arom.).

3-(2-chloro-6-fluorophenyl)-5-{1-[(2R)-2-hydroxypropyl]-5-(trifluoromethyl)-1H-pyrazol-4-yl}-1,2-oxazole-4-carboxylic acid as off-white solid, 75% yield;

Result of LC/MS [M+H]⁺: 433.9;
¹H NMR (CDCl₃): δ1.30 (3H, d, CH₃), 4.24 (1H, dd, CH), 4.47-4.28 (2H, m, CH₂), 7.12 (1H, td, CH-arom.), 7.32 (1H, dt, CH-arom.), 7.47-7.36 (1H, m, CH-arom.), 7.98 (1H, s, CH-arom.).

Crude acetic acid derivative (1.0 mmol), N,O-dimethylhydroxylamine hydrochloride (1.2 eq.), 1-hydroxybenzotriazole (1.1 eq.) and 1-(3-dimethylaminopropyl)-3-ethylcarbodiimide hydrochloride (EDCI; 1.2 eq.) were dissolved in dry DMF (Sure/Seal, 4 mL/mmol). N-Methylmorpholine (5 eq.) was added and the reaction was stirred at room temperature for 18 h.

The mixture was poured into ice water and extracted with CH₂Cl₂. Combined organic phases were washed with water and dried over MgSO₄ and concentrated under reduced pressure:

3-(2-chloro-6-fluorophenyl)-5-(1-(2-hydroxy-2-methyl-propyl)-5-(trifluoromethyl)-1H-pyrazol-4-yl)-N-methoxy-N-methyl-1,2-oxazole-4-carboxamide; pTLC (eluent: CH₂Cl₂/MeOH 95:5), as pale yellow solid, 68% yield;

Result of LC/MS [M+H]⁺: 491.3;
¹H NMR (CDCl₃): δ1.23 (6H, s, 2xCH₃), 3.11 (3H, s, NCH₃), 3.38 (3H, s, OCH₃), 4.13 (1H, s, OH), 4.29 (2H, s, CH₂), 7.12 (1H, td, CH-arom.), 7.32 (1H, dt, CH-arom.), 7.45-7.35 (1H, m, CH-arom.), 7.99 (1H, s, CH-arom.).

3-(2-chloro-6-fluorophenyl)-5-{1-[(2R)-2-hydroxypropyl]-5-(trifluoromethyl)-1H-pyrazol-4-yl}-N-methoxy-N-methyl-1,2-oxazole-4-carboxamide, crude material as orange oil, 95% yield;

Result of LC/MS [M+H]⁺: 476.8;

The respective Weinreb amide was dissolved in THF (Sure/Seal; 5 mL/mmol) at 0° C. Methylmagnesium bromide (5.0 eq.; 3.2 M in 2-methyl-THF) was added slowly and the mixture was stirred at 0° C. for 1.5 h. If LCMS indicated incomplete conversion, the mixture was stirred at room temperature for additional 5 h. If necessary, an additional MeMgBr (3 eq.) was added at 0° C. again and the mixture was kept at room temperature for another 18 h. The mixture was quenched with water and partitioned between CH₂Cl₂ and water. Combined organic layers were dried over MgSO₄, filtrated and concentrated under reduced pressure.

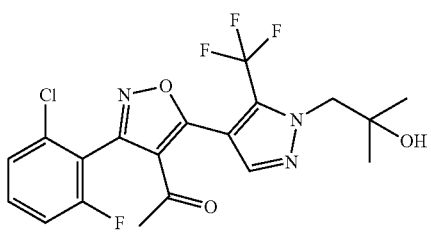 [SMILES: CC(=O)c1c(-c2c(F)cccc2Cl)noc1-c1cnn(CC(C)(C)O)c1C(F)(F)F]

Example 34: 1-(3-(2-chloro-6-fluorophenyl)-5-(1-(2-hydroxy-2-methylpropyl)-5-(trifluoromethyl)-1H-pyrazol-4-yl)-1,2-oxazol-4-yl)ethanone The title compound was isolated by prep. TLC on silica gel (eluent: $CH_2Cl_2$/MeOH 95:5) as a dark yellow oil in 8% yield.

Result of LC/MS [M+H]$^+$: 490.7;

$^1$H NMR (CDCl$_3$): δ1.25 (6H, s, CH$_3$), 2.06 (3H, s, CH$_3$), 4.12 (1H, s, OH), 4.32 (2H, s, CH$_2$), 7.18 (1H, td, CH-arom.), 7.37 (1H, d, CH-arom), 7.47 (1H, m, CH-arom.), 7.99 (1H, s, CH-arom).

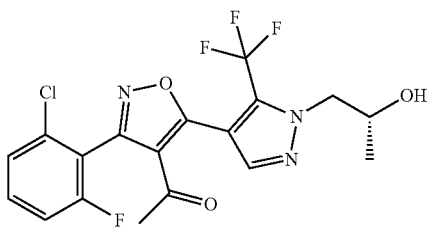 [SMILES: CC(=O)c1c(-c2c(F)cccc2Cl)noc1-c1cnn(C[C@@H](C)O)c1C(F)(F)F]

Example 35: 1-[3-(2-chloro-6-fluorophenyl)-5-{1-[(2R)-2-hydroxypropyl]-5-(trifluoromethyl)-1H-pyrazol-4-yl}-1,2-oxazol-4-yl]ethan-1-one The title compound was isolated by prep. TLC on silica gel (eluent: petroleum ether/ethyl acetate 1:1) as a yellow oil in 10% yield.

Result of LC/MS [M+H]$^+$: 431.8;

$^1$H NMR (CDCl$_3$): δ1.32 (3H, d, CH$_3$), 2.06 (3H, s, CH$_3$), 3.22 (1H, s, CH), 4.26 (1H, dd, CH$_2$), 4.37 (3H, dd, OH, CH$_2$), 7.18 (1H, td, CH-arom.), 7.37 (1H, d, CH-arom), 7.47 (1H, m, CH-arom.), 7.98 (1H, s, CH-arom).

Examples 36, 37 and 38

Preparation of the grignard reagent: To a suspension of magnesium (1.25 eq.) in Et$_2$O (5 mL) was added (bromomethyl)cyclobutane or cyclopropylmethyl bromide (10 mmol). After the completion of the Grignard reaction the solution was separated from the rest of magnesium and further used as such (4 ml of the respective Grignard reagent in Et$_2$O). 3-(2-chloro-6-fluorophenyl)-5-(1-(2-hydroxy-2-methylpropyl)-5-(trifluoromethyl)-1H-pyrazol-4-yl)-N-methoxy-N-methylisoxazole-4-carboxamide (0.25 mmol) was dissolved in THF and the reaction mixture was cooled to 0° C. The Grignard solution (4 mL, as described above) was added dropwise at 0° C. over a period of 5 h. After addition the mixture was stirred for 1 h at 0° C. (in the case of the cyclobutane-Grignard) or for 4 h with slow warming to room temperature (in the case of the cyclopropylmethyl-Grignard). The reaction was quenched by the addition of water and an aqueous 1 M HCl solution and extracted with $CH_2Cl_2$. Organic layers were combined, dried over MgSO$_4$, filtered and concentrated under reduced pressure. The residue was purified by preparative TLC on silica gel (eluent: $CH_2Cl_2$/MeOH 98:2).

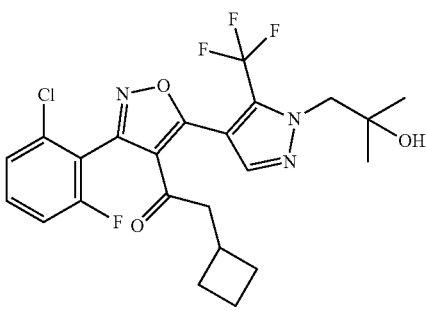 [SMILES: CC(C)(O)Cn1ncc(-c2onc(-c3c(F)cccc3Cl)c2C(=O)CC2CCC2)c1C(F)(F)F]

Example 36: 1-[3-(2-chloro-6-fluorophenyl)-5-[1-(2-hydroxy-2-methylpropyl)-5-(trifluoromethyl)-1H-pyrazol-4-yl]-1,2-oxazol-4-yl]-2-cyclobutylethan-1-one The title compound was obtained as a colorless oil (33% yield).

Result of LC/MS [M+H]$^+$: 500.3;

$^1$H NMR (CDCl$_3$): δ1.25 (6H, s, 2x CH$_3$), 1.42 (2H, m, CH$_2$), 1.80 (2H, m, CH$_2$), 1.98 (2H, m, CH$_2$), 2.39 (2H, d, CH$_2$), 2.58 (1H, m, CH), 4.13) 1H, s, OH), 4.32 (2H, s, CH$_2$), 7.17 (1H, td, CH-arom.), 7.36 (1H, dt, CH-arom), 7.47 (1H, m, CH-arom.), 7.97 (1H, s, CH-arom).

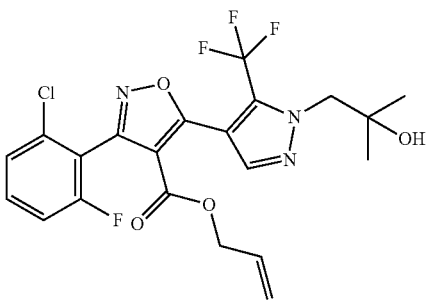 [SMILES: C=CCOC(=O)c1c(-c2c(F)cccc2Cl)noc1-c1cnn(CC(C)(C)O)c1C(F)(F)F]

Example 37: 1-[3-(2-chloro-6-fluorophenyl)-5-[1-(2-hydroxy-2-methylpropyl)-5-(trifluoromethyl)-1H-pyrazol-4-yl]-1,2-oxazol-4-yl]pent-4-en-1-one A rearrangement of the cyclopropylmethyl unit to give a butenyl substituent was observed. The obtained crude product was further purified by preparative HPLC/MS to give the title compound as a colorless oil (9% yield).

Result of LC/MS [M−H$_2$O+H]$^+$: 468.3;

$^1$H NMR (CDCl$_3$): δ1.25 (6H, s, 2xCH$_3$), 2.89-2.17 (2H, m, CH$_2$), 2.42-2.33 (2H, m, CH$_2$), 4.11 (1H, s, OH), 4.32 (2H, s, CH$_2$), 4.91-4.77 (2H, m, CH$_2$), 5.70-5.52 (1H, m, CH), 7.18 (1H, td, CH-arom.), 7.37 (1H, d, CH-arom.), 7.54-7.42 (1H, m, CH-arom.), 7.99 (1H, s, CH-arom.).

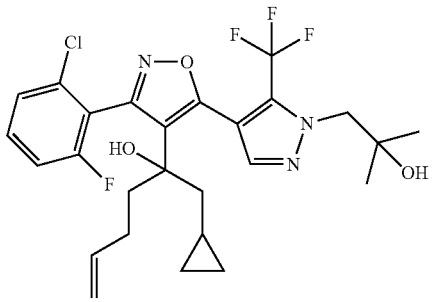 [SMILES: C=CCCC(O)(CC1CC1)c1c(-c2c(F)cccc2Cl)noc1-c1cnn(CC(C)(C)O)c1C(F)(F)F]

Example 38: 2-[3-(2-chloro-6-fluorophenyl)-5-[1-(2-hydroxy-2-methylpropyl)-5-(trifluoromethyl)-1H-pyrazol-4-yl]-1,2-oxazol-4-yl]-1-cyclopropylhex-5-en-2-ol (Racemic)

If the addition of the cyclopropylmethyl-Grignard is conducted at room temperature and stirring of the mixture is continued at this temperature for 3 h, a second addition of the Grignard reagent to the Weinreb amide was observed, which did not rearrange in a similar fashion as the first cyclopropylmethyl group (cf. Example 37). Compound purification was achieved using preparative HPLC/MS to give the title compound as a light yellow oil (14% yield).

Result of LC/MS [M+H]$^+$: 542.2;

$^1$H NMR (CDCl$_3$): δ1.09-0.91 (1H, m, CH-diastereotopic), 1.24-1.09 (1H, m, CH-diastereotopic), 1.26 (6H, s, 2xCH$_3$), 1.45-1.30 (1H, m, CH-diastereotopic), 1.71-1.58 (1H, m, CH-diastereotopic), 1.93-1.80 (2H, m, CH$_2$), 3.11-2.99 (1H, m, CH), 4.11 (1H, s, CH), 4.31 (2H, s, CH$_2$), 4.68 (1H, d, CH), 4.90-4.86 (1H, m, CH), 4.96-4.90 (1H, m, CH), 5.01 (1H, dd, CH), 5.76-5.44 (2H, m, 2xCH), 7.18 (1H, td, CH-arom.), 7.37 (1H, dt, CH-arom.), 7.54-7.42 (1H, m, CH-arom.), 7.97 (1H, s, CH-arom.).

Examples 39 and 40

To a solution of either 1-[3-(2-chloro-6-fluorophenyl)-5-[1-(2-hydroxy-2-methylpropyl)-5-(trifluoromethyl)-1H-pyrazol-4-yl]-1,2-oxazol-4-yl]ethan-1-one or 1-[3-(2-chloro-6-fluorophenyl)-5-{1-[(2R)-2-hydroxypropyl]-5-(trifluoromethyl)-1H-pyrazol-4-yl}-1,2-oxazol-4-yl]ethan-1-one (0.3 mmol) in acetonitrile (1 ml) were added NBS (1.02 eq.) and p-toluenesulfonic acid (1.0 eq.) and the mixture was stirred at 50° C. for 18 h. If conversion was not complete, additional NBS (1.02 eq.) and p-toluenesulfonic acid (1.0 eq.) were added and stirring continued at 50° C. for 5 h. The solvent was evaporated under reduced pressure and saturated aq. NaHCO$_3$ was added. The mixture was extracted with CH$_2$Cl$_2$, combined organic layers were dried over MgSO$_4$, filtrated and concentrated under reduced pressure. Crude bromoacetyl derivatives were obtained as brownish oil in around 95% yield.

2-bromo-1-[3-(2-chloro-6-fluorophenyl)-5-[1-(2-hydroxy-2-methylpropyl)-5-(trifluoromethyl)-1H-pyrazol-4-yl]-1,2-oxazol-4-yl]ethan-1-one
Result of LC/MS [M+H]$^+$: 523.6.

2-bromo-1-[3-(2-chloro-6-fluorophenyl)-5-{1-[(2R)-2-hydroxypropyl]-5-(trifluoromethyl)-1H-pyrazol-4-yl}-1,2-oxazol-4-yl]ethan-1-one
Result of LC/MS [M+H]$^+$: 509.6.

The crude bromoacetyl derivatives were taken up in methanol (2 mL) and BF$_3$*Et$_2$O (1.1 eq.) and Ag$_2$CO$_3$ (1.1 eq.) were added. The mixture was stirred at 50° C. for 18 h, upon which it was partitioned between CH$_2$Cl$_2$ and saturated aq. NH$_4$Cl. Combined organic layers were dried over sodium sulfate, filtered and concentrated under reduced pressure. Residue was purified via prep. TLC (eluent: petroleum ether/ethyl acetate 2:1).

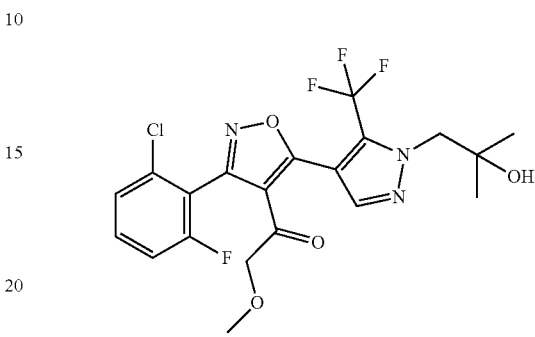

Example 39: 1-[3-(2-chloro-6-fluorophenyl)-5-[1-(2-hydroxy-2-methylpropyl)-5-(trifluoromethyl)-1H-pyrazol-4-yl]-1,2-oxazol-4-yl]-2-methoxyethan-1-one Title compound was obtained as yellowish oil (10%).

Result of LC/MS [M+H]$^+$: 475.8;

$^1$H NMR (CDCl$_3$): δ1.52 (6H, s, 2x CH$_3$), 3.15 (3H, s, CH$_3$), 3.89 (2H, s, CH$_2$), 4.10 (1H, s, OH), 4.32 (2H, s, CH$_2$), 7.19 (1H, td, CH-arom.), 7.38 (1H, dt, CH-arom), 7.48 (1H, m, CH-arom.), 8.02 (1H, s, CH-arom).

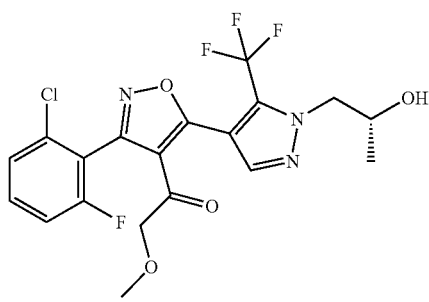 [SMILES: COCC(=O)c1c(-c2c(F)cccc2Cl)noc1-c1cnn(C[C@@H](C)O)c1C(F)(F)F]

Example 40: 1-[3-(2-chloro-6-fluorophenyl)-5-{1-[(2R)-2-hydroxypropyl]-5-(trifluoromethyl)-1H-pyrazol-4-yl}-1,2-oxazol-4-yl]-2-methoxyethan-1-one Title compound was obtained as brownish oil (12%).

Result of LC/MS [M+H]$^+$: 461.7;

$^1$H NMR (CDCl$_3$): δ1.32 (3H, d, CH$_3$), 3.15 (3H, s, CH$_3$), 1.80 (2H, m, CH$_2$), 4.25 (1H, dd, CH$_2$), 4.37 (2H, dd, OH, CH$_2$), 7.18 (1H, td, CH-arom.), 7.37 (1H, dt, CH-arom), 7.47 (1H, m, CH-arom.), 7.99 (1H, s, CH-arom).

Synthesis of Isoxazoles-4-Carboxamides

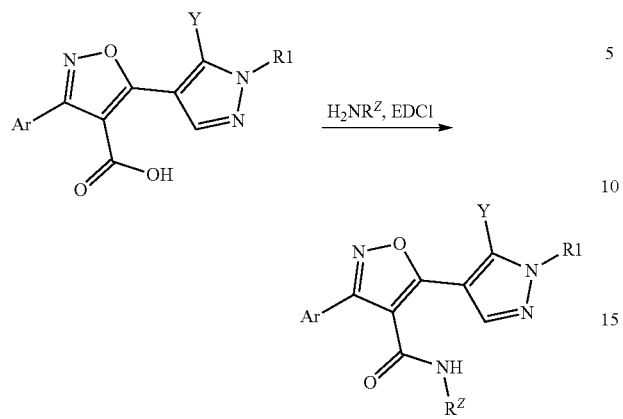

Either 3-(2-chloro-6-fluorophenyl)-5-(1-(2-hydroxy-2-methylpropyl)-5-(trifluoromethyl)-1H-pyrazol-4-yl)isoxazole-4-carboxylic acid or 3-(2-chloro-6-fluorophenyl)-5-{1-[(2R)-2-hydroxypropyl]-5-(trifluoromethyl)-1H-pyrazol-4-yl}-1,2-oxazole-4-carboxylic acid (0.15 mmol), the respective amine (1.8 eq.), 1-hydroxybenzotriazole (1.5 eq.) and 1-(3-dimethylaminopropyl)-3-ethylcarbodiimide hydrochloride (EDCI; 1.7 eq.) were dissolved in 1 mL dry DMF. N-Methylmorpholine (10. eq.) was added and the mixture was stirred at room temperature for 18 h. The mixture was partitioned between saturated aq. NH$_4$Cl-solution and CH$_2$Cl$_2$, combined organic layers were washed with water and brine and dried over MgSO$_4$, filtrated and concentrated under reduced pressure. Product purification was achieved by prep. TLC on silica gel.

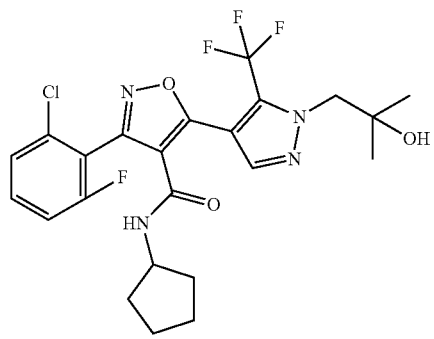 [SMILES: CC(C)(O)Cn1ncc(-c2onc(-c3c(F)cccc3Cl)c2C(=O)NC2CCCC2)c1C(F)(F)F]

Example 41: 3-(2-chloro-6-fluorophenyl)-N-cyclopentyl-5-(1-(2-hydroxy-2-methylpropyl)-5-(trifluoromethyl)-1H-pyrazol-4-yl)isoxazole-4-carboxamide Title compound was synthesized from 3-(2-chloro-6-fluorophenyl)-5-(1-(2-hydroxy-2-methylpropyl)-5-(trifluoromethyl)-1H-pyrazol-4-yl)isoxazole-4-carboxylic acid and cyclopentylamine as yellowish solid in 42% yield (pTLC, eluent: petroleum ether/ethyl acetate 1:1).

Result of LC/MS [M+H]$^+$: 514.8;

$^1$H NMR (CDCl$_3$): δ1.13 (2H, m, CH$_2$), 1.25 (6H, s, 2x CH$_3$), 1.37 (2H, m, CH$_2$), 1.50 (2H, m, CH$_2$), 1.82 (2H, m, CH$_2$), 4.18 (2H, m, CH$_2$), 4.30 (2H, s, CH$_2$), 5.24 (1H, s, OH), 7.21 (1H, td, CH-arom.), 7.40 (1H, dt, CH-arom), 7.51 (1H, m, CH-arom.), 8.11 (1H, s, CH-arom).

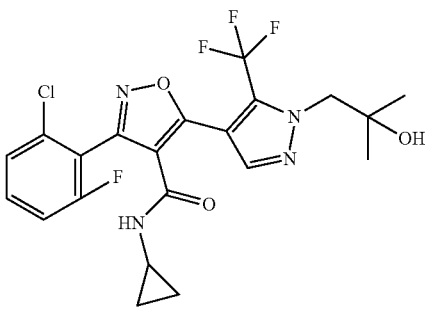 [SMILES: CC(C)(O)Cn1ncc(-c2onc(-c3c(F)cccc3Cl)c2C(=O)NC2CC2)c1C(F)(F)F]

Example 42: 3-(2-chloro-6-fluorophenyl)-N-cyclopropyl-5-(1-(2-hydroxy-2-methylpropyl)-5-(trifluoromethyl)-1H-pyrazol-4-yl)isoxazole-4-carboxamide Title compound was synthesized from 3-(2-chloro-6-fluorophenyl)-5-(1-(2-hydroxy-2-methylpropyl)-5-(trifluoromethyl)-1H-pyrazol-4-yl)isoxazole-4-carboxylic acid and cyclopropylamine as greenish oil in 23% yield (pTLC, eluent: petroleum ether/ethyl acetate 1:2).

Result of LC/MS [M+H]$^+$: 486.9;

$^1$H NMR (CDCl$_3$): δ0.22 (2H, m, CH$_2$), 0.69 (2H, m, CH$_2$), 1.24 (6H, s, 2x CH$_3$), 2.64 (1H, m, CH), 4.13 (1H, s, CH), 4.30 (2H, s, CH$_2$), 5.42 (1H, s, OH), 7.19 (1H, td, CH-arom.), 7.38 (1H, d, CH-arom), 7.49 (1H, m, CH-arom.), 8.10 (1H, s, CH-arom).

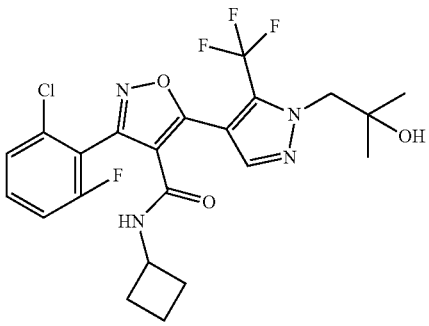 [SMILES: CC(C)(O)Cn1ncc(-c2onc(-c3c(F)cccc3Cl)c2C(=O)NC2CCC2)c1C(F)(F)F]

Example 43: 3-(2-chloro-6-fluorophenyl)-N-cyclobutyl-5-(1-(2-hydroxy-2-methylpropyl)-5-(trifluoromethyl)-1H-pyrazol-4-yl)isoxazole-4-carboxamide Title compound was synthesized from 3-(2-chloro-6-fluorophenyl)-5-(1-(2-hydroxy-2-methylpropyl)-5-(trifluoromethyl)-1H-pyrazol-4-yl)isoxazole-4-carboxylic acid and cyclobutylamine as greyish solid in 13% yield (pTLC, eluent: petroleum ether/ethyl acetate 1:2).

Result of LC/MS [M+H]$^+$: 500.9;

$^1$H NMR (CDCl$_3$): δ1.24 (6H, s, 2x CH$_3$), 1.58 (4H, m, 2x CH$_2$), 2.23 (2H, m, CH$_2$), 4.30 (2H, s, CH$_2$), 4.32 (1H, m, CH), 5.41 (1H, s, OH), 7.21 (1H, td, CH-arom.), 7.41 (1H, d, CH-arom), 7.51 (1H, m, CH-arom.), 8.08 (1H, s, CH-arom).

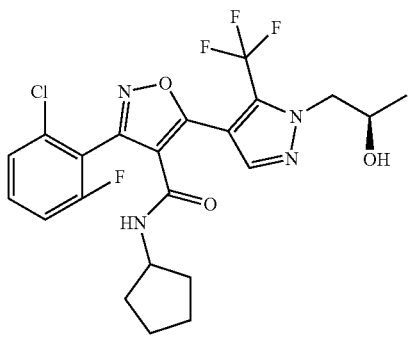 [SMILES: C[C@@H](O)Cn1ncc(-c2onc(-c3c(F)cccc3Cl)c2C(=O)NC2CCCC2)c1C(F)(F)F]

Example 44: 3-(2-chloro-6-fluorophenyl)-N-cyclopentyl-5-{1-[1-(2R)-2-hydroxypropyl]-5-(trifluoromethyl)-1H-pyrazol-4-yl}-1,2-oxazole-4-carboxamide Title compound was synthesized from 3-(2-chloro-6-fluorophenyl)-5-{1-[(2R)-2-hydroxypropyl]-5-(trifluoromethyl)-1H-pyrazol-4-yl}-1,2-oxazole-4-carboxylic acid and cyclopentylamine as orange oil in 12% yield (pTLC, eluent: petroleum ether/ethyl acetate 1:1).

Result of LC/MS [M+H]$^+$: 500.8;

$^1$H NMR (CDCl$_3$): δ1.20-1.05 (3H, s, 3x CH-diastereotopic), 1.32 (3H, d, CH$_3$), 1.42-1.34 (2H, m, 2x CH-diastereotopic), 1.91-1.74 (3H, m, 3x CH-diastereotopic), 4.21-4.13 (1H, m, CH), 4.29-4.22 (1H, m, CH), 4.44-4.30 (2H, m, CH$_2$), 5.25 (1H, br, OH), 7.21 (1H, td, CH-arom.), 7.40 (1H, dt, CH-arom.), 7.56-7.46 (1H, m, CH-arom.), 8.08 (1H, s, CH-arom.).

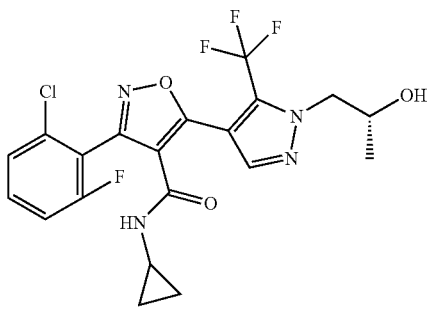 [SMILES: C[C@@H](O)Cn1ncc(-c2onc(-c3c(F)cccc3Cl)c2C(=O)NC2CC2)c1C(F)(F)F]

Example 45: 3-(2-chloro-6-fluorophenyl)-N-cyclopropyl-5-(1-((2R)-2-hydroxypropyl)-5-(trifluoromethyl)-1H-pyrazol-4-yl)isoxazole-4-carboxamide Title compound was synthesized from 3-(2-chloro-6-fluorophenyl)-5-{1-[(2R)-2-hydroxypropyl]-5-(trifluoromethyl)-1H-pyrazol-4-yl}-1,2-oxazole-4-carboxylic acid and cyclopropylamine as greenish solid in 27% yield (pTLC, eluent: petroleum ether/ethyl acetate 1:2).

Result of LC/MS [M+H]$^+$: 472.8;

$^1$H NMR (CDCl$_3$): δ0.24 (2H, m, CH$_2$), 0.68 (2H, m, CH$_2$), 1.31 (3H, d, CH$_3$), 2.63 (1H, m, CH), 3.34 (1H, s, CH), 4.23 (1H, dd, CH), 4.35 (2H, m, CH, OH), 5.46 (1H, s, NH), 7.18 (1H, t, CH-arom.), 7.37 (1H, d, CH-arom.), 7.48 (1H, m, CH-arom.), 8.05 (1H, s, CH-arom).

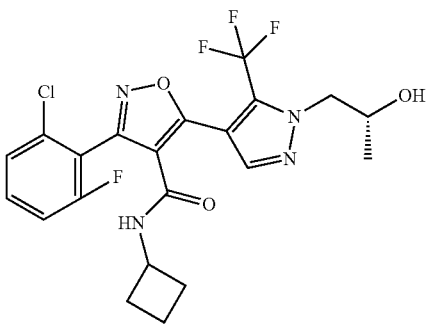 [SMILES: C[C@@H](O)Cn1ncc(-c2onc(-c3c(F)cccc3Cl)c2C(=O)NC2CCC2)c1C(F)(F)F]

Example 46: 3-(2-chloro-6-fluorophenyl)-N-cyclobutyl-5-(1-((2R)-2-hydroxypropyl)-5-(trifluoromethyl)-1H-pyrazol-4-yl)isoxazole-4-carboxamide Title compound was synthesized from 3-(2-chloro-6-fluorophenyl)-5-{1-[(2R)-2-hydroxypropyl]-5-(trifluoromethyl)-1H-pyrazol-4-yl}-1,2-oxazole-4-carboxylic acid and cyclobutylamine as yellowish solid in 41% yield (pTLC, eluent: petroleum ether/ethyl acetate 1:2).

Result of LC/MS [M+H]$^+$: 486.9;

$^1$H NMR (CDCl$_3$): δ1.30 (3H, d, CH$_3$), 1.56 (4H, m, CH$_2$), 2.22 (2H, m, CH$_2$), 3.35 (1H, s, CH), 4.28 (4H, m, CH$_2$, OH), 5.45 (1H, s, NH), 7.20 (1H, t, CH-arom.), 7.39 (1H, d, CH-arom.), 7.50 (1H, m, CH-arom.), 8.04 (1H, s, CH-arom).

Synthesis of Isoxazole-4-Carboxylic Acid Esters

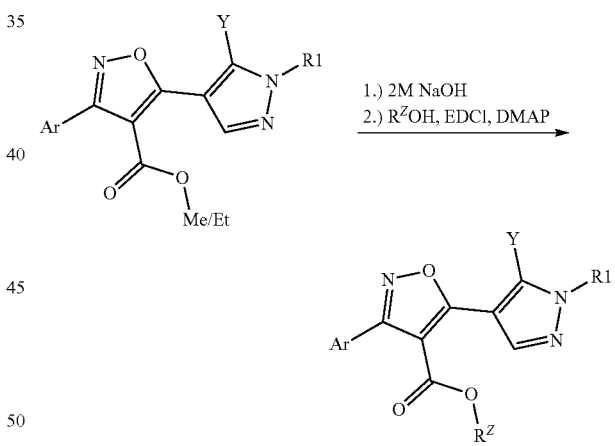

Starting from respective methyl or ethyl esters (0.3 mmol), corresponding carboxylic acids were generated by saponification according to the general procedure described above within the synthesis of 4-acyl isoxazoles (described there starting with Example 8 or Example 12):

- 3-(2-chloro-6-fluorophenyl)-5-(1-(2-hydroxy-2-methylpropyl)-5-(trifluoromethyl)-1H-pyrazol-4-yl)isoxazole-4-carboxylic acid, cf. above.
- 3-(2-chloro-6-fluorophenyl)-5-{1-[(2R)-2-hydroxypropyl]-5-(trifluoromethyl)-1H-pyrazol-4-yl}-1,2-oxazole-4-carboxylic acid, cf. above.
- 3-(2-chloro-6-fluorophenyl)-5-{1-[(2S)-2-hydroxypropyl]-5-(trifluoromethyl)-1H-pyrazol-4-yl}-1,2-oxazole-4-carboxylic acid from Example 13 as off-white solid, 81% yield;

Result of LC/MS [M+H]$^+$: 434.2;
$^1$H NMR (CDCl$_3$): δ1.30 (3H, d, CH$_3$), 4.24 (1H, dd, CH), 4.46-4.31 (2H, m, CH$_2$), 7.12 (1H, td, CH-arom.), 7.32 (1H, dt, CH-arom.), 7.48-7.36 (1H, m, CH-arom.), 7.97 (1H, s, CH-arom.).

3-(2-chlorophenyl)-5-{5-methyl-1-[3-hydroxy-3-methyl-cyclobutyl]-1H-pyrazol-4-yl}-1,2-oxazole-4-carbox-ylic acid from Examples 17/18 (syn/anti mixture not separated at this stage) as brownish oil, 52% yield;
Result of LC/MS [M+H]$^+$: 388.2;

3-(2-chlorophenyl)-5-{1-[(2S)-2-hydroxypropyl]-5-methyl-1H-pyrazol-4-yl}-1,2-oxazole-4-carboxylic acid from Example 24 as brownish oil, 64% yield;

3-(2-chloro-6-fluorophenyl)-5-{5-methyl-1-[3-hydroxy-3-methylcyclobutyl]-1H-pyrazol-4-yl}-1,2-oxazole-4-carboxylic acid (syn/anti-mixture) as off-white solid, 83% yield;
Result of LC/MS [M+H]$^+$: 406.2;

The required ester methyl 3-(2-chloro-6-fluorophenyl)-5-{5-methyl-1-[3-hydroxy-3-methylcyclobutyl]-1H-pyrazol-4-yl}-1,2-oxazole-4-carboxylate was synthesized as described above from methyl (Z)-3-(2-chloro-6-fluorophenyl)-5-(1-(dimethylamino)-3-oxobut-1-en-2-yl)isoxazole-4-carboxylate (0.80 mmol) and 3-hydrazinyl-1-methylcyclobutan-1-ol (syn/anti mixture) as an off-white solid (54% crude) as a mixture of syn/anti-configurations within the cyclobutanol unit.
Result of LC/MS [M+H]$^+$: 420.2;

3-(2-chlorophenyl)-5-[1-(3-hydroxy-3-methylcy-clobutyl)-5-(trifluoromethyl)-1H-pyrazol-4-yl]-1,2-oxazole-4-carboxylic acid (syn/anti-mixture) as yellowish solid, 96% yield;
Result of LC/MS [M+H]$^+$: 442.2;

The required ester ethyl 3-(2-chlorophenyl)-5-[1-(3-hydroxy-3-methylcyclobutyl)-5-(trifluoromethyl)-1H-pyrazol-4-yl]-1,2-oxazole-4-carboxylate was synthesized as described above from ethyl (Z)-3-(2-chlorophenyl)-5-(1-(dimethylamino)-4,4,4-trifluoro-3-oxobut-1-en-2-yl)isoxazole-4-carboxylate (1.0 mmol) and 3-hydrazinyl-1-methylcyclobutan-1-ol (syn/anti mixture) as a yellowish oil (11%; pTLC, eluent: CH$_2$Cl$_2$/MeOH 95:5 and pTLC, eluent: petroleum ether/ethyl acetate 1:1) as a mixture of syn/anti-configurations within the cyclobutanol unit.
Result of LC/MS [M+H]$^+$: 470.2;

3-(2-chloro-6-fluorophenyl)-5-[1-(3-hydroxy-3-methyl-cyclobutyl)-5-(trifluoromethyl)-1H-pyrazol-4-yl]-1,2-oxazole-4-carboxylic acid (syn/anti-mixture) as orange solid, 78% yield;
Result of LC/MS [M+H]$^+$: 460.1;

The required ester ethyl 3-(2-chloro-6-fluorophenyl)-5-[1-(3-hydroxy-3-methylcyclobutyl)-3-(trifluorom-ethyl)-1H-pyrazol-4-yl]-1,2-oxazole-4-carboxylate was synthesized as described above from ethyl (Z)-3-(2-chloro-6-fluorophenyl)-5-(1-(dimethylamino)-4,4,4-trifluoro-3-oxobut-1-en-2-yl)isoxazole-4-carboxylate (0.35 mmol) and 3-hydrazinyl-1-methylcyclobutan-1-ol (syn/anti mixture) as a brownish oil (65% crude) as a mixture of syn/anti-configurations within the cyclobutanol unit.
Result of LC/MS [M+H]$^+$: 488.2;

To a mixture of the respective carboxylic acid (0.05 mmol) and the respective alcohol (3.0 eq.) in CH$_2$Cl$_2$ (4 mL) were added EDCI (1.5 eq.) and DMAP (0.2 eq.) at room temperature. The reaction mixture was stirred at room temperature for 18 h. All volatiles were removed under reduced pressure. The residue was purified by preparative TLC on silica gel (eluent: PE/EtOAc 1:1).

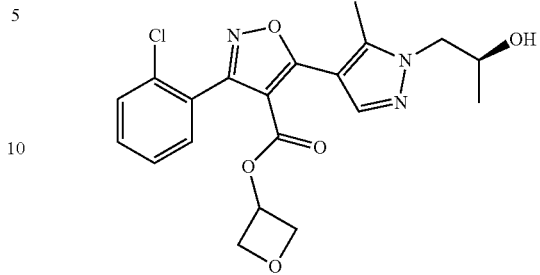

Example 47: oxetan-3-yl 3-(2-chlorophenyl)-5-{1-[(2S)-2-hydroxypropyl]-5-methyl-1H-pyrazol-4-yl}-1,2-oxazole-4-carboxylate Title compound was synthesized from 3-(2-chlorophenyl)-5-{1-[(2S)-2-hydroxypropyl]-5-methyl-1H-pyrazol-4-yl}-1,2-oxazole-4-carboxylic acid and oxetan-3-ol as off-white solid in 24% yield (pTLC, eluent: petroleum ether/ethyl acetate 1:1).
Result of LC/MS [M+H]$^+$: 418.2;
$^1$H NMR (CDCl$_3$): δ1.30 (3H, d, CH$_3$), 2.63 (3H, s, CH$_3$), 3.37 (1H, d, CH$_2$), 4.01 (1H, dd, CH), 4.15 (1H, dd, CH$_2$) 4.28-4.19 (2H, m, CH$_2$), 4.33 (1H, br, OH), 4.74 (2H, t, CH$_2$), 5.51-5.40 (m, 1H, CH), 7.56-7.35 (4H, m, 4xCH-arom.), 8.41 (1H, s, CH-arom.).

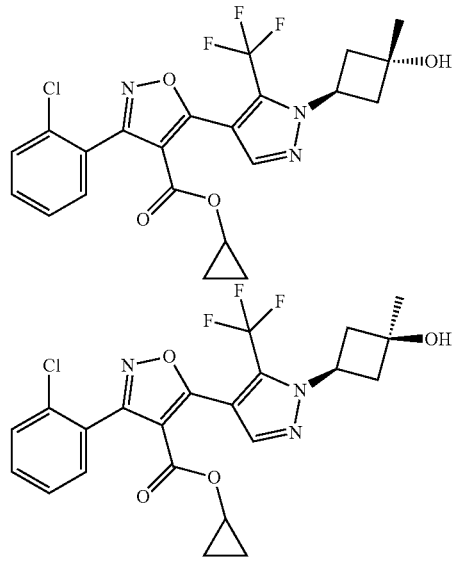

Examples 48 and 49: cyclopropyl 3-(2-chlorophe-nyl)-5-(1-(3-hydroxy-3-methylcyclobutyl)-5-(trifluo-romethyl)-1H-pyrazol-4-yl)isoxazole-4-carboxylate (Anti- and Syn-Configuration)

Title compounds were synthesized from 3-(2-chlorophenyl)-5-[1-(3-hydroxy-3-methylcyclobutyl)-5-(trifluorom-ethyl)-1H-pyrazol-4-yl]-1,2-oxazole-4-carboxylic acid (syn/anti-mixture) and cyclopropanol as pale yellow oils; pTLC, eluent: CH$_2$Cl$_2$/MeOH 95:5 and pTLC, eluent: petroleum ether/ethyl acetate 7:3.

Example 48: cyclopropyl 3-(2-chlorophenyl)-5-(1-(3-hydroxy-3-methylcyclobutyl)-5-(trifluoromethyl)-1H-pyrazol-4-yl)isoxazole-4-carboxylate (anti-configuration), 39% yield;

Result of LC/MS [M+H]$^+$: 482.2;

$^1$H NMR (CDCl$_3$): δ0.34 (2H, m, CH$_2$), 0.58 (2H, m, CH$_2$), 1.56 (3H, s, CH$_3$), 2.64 (2H, m, CH$_2$), 2.84 (2H, m, CH$_2$), 4.11 (1H, m, CH), 5.26 (1H, quint., CH), 7.38 (1H, m, CH-arom.), 7.46 (3H, m, CH-arom), 7.97 (1H, s, CH-arom).

Example 49: cyclopropyl 3-(2-chlorophenyl)-5-(1-(3-hydroxy-3-methylcyclobutyl)-5-(trifluoromethyl)-1H-pyrazol-4-yl)isoxazole-4-carboxylate (syn-configuration), 25% yield.

Result of LC/MS [M+H]$^+$: 482.2;

$^1$H NMR (CDCl$_3$): δ0.34 (2H, m, CH$_2$), 0.58 (2H, m, CH$_2$), 1.49 (3H, s, CH$_3$), 2.80 (4H, m, 2x CH$_2$), 4.12 (1H, m, CH), 4.72 (1H, quint., CH), 5.42 (1H, s, OH), 7.99 (1H, m, CH-arom.), 7.46 (3H, m, CH-arom), 8.01 (1H, s, CH-arom).

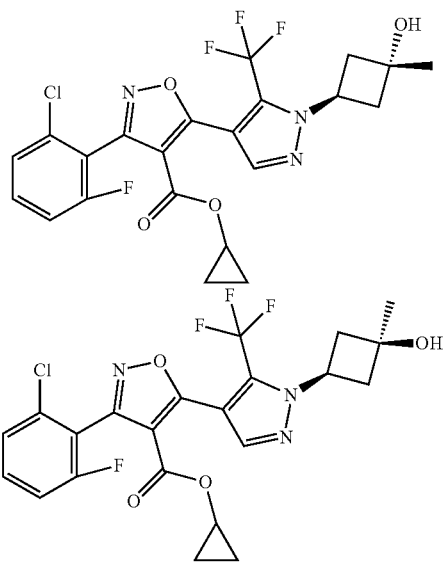

Examples 50 and 51: cyclopropyl 3-(2-chloro-6-fluorophenyl)-5-(1-(3-hydroxy-3-methylcyclobutyl)-5-(trifluoromethyl)-1H-pyrazol-4-yl)isoxazole-4-carboxylate (Anti- and Syn-Configuration)

Title compounds were synthesized from 3-(2-chloro-6-fluorophenyl)-5-[1-(3-hydroxy-3-methylcyclobutyl)-5-(trifluoromethyl)-1H-pyrazol-4-yl]-1,2-oxazole-4-carboxylic acid (syn/anti-mixture) and cyclopropanol as yellowish oils; pTLC, eluent: petroleum ether/ethyl acetate 7:3 and again pTLC, eluent: petroleum ether/ethyl acetate 7:3.

Example 50: cyclopropyl 3-(2-chloro-6-fluorophenyl)-5-(1-(3-hydroxy-3-methylcyclobutyl)-5-(trifluoromethyl)-1H-pyrazol-4-yl)isoxazole-4-carboxylate (anti-configuration), 1% yield.

Result of LC/MS [M+H]$^+$: 500.2;

$^1$H NMR (CDCl$_3$): δ0.32 (2H, m, CH$_2$), 0.58 (2H, m, CH$_2$), 1.58 (3H, s, CH$_3$), 2.65 (2H, m, CH$_2$), 2.83 (2H, m, CH$_2$), 4.12 (1H, m, CH), 5.26 (1H, quint., CH), 7.12 (1H, t, CH-arom.), 7.31 (1H, d, CH-arom.), 7.42 (1H, m, CH-arom), 7.96 (1H, s, CH-arom).

Example 51: cyclopropyl 3-(2-chloro-6-fluorophenyl)-5-{1-[3-hydroxy-3-methylcyclobutyl]-5-(trifluoromethyl)-1H-pyrazol-4-yl}-1,2-oxazole-4-carboxylate (syn-configuration), 1% yield.

Result of LC/MS [M+H]$^+$: 500.2;

$^1$H NMR (CDCl$_3$): δ0.32 (2H, m, CH$_2$), 0.59 (2H, m, CH$_2$), 1.56 (3H, s, CH$_3$), 2.82 (4H, m, 2x CH$_2$), 4.13 (1H, m, CH), 4.71 (1H, quint., CH), 7.13 (1H, t, CH-arom.), 7.32 (1H, d, CH-arom.), 7.43 (1H, m, CH-arom), 8.00 (1H, s, CH-arom).

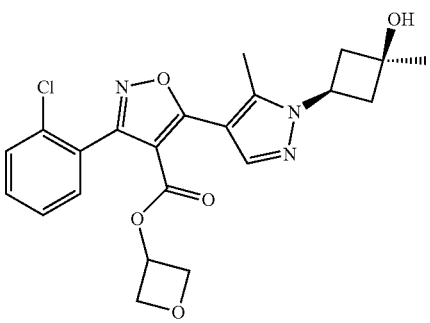 [SMILES: Cc1c(-c2onc(-c3ccccc3Cl)c2C(=O)OC2COC2)cnn1[C@H]1C[C@@](C)(O)C1]

Example 52: oxetan-3-yl 3-(2-chlorophenyl)-5-(1-(3-hydroxy-3-methylcyclobutyl)-5-methyl-1H-pyrazol-4-yl)isoxazole-4-carboxylate (Syn-Configuration)

Title compound was synthesized from 3-(2-chlorophenyl)-5-{5-methyl-1-[3-hydroxy-3-methylcyclobutyl]-1H-pyrazol-4-yl}-1,2-oxazole-4-carboxylic acid (syn-configuration, resulting from saponification of Example 18) and oxetan-3-ol as pale yellow oil in 7% yield (pTLC, eluent: petroleum ether/ethyl acetate 1:1).

Result of LC/MS [M+H]$^+$: 444.3;

$^1$H NMR (CDCl$_3$): δ1.47 (3H, s, CH$_3$), 2.59 (3H, s, CH$_3$), 2.79-2.69 (4H, m, CH$_2$), 3.64 (1H, br, OH), 4.24 (2H, t, CH$_2$), 4.55 (1H, quint, CH), 4.74 (2H, t, CH$_2$), 5.45 (1H, quint, CH), 7.55-7.36 (4H, m, 4xCH-arom.), 8.42 (1H, s, CH-arom.).

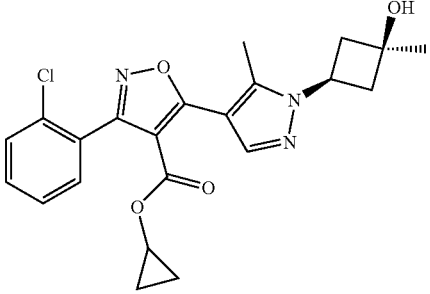

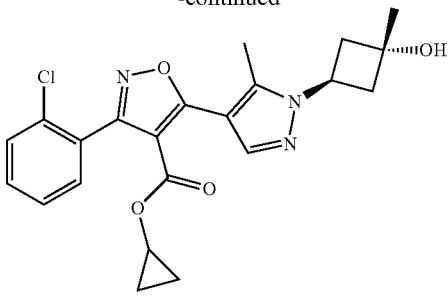

Examples 53 and 54: cyclopropyl 3-(2-chlorophenyl)-5-{5-methyl-1-[3-hydroxy-3-methylcyclobutyl]-1H-pyrazol-4-yl}-1,2-oxazole-4-carboxylate (Syn- and Anti-Configuration)

Title compounds were synthesized from 3-(2-chlorophenyl)-5-{5-methyl-1-[3-hydroxy-3-methylcyclobutyl]-1H-pyrazol-4-yl}-1,2-oxazole-4-carboxylic acid (syn/anti mixture) and cyclopropanol as colorless oils; pTLC, eluent: petroleum ether/ethyl acetate 7:3 and again pTLC, eluent: petroleum ether/ethyl acetate 7:3.

Example 53: cyclopropyl 3-(2-chlorophenyl)-5-{5-methyl-1-[3-hydroxy-3-methylcyclobutyl]-1H-pyrazol-4-yl}-1,2-oxazole-4-carboxylate (syn-configuration), 2% yield;

Result of LC/MS [M+H]$^+$: 428.3;

$^1$H NMR (CDCl$_3$): δ0.33 (2H, m, CH$_2$), 0.58 (2H, m, CH$_2$), 1.47 (3H, s, CH$_3$), 2.58 (3H, s, CH$_3$), 2.74 (4H, m, 2x CH$_2$), 4.15 (1H, m, CH), 4.55 (1H, quint., CH), 7.41 (4H, m, CH-arom.), 8.43 (1H, s, CH-arom).

Example 54: cyclopropyl 3-(2-chlorophenyl)-5-{5-methyl-1-[3-hydroxy-3-methylcyclobutyl]-1H-pyrazol-4-yl}-1,2-oxazole-4-carboxylate (anti-configuration), 3% yield.

Result of LC/MS [M+H]$^+$: 428.3;

$^1$H NMR (CDCl$_3$): δ0.33 (2H, m, CH$_2$), 0.58 (2H, m, CH$_2$), 1.55 (3H, s, CH$_3$), 2.58 (5H, m, CH$_3$, CH$_2$), 2.80 (2H, m, CH$_2$), 4.15 (1H, m, CH), 5.04 (1H, quint., CH), 7.41 (4H, m, CH-arom.), 8.38 (1H, s, CH-arom).

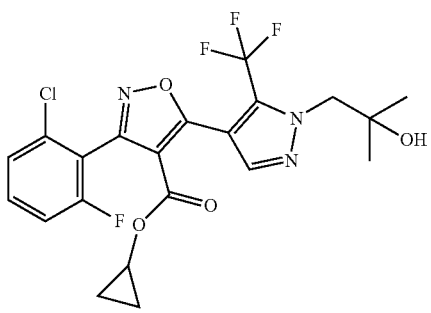 [SMILES: CC(C)(O)Cn1ncc(-c2onc(-c3c(F)cccc3Cl)c2C(=O)OC2CC2)c1C(F)(F)F]

Example 55: cyclopropyl 3-(2-chloro-6-fluorophenyl)-5-[1-(2-hydroxy-2-methylpropyl)-5-(trifluoromethyl)-1H-pyrazol-4-yl]-1,2-oxazole-4-carboxylate Title compound was synthesized from 3-(2-chloro-6-fluorophenyl)-5-(1-(2-hydroxy-2-methylpropyl)-5-(trifluoromethyl)-1H-pyrazol-4-yl)isoxazole-4-carboxylic acid and cyclopropanol as pale yellow solid in 33% yield (pTLC, eluent: petroleum ether/ethyl acetate 1:1).

Result of LC/MS [M+H]$^+$: 487.8;

$^1$H NMR (CDCl$_3$): δ0.33 (2H, m, CH$_2$), 0.60 (2H, m, CH$_2$), 1.25 (6H, s, 2x CH$_3$), 4.13 (1H, m, CH), 4.18 (1H, s, OH), 4.31 (2H, s, CH$_2$), 7.13 (1H, t, CH-arom.), 7.33 (1H, d, CH-arom.), 7.47 (1H, m, CH-arom), 8.05 (1H, s, CH-arom).

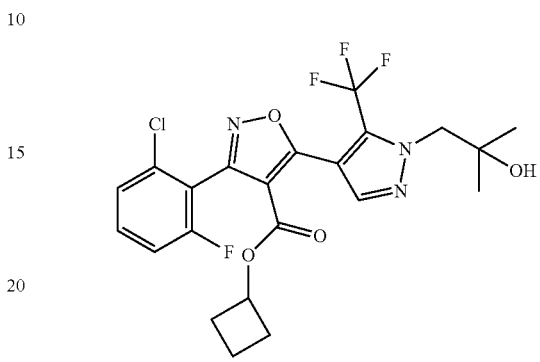

Example 56: cyclobutyl 3-(2-chloro-6-fluorophenyl)-5-[1-(2-hydroxy-2-methylpropyl)-5-(trifluoromethyl)-1H-pyrazol-4-yl]-1,2-oxazole-4-carboxylate Title compound was synthesized from 3-(2-chloro-6-fluorophenyl)-5-(1-(2-hydroxy-2-methylpropyl)-5-(trifluoromethyl)-1H-pyrazol-4-yl)isoxazole-4-carboxylic acid and cyclobutanol as pale yellow oil in 47% yield (pTLC, eluent: petroleum ether/ethyl acetate 1:1).

Result of LC/MS [M+H]$^+$: 501.8;

$^1$H NMR (CDCl$_3$): δ1.25 (6H, s, 2x CH$_3$), 1.55 (2H, m, CH$_2$), 1.69 (2H, m, CH$_2$), 2.19 (2H, m, CH$_2$), 4.21 (1H, s, OH), 4.31 (2H, s, CH$_2$), 4.97 (1H, m, CH), 7.15 (1H, t, CH-arom.), 7.35 (1H, d, CH-arom.), 7.45 (1H, m, CH-arom), 8.06 (1H, s, CH-arom).

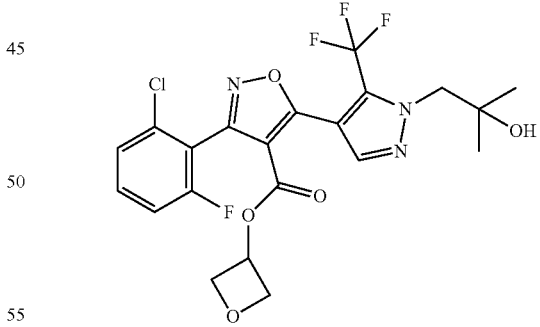

Example 57: oxetan-3-yl 3-(2-chloro-6-fluorophenyl)-5-[1-(2-hydroxy-2-methylpropyl)-5-(trifluoromethyl)-1H-pyrazol-4-yl]-1,2-oxazole-4-carboxylate Title compound was synthesized from 3-(2-chloro-6-fluorophenyl)-5-(1-(2-hydroxy-2-methylpropyl)-5-(trifluoromethyl)-1H-pyrazol-4-yl)isoxazole-4-carboxylic acid and oxetan-3-ol as colorless solid in 38% yield (pTLC, eluent: petroleum ether/ethyl acetate 1:1).

Result of LC/MS [M+H]⁺: 504.0;
¹H NMR (CDCl₃): δ1.26 (6H, s, 2xCH₃), 4.11 (1H, br, OH), 4.29-4.21 (2H, m, CH₂), 4.31 (2H, s, CH₂), 4.80-4.70 (2H, m, CH₂), 5.49-5.38 (1H, m, CH), 7.17 (1H, td, CH-arom.), 7.37 (1H, dt, CH-arom.), 7.52-7.42 (1H, m, CH-arom.), 8.05 (1H, s, CH-arom.).

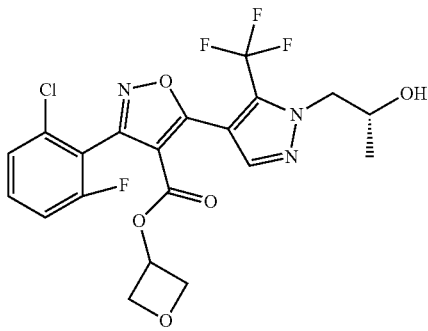 [SMILES: C[C@@H](O)Cn1ncc(-c2onc(-c3c(F)cccc3Cl)c2C(=O)OC2COC2)c1C(F)(F)F]

Example 58: oxetan-3-yl 3-(2-chloro-6-fluorophenyl)-5-{1-[(2R)-2-hydroxypropyl]-5-(trifluoromethyl)-1H-pyrazol-4-yl}-1,2-oxazole-4-carboxylate Title compound was synthesized from 3-(2-chloro-6-fluorophenyl)-5-{1-[(2R)-2-hydroxypropyl]-5-(trifluoromethyl)-1H-pyrazol-4-yl}-1,2-oxazole-4-carboxylic acid and oxetan-3-ol as colorless solid in 21% yield (pTLC, eluent: petroleum ether/ethyl acetate 1:1).
Result of LC/MS [M+H]⁺: 490.2;
¹H NMR (CDCl₃): δ1.32 (3H, d, CH₃), 3.20 (1H, br, OH), 4.32-4.19 (3H, m, CH and CH₂), 4.47-4.32 (2H, m, CH₂), 4.75 (2H, t, CH₂), 5.49-5.39 (1H, m, CH), 7.17 (1H, td, CH-arom.), 7.37 (1H, td, CH-arom.), 7.52-7.42 (1H, m, CH-arom.), 8.03 (1H, s, CH-arom.).

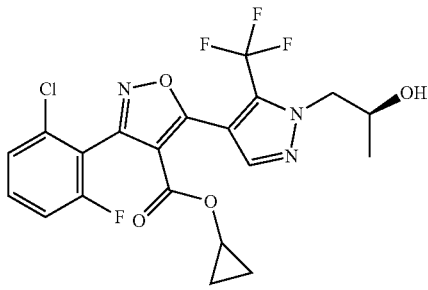 [SMILES: C[C@H](O)Cn1ncc(-c2onc(-c3c(F)cccc3Cl)c2C(=O)OC2CC2)c1C(F)(F)F]

Example 59: cyclopropyl 3-(2-chloro-6-fluorophenyl)-5-{1-[(2S)-2-hydroxypropyl]-5-(trifluoromethyl)-1H-pyrazol-4-yl}-1,2-oxazole-4-carboxylate Title compound was synthesized from 3-(2-chloro-6-fluorophenyl)-5-{1-[(2S)-2-hydroxypropyl]-5-(trifluoromethyl)-1H-pyrazol-4-yl}-1,2-oxazole-4-carboxylic acid and cyclopropanol as pale yellow oil in 30% yield (pTLC, eluent: petroleum ether/ethyl acetate 1:1).
Result of LC/MS [M+H]⁺: 474.2;
¹H NMR (CDCl₃): δ0.32 (2H, m, CH₂), 0.59 (2H, m, CH₂), 1.32 (3H, d, CH₃), 3.26 (1H, s, OH), 4.13 (1H, quint., CH), 4.25 (1H, dd, CH), 4.37 (2H, m, 2x CH), 7.13 (1H, t, CH-arom.), 7.32 (1H, d, CH-arom.), 7.44 (1H, m, CH-arom), 8.03 (1H, s, CH-arom).

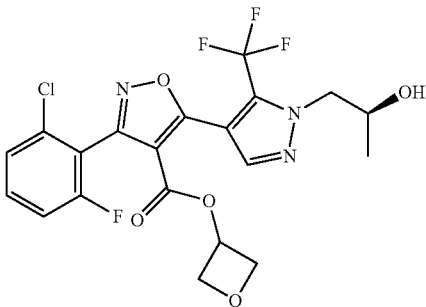 [SMILES: C[C@H](O)Cn1ncc(-c2onc(-c3c(F)cccc3Cl)c2C(=O)OC2COC2)c1C(F)(F)F]

Example 60: oxetan-3-yl 3-(2-chloro-6-fluorophenyl)-5-{1-[(2S)-2-hydroxypropyl]-5-(trifluoromethyl)-1H-pyrazol-4-yl}-1,2-oxazole-4-carboxylate Title compound was synthesized from 3-(2-chloro-6-fluorophenyl)-5-{1-[(2S)-2-hydroxypropyl]-5-(trifluoromethyl)-1H-pyrazol-4-yl}-1,2-oxazole-4-carboxylic acid and oxetan-3-ol as pale yellow solid in 29% yield (pTLC, eluent: petroleum ether/ethyl acetate 1:1).
Result of LC/MS [M+H]⁺: 490.2;
¹H NMR (CDCl₃): δ1.32 (3H, d, CH₃), 3.21 (1H, br, OH), 4.31-4.20 (3H, m, CH and CH₂), 4.47-4.31 (2H, m, CH₂), 4.75 (2H, t, CH₂), 5.50-5.38 (1H, m, CH), 7.17 (1H, td, CH-arom.), 7.37 (1H, dt, CH-arom.), 7.52-7.42 (1H, m, CH-arom.), 8.03 (1H, s, CH-arom.).

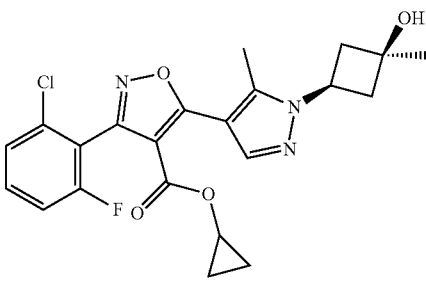

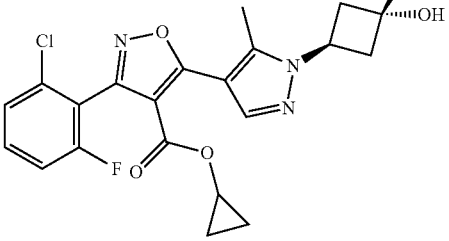

Examples 61 and 62: cyclopropyl 3-(2-chloro-6-fluorophenyl)-5-{5-methyl-1-[3-hydroxy-3-methylcyclobutyl]-1H-pyrazol-4-yl}-1,2-oxazole-4-carboxylate (Syn- and Anti-Configuration)

Title compounds were synthesized from 3-(2-chloro-6-fluorophenyl)-5-{5-methyl-1-[3-hydroxy-3-methylcyclobutyl]-1H-pyrazol-4-yl}-1,2-oxazole-4-carboxylic acid (syn/anti mixture) and cyclopropanol as yellowish oils; pTLC, eluent: petroleum ether/ethyl acetate 7:3 and again pTLC, eluent: petroleum ether/ethyl acetate 7:3.

Example 61: cyclopropyl 3-(2-chloro-6-fluorophenyl)-5-{5-methyl-1-[3-hydroxy-3-methylcyclobutyl]-1H-pyrazol-4-yl}-1,2-oxazole-4-carboxylate (syn-configuration), 7% yield;
Result of LC/MS [M+H]$^+$: 446.3;
$^1$H NMR (CDCl$_3$): δ0.29 (2H, m, CH$_2$), 0.58 (2H, m, CH$_2$), 1.53 (3H, s, CH$_3$), 2.58 (4H, m, CH, CH$_3$), 2.77 (3H, m, CH, CH$_2$), 4.16 (1H, m, CH), 5.03 (1H, quint., CH), 7.10 (1H, t, CH-arom.), 7.30 (1H, d, CH-arom.), 7.40 (1H, m, CH-arom), 8.41 (1H, s, CH-arom).

Example 62: cyclopropyl 3-(2-chloro-6-fluorophenyl)-5-{5-methyl-1-[3-hydroxy-3-methylcyclobutyl]-1H-pyrazol-4-yl}-1,2-oxazole-4-carboxylate (anti-configuration), 14% yield.
Result of LC/MS [M+H]$^+$: 446.3;
$^1$H NMR (CDCl$_3$): δ0.30 (2H, m, CH$_2$), 0.58 (2H, m, CH$_2$), 1.47 (3H, s, CH$_3$), 2.59 (3H, s, CH$_3$), 2.74 (4H, m, 2x CH$_2$), 3.63 (1H, s, OH), 4.16 (1H, m, CH), 4.55 (1H, quint., CH), 7.12 (1H, t, CH-arom.), 7.31 (1H, d, CH-arom.), 7.39 (1H, m, CH-arom), 8.48 (1H, s, CH-arom).

Synthesis of 4-Alkoxymethyl Isoxazoles 2-methylbutan-2-ol from Example 9 (1.0 mmol) as pale yellow oil (87%).
Result of LC/MS [M+H]$^+$: 448.2;

$^1$H NMR (CDCl$_3$): δ1.32 (6H, s, 2xCH$_3$), 2.18-2.08 (2H, m, CH$_2$), 3.79-3.71 (1H, m, OH), 4.08 (1H, dq, OH), 4.40 (2H, s, CH$_2$), 4.58-4.48 (2H, m, CH$_2$), 7.15 (1H, td, CH-arom.), 7.35 (1H, dt, CH-arom.), 7.48-7.39 (1H, m, CH-arom.), 7.92 (1H, s, CH-arom.).

3-{4-[3-(2-chloro-6-fluorophenyl)-4-(hydroxymethyl)-1,2-oxazol-5-yl]-5-(trifluoromethyl)-1H-pyrazol-1-yl}-1-methylcyclobutan-1-ol (syn/anti-mixture) from Examples 10/11 (0.6 mmol) as syn/anti-mixture (for this synthesis, syn- and anti-isomers were not separated at the ester level) (quant.).

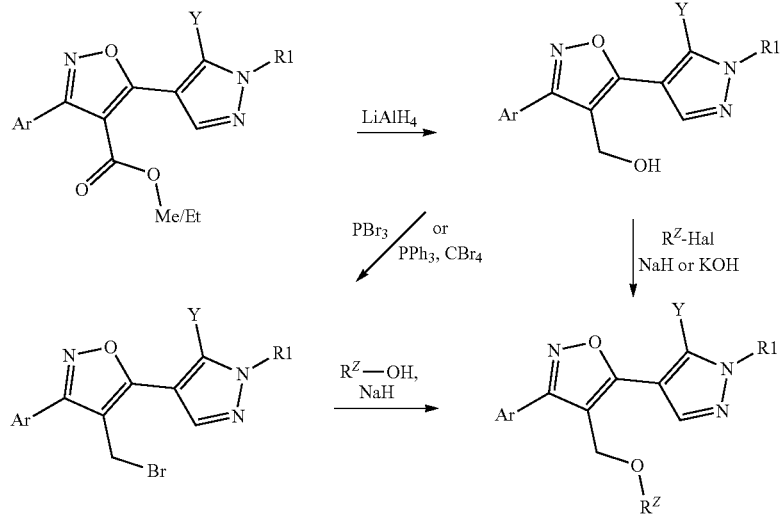

Reduction Step with LiAlH$_4$

Respective isoxazole-4-carboxylic acid methyl or ethyl esters were dissolved in dry THF (Sure/Seal; 4 mL/mmol) and the solution was cooled to 0° C. LiAlH$_4$ (1 M in THF; 1.5 eq.) was slowly added and the mixture was stirred at 0° C. for 1.5 h. The mixture was then quenched with Rochelle's salt and the resulting mixture was extracted with CH$_2$Cl$_2$. Combined organic layers were dried over MgSO$_4$, filtrated and concentrated under reduced pressure to give crude material, which was directly used for next steps.

(2S)-1-(4-(3-(2-chloro-6-fluorophenyl)-4-(hydroxymethyl)isoxazol-5-yl)-5-(trifluoromethyl)-1H-pyrazol-1-yl)propan-2-ol from Example 13 (0.4 mmol) as an orange solid (80%).
Result of LC/MS [M+H]$^+$: 419.7;

4-{4-[3-(2-chloro-6-fluorophenyl)-4-(hydroxymethyl)-1,2-oxazol-5-yl]-5-(trifluoromethyl)-1H-pyrazol-1-yl}-

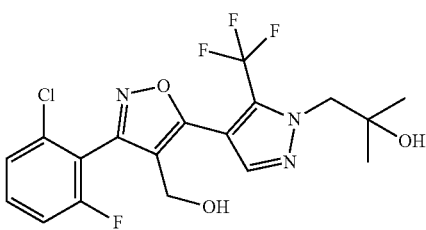 [SMILES: CC(C)(O)Cn1ncc(-c2onc(-c3c(F)cccc3Cl)c2CO)c1C(F)(F)F]

Example 63

1-(4-(3-(2-chloro-6-fluorophenyl)-4-(hydroxymethyl)isoxazol-5-yl)-5-(trifluoromethyl)-1H-pyrazol-1-yl)-2-methylpropan-2-ol from Example 8 (0.3 mmol) as yellowish solid (pTLC, eluent: petroleum ether/ethyl acetate 1:1; 24%).
Result of LC/MS [M+H]$^+$: 433.8;
$^1$H NMR (CDCl$_3$): δ1.24 (6H, s, 2x CH$_3$), 1.67 (1H, s, OH), 4.16 (1H, s, OH), 4.31 (2H, s, CH$_2$), 4.41 (2H, d, CH$_2$), 7.16 (1H, td, CH-arom.), 7.36 (1H, td, CH-arom.), 7.44 (1H, m, CH-arom), 8.01 (1H, s, CH-arom).

(2R)-1-(4-(3-(2-chloro-6-fluorophenyl)-4-(hydroxymethyl)isoxazol-5-yl)-5-(trifluoromethyl)-1H-pyrazol-1-yl)propan-2-ol from Example 12 (0.55 mmol) as orange solid (75%).

Result of LC/MS [M+H]$^+$: 419.7;

Ester methyl 3-(2-chlorophenyl)-5-[1-(3-hydroxy-3-methylbutyl)-5-(trifluoromethyl)-1H-pyrazol-4-yl]-1,2-oxazole-4-carboxylate was synthesized as described above from methyl (Z)-3-(2-chlorophenyl)-5-(1-(dimethylamino)-4,4,4-trifluoro-3-oxobut-1-en-2-yl)isoxazole-4-carboxylate (1.2 mmol) and 4-hydrazinyl-2-methylbutan-2-ol as a yellow oil (33%; pTLC, eluent: CH$_2$Cl$_2$/MeOH 95:5).

Result of LC/MS [M+H]$^+$: 440.3;

$^1$H NMR (CDCl$_3$): δ1.32 (6H, s, 2xCH$_3$), 2.20-2.10 (2H, m, CH$_2$), 3.63 (3H, s, OCH$_3$), 4.58-4.48 (2H, m, CH$_2$), 7.59-7.33 (4H, m, 4xCH-arom.), 7.95 (1H, s, CH-arom.).

From this ester (0.4 mmol), 4-{4-[3-(2-chlorophenyl)-4-(hydroxymethyl)-1,2-oxazol-5-yl]-5-(trifluoromethyl)-1H-pyrazol-1-yl}-2-methylbutan-2-ol was synthesized quantitatively according to the standard procedure.

Result of LC/MS [M+H]$^+$: 430.3;

(2S)-1-{4-[3-(2-chlorophenyl)-4-(hydroxymethyl)-1,2-oxazol-5-yl]-5-(trifluoromethyl)-1H-pyrazol-1-yl}propan-2-ol from Example 22 (1.5 mmol) (90%).

3-{4-[3-(2-chlorophenyl)-4-(hydroxymethyl)-1,2-oxazol-5-yl]-5-(trifluoromethyl)-1H-pyrazol-1-yl}-1-methylcyclobutan-1-ol (syn/anti-mixture) from ethyl 3-(2-chlorophenyl)-5-[1-(3-hydroxy-3-methylcyclobutyl)-5-(trifluoromethyl)-1H-pyrazol-4-yl]-1,2-oxazole-4-carboxylate (0.8 mmol) (syn/anti-mixture; synthesis described above) (63%).

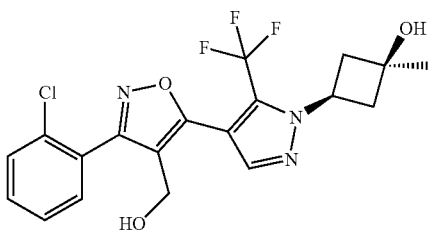 [SMILES: C[C@]1(O)C[C@@H](n2ncc(-c3onc(-c4ccccc4Cl)c3CO)c2C(F)(F)F)C1]

Example 64: 3-(4-(3-(2-chlorophenyl)-4-(hydroxymethyl)-1,2-oxazol-5-yl)-5-(trifluoromethyl)-1H-pyrazol-1-yl)-1-methylcyclobutan-1-ol (Syn-Configuration)

From the mixture of syn- and anti-isomers, the syn isomer was separated by prep. TLC (eluent petroleum ether/ethyl acetate 1:1).

Result of LC/MS [M+H]$^+$: 427.9;

$^1$H NMR (CDCl$_3$): δ1.49 (3H, s, CH$_3$), 2.94-2.68 (4H, m, 2xCH$_2$), 3.49 (1H, s, OH), 4.45 (2H, s, CH$_2$), 4.73 (1H, quint, CH), 7.63-7.34 (4H, m, 4xCH-arom), 7.99 (1H, s, CH-arom.).

4-{4-[3-(2-chlorophenyl)-4-(hydroxymethyl)-1,2-oxazol-5-yl]-5-methyl-1H-pyrazol-1-yl}-2-methylbutan-2-ol from Example 19 (0.4 mmol) as yellow solid (84%).

Result of LC/MS [M+H]$^+$: 376.0;

3-{4-[3-(2-chlorophenyl)-4-(hydroxymethyl)-1,2-oxazol-5-yl]-5-methyl-1H-pyrazol-1-yl}-1-methylcyclobutan-1-ol (syn/anti-mixture) from Examples 17/18 (1.1 mmol) as syn/anti-mixture (for this synthesis, syn- and anti-isomers were not separated at the ester level) (quant.).

Result of LC/MS [M+H]$^+$: 374.3;

4-{4-[3-(2-chloro-6-fluorophenyl)-4-(hydroxymethyl)-1,2-oxazol-5-yl]-5-methyl-1H-pyrazol-1-yl}-2-methylbutan-2-ol from Example 20 (2.0 mmol) as yellowish solid (94%).

Result of LC/MS [M+H]$^+$: 394.1;

$^1$H NMR (CDCl$_3$): δ1.30 (6H, s, 2xCH$_3$), 2.08-2.00 (2H, m, CH$_2$), 2.65 (3H, s, CH$_3$), 4.36-4.28 (2H, m, CH$_2$), 4.45 (2H, d, CH$_2$), 7.16 (1H, td, CH-arom.), 7.36 (1H, dt, CH-arom.), 7.49-7.39 (1H, m, CH-arom.), 7.97 (1H, s, CH-arom.).

3-{4-[3-(2-chloro-6-fluorophenyl)-4-(hydroxymethyl)-1,2-oxazol-5-yl]-5-methyl-1H-pyrazol-1-yl}-1-methylcyclobutan-1-ol (syn/anti-mixture) from methyl 3-(2-chloro-6-fluorophenyl)-5-{5-methyl-1-[3-hydroxy-3-methylcyclobutyl]-1H-pyrazol-4-yl}-1,2-oxazole-4-carboxylate (1.1 mmol) (syn/anti-mixture; synthesis described above) as yellowish solid (89%).

Result of LC/MS [M+H]$^+$: 392.2;

3-(4-{3-[3-(benzyloxy)-2-chlorophenyl]-4-(hydroxymethyl)-1,2-oxazol-5-yl}-5-(trifluoromethyl)-1H-pyrazol-1-yl)-1-methylcyclobutan-1-ol (syn/anti-mixture) from ethyl 3-(3-(benzyloxy)-2-chlorophenyl)-5-(1-(3-hydroxy-3-methylcyclobutyl)-5-(trifluoromethyl)-1H-pyrazol-4-yl)isoxazole-4-carboxylate (0.9 mmol) (syn/anti-mixture) as orange-brown solid (quant.).

Result of LC/MS [M+H]$^+$: 534.3;

$^1$H NMR (CDCl$_3$): δ1.55 (3H, s, CH$_3$), 2.94-2.55 (4H, m, 2xCH$_2$), 3.83-3.68 (1H, m, CH), 4.44 (2H, s, OCH$_2$), 5.22 (2H, s, OCH$_2$), 7.19-7.09 (2H, m, 2xCH-arom.), 7.54-7.30 (6H, m, 6xCH-arom.), 7.97 (1H, s, CH-arom.).

4-(4-(3-(3-(benzyloxy)-2-chlorophenyl)-4-(hydroxymethyl)isoxazol-5-yl)-5-(trifluoromethyl)-1H-pyrazol-1-yl)-2-methylbutan-2-ol from ethyl 3-(3-(benzyloxy)-2-chlorophenyl)-5-(1-(3-hydroxy-3-methylbutyl)-5-(trifluoromethyl)-1H-pyrazol-4-yl)isoxazole-4-carboxylate as brown oil (91%).

Result of LC/MS [M+H]$^+$: 536.1;

$^1$H NMR (CDCl$_3$): δ1.33 (6H, s, 2x CH$_3$), 1.86 (4H, m, 2x CH$_2$), 3.75 (2H, s, CH$_2$), 5.23 (2H, d, CH$_2$), 7.12 (1H, m, CH-arom.), 7.41 (6H, m, CH-arom.), 7.95 (1H, s, CH-arom.).

Conversion of a hydroxymethyl-isoxazole into a bromomethyl-isoxazole was achieved by two methods:

A) The respective hydroxymethyl-isoxazole was dissolved in diethylether, THF or CH$_2$Cl$_2$ (3 mL/mmol) at 0° C. and phosphorus tribromide (0.5 eq.) dissolved in diethylether (3 mL/mmol) was added slowly. The mixture was stirred at 0° C. for 10-30 min. The mixture was treated with NaHCO$_3$ (5%) and extracted twice with CH$_2$Cl$_2$. Combined organic layers were dried over MgSO$_4$, and the solvent was removed in vacuo to give crude material, which was used as such in further steps.

B) The respective hydroxymethyl-isoxazole and PPh$_3$ (1.5 eq.) were dissolved in dry THF (Sure/Seal; 4 mL/mmol) and cooled to 0° C. CBr$_4$ (1.5 eq.) was added, and the mixture was stirred at 0° C. for 15 min and then at room temperature for 2 h. The mixture was quenched with water and the resulting mixture was extracted twice with CH$_2$Cl$_2$. Combined organic layers were dried over MgSO$_4$, and the solvent was removed in vacuo to give crude material. In order to remove bulk material of OPPh$_3$, the solid material was treated with Et$_2$O, sonicated, centrifuged and decanted; alternatively, material was purified by prep. TLC on silica gel (eluent: CH$_2$Cl$_2$/ MeOH 95:5).

4-{4-[4-(bromomethyl)-3-(2-chloro-6-fluorophenyl)-1,2-oxazol-5-yl]-5-(trifluoromethyl)-1H-pyrazol-1-yl}-2-methylbutan-2-ol from 4-{4-[3-(2-chloro-6-fluorophenyl)-4-(hydroxymethyl)-1,2-oxazol-5-yl]-5-(trifluoromethyl)-1H-pyrazol-1-yl}-2-methylbutan-2-ol (0.25 mmol) according to method A (Et$_2$O, 10 min) as yellow solid (93%).
Result of LC/MS [M+H]$^+$: 510.1;
$^1$H NMR (CDCl$_3$): δ1.32 (6H, s, 2x CH$_3$), 2.12 (2H, m, CH$_2$), 4.15 (2H, s, CH$_2$), 4.53 (2H, m, CH$_2$), 7.17 (1H, t, CH-arom.), 7.37 (1H, d, CH-arom.), 7.44 (1H, m, CH-arom.), 7.92 (1H, s, CH-arom.).

4-{4-[4-(bromomethyl)-3-(2-chlorophenyl)-1,2-oxazol-5-yl]-5-(trifluoromethyl)-1H-pyrazol-1-yl}-2-methylbutan-2-ol from 4-{4-[3-(2-chlorophenyl)-4-(hydroxymethyl)-1,2-oxazol-5-yl]-5-(trifluoromethyl)-1H-pyrazol-1-yl}-2-methylbutan-2-ol (0.40 mmol) according to method A (CH$_2$Cl$_2$, 30 min) as orange oil (60%; pTLC, eluent: CH$_2$Cl$_2$/MeOH 95:5).
Result of LC/MS [M+H]$^+$: 492.2;
$^1$H NMR (CDCl$_3$): δ1.32 (6H, s, 2x CH$_3$), 2.13 (2H, m, CH$_2$), 4.23 (2H, s, CH$_2$), 4.55 (2H, m, CH$_2$), 7.45 (1H, m, CH-arom.), 7.54 (2H, m, CH-arom.), 7.65 (1H, m, CH-arom.), 7.92 (1H, s, CH-arom.).

4-{4-[4-(bromomethyl)-3-(2-chlorophenyl)-1,2-oxazol-5-yl]-5-methyl-1H-pyrazol-1-yl}-2-methylbutan-2-ol from 4-{4-[3-(2-chlorophenyl)-4-(hydroxymethyl)-1,2-oxazol-5-yl]-5-methyl-1H-pyrazol-1-yl}-2-methylbutan-2-ol (0.25 mmol) according to method A (THF, 20 min) as yellow solid (84%); a partial additional hydroxy-bromine exchange in methylbutanol unit was observed (5-[1-(3-bromo-3-methylbutyl)-5-methyl-1H-pyrazol-4-yl]-4-(bromomethyl)-3-(2-chlorophenyl)-1,2-oxazole).
Result of LC/MS [M–H$_2$O+H]$^+$: 419.9 (title compound);
Result of LC/MS [M+H]$^+$: 499.8 (M+(additional OH—Br-exchange);

4-{4-[4-(bromomethyl)-3-(2-chloro-6-fluorophenyl)-1,2-oxazol-5-yl]-5-methyl-1H-pyrazol-1-yl}-2-methylbutan-2-ol from 4-{4-[3-(2-chloro-6-fluorophenyl)-4-(hydroxymethyl)-1,2-oxazol-5-yl]-5-methyl-1H-pyrazol-1-yl}-2-methylbutan-2-ol (2.0 mmol) according to method B as yellowish oil (95%).
Result of LC/MS [M–H$_2$O+H]$^+$: 437.9;
$^1$H NMR (CDCl$_3$): δ1.32 (6H, s, 2x CH$_3$), 2.05 (2H, m, CH$_2$), 2.63 (3H, s, CH$_3$), 4.29 (2H, s, CH$_2$), 4.33 (2H, m, CH$_2$), 7.17 (1H, t, CH-arom.), 7.36 (1H, d, CH-arom.), 7.45 (1H, m, CH-arom.), 7.95 (1H, s, CH-arom.).

3-{4-[4-(bromomethyl)-3-(2-chloro-6-fluorophenyl)-1,2-oxazol-5-yl]-5-methyl-1H-pyrazol-1-yl}-1-methylcyclobutan-1-ol (syn/anti-mixture) from 3-{4-[3-(2-chloro-6-fluorophenyl)-4-(hydroxymethyl)-1,2-oxazol-5-yl]-5-methyl-1H-pyrazol-1-yl}-1-methylcyclobutan-1-ol (0.4 mmol; syn/anti-mixture) according to method B as yellowish solid (89%).
Result of LC/MS [M+H]$^+$: 454.1;

3-{4-[4-(bromomethyl)-3-(2-chlorophenyl)-1,2-oxazol-5-yl]-5-methyl-1H-pyrazol-1-yl}-1-methylcyclobutan-1-ol (syn/anti-mixture) from 3-{4-[3-(2-chlorophenyl)-4-(hydroxymethyl)-1,2-oxazol-5-yl]-5-methyl-1H-pyrazol-1-yl}-1-methylcyclobutan-1-ol (0.15 mmol; syn/anti-mixture) according to method B (quant.)
Result of LC/MS [M+H]$^+$: 436.2;

(2R)-1-{4-[4-(bromomethyl)-3-(2-chloro-6-fluorophenyl)-1,2-oxazol-5-yl]-5-(trifluoromethyl)-1H-pyrazol-1-yl}propan-2-ol from (2R)-1-(4-(3-(2-chloro-6-fluorophenyl)-4-(hydroxymethyl)isoxazol-5-yl)-5-(trifluoromethyl)-1H-pyrazol-1-yl)propan-2-ol (0.3 mmol) according to method B (87%).

(2S)-1-{4-[4-(bromomethyl)-3-(2-chlorophenyl)-1,2-oxazol-5-yl]-5-(trifluoromethyl)-1H-pyrazol-1-yl}propan-2-ol from (2S)-1-{4-[3-(2-chlorophenyl)-4-(hydroxymethyl)-1,2-oxazol-5-yl]-5-(trifluoromethyl)-1H-pyrazol-1-yl}propan-2-ol (0.35 mmol) according to method B (55%).

3-{4-[4-(bromomethyl)-3-(2-chlorophenyl)-1,2-oxazol-5-yl]-5-(trifluoromethyl)-1H-pyrazol-1-yl}-1-methylcyclobutan-1-ol (syn/anti-mixture) from 3-{4-[3-(2-chlorophenyl)-4-(hydroxymethyl)-1,2-oxazol-5-yl]-5-(trifluoromethyl)-1H-pyrazol-1-yl}-1-methylcyclobutan-1-ol (0.3 mmol; syn/anti-mixture) according to method B (92%).

3-{4-[4-(bromomethyl)-3-(2-chloro-6-fluorophenyl)-1,2-oxazol-5-yl]-5-(trifluoromethyl)-1H-pyrazol-1-yl}-1-methylcyclobutan-1-ol (syn/anti-mixture) from 3-{4-[3-(2-chloro-6-fluorophenyl)-4-(hydroxymethyl)-1,2-oxazol-5-yl]-5-(trifluoromethyl)-1H-pyrazol-1-yl}-1-methylcyclobutan-1-ol (0.35 mmol; syn/anti-mixture) according to method B (77%).

3-(4-(3-(3-(benzyloxy)-2-chlorophenyl)-4-(bromomethyl)isoxazol-5-yl)-5-(trifluoromethyl)-1H-pyrazol-1-yl)-1-methylcyclobutan-1-ol (syn/anti-mixture) from 3-(4-{3-[3-(benzyloxy)-2-chlorophenyl]-4-(hydroxymethyl)-1,2-oxazol-5-yl}-5-(trifluoromethyl)-1H-pyrazol-1-yl)-1-methylcyclobutan-1-ol (syn/anti-mixture) (1.0 mmol) according to method A (Et$_2$O, 10 min) as yellow oil (quant.).
Result of LC/MS [M+H]$^+$: 596.2;
$^1$H NMR (CDCl$_3$): δ1.51 (3H, s, CH$_3$), 2.78 (4H, m, 2x CH$_2$), 4.24 (2H, s, CH$_2$), 4.73 (1H, m, CH), 5.23 (2H, s, CH$_2$), 7.15 (2H, d, CH-arom.), 7.39 (6H, d, CH-arom.), 7.97 (1H, s, CH-arom.).

4-(4-(3-(3-(benzyloxy)-2-chlorophenyl)-4-(bromomethyl)isoxazol-5-yl)-5-(trifluoromethyl)-1H-pyrazol-1-yl)-2-methylbutan-2-ol from 4-(4-(3-(3-(benzyloxy)-2-chlorophenyl)-4-(hydroxymethyl)isoxazol-5-yl)-5-(trifluoromethyl)-1H-pyrazol-1-yl)-2-methylbutan-2-ol (2.5 mmol) according to method A (CH$_2$Cl$_2$, 15 min) as yellow solid (94%).
Result of LC/MS [M+H]$^+$–H$_2$O: 580.0;
$^1$H NMR (CDCl$_3$): δ1.34 (6H, s, 2x CH$_3$), 1.94 (4H, m, 2x CH$_2$), 3.45 (2H, s, CH$_2$), 5.23 (2H, s, CH$_2$), 7.15 (2H, m, CH-arom.), 7.39 (6H, m, CH-arom.), 7.99 (1H, s, CH-arom.).

Final generation of 4-alkoxymethyl isoxazoles; alternative methods:

A) To a stirred solution of the respective 4-hydroxymethyl isoxazole in 2-methyltetrahydrofurane (5 ml/mmol) was added potassium hydroxide (powder, 4.0 eq.) and the resulting suspension was stirred for 10 min at room temperature. Iodomethane (4.0 eq.) was then added and the mixture was stirred at room temperature for 18 h. The mixture was partitioned between water and CH$_2$Cl$_2$. Combined organic layers were dried over MgSO$_4$, filtrated and concentrated under reduced pressure. Purification was achieved by preparative TLC on silica gel.

B) Sodium hydride (1.1 eq.) was suspended in THF (Sure/Seal; 2 mL/mmol) and cooled to 0° C. The respective 4-hydroxymethyl isoxazole was dissolved in THF (Sure/Seal; 2 mL/mmol), cooled to 0° C. and added to the NaH suspension. The mixture was stirred for 10 min at 0° C. and for 0.5 h at room temperature. Alkylbromide (2.0 eq.) was added and stirring continued at r.t. for 18 h. The reaction was quenched by addition of water, the mixture was partitioned between water and CH$_2$Cl$_2$. Combined organic layers were dried over MgSO$_4$, filtrated and concentrated under reduced pressure. Purification was achieved by preparative TLC on silica gel.

C) At 0° C. NaH (1.5 eq.) was dissolved in THF (2 mL/mmol) and cyclopropanol was added. Mixture was stirred at 0° C. for 20 min. The respective 4-bromomethyl isoxazole was dissolved in DMF (2 mL/mmol) and was added to the NaH suspension. The mixture was stirred at 0° C. for 1 h, warmed to room temperature and stirred at this temperature for 18 h. Water was added and the mixture was extracted with ethyl acetate. Combined organic layers were dried over MgSO$_4$ and concentrated under reduced pressure. Product was purified by preparative TLC on silica gel (eluent: CH$_2$Cl$_2$/MeOH 95:5).

D) To a stirred solution of the respective 4-bromomethyl isoxazole in THF (4 ml/mmol) was added the respective alcohol (3.0 eq.), KOtBu (3.0 eq.) and 18-crown-6 ether (1.0 eq.). The mixture was stirred at room temperature for 18 h. The mixture was partitioned between water and CH$_2$Cl$_2$. Combined organic layers were dried over MgSO$_4$, filtrated and concentrated under reduced pressure. Purification was achieved by preparative TLC on silica gel.

s, CH$_2$), 7.15 (1H, td, CH-arom.), 7.35 (1H, td, CH-arom.), 7.43 (1H, m, CH-arom), 7.94 (1H, s, CH-arom).

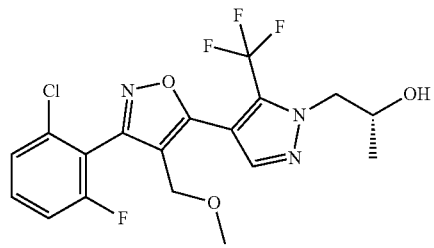

Example 66: (2R)-1-(4-(3-(2-chloro-6-fluorophenyl)-4-(methoxymethyl)isoxazol-5-yl)-5-(trifluoromethyl)-1H-pyrazol-1-yl)propan-2-ol method A, from (2R)-1-(4-(3-(2-chloro-6-fluorophenyl)-4-(hydroxymethyl)isoxazol-5-yl)-5-(trifluoromethyl)-1H-pyrazol-1-yl)propan-2-ol (0.4 mmol) as yellowish oil (5%; pTLC, eluent: petroleum ether/ethyl acetate 1:1 and pTLC, eluent: petroleum ether/ethyl acetate 4:1).

Result of LC/MS [M+H]$^+$: 433.8;

$^1$H NMR (CDCl$_3$): δ1.31 (3H, d, CH$_3$), 3.15 (3H, s, CH$_3$), 3.27 (1H, m, CH), 4.19 (2H, s, CH$_2$), 4.27 (1H, m, CH), 4.37 (2H, m, OH, CH), 7.15 (1H, td, CH-arom.), 7.35 (1H, td, CH-arom.), 7.43 (1H, m, CH-arom), 7.91 (1H, s, CH-arom).

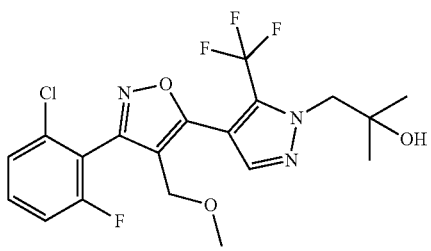 [SMILES: COCc1c(-c2c(F)cccc2Cl)noc1-c1cnn(CC(C)(C)O)c1C(F)(F)F]

Example 65: 1-(4-(3-(2-chloro-6-fluorophenyl)-4-(methoxymethyl)isoxazol-5-yl)-5-(trifluoromethyl)-1H-pyrazol-1-yl)-2-methylpropan-2-ol method A, from 1-(4-(3-(2-chloro-6-fluorophenyl)-4-(hydroxymethyl)isoxazol-5-yl)-5-(trifluoromethyl)-1H-pyrazol-1-yl)-2-methylpropan-2-ol (0.1 mmol) as yellowish oil (30%; pTLC, eluent: petroleum ether/ethyl acetate 1:1 and pTLC, eluent: petroleum ether/ethyl acetate 2:1).

Result of LC/MS [M+H]$^+$: 447.8;

$^1$H NMR (CDCl$_3$): δ1.23 (6H, s, 2x CH$_3$), 3.14 (3H, s, CH$_3$), 4.18 (1H, s, OH), 4.19 (2H, s, CH$_2$), 4.31 (2H,

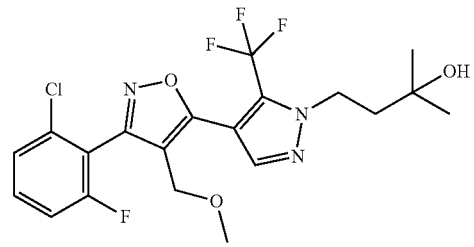 [SMILES: COCc1c(-c2c(F)cccc2Cl)noc1-c1cnn(CCC(C)(C)O)c1C(F)(F)F]

Example 67: 4-{4-[3-(2-chloro-6-fluorophenyl)-4-(methoxymethyl)-1,2-oxazol-5-yl]-5-(trifluoromethyl)-1H-pyrazol-1-yl}-2-methylbutan-2-ol method A, from 4-{4-[3-(2-chloro-6-fluorophenyl)-4-(hydroxymethyl)-1,2-oxazol-5-yl]-5-(trifluoromethyl)-1H-pyrazol-1-yl}-2-methylbutan-2-ol (1.5 mmol) as pale yellow oil (29%; pTLC, eluent: petroleum ether/ethyl acetate 3:2 and pTLC, eluent: CH$_2$Cl$_2$/MeOH 95:5).

Result of LC/MS [M+H]$^+$: 462.3;

$^1$H NMR (CDCl$_3$): δ1.33 (6H, s, 2x CH$_3$), 2.13 (2H, m, CH$_2$), 3.13 (3H, s, CH$_3$), 4.19 (2H, s, CH$_2$), 4.53 (2H, m, CH$_2$), 7.14 (1H, td, CH-arom.), 7.35 (1H, d, CH-arom.), 7.42 (1H, m, CH-arom), 7.85 (1H, s, CH-arom).

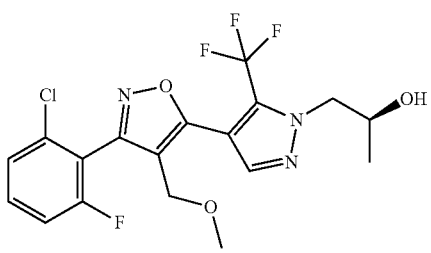 [SMILES: COCc1c(-c2c(F)cccc2Cl)noc1-c1cnn(C[C@H](C)O)c1C(F)(F)F]

Example 68: (2S)-1-(4-(3-(2-chloro-6-fluorophenyl)-4-(methoxymethyl)isoxazol-5-yl)-5-(trifluoromethyl)-1H-pyrazol-1-yl)propan-2-ol method A, from (2S)-1-(4-(3-(2-chloro-6-fluorophenyl)-4-(hydroxymethyl)isoxazol-5-yl)-5-(trifluoromethyl)-1H-pyrazol-1-yl)propan-2-ol (0.3 mmol) as yellowish oil (6%; pTLC, eluent: petroleum ether/ethyl acetate 1:1 and pTLC, eluent: $CH_2Cl_2$/MeOH 95:5).
Result of LC/MS [M+H]$^+$: 433.8;
$^1$H NMR (CDCl$_3$): δ1.32 (3H, d, CH$_3$), 3.15 (3H, s, CH$_3$), 3.27 (1H, m, CH), 4.20 (2H, s, CH$_2$), 4.26 (1H, m, CH), 4.37 (2H, m, OH, CH), 7.15 (1H, td, CH-arom.), 7.35 (1H, td, CH-arom.), 7.43 (1H, m, CH-arom), 7.92 (1H, s, CH-arom).

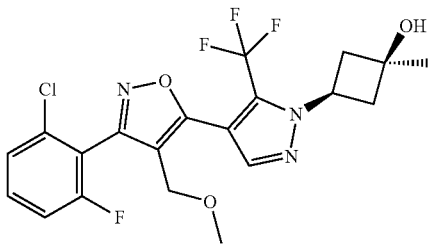 [SMILES: COCc1c(-c2c(F)cccc2Cl)noc1-c1cnn([C@H]2C[C@@](C)(O)C2)c1C(F)(F)F]

Example 69: 3-(4-(3-(2-chloro-6-fluorophenyl)-4-(methoxymethyl)isoxazol-5-yl)-5-(trifluoromethyl)-1H-pyrazol-1-yl)-1-methylcyclobutan-1-ol (Syn-Configuration)

method A, from 3-{4-[3-(2-chloro-6-fluorophenyl)-4-(hydroxymethyl)-1,2-oxazol-5-yl]-5-(trifluoromethyl)-1H-pyrazol-1-yl}-1-methylcyclobutan-1-ol (syn/anti-mixture) (0.5 mmol) (17%; pTLC, eluent: petroleum ether/ethyl acetate 1:1 and pTLC, eluent: $CH_2Cl_2$/MeOH 95:5; only syn diastereomer isolated).
$^1$H NMR (CDCl$_3$): δ1.50 (3H, s, CH$_3$), 2.95-2.71 (4H, m, 2xCH$_2$), 3.14 (3H, s, OCH$_3$), 4.19 (2H, s, CH$_2$), 4.72 (1H, quint, CH), 7.15 (1H, td, CH-arom.), 7.35 (1H, d, CH-arom.), 7.49-7.38 (1H, m, CH-arom.), 7.91 (1H, s, CH-arom.).

Examples 70 and 71: 3-{4-[3-(2-chloro-6-fluorophenyl)-4-(methoxymethyl)-1,2-oxazol-5-yl]-5-methyl-1H-pyrazol-1-yl}-1-methylcyclobutan-1-ol (Syn-Configuration) and 3-{4-[3-(2-chloro-6-fluorophenyl)-4-(methoxymethyl)-1,2-oxazol-5-yl]-5-methyl-1H-pyrazol-1-yl}-1-methylcyclobutan-1-ol (Anti-Configuration)

method A, from 3-{4-[3-(2-chloro-6-fluorophenyl)-4-(hydroxymethyl)-1,2-oxazol-5-yl]-5-methyl-1H-pyrazol-1-yl]-1-methylcyclobutan-1-ol (syn/anti-mixture) (0.3 mmol) (pTLC, eluent: $CH_2Cl_2$/MeOH 95:5 and again pTLC, eluent: $CH_2Cl_2$/MeOH 95:5);

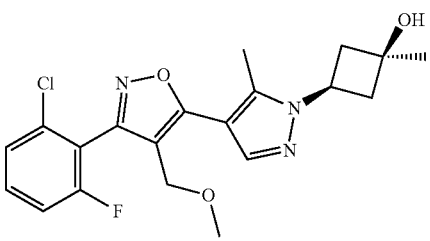 [SMILES: COCc1c(-c2c(F)cccc2Cl)noc1-c1cnn([C@H]2C[C@@](C)(O)C2)c1C]

Example 70: (syn-configuration), 10% yield;
Result of LC/MS [M+H]$^+$: 406.3;
$^1$H NMR (CDCl$_3$): δ1.52 (3H, s, CH$_3$), 2.59 (3H, s, CH$_3$), 2.64 (4H, m, 2x CH$_2$), 3.17 (3H, s, CH$_3$), 4.20 (2H, s, CH$_2$), 4.95 (1H, m, CH), 7.14 (1H, td, CH-arom.), 7.35 (1H, d, CH-arom.), 7.43 (1H, m, CH-arom), 7.88 (1H, s, CH-arom).

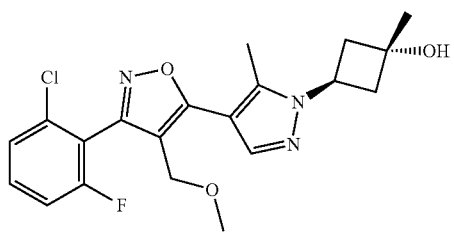 [SMILES: COCc1c(-c2c(F)cccc2Cl)noc1-c1cnn([C@H]2C[C@](C)(O)C2)c1C]

Example 71: (anti-configuration), 18% yield;
Result of LC/MS [M+H]$^+$: 406.3;
$^1$H NMR (CDCl$_3$): δ1.54 (3H, s, CH$_3$), 2.59 (5H, m, CH$_2$, CH$_3$), 2.76 (2H, m, CH$_2$), 3.20 (3H, s, CH$_3$), 4.24 (2H, s, CH$_2$), 5.03 (1H, m, CH), 7.14 (1H, td, CH-arom.), 7.34 (1H, d, CH-arom.), 7.42 (1H, m, CH-arom), 7.90 (1H, s, CH-arom).

Examples 72 and 73: 3-{4-[3-(2-chlorophenyl)-4-(methoxymethyl)-1,2-oxazol-5-yl]-5-methyl-1H-pyrazol-1-yl}-1-methylcyclobutan-1-ol (Syn-Configuration) and 3-{4-[3-(2-chlorophenyl)-4-(methoxymethyl)-1,2-oxazol-5-yl]-5-methyl-1H-pyrazol-1-yl}-1-methylcyclobutan-1-ol (Anti-Configuration)

method A, from 3-{4-[3-(2-chlorophenyl)-4-(hydroxymethyl)-1,2-oxazol-5-yl]-5-methyl-1H-pyrazol-1-yl}-1-methylcyclobutan-1-ol (syn/anti-mixture) (0.3 mmol) (pTLC, eluent: $CH_2Cl_2$/MeOH 95:5 and again pTLC, eluent: $CH_2Cl_2$/MeOH 95:5);

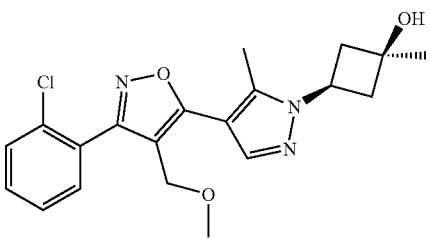 [SMILES: COCc1c(-c2ccccc2Cl)noc1-c1cnn([C@H]2C[C@@](C)(O)C2)c1C]

Example 72: (syn-configuration), 4% yield;

Result of LC/MS [M+H]+: 388.3;

1H NMR (CDCl3): δ1.48 (3H, s, CH3), 2.59 (3H, s, CH3), 2.72 (4H, m, 2x CH2), 3.25 (3H, s, CH3), 4.24 (2H, s, CH2), 4.53 (1H, quint., CH), 7.45 (4H, m, CH-arom.), 7.92 (1H, s, CH-arom).

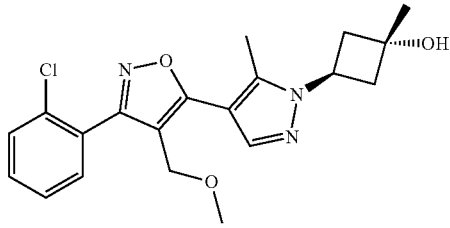 [SMILES: COCc1c(-c2ccccc2Cl)noc1-c1cnn([C@H]2C[C@](C)(O)C2)c1C]

Example 73: (anti-configuration), 4% yield;

Result of LC/MS [M+H]+: 388.3;

1H NMR (CDCl3): δ1.53 (3H, s, CH3), 2.58 (5H, m, CH2, CH3), 2.77 (2H, m, CH2), 3.25 (3H, s, CH3), 4.24 (2H, s, CH2), 5.03 (1H, quint., CH), 7.45 (4H, m, CH-arom.), 7.89 (1H, s, CH-arom).

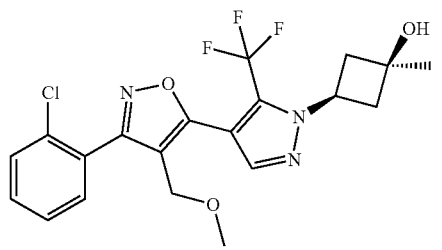 [SMILES: COCc1c(-c2ccccc2Cl)noc1-c1cnn([C@H]2C[C@@](C)(O)C2)c1C(F)(F)F]

Example 74: 3-(4-(3-(2-chlorophenyl)-4-(methoxymethyl)isoxazol-5-yl)-5-(trifluoromethyl)-1H-pyrazol-1-yl)-1-methylcyclobutan-1-ol (Syn-Configuration)

method A, from 3-{4-[3-(2-chlorophenyl)-4-(hydroxymethyl)-1,2-oxazol-5-yl]-5-(trifluoromethyl)-1H-pyrazol-1-yl}-1-methylcyclobutan-1-ol (syn/anti-mixture) 0.5 mmol) (14%; pTLC, eluent: petroleum ether/ethyl acetate 1:1 and pTLC, eluent: CH2Cl2/MeOH 95:5; only syn diastereomer isolated).

Result of LC/MS [M+H]+: 441.9;

1H NMR (CDCl3): δ1.49 (3H, s, CH3), 2.90-2.72 (4H, m, 2xCH2), 3.17 (3H, s, OCH3), 4.20 (2H, s, OCH2), 4.81 (1H, m, CH), 5.04 (1H, br, OH), 7.57-7.35 (4H, m, 4xCH-arom.), 7.90 (1H, s, CH-arom.).

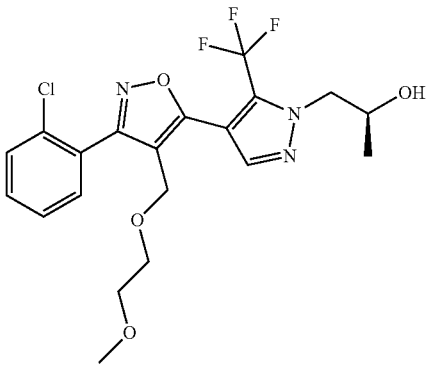 [SMILES: COCCOCc1c(-c2ccccc2Cl)noc1-c1cnn(C[C@H](C)O)c1C(F)(F)F]

Example 75: (2S)-1-{4-[3-(2-chlorophenyl)-4-[(2-methoxyethoxy)methyl]-1,2-oxazol-5-yl]-5-(trifluoromethyl)-1H-pyrazol-1-yl}propan-2-ol method B, from (2S)-1-{4-[3-(2-chlorophenyl)-4-(hydroxymethyl)-1,2-oxazol-5-yl]-5-(trifluoromethyl)-1H-pyrazol-1-yl}propan-2-ol (0.2 mmol) and 2-bromoethyl methyl ether (57%; pTLC, eluent: petroleum ether/ethyl acetate 1:1 and pTLC, eluent: CH2Cl2/MeOH 95:5).

Result of LC/MS [M+H]+: 459.8;

1H NMR (CDCl3): δ1.32 (3H, d, CH3), 3.26 (3H, s, OCH3), 3.48-3.32 (5H, m, 2xCH2 and CH), 4.24 (1H, dd, CH), 4.47-4.30 (4H, m, 2xCH2), 7.48-7.34 (2H, m, 2xCH-arom.), 7.57-7.49 (2H, m, 2xCH-arom.), 7.98 (1H, s, CH-arom.).

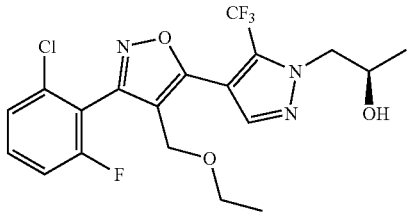 [SMILES: CCOCc1c(-c2c(F)cccc2Cl)noc1-c1cnn(C[C@@H](C)O)c1C(F)(F)F]

Example 76: (2R)-1-{4-[3-(2-chloro-6-fluorophenyl)-4-(ethoxymethyl)-1,2-oxazol-5-yl]-5-(trifluoromethyl)-1H-pyrazol-1-yl}propan-2-ol method B, from (2R)-1 (2-chloro-6-fluorophenyl)-4-(hydroxymethyl)isoxazol-5-yl)-5-(trifluoromethyl)-1H-pyrazol-1-yl)propan-2-ol (0.5 mmol) and ethyl bromide (46%; pTLC, eluent: petroleum ether/ethyl acetate 1:1 and pTLC, eluent: CH2Cl2/MeOH 95:5).

Result of LC/MS [M+H]+: 447.8;

1H NMR (CDCl3): δ0.99 (3H, t, CH3), 1.32 (3H, d, CH3), 3.28 (2H, q, CH2), 4.31-4.18 (3H, m, CH and CH2), 4.45-4.31 (2H, m, CH2), 7.14 (1H, td, CH-arom.), 7.35 (1H, d, CH-arom.), 7.48-7.38 (1H, m, CH-arom.), 7.93 (1H, s, CH-arom.).

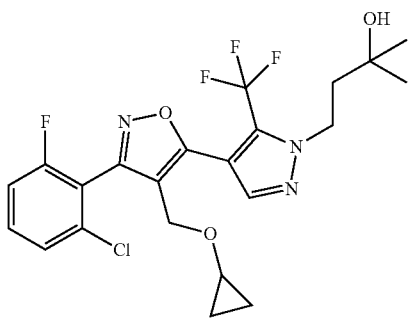 [SMILES: CC(C)(O)CCn1ncc(-c2onc(-c3c(F)cccc3Cl)c2COC2CC2)c1C(F)(F)F]

Example 77: 4-{4-[3-(2-chloro-6-fluorophenyl)-4-(cyclopropoxymethyl)-1,2-oxazol-5-yl]-5-(trifluoromethyl)-1H-pyrazol-1-yl}-2-methylbutan-2-ol method C, from 4-{4-[4-(bromomethyl)-3-(2-chloro-6-fluorophenyl)-1,2-oxazol-5-yl]-5-(trifluoromethyl)-1H-pyrazol-1-yl}-2-methylbutan-2-ol (0.25 mmol) and cyclopropanol as pale yellow oil (11%).

Result of LC/MS [M+H]$^+$: 488.30;

$^1$H NMR (CDCl$_3$): δ0.28 (3H, s, CH$_3$), 1.33 (6H, s, 2x CH$_3$), 2.14 (2H, m, CH$_2$), 3.12 (1H, m, CH), 4.27 (2H, s, CH$_2$), 4.53 (2H, m, CH$_2$), 7.14 (1H, td, CH-arom.), 7.34 (1H, t, CH-arom.), 7.43 (1H, m, CH-arom), 7.85 (1H, s, CH-arom.).

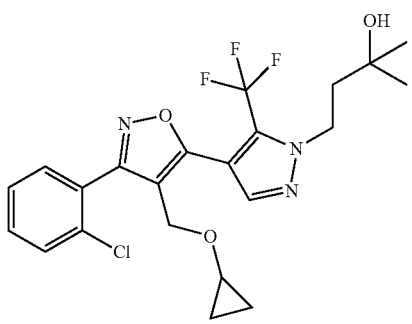 [SMILES: CC(C)(O)CCn1ncc(-c2onc(-c3ccccc3Cl)c2COC2CC2)c1C(F)(F)F]

Example 78: 4-{4-[3-(2-chlorophenyl)-4-(cyclopropoxymethyl)-1,2-oxazol-5-yl]-5-(trifluoromethyl)-1H-pyrazol-1-yl}-2-methylbutan-2-ol method C, from 4-{4-[4-(bromomethyl)-3-(2-chlorophenyl)-1,2-oxazol-5-yl]-5-(trifluoromethyl)-1H-pyrazol-1-yl}-2-methylbutan-2-ol (0.25 mmol) and cyclopropanol as colorless oil (28%).

Result of LC/MS [M+H]$^+$: 470.30;

$^1$H NMR (CDCl$_3$): δ0.30 (4H, m, 2x CH$_2$), 1.33 (6H, s, 2x CH$_3$), 2.13 (2H, m, CH$_2$), 3.12 (1H, m, CH), 4.29 (2H, s, CH$_2$), 4.53 (2H, m, CH$_2$), 7.44 (5H, m, CH-arom.), 7.84 (1H, s, CH-arom.).

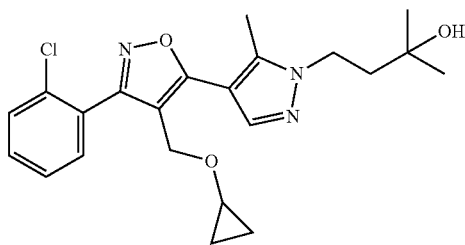 [SMILES: Cc1c(-c2onc(-c3ccccc3Cl)c2COC2CC2)cnn1CCC(C)(C)O]

Example 79: 4-{4-[3-(2-chlorophenyl)-4-(cyclopropoxymethyl)-1,2-oxazol-5-yl]-5-methyl-1H-pyrazol-1-yl}-2-methylbutan-2-ol method C, from 4-{4-[4-(bromomethyl)-3-(2-chlorophenyl)-1,2-oxazol-5-yl]-5-methyl-1H-pyrazol-1-yl}-2-methylbutan-2-ol (0.25 mmol) and cyclopropanol (6%).

Result of LC/MS [M+H]$^+$: 416.0;

$^1$H NMR (CDCl$_3$): δ0.34 (2H, m, CH$_2$), 0.41 (2H, m, CH$_2$), 1.27 (6H, s, 2x CH$_3$), 2.03 (2H, m, CH$_2$), 2.61 (3H, s, CH$_3$), 3.18 (1H, m, CH), 4.32 (2H, m, CH$_2$), 4.34 (2H, s, CH$_2$), 7.43 (3H, m, CH-arom.), 7.53 (1H, d, CH-arom.), 7.87 (1H, s, CH-arom).

Example 80 and 81: 3-{4-[3-(2-chlorophenyl)-4-(cyclopropoxymethyl)-1,2-oxazol-5-yl]-5-methyl-1H-pyrazol-1-yl}-1-methylcyclobutan-1-ol, Syn- and Anti-Configuration method C, from 3-{4-[4-(bromomethyl)-3-(2-chlorophenyl)-1,2-oxazol-5-yl]-5-methyl-1H-pyrazol-1-yl}-1-methylcyclobutan-1-ol (syn/anti-mixture) (0.2 mmol) and cyclopropanol;

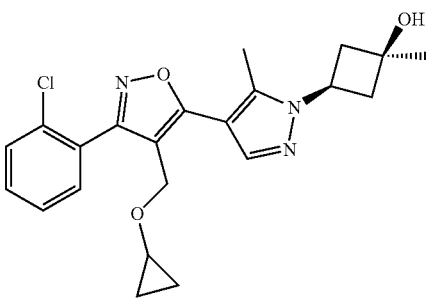 [SMILES: Cc1c(-c2onc(-c3ccccc3Cl)c2COC2CC2)cnn1[C@H]1C[C@@](C)(O)C1]

Example 80: (syn-configuration), 2% yield;

Result of LC/MS [M+H]$^+$: 414.3;

$^1$H NMR (CDCl$_3$): δ0.33 (2H, m, CH$_2$), 0.40 (2H, m, CH$_2$), 1.47 (3H, s, CH$_3$), 2.57 (3H, s, CH$_3$), 2.63 (2H, m, CH$_2$), 2.75 (2H, m, CH$_2$), 3.16 (1H, m, CH), 3.76 (1H, m, CH), 4.31 (2H, s, CH$_2$), 7.44 (4H, m, CH-arom.), 7.85 (1H, s, CH-arom).

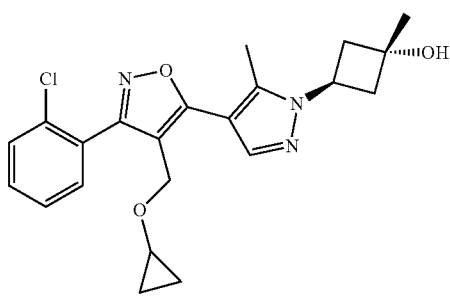 [SMILES: Cc1c(-c2onc(-c3ccccc3Cl)c2COC2CC2)cnn1[C@H]1C[C@](C)(O)C1]

Example 81: (anti-configuration), 4% yield.
Result of LC/MS [M+H]⁺: 414.3;
¹H NMR (CDCl₃): δ0.34 (2H, m, CH₂), 0.42 (2H, m, CH₂), 1.57 (3H, s, CH₃), 2.58 (5H, m, CH₂, CH₃), 2.77 (2H, m, CH₂), 3.18 (1H, m, CH), 4.33 (2H, s, CH₂), 5.03 (1H, m, CH), 7.45 (4H, m, CH-arom.), 7.89 (1H, s, CH-arom).

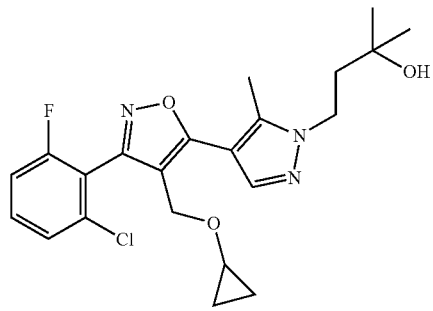 [SMILES: Cc1c(-c2onc(-c3c(F)cccc3Cl)c2COC2CC2)cnn1CCC(C)(C)O]

Example 82: 4-{4-[3-(2-chloro-6-fluorophenyl)-4-(cyclopropoxymethyl)-1,2-oxazol-5-yl]-5-methyl-1H-pyrazol-1-yl}-2-methylbutan-2-ol method C, from 4-{4-[4-(bromomethyl)-3-(2-chloro-6-fluorophenyl)-1,2-oxazol-5-yl]-5-methyl-1H-pyrazol-1-yl}-2-methylbutan-2-ol (0.3 mmol) and cyclopropanol as yellowish oil (19%).
Result of LC/MS [M+H]⁺: 434.1;
¹H NMR (CDCl₃): δ0.41-0.26 (4H, m, 2xCH₂), 1.30 (6H, s, 2xCH₃), 2.04 (2H, t, CH₂), 2.63 (3H, s, CH₃), 3.23-3.14 (1H, m, CH), 4.35-4.27 (4H, m, 2xCH₂), 7.14 (1H, td, CH-arom.), 7.34 (1H, d, CH-arom.), 7.48-7.38 (1H, m, CH-arom.), 7.89 (1H, s, CH-arom.).

Example 83 and 84: 3-{4-[3-(2-chloro-6-fluorophenyl)-4-(cyclopropoxymethyl)-1,2-oxazol-5-yl]-5-methyl-1H-pyrazol-1-yl}-1-methylcyclobutan-1-ol, Syn- and Anti-Configuration method C, from 3-{4-[4-(bromomethyl)-3-(2-chloro-6-fluorophenyl)-1,2-oxazol-5-yl]-5-methyl-1H-pyrazol-1-yl}-1-methylcyclobutan-1-ol (syn/anti-mixture) (0.4 mmol) and cyclopropanol as colorless oil (additional pTLC, eluent: petroleum ether/ethyl acetate 1:1);

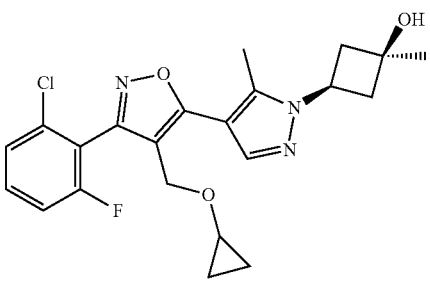 [SMILES: Cc1c(-c2onc(-c3c(F)cccc3Cl)c2COC2CC2)cnn1[C@H]1C[C@@](C)(O)C1]

Example 83: (syn-configuration), 15% yield;
Result of LC/MS [M+H]⁺: 432.3;
¹H NMR (CDCl₃): δ0.30 (2H, m, CH₂), 0.36 (2H, m, CH₂), 1.47 (3H, s, CH₃), 1.76 (1H, s, OH), 2.58 (3H, s, CH₃), 2.72 (2H, m, CH₂), 2.74 (2H, m, CH₂), 3.18 (1H, m, CH), 4.33 (2H, s, CH₂), 4.53 (1H, quint., CH), 7.14 (1H, td, CH-arom.), 7.34 (1H, d, CH-arom.), 7.42 (1H, m, CH-arom), 7.95 (1H, s, CH-arom).

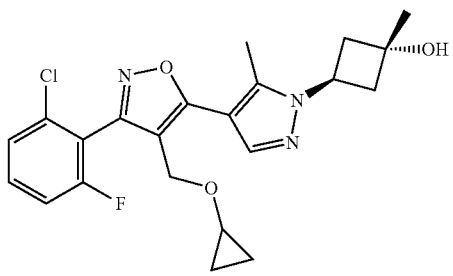 [SMILES: Cc1c(-c2onc(-c3c(F)cccc3Cl)c2COC2CC2)cnn1[C@H]1C[C@](C)(O)C1]

Example 84: (anti-configuration), 16% yield;
Result of LC/MS [M+H]⁺: 432.3;
¹H NMR (CDCl₃): δ0.31 (2H, m, CH₂), 0.36 (2H, m, CH₂), 1.53 (3H, s, CH₃), 1.68 (1H, s, OH), 2.57 (5H, m, CH₃, CH₂), 2.75 (2H, m, CH₂), 3.18 (1H, m, CH), 4.32 (2H, s, CH₂), 5.03 (1H, quint., CH), 7.13 (1H, td, CH-arom.), 7.34 (1H, d, CH-arom.), 7.42 (1H, m, CH-arom), 7.91 (1H, s, CH-arom).

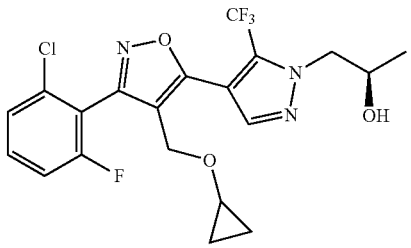 [SMILES: C[C@@H](O)Cn1ncc(-c2onc(-c3c(F)cccc3Cl)c2COC2CC2)c1C(F)(F)F]

Example 85: (2R)-1-(4-(3-(2-chloro-6-fluorophenyl)-4-(cyclopropoxymethyl)isoxazol-5-yl)-5-(trifluoromethyl)-1H-pyrazol-1-yl)propan-2-ol method C, from (2R)-1-{4-[4-(bromomethyl)-3-(2-chloro-6-fluorophenyl)-1,2-oxazol-5-yl]-5-(trifluoromethyl)-1H-pyrazol-1-yl}propan-2-ol (0.3 mmol) and cyclopropanol (9%).
Result of LC/MS [M+H]⁺: 459.8;
¹H NMR (CDCl₃): δ0.94-0.80 (4H, m, 2xCH₂), 1.32 (3H, d, CH₃), 3.19-3.07 (1H, m, CH), 4.25 (1H, dd, CH), 4.27 (2H, s, OCH₂), 4.45-4.32 (2H, m, CH₂), 7.15 (1H, td, CH-arom.), 7.35 (1H, dt, CH-arom.), 7.49-7.39 (1H, m, CH-arom.), 7.92 (1H, s, CH-arom.).

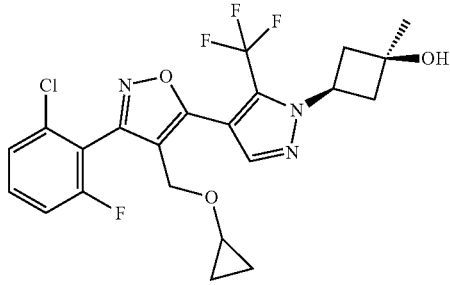 [SMILES: C[C@]1(O)C[C@@H](n2ncc(-c3onc(-c4c(F)cccc4Cl)c3COC3CC3)c2C(F)(F)F)C1]

Example 86: 3-(4-(3-(2-chloro-6-fluorophenyl)-4-(cyclopropoxymethyl)isoxazol-5-yl)-5-(trifluoromethyl)-1H-pyrazol-1-yl)-1-methylcyclobutan-1-ol (Syn-Configuration)

method C, from 3-{4-[4-(bromomethyl)-3-(2-chloro-6-fluorophenyl)-1,2-oxazol-5-yl]-5-(trifluoromethyl)-1H-pyrazol-1-yl}-1-methylcyclobutan-1-ol (syn/anti-mixture) (0.2 mmol) and cyclopropanol (52%; only syn diastereomer isolated).
Result of LC/MS [M+H]⁺: 486.0;
¹H NMR (CDCl₃): δ0.27 (4H, d, 2xCH₂), 1.50 (3H, s, CH₃), 2.91-2.71 (4H, m, 2xCH₂), 3.16-3.08 (1H, m, CH), 4.26 (2H, s, OCH₂), 4.81-4.65 (1H, m, CH), 7.14 (1H, td, CH-arom.), 7.34 (1H, dt, CH-arom.), 7.48-7.38 (1H, m, CH-arom.), 7.91 (1H, s, CH-arom.).

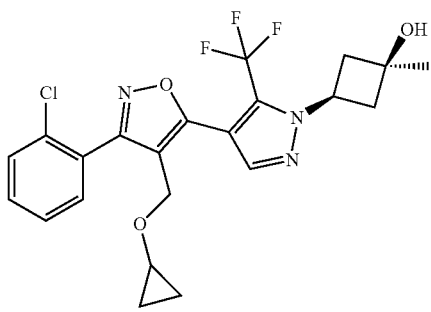 [SMILES: C[C@]1(O)C[C@@H](n2ncc(-c3onc(-c4ccccc4Cl)c3COC3CC3)c2C(F)(F)F)C1]

Example 87: 3-{4-[3-(2-chlorophenyl)-4-(cyclopropoxymethyl)-1,2-oxazol-5-yl]-5-(trifluoromethyl)-1H-pyrazol-1-yl}-1-methylcyclobutan-1-ol (Syn-Configuration)

method C, from 3-{4-[4-(bromomethyl)-3-(2-chlorophenyl)-1,2-oxazol-5-yl]-5-(trifluoromethyl)-1H-pyrazol-1-yl}-1-methylcyclobutan-1-ol (syn/anti-mixture) (0.25 mmol) and cyclopropanol (26%; only syn diastereomer isolated).
Result of LC/MS [M+H]⁺: 467.9;
¹H NMR (CDCl₃): δ0.35-0.25 (4H, m, 2xCH₂), 1.50 (3H, s, CH₃), 2.91 (4H, br, 2xCH₂), 3.17-3.07 (1H, m, CH), 4.29 (2H, s, OCH₂), 4.72 (1H, quint, CH), 7.56-7.34 (4H, m, 4xCH-arom.), 7.89 (1H, s, CH-arom.).

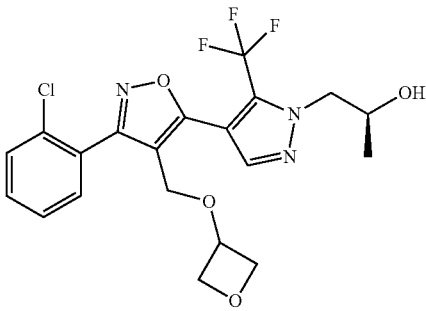 [SMILES: C[C@H](O)Cn1ncc(-c2onc(-c3ccccc3Cl)c2COC2COC2)c1C(F)(F)F]

Example 88: (S)-1-(4-(3-(2-chlorophenyl)-4-((oxetan-3-yloxy)methyl)isoxazol-5-yl)-5-(trifluoromethyl)-1H-pyrazol-1-yl)propan-2-ol method C, from (2S)-1-{4-[4-(bromomethyl)-3-(2-chlorophenyl)-1,2-oxazol-5-yl]-5-(trifluoromethyl)-1H-pyrazol-1-yl}propan-2-ol (0.25 mmol) and oxetan-3-ol (11%).
Result of LC/MS [M+H]⁺: 458.3;
¹H NMR (CDCl₃): δ1.32 (3H, d, CH₃), 4.21 (2H, s, OCH₂), 4.46-4.23 (6H, m, 2xCH₂ and 2xCH), 4.59-4.51 (2H, m, CH₂), 7.58-7.37 (4H, m, 4xCH-arom.), 7.91 (1H, s, CH-arom.).

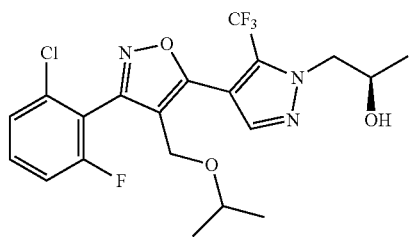 [SMILES: CC(C)OCc1c(-c2c(F)cccc2Cl)noc1-c1cnn(C[C@@H](C)O)c1C(F)(F)F]

Example 89: (2R)-1-{4-[3-(2-chloro-6-fluorophenyl)-4-[(propan-2-yloxy)methyl]-1,2-oxazol-5-yl]-5-(trifluoromethyl)-1H-pyrazol-1-yl}propan-2-ol method D, from (2R)-1-{4-[4-(bromomethyl)-3-(2-chloro-6-fluorophenyl)-1,2-oxazol-5-yl]-5-(trifluoromethyl)-1H-pyrazol-1-yl}propan-2-ol (0.25 mmol) and isopropanol (21%).
Result of LC/MS [M+H]⁺: 462.1;
¹H NMR (CDCl₃): δ0.92 (6H, d, 2xCH₃), 1.32 (3H, d, CH₃), 3.28 (1H, br, OH), 3.40 (1H, sept, CH), 4.29-4.19 (3H, m, CH and CH₂), 4.45-4.31 (2H, m, CH₂), 7.14 (1H, td, CH-arom.), 7.34 (1H, d, CH-arom.), 7.47-7.38 (1H, m, CH-arom.), 7.93 (1H, s, CH-arom.).

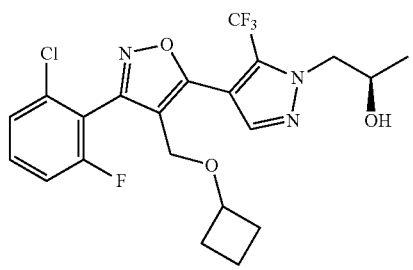 [SMILES: C[C@@H](O)Cn1ncc(-c2onc(-c3c(F)cccc3Cl)c2COC2CCC2)c1C(F)(F)F]

Example 90: (2R)-1-(4-(3-(2-chloro-6-fluorophenyl)-4-(cyclobutoxymethyl)isoxazol-5-yl)-5-(trifluoromethyl)-1H-pyrazol-1-yl)propan-2-ol method C, from (2R)-1-{4-[4-(bromomethyl)-3-(2-chloro-6-fluorophenyl)-1,2-oxazol-5-yl]-5-(trifluoromethyl)-1H-pyrazol-1-yl}propan-2-ol (0.25 mmol) and cyclobutanol (17%).
Result of LC/MS [M+H]⁺: 474.1;
¹H NMR (CDCl₃): δ1.31 (3H, d, CH₃), 1.74-1.55 (4H, m, 2xCH₂), 2.02-1.88 (2H, m, CH₂), 3.27 (1H, br, OH), 3.75 (1H, quint, CH), 4.14 (2H, s, CH), 4.25 (1H, d, CH), 4.45-4.31 (2H, m, CH₂), 7.15 (1H, td, CH-arom.), 7.35 (1H, d, CH-arom.), 7.49-7.39 (1H, m, CH-arom.), 7.94 (1H, s, CH-arom.).

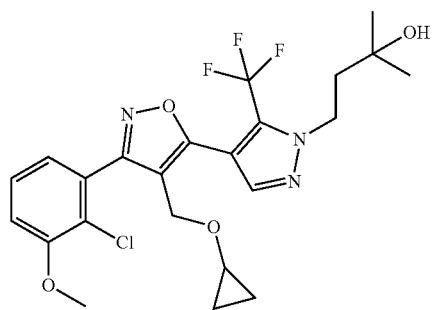 [SMILES: COc1cccc(-c2noc(-c3cnn(CCC(C)(C)O)c3C(F)(F)F)c2COC2CC2)c1Cl]

Example 91: 4-{4-[3-(2-chloro-3-methoxyphenyl)-4-(cyclopropoxymethyl)-1,2-oxazol-5-yl]-5-(trifluoromethyl)-1H-pyrazol-1-yl}-2-methylbutan-2-ol 1.) 4-(4-(3-(3-(benzyloxy)-2-chlorophenyl)-4-(cyclopropoxymethyl)isoxazol-5-yl)-5-(trifluoromethyl)-1H-pyrazol-1-yl)-2-methylbutan-2-ol
method C, from 4-(4-(3-(3-(benzyloxy)-2-chlorophenyl)-4-(bromomethyl)isoxazol-5-yl)-5-(trifluoromethyl)-1H-pyrazol-1-yl)-2-methylbutan-2-ol (1.0 mmol) and cyclopropanol as colorless oil (20%).
Result of LC/MS [M+H]⁺: 576.5;
¹H NMR (CDCl₃): δ0.38-0.20 (4H, m, 2xCH₂), 1.32 (6H, s, 2xCH₃), 2.19 (2H, m, CH₂), 3.14-3.06 (1H, m, OH), 4.58-4.47 (2H, m, CH₂), 5.22 (2H, s, OCH₂), 5.23 (2H, s, OCH₂), 7.10 (1H, td, CH-arom.), 7.52-7.28 (6H, m, 6xCH-arom.), 7.84 (1H, s, CH-arom.).

2.) 2-chloro-3-[4-(cyclopropoxymethyl)-5-[1-(3-hydroxy-3-methylbutyl)-5-(trifluoromethyl)-1H-pyrazol-4-yl]-1,2-oxazol-3-yl]phenol
4-(4-(3-(3-(benzyloxy)-2-chlorophenyl)-4-(cyclopropoxymethyl)isoxazol-5-yl)-5-(trifluoromethyl)-1H-pyrazol-1-yl)-2-methylbutan-2-ol (0.2 mmol) was dissolved in iPrOH/ethyl acetate (1:1; 1 ml) and Pd/C (10%; 0.3 eq.) was added. The atmosphere was replaced with hydrogen and the mixture was stirred at room temperature for 18 h. The mixture was filtrated over celite, the filter cake was washed with ethyl acetate, and the filtrate was concentrated under reduced pressure to give crude material (yellow oil; 90%), which was used as such for the next step.
Result of LC/MS [M+H]⁺: 486.3;
¹H NMR (CDCl₃): δ0.38-0.24 (4H, m, 2xCH₂), 1.32 (6H, s, 2xCH₃), 2.18-2.08 (2H, m, CH₂), 3.18-3.06 (1H, m, CH), 4.26 (2H, s, OCH₂), 4.58-4.45 (2H, m, CH₂), 7.20-6.97 (2H, m, 2xCH-arom.), 7.84 (1H, s, CH-arom.).

3.) NaH (1.4 eq.) was suspended in THF (Sure/Seal; 2 mL/mmol) and the solution was cooled to 0° C. A solution of 2-chloro-3-[4-(cyclopropoxymethyl)-5-[1-(3-hydroxy-3-methylbutyl)-5-(trifluoromethyl)-1H-pyrazol-4-yl]-1,2-oxazol-3-yl]phenol (0.6 mmol) in THF (Sure/Seal: 4 mL/mmol) was added dropwise to the mixture. The mixture was stirred at 0° C. for 15 min, then MeI (3.3 eq.) was added. The mixture was allowed to warm to room temperature and was stirred at this temperature for 18 h. Water was added and the mixture was extracted with CH₂Cl₂ and ethyl acetate. Combined organic layers were dried over MgSO₄, filtered and concentrated under reduced pressure. The title compound was obtained by preparative TLC on silica gel (eluent: CH₂Cl₂/MeOH 98:2 and petroleum/ether/ethyl acetate 3:2) as yellow oil (16% yield).
Result of LC/MS [M+H]⁺: 500.40
¹H NMR (CDCl₃): δ0.30 (4H, m, 2x CH₂), 1.32 (6H, s, 2x CH₃), 2.13 (2H, m, CH₂), 3.11 (1H, m, CH), 3.96 (3H, s, CH₃), 4.29 (2H, s, CH₂), 4.53 (2H, m, CH₂), 7.07 (2H, m, CH-arom.), 7.34 (1H, t, CH-arom.), 7.84 (1H, s, CH-arom.).

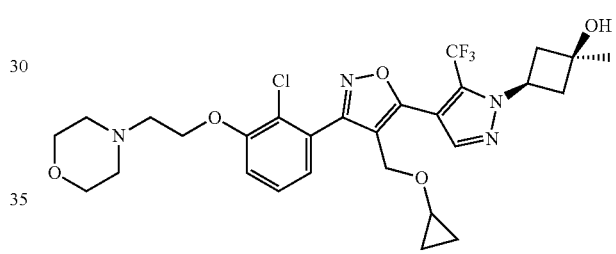

Example 92: 3-(4-(3-(2-chloro-3-(2-morpholinoethoxy)phenyl)-4-(cyclopropoxymethyl)isoxazol-5-yl)-5-(trifluoromethyl)-1H-pyrazol-1-yl)-1-methylcyclobutan-1-ol (Syn-Configuration)

1.) 3-(4-(3-(3-(benzyloxy)-2-chlorophenyl)-4-(cyclopropoxymethyl)isoxazol-5-yl)-5-(trifluoromethyl)-1H-pyrazol-1-yl)-1-methylcyclobutan-1-ol (syn/anti-mixture)
method C, from 3-(4-(3-(3-(benzyloxy)-2-chlorophenyl)-4-(bromomethyl)isoxazol-5-yl)-5-(trifluoromethyl)-1H-pyrazol-1-yl)-1-methylcyclobutan-1-ol (syn/anti-mixture) (0.30 mmol) and cyclopropanol as colorless oil (28%).
Result of LC/MS [M+H]⁺: 574.3;
¹H NMR (CDCl₃): δ0.58-0.24 (4H, m, 2xCH₂), 1.49 (3H, s, CH₃), 2.92-2.68 (4H, m, 2xCH₂), 3.17-3.05 (1H, m, CH), 4.29 (2H, s, OCH₂), 4.80-4.64 (1H, m, CH), 5.24 (2H, s, OCH₂), 7.13-7.07 (1H, m, CH-arom.), 7.44-7.28 (5H, m, 5xCH-arom.), 7.52-7.46 (1H, m, CH-arom.), 7.90 (1H, s, CH-arom.).

2.) 2-chloro-3-(4-(cyclopropoxymethyl)-5-(1-(3-hydroxy-3-methylcyclobutyl)-5-(trifluoromethyl)-1H-pyrazol-4-yl)isoxazol-3-yl)phenol (syn/anti-mixture) O-debenzylation was achieved according to the procedure described for Example 91, step 2; starting from 3-(4-(3-(3-(benzyloxy)-2-chlorophenyl)-4-(cyclopropoxymethyl)isoxazol-5-yl)-5-(trifluoromethyl)-1H- pyrazol-1-yl)-1-methylcyclobutan-1-ol (syn/anti-mixture) (0.09 mmol) (reaction time 1 h). Crude material was obtained as colorless oil in 52% yield.
Result of LC/MS [M+H]$^+$: 484.3;
3.) 2-chloro-3-(4-(cyclopropoxymethyl)-5-(1-(3-hydroxy-3-methylcyclobutyl)-5-(trifluoromethyl)-1H-pyrazol-4-yl)isoxazol-3-yl)phenol (syn/anti mixture) (0.045 mmol) and K$_2$CO$_3$ (3.0 eq.) were suspended in dry DMF (Sure/Seal; 1 mL). N-(2-Chloroethyl)morpholine hydrochloride was added (1.2 eq.) and the mixture was stirred at 50° C. for 2.5 h. The mixture was partitioned between water and CH$_2$Cl$_2$, combined organic layers were dried over MgSO$_4$ and concentrated under reduced pressure. The title compound was isolated from prep. TLC on silica gel (eluent: petroleum ether/ethyl acetate 1:1) (14% yield).
Result of LC/MS [M+H]$^+$: 597.3;
$^1$H NMR (CDCl$_3$): δ0.30 (4H, m, 2x CH$_2$), 2.64 (4H, m, 2x CH$_2$), 2.80 (4H, m, 2x CH$_2$), 2.89 (2H, t, CH$_2$), 3.10 (1H, m, CH), 3.73 (4H, m, 2x CH$_2$), 4.24 (2H, t, CH$_2$), 4.27 (2H, s, CH$_2$), 4.72 (1H, m, CH), 7.08 (2H, m, CH-arom.), 7.31 (1H, t, CH-arom.), 7.89 (1H, s, CH-arom).

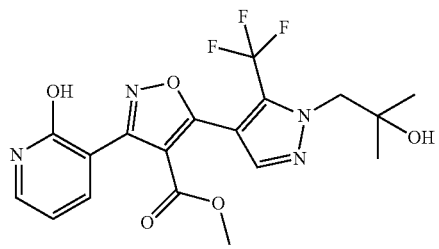 [SMILES: COC(=O)c1c(-c2cccnc2O)noc1-c1cnn(CC(C)(C)O)c1C(F)(F)F]

Example 93: methyl 5-[1-(2-hydroxy-2-methylpropyl)-5-(trifluoromethyl)-1H-pyrazol-4-yl]-3-(2-hydroxypyridin-3-yl)-1,2-oxazole-4-carboxylate Methyl 5-(1-(2-hydroxy-2-methylpropyl)-5-(trifluoromethyl)-1H-pyrazol-4-yl)-3-(2-methoxypyridin-3-yl)isoxazole-4-carboxylate (synthesized in analogy to Example 21 using 1-hydrazinyl-2-methylpropan-2-ol instead of (R)-1-hydrazinylpropan-2-ol; 0.025 mmol) and sodium iodide (3.0 eq.) were stirred together in acetonitrile (0.150 mL). To this solution chlorotrimethylsilane (3.0 eq.) was added dropwise. The mixture was stirred at room temperature for 2 h, then diluted with ethyl acetate. The organic phase was washed with water and saturated aq. NaHCO$_3$ and dried over MgSO$_4$, filtered and concentrated under reduced pressure to give the title compound as pale yellow oil (82%).
Result of LC/MS [M+H]$^+$: 433.8;
$^1$H NMR (CDCl$_3$): δ1.24 (6H, s, 2x CH$_3$), 3.67 (3H, s, CH$_3$), 4.30 (2H, s, CH$_2$), 6.43 (1H, td, CH-arom.), 7.48 (1H, dd, CH-arom.), 7.85 (1H, dd, CH-arom), 8.06 (1H, s, CH-arom).

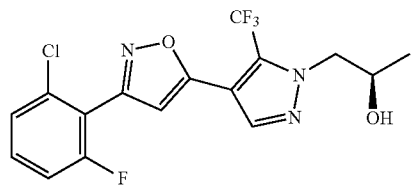 [SMILES: C[C@@H](O)Cn1ncc(-c2cc(-c3c(F)cccc3Cl)no2)c1C(F)(F)F]

Example 94: (2R)-1-(4-(3-(2-chloro-6-fluorophenyl) isoxazol-5-yl)-5-(trifluoromethyl)-1H-pyrazol-1-yl) propan-2-ol 1. The hydroxyl group of the alcoholic moiety of ethyl 3-(2-chloro-6-fluorophenyl)-5-{1-[(2R)-2-hydroxypropyl]-5-(trifluoromethyl)-1H-pyrazol-4-yl}-1,2-oxazole-4-carboxylate (Example 12) was TBS protected according to method A, "General O-silylation" described below;
2. The ethyl oxazole-4-carboxylate group was saponified according to the procedure described as first step in "Synthesis of 4-acyl isoxazoles" above;
3. Decarboxylation of the resulting oxazole-4-carboxylic acid was performed according to Adv. Synth. Catal. 2013, 355, 790 (Table 3, entry 15) using catalytic Cu(I) oxide and TMEDA in NMP at 140° C., simultaneously removing the silyl protecting group to give the title compound upon purification by prep. TLC (eluent: petroleum ether/ethyl acetate 1:1) in 15% yield.
Result of LC/MS [M+H]$^+$: 389.8;
$^1$H NMR (CDCl$_3$): δ1.31 (3H, d, CH$_3$), 4.24 (1H, dd, CH), 4.44-4.31 (2H, m, CH$_2$), 6.62 (1H, s, CH-arom.), 7.14 (1H, td, CH-arom.), 7.46-7.31 (2H, m, 2xCH-arom.), 8.04 (1H, s, CH-arom.).

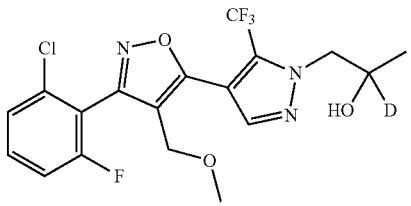 [SMILES: [2H]C(C)(O)Cn1ncc(-c2onc(-c3c(F)cccc3Cl)c2COC)c1C(F)(F)F]

Example 95: 1-{4-[3-(2-chloro-6-fluorophenyl)-4-(methoxymethyl)-1,2-oxazol-5-yl]-5-(trifluoromethyl)-1H-pyrazol-1-yl}(2-$^2$H)propan-2-ol (Racemic)

To a stirred solution of Example 66 (0.25 mmol) in CH$_2$Cl$_2$ (1.5 mL) was added Dess-Martin periodinane (3.5 eq.). The reaction mixture was stirred at room temperature for 18 h. The reaction mixture was quenched by adding aq. Na$_2$S$_2$O$_3$ and extracted with CH$_2$Cl$_2$. Combined organic layers were washed with saturated aq. NaHCO$_3$ and brine, dried over anhydrous Na$_2$SO$_4$, and concentrated under reduced pressure. The residue was purified by prep. TLC on silica gel (eluent: petroleum ether/ethyl acetate 3:1) to give 1-{4-[3-(2-chloro-6-fluorophenyl)-4-(methoxymethyl)-1,2-oxazol-5-yl]-5-(trifluoromethyl)-1H-pyrazol-1-yl}propan-2-one (41%).
This propanone was dissolved in THF (10 mL/mmol) and cooled to 0° C. NaBD$_4$ (1.1 eq.) was added and the mixture was stirred at 0° C. for 1 h. The mixture was quenched with water and partitioned between CH$_2$Cl$_2$ and water. Combined organic layers were dried over MgSO$_4$, filtrated and concentrated under reduced pressure. Title compound was purified by preparative TLC on silica gel (eluent: CH$_2$Cl$_2$/MeOH 95:5) and isolated in 65% yield.
Result of LC/MS [M+H]$^+$: 435.1;
$^1$H NMR (CDCl$_3$): δ1.31 (3H, s, CH$_3$), 3.14 (3H, s, OCH$_3$), 3.24 (1H, s, OH), 4.19 (2H, s, CH$_2$), 4.31 (2H, q, CH$_2$), 7.15 (1H, td, CH-arom.), 7.35 (1H, d, CH-arom.), 7.49-7.38 (1H, m, CH-arom.), 7.91 (1H, s, CH-arom.).

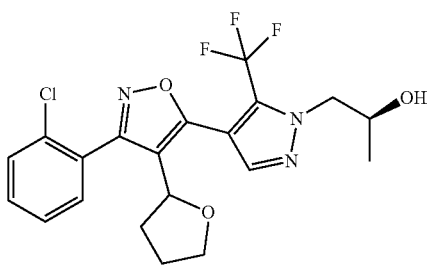 [SMILES: C[C@H](O)Cn1ncc(-c2onc(-c3ccccc3Cl)c2C2CCCO2)c1C(F)(F)F]

Example 96: (2S)-1-{4-[3-(2-chlorophenyl)-4-(oxolan-2-yl)-1,2-oxazol-5-yl]-5-(trifluoromethyl)-1H-pyrazol-1-yl}propan-2-ol (as Mixture of Diastereomers)

MeMgBr (1.0 eq., 1 M in THF) in THF at 0° C., followed by addition of Mg (2.0 eq.) and 1,2-dibromoethane (0.1 eq.) and stirring under reflux for 20 min Upon cooling to room temperature, the solution was separated from the rest of magnesium and directly added to (2S)-5-(1-(2-((tert-butyldimethylsilyl)oxy)propyl)-5-(trifluoromethyl)-1H-pyrazol-4-yl)-3-(2-chlorophenyl)isoxazole-4-carbaldehyde in THF to give 1-(5-(1-((2S)-2-((tert-butyldimethylsilyl)oxy)propyl)-5-(trifluoromethyl)-1H-pyrazol-4-yl)-3-(2-chlorophenyl)isoxazol-4-yl)butane-1,4-diol in 60% yield. Cyclization of the butane-1,4-diol unit to the respective tetrahydrofuran ring was achieved with mesyl chloride in THF and triethylamine under reflux in 31% yield. Final O-deprotection with HCl/MeOH (3.0 M) (described below as step2 in "Cycloaddition reaction") gave the title compound as mixture of diastereomers in 31% yield.

Result of LC/MS [M+H]$^+$: 442.3;
$^1$H NMR (CDCl$_3$): δ1.31 (3H, d, CH$_3$), 1.69-1.39 (4H, m, 2xCH$_2$), 3.66-3.47 (2H, m, CH$_2$), 4.22 (1H, dd, OCH$_2$), 4.44-4.29 (2H, m, CH$_2$), 4.65 (1H, t, CH), 7.55-7.32 (4H, m, 4xCH-arom.), 7.83 (1H, s, CH-arom.).

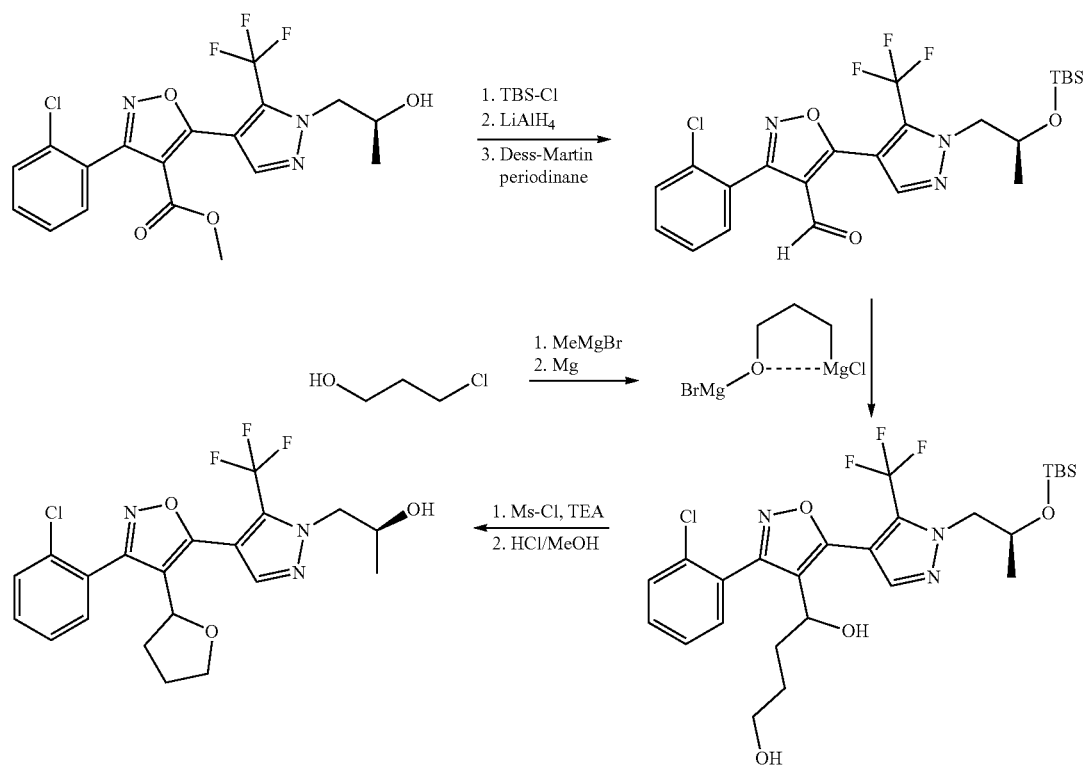

Starting from methyl (2S)-3-(2-chlorophenyl)-5-(1-(2-hydroxypropyl)-5-(trifluoromethyl)-1H-pyrazol-4-yl)isoxazole-4-carboxylate (Example 22), the alcohol group was tert-butyldimethylsilyl protected (cf. below "General O-silylation procedures", method A), the methyl isoxazol-4-carboxylate was reduced using LiAlH$_4$ (cf. general procedure as first step described above in "Synthesis of 4-alkoxymethyl isoxazoles") and oxidized with Dess-Martin periodinane to give the corresponding isoxazol-4-aldehyde (64%; cf. first step described above for Example 95). The Grignard reagent was prepared from 3-chloropropan-1-ol and Alternative Route to Pyrazolyl-Isoxazoles

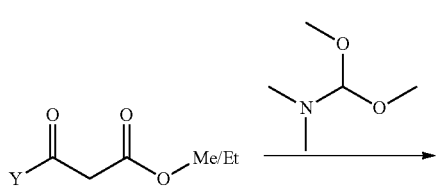

-continued

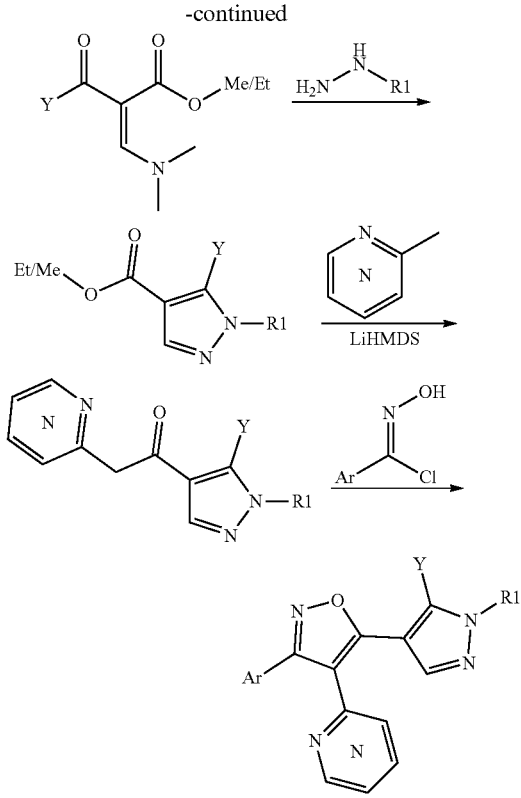

Synthesis of 2-(dimethylamino)methylene)-oxobutanoates

A) ethyl 2-((dimethylamino)methylene)-4,4,4-trifluoro-3-oxobutanoate

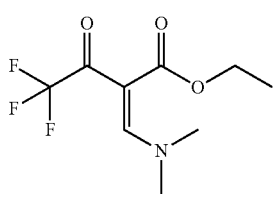 [SMILES: CCOC(=O)/C(=C\N(C)C)C(=O)C(F)(F)F]

To a solution of ethyl 4,4,4-trifluoro-3-oxobutanoate (18.5 g, 77.3 mmol) in toluene (30.0 mL) at 0° C. was added (dimethoxymethyl)dimethylamine (9.21 g, 77.3 mmol). The reaction was stirred at room temperature for ca. 3 h until ethyl 4,4,4-trifluoro-3-oxobutanoate was completely consumed. Toluene was removed under reduced pressure. The residue was purified by column chromatography on silica gel to give ethyl 2-((dimethylamino)methylene)-4,4,4-trifluoro-3-oxobutanoate (15 g, yield: 81%).

Result of LC/MS [M+H]$^+$: 240.0;

$^1$H NMR (CDCl$_3$): δ1.30 (3H, t, CH$_3$), 2.90 (3H, br, NCH$_3$), 3.32 (3H, br, NCH$_3$), 4.22 (2H, q, OCH$_2$), 7.68 (1H, s, CH).

B) methyl 2-((dimethylamino)methylene)-3-oxobutanoate or ethyl 2-((dimethylamino)methylene)-3-oxobutanoate

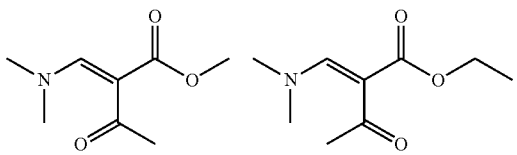

Methyl or ethyl acetoacetate (20 mmol) was dissolved in N,N-dimethylformamide dimethyl acetal (3.0 eq.) and the mixture was heated by microwave irradiation to 80° C. for 3 h. The reaction mixture was concentrated under reduced pressure and the crude material (brown oil) was taken up in a small volume of ethyl acetate and crystallized by addition of petroleum ether to give the product as brown solid (53-62%).

Methyl ester:

Result of LC/MS [M+H]$^+$: 172.0;

$^1$H NMR (CDCl$_3$): δ2.32 (3H, s, CH$_3$), 3.04 (6H, br, 2xNCH$_3$), 3.75 (3H, s, CH$_3$), 7.70 (1H, s, CH).

Ethyl ester:

Result of LC/MS [M+H]$^+$: 186.0;

$^1$H NMR (CDCl$_3$): δ1.32 (3H, t, CH$_3$), 2.32 (3H, s, CH$_3$), 3.03 (6H, br, 2xNCH$_3$), 4.23 (2H, q, OCH$_2$), 7.66 (1H, s, CH).

Formation of Pyrazole Building Blocks from 2-(dimethylamino)methylene)-oxobutanoates To a solution of either ethyl 2-((dimethylamino)methylene)-4,4,4-trifluoro-3-oxobutanoate or methyl or ethyl 2-((dimethylamino)methylene)-3-oxobutanoate (10.0 mmol) in EtOH (5 mL/mmol) was added N,N-diisopropylethylamine (3.0 eq.) and the respective hydrazinyl-alcohol (usually as hydrochloride; 1.1 eq.). The reaction was stirred at room temperature for 18 h. The mixture was partitioned between water and ethyl acetate, combined organic layers were washed with brine and dried over MgSO$_4$, filtered and concentrated under reduced pressure.

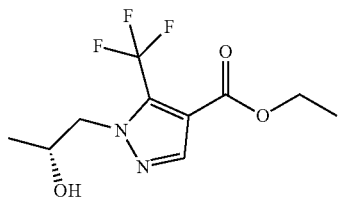 [SMILES: CCOC(=O)c1cnn(C[C@@H](C)O)c1C(F)(F)F]

Using ethyl 2-((dimethylamino)methylene)-4,4,4-trifluoro-3-oxobutanoate and (R)-1-hydrazinylpropan-2-ol hydrochloride: The residue was purified by column chromatography on silica gel (eluent: petroleum ether/ethyl acetate 3:1) to give ethyl (R)-1-(2-hydroxypropyl)-5-(trifluoromethyl)-1H-pyrazole-4-carboxylate (82% yield);

Result of LC/MS [M+H]$^+$: 267.0;

$^1$H NMR (CDCl$_3$): δ1.27 (3H, d, CH$_3$), 1.36 (3H, t, CH$_3$), 3.00 (1H, d, OH), 4.31-4.17 (2H, m, CH$_2$), 4.34 (2H, q, CH$_2$), 7.98 (1H, s, CH-arom.).

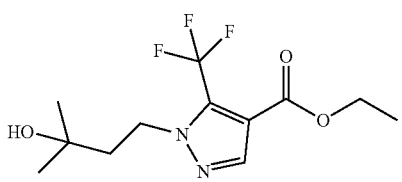 [SMILES: CCOC(=O)c1cnn(CCC(C)(C)O)c1C(F)(F)F]

Using ethyl 2-((dimethylamino)methylene)-4,4,4-trifluoro-3-oxobutanoate and 4-hydrazinyl-2-methylbutan-2-ol: crude ethyl 1-(3-hydroxy-3-methylbutyl)-5-(trifluoromethyl)-1H-pyrazole-4-carboxylate was obtained as orange oil (79%);
Result of LC/MS [M+H]⁺: 295.3;
¹H NMR (CDCl₃): δ1.29 (6H, s, 2xCH₃), 1.35 (3H, t, CH₃), 2.09-1.97 (2H, m, CH₂), 4.32 (2H, q, OCH₂), 4.55-4.46 (2H, m, CH₂), 7.93 (1H, s, CH-arom.).

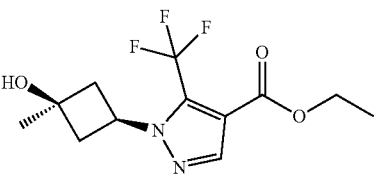 [SMILES: CCOC(=O)c1cnn([C@H]2C[C@@](C)(O)C2)c1C(F)(F)F]

Using ethyl 2-((dimethylamino)methylene)-4,4,4-trifluoro-3-oxobutanoate and 3-hydrazinyl-1-methylcyclobutanol (syn/anti-mixture): The residue was purified by column chromatography on silica gel (eluent: petroleum ether/ethyl acetate 5:1) to give ethyl 1-(3-hydroxy-3-methylcyclobutyl)-5-(trifluoromethyl)-1H-pyrazole-4-carboxylate (syn/anti-mixture) as yellow oil (9% yield);
Result of LC/MS [M+H]⁺: 293.3;
¹H NMR (CDCl₃, mixture of diasteromers=isomers 1 and 2): δ1.34 (6H, t, CH₃ $_{Isomer1+2}$), 1.46 (3H, s, CH₃ $_{Isomer2}$), 1.50 (3H, s, CH₃ $_{Isomer1}$), 2.88-2.55 (8H, m, CH₂ $_{Isomere1+2}$), 4.31 (2H, t, CH₂ $_{Isomer2}$), 4.32 (2H, t, CH₂ $_{Isomer1}$), 4.75-4.65 (1H, m, CH$_{Isomer2}$), 5.28-5.17 (1H, m, CH$_{Isomer1}$), 7.93 (1H, s, pyrazole-H$_{Isomer2}$), 7.97 (1H, s, pyrazole-H$_{Isomer1}$).

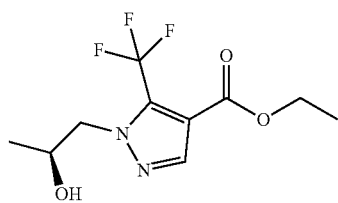 [SMILES: CCOC(=O)c1cnn(C[C@H](C)O)c1C(F)(F)F]

Using ethyl 2-((dimethylamino)methylene)-4,4,4-trifluoro-3-oxobutanoate and (S)-1-hydrazinylpropan-2-ol: crude ethyl (S)-1-(2-hydroxypropyl)-5-(trifluoromethyl)-1H-pyrazole-4-carboxylate was obtained in 35% yield;
Result of LC/MS [M+H]⁺: 267.0;

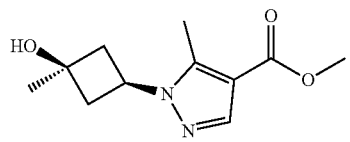 [SMILES: COC(=O)c1cnn([C@H]2C[C@@](C)(O)C2)c1C]

Using methyl 2-((dimethylamino)methylene)-3-oxobutanoate and 3-hydrazinyl-1-methylcyclobutanol (syn/anti-mixture): The residue was purified by column chromatography on silica gel (eluent: petroleum ether/ethyl acetate 1:1) to give methyl 1-(3-hydroxy-3-methylcyclobutyl)-5-methyl-1H-pyrazole-4-carboxylate (syn-configuration) (39%; a second fraction yielded the anti-diastereomer in a similar amount).
Result of LC/MS [M+H]⁺: 225.1;
¹H NMR (CDCl₃): δ1.52 (3H, s, CH₃), 2.53 (3H, s, CH₃), 2.56 (4H, m, 2x CH₂), 2.82 (3H, s, CH₃), 4.46 (1H, m, CH), 7.91 (1H, s, CH-arom.).

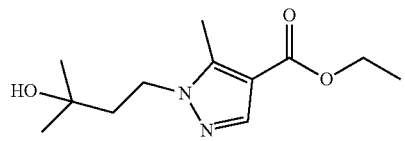 [SMILES: CCOC(=O)c1cnn(CCC(C)(C)O)c1C]

Using ethyl 2-((dimethylamino)methylene)-3-oxobutanoate and 4-hydrazinyl-2-methylbutan-2-ol: The residue was purified by column chromatography on silica gel (eluent: petroleum ether/ethyl acetate 1:1) to give ethyl 1-(3-hydroxy-3-methylbutyl)-5-methyl-1H-pyrazole-4-carboxylate as a reddish oil (92%).
Result of LC/MS [M+H]⁺: 241.1;
¹H NMR (CDCl₃): δ1.27 (6H, s, 2xCH₃), 3.90 (3H, t, CH₃), 2.02-1.93 (2H, m, CH₂), 2.55 (3H, s, CH₃), 4.34-4.17 (4H, m, 2xCH₂), 7.84 (1H, s, CH-arom.).
General O-Silylation Procedures
A) To a solution of ethyl 1-(2-hydroxypropyl)-5-(trifluoromethyl)-1H-pyrazole-4-carboxylate 4 (2.67 g, 10.0 mmol) (R or S configuration) in CH₂Cl₂ (20.0 mL) were added imidazole (1.02 g, 15.0 mmol), DMAP (122 mg, 1.0 mmol) and then tert-butyldimethylsilyl chloride (1.95 g, 13.0 mmol in CH₂Cl₂, 5.0 mL) at 0° C. The resulting solution was stirred at room temperature for 18 h. The reaction was quenched with saturated aq. NaHCO₃ and extracted with CH₂Cl₂. Combined organic phases were washed with 0.1 M aq. HCl and dried over MgSO₄, filtered and concentrated under reduced pressure. The residue was purified by column chromatography on silica gel.
1.

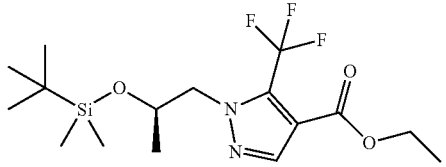 [SMILES: CCOC(=O)c1cnn(C[C@@H](C)O[Si](C)(C)C(C)(C)C)c1C(F)(F)F]

Starting from the (R)-alcohol to give ethyl (R)-1-(2-((tert-butyldimethylsilyl)oxy)propyl)-5-(trifluoromethyl)-1H-pyrazole-4-carboxylate (84%).

Result of LC/MS [M+H]⁺: 381.1;
¹H NMR (CDCl₃): δ −0.21 (3H, s, CH₃), −0.03 (3H, s, CH₃), 0.80 (9H, s, 3xCH₃), 1.19 (3H, d, CH₃), 1.35 (3H, t, CH₃), 4.40-4.25 (4H, m, CH₂ and OCH₂), 7.94 (1H, s, CH-arom.).

2.

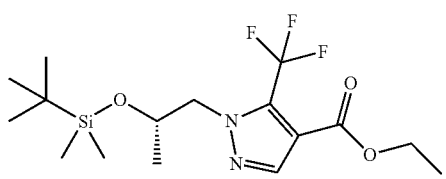 [SMILES: CCOC(=O)c1cnn(C[C@H](C)O[Si](C)(C)C(C)(C)C)c1C(F)(F)F]

Starting from the (S)-alcohol to give ethyl (S)-1-(2-((tert-butyldimethylsilyl)oxy)propyl)-5-(trifluoromethyl)-1H-pyrazole-4-carboxylate (55%).

B) To a stirred mixture of either ethyl 1-(3-hydroxy-3-methylcyclobutyl)-5-(trifluoromethyl)-1H-pyrazole-4-carboxylate (syn/anti-mixture) or methyl 1-(3-hydroxy-3-methylcyclobutyl)-5-methyl-1H-pyrazole-4-carboxylate (syn-configuration) (3.0 mmol) and N,N-diisopropylethylamine (3.0 eq.) in CH₂Cl₂ (5 mL/mmol) was added tert-butyldimethylsilyl triflate (1.5 eq.) slowly at 0° C. The reaction mixture was stirred at room temperature for 3 h and was then diluted with water and extracted with CH₂Cl₂. Combined organic phases were washed with brine, dried over anhydrous MgSO₄, filtrated, and concentrated.

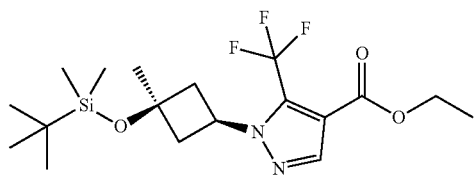 [SMILES: CCOC(=O)c1cnn([C@H]2C[C@@](C)(O[Si](C)(C)C(C)(C)C)C2)c1C(F)(F)F]

Using ethyl 1-(3-hydroxy-3-methylcyclobutyl)-5-(trifluoromethyl)-1H-pyrazole-4-carboxylate (syn-configuration): The residue was purified by column chromatography on silica gel (eluent: petroleum ether/ethyl acetate 50:1 to 20:1) to give ethyl 1-(3-((cert-butyldimethylsilyl)oxy)-3-methylcyclobutyl)-5-(trifluoromethyl)-1H-pyrazole-4-carboxylate as a brown oil; a separation of syn- and anti-diastereomers can be achieved at this level; combined yield of 84%.

¹H NMR (CDCl₃, diastereomer 1): δ −0.01 (6H, s, 2x CH₃), 0.77 (9H, s, tBu), 1.13 (3H, t, CH₃), 1.34 (3H, s, CH₃), 2.53 (4H, m, CH₂), 4.19 (2H, q, CH₂), 5.03 (1H, m, CH), 7.82 (1H, s, CH-arom.)

¹H NMR (CDCl₃, diastereomer 2): δ −0.02 (6H, s, 2x CH₃), 0.79 (9H, s, tBu), 1.13 (3H, t, CH₃), 1.34 (3H, s, CH₃), 2.53 (4H, m, CH₂), 4.19 (2H, q, CH₂), 5.03 (1H, m, CH), 7.80 (1H, s, CH-arom.)

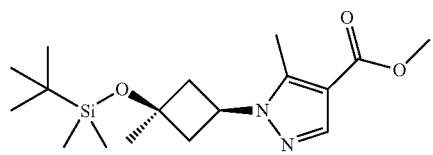 [SMILES: COC(=O)c1cnn([C@H]2C[C@@](C)(O[Si](C)(C)C(C)(C)C)C2)c1C]

Using methyl 1-(3-hydroxy-3-methylcyclobutyl)-5-methyl-1H-pyrazole-4-carboxylate (syn-configuration): The residue was purified by column chromatography on silica gel (eluent: petroleum ether/ethyl acetate 8:1) to give methyl 1-(3-((tert-butyldimethylsilyl)oxy)-3-methylcyclobutyl)-5-methyl-1H-pyrazole-4-carboxylate (syn-configuration) (38%).

Result of LC/MS [M+H]⁺: 339.1;
¹H NMR (CDCl₃): δ 0.11 (6H, 2, 2xCH₃), 0.89 (9H, s, 3xCH₃), 1.46 (3H, s, CH₃), 2.50 (3H, s, CH₃), 2.59-2.51 (2H, m, CH₂), 2.90-2.76 (2H, m, CH₂), 3.81 (3H, s, OCH₃), 4.33-4.17 (1H, m, CH), 7.86 (1H, s, CH-arom.).

C) ethyl 1-(3-hydroxy-3-methylbutyl)-5-(trifluoromethyl)-1H-pyrazole-4-carboxylate or ethyl 1-(3-hydroxy-3-methylbutyl)-5-methyl-1H-pyrazole-4-carboxylate (4 mmol) was taken up in bis(trimethylsilyl)amine (10 mL) and chlorotrimethylsilane (1.0 eq.) was added. The mixture was stirred at room temperature for 18 h. The mixture was diluted with CH₂Cl₂ and washed with water and saturated aq. NH₄Cl. The organic phase was dried over MgSO₄, filtered and concentrated under reduced pressure.

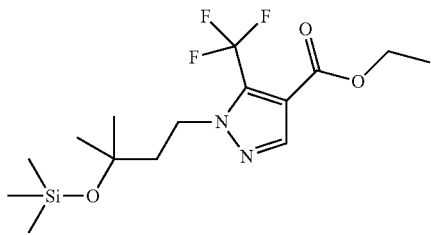 [SMILES: CCOC(=O)c1cnn(CCC(C)(C)O[Si](C)(C)C)c1C(F)(F)F]

Using ethyl 1-(3-hydroxy-3-methylbutyl)-5-(trifluoromethyl)-1H-pyrazole-4-carboxylate: Crude product was purified by prep. TLC on silica gel (eluent: CH₂Cl₂/MeOH 95:5) and again pTLC (eluent: petroleum ether/ethyl acetate 4:1) to give ethyl 1-(3-methyl-3-((trimethylsilyl)oxy)butyl)-5-(trifluoromethyl)-1H-pyrazole-4-carboxylate as orange oil (75%).

Result of LC/MS [M+H]⁺: 367.3;
¹H NMR (CDCl₃): δ 0.13 (9H, s, 3xCH₃), 1.29 (6H, s, 2xCH₃), 1.35 (3H, t, CH₃), 2.02-1.92 (2H, m, CH₂), 4.32 (2H, q, OCH₂), 4.50-4.40 (2H, m, CH₂), 7.92 (1H, s, CH-arom.).

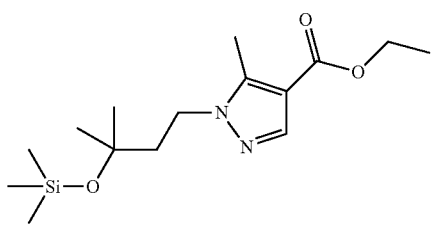 [SMILES: CCOC(=O)c1cnn(CCC(C)(C)O[Si](C)(C)C)c1C]

Using ethyl 1-(3-hydroxy-3-methylbutyl)-5-methyl-1H-pyrazole-4-carboxylate: if reaction is not reaching completion, another eq. chlorotrimethylsilane can be added and stirring to be continued under reflux. Crude material ethyl 5-methyl-1-(3-methyl-3-((trimethylsilyl)oxy)butyl)-1H-pyrazole-4-carboxylate was obtained as a reddish oil (88%) and was used as such in the next reaction step.

Result of LC/MS [M+H]⁺: 313.1;

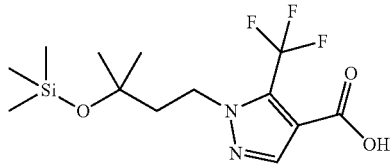 [SMILES: CC(C)(CCn1ncc(C(=O)O)c1C(F)(F)F)O[Si](C)(C)C]

Using 1-(3-hydroxy-3-methylbutyl)-5-(trifluoromethyl)-1H-pyrazole-4-carboxylic acid (1.1 mmol; which was obtained from ethyl 1-(3-hydroxy-3-methylbutyl)-5-(trifluoromethyl)-1H-pyrazole-4-carboxylate by saponification using 4 N aq. NaOH in THF (room temperature, 18 h), isolated in 48% yield as brown oil upon acidification with 6 N aq. HCl and extraction with CH₂Cl₂): mixture was stirred at 60° C. in a sealed tube for 18 h, upon which more chlorotrimethylsilane was added an stirring continued for another day, until conversion was completed; crude product 1-{3-methyl-3-[(trimethylsilyl)oxy]butyl}-5-(trifluoromethyl)-1H-pyrazole-4-carboxylic acid (84%) was used as such in next step.

Result of LC/MS [M+H]⁺: 339.0;

Condensation of Alkyl Pyrazole-4-Carboxylates with Heteroaryl-Methyl Anions

To a solution of 2-methylpyrimidine/2-methylpyrazine/4-methylpyrimidine (1.2 eq.) in THF (1 mL/mmol) was added LiHMDS (1.0 M in THF; 2.2 eq.) at −10° C. under Na atmosphere. The mixture was stirred at this temperature for 30 min and the respective alkyl pyrazole-4-carboxylate (1.0 eq. in THF, 1 mL/mmol) was added, and the mixture was stirred at room temperature for 2-18 h (based on progress control). The reaction was quenched with ice water and the resulting mixture was extracted with EtOAc. Combined organic phases were washed with brine, dried over MgSO₄, filtered and concentrated in vacuo.

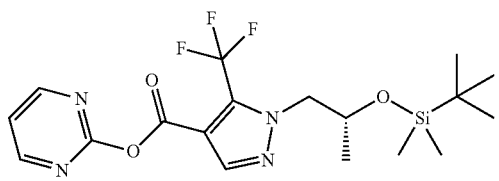 [SMILES: C[C@H](Cn1ncc(C(=O)Oc2ncccn2)c1C(F)(F)F)O[Si](C)(C)C(C)(C)C]

Using ethyl (R)-1-(2-((tert-butyldimethylsilyl)oxy)propyl)-5-(trifluoromethyl)-1H-pyrazole-4-carboxylate (10 mmol) and 2-methylpyrimidine: The residue was purified by chromatography on silica gel to give (R)-1-(1-(2-((tert-butyldimethylsilyl)oxy)propyl)-5-(trifluoromethyl)-1H-pyrazol-4-yl)-2-(pyrimidin-2-yl)ethan-1-one (yield: 77%);

Result of LC/MS [M+H]⁺: 429.0.

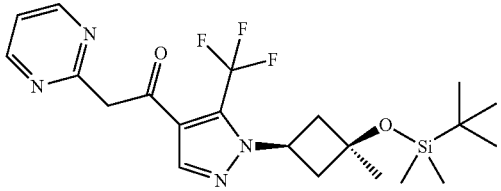 [SMILES: CC(C)(C)[Si](C)(C)O[C@]1(C)C[C@H](n2ncc(C(=O)Cc3ncccn3)c2C(F)(F)F)C1]

Using ethyl 1-(3-((tert-butyldimethylsilyl)oxy)-3-methylcyclobutyl)-5-(trifluoromethyl)-1H-pyrazole-4-carboxylate (syn-configuration) (0.3 mmol) and 2-methylpyrimidine: The residue was purified by prep. TLC on silica gel (eluent: petroleum ether/ethyl acetate 3:1) to give 1-(1-(3-((tert-butyldimethylsilyl)oxy)-3-methylcyclobutyl)-5-(trifluoromethyl)-1H-pyrazol-4-yl)-2-(pyrimidin-2-yl)ethanone (syn-configuration) as a yellow oil (46%).

Result of LC/MS [M+H]⁺: 455.1;

¹H NMR (CDCl₃): δ −0.01 (6H, s, 2x CH₃), 0.80 (9H, s, tBu), 1.35 (3H, s, CH₃), 2.53 (4H, m, CH₂), 4.38 (2H, s, CH₂), 5.02 (1H, m, CH), 6.89 (1H, t, CH-arom.), 7.65 (1H, d, CH-arom.), 7.82 (1H, s, CH-arom.), 8.60 (1H, d, CH-arom.).

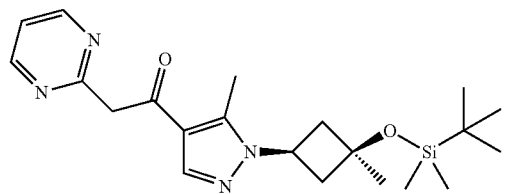 [SMILES: Cc1c(C(=O)Cc2ncccn2)cnn1[C@H]1C[C@@](C)(O[Si](C)(C)C(C)(C)C)C1]

Using methyl 1-(3-((tert-butyldimethylsilyl)oxy)-3-methylcyclobutyl)-5-methyl-1H-pyrazole-4-carboxylate (syn-configuration) (1.6 mmol) and 2-methylpyrimidine: The residue was purified by prep. TLC on silica gel (eluent: petroleum ether/ethyl acetate 1:2) to give 1-(1-(3-((tert-butyldimethylsilyl)oxy)-3-methylcyclobutyl)-5-methyl-1H-pyrazol-4-yl)-2-(pyrimidin-2-yl)ethan-1-one (syn-configuration) as colorless solid (17%).

Result of LC/MS [M+H]⁺: 401.1.

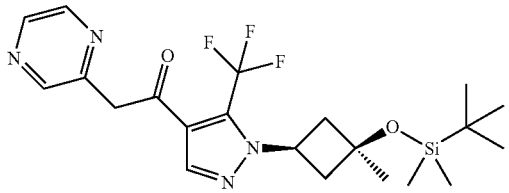 [SMILES: CC(C)(C)[Si](C)(C)O[C@]1(C)C[C@H](n2ncc(C(=O)Cc3cnccn3)c2C(F)(F)F)C1]

Using ethyl 1-(3-((tert-butyldimethylsilyl)oxy)-3-methylcyclobutyl)-5-(trifluoromethyl)-1H-pyrazole-4-carboxylate (syn-configuration) (0.3 mmol) and 2-methylpyrazine: The residue was purified by prep. TLC on silica gel (eluent: petroleum ether/ethyl acetate 3:1) to give 1-(1-{3-[(tert-butyldimethylsilyl)oxy]-3-methylcyclobutyl}-5-(trifluoromethyl)-1H-pyrazol-4-yl)-2-(pyrazin-2-yl)ethan-1-one (syn-configuration) (48%).

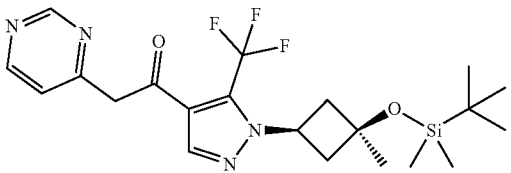 [SMILES: CC(C)(C)[Si](C)(C)O[C@]1(C)C[C@H](n2ncc(C(=O)Cc3ccncn3)c2C(F)(F)F)C1]

Using ethyl 1-(3-((tert-butyldimethylsilyl)oxy)-3-methylcyclobutyl)-5-(trifluoromethyl)-1H-pyrazole-4-carboxylate (syn-configuration) (0.3 mmol) and 4-methylpyrimidine: The residue was purified by prep. TLC on silica gel (eluent: petroleum ether/ethyl acetate 3:1) to give 1-(1-{3-[(tert-butyldimethylsilyl)oxy]-3-methylcyclobutyl}-5-(trifluoromethyl)-1H-pyrazol-4-yl)-2-(pyrimidin-4-yl)ethan-1-one (syn-configuration) (63%).

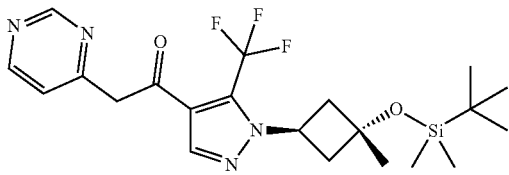 [SMILES: CC(C)(C)[Si](C)(C)O[C@]1(C)C[C@@H](n2ncc(C(=O)Cc3ccncn3)c2C(F)(F)F)C1]

The corresponding anti-diastereomer was obtained accordingly, starting from the respective anti-building-block.

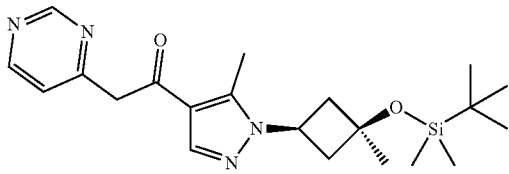 [SMILES: Cc1c(C(=O)Cc2ccncn2)cnn1[C@H]1C[C@@](C)(O[Si](C)(C)C(C)(C)C)C1]

Using methyl 1-(3-((tert-butyldimethylsilyl)oxy)-3-methylcyclobutyl)-5-methyl-1H-pyrazole-4-carboxylate (syn-configuration) (0.3 mmol) and 4-methylpyrimidine: The residue was purified by prep. TLC on silica gel (eluent: petroleum ether/ethyl acetate 3:1) to give 1-(1-{3-[(tert-butyldimethylsilyl)oxy]-3-methylcyclobutyl}-5-methyl-1H-pyrazol-4-yl)-2-(pyrimidin-4-yl)ethan-1-one (syn-configuration) (76%).

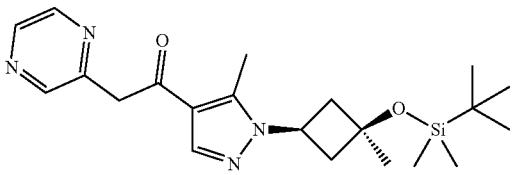 [SMILES: Cc1c(C(=O)Cc2cnccn2)cnn1[C@H]1C[C@@](C)(O[Si](C)(C)C(C)(C)C)C1]

Using methyl 1-(3-((tert-butyldimethylsilyl)oxy)-3-methylcyclobutyl)-5-methyl-1H-pyrazole-4-carboxylate (syn-configuration) (0.3 mmol) and 2-methylpyrazine: The residue was purified by prep. TLC on silica gel (eluent: petroleum ether/ethyl acetate 3:1) to give 1-(1-{3-[(tert-butyldimethylsilyl)oxy]-3-methylcyclobutyl}-5-methyl-1H-pyrazol-4-yl)-2-(pyrazin-2-yl)ethan-1-one (syn-configuration) (79%).

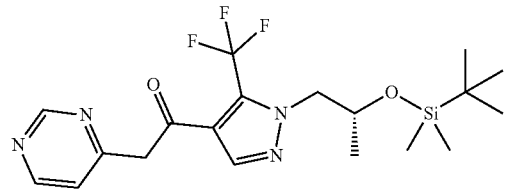 [SMILES: C[C@H](Cn1ncc(C(=O)Cc2ccncn2)c1C(F)(F)F)O[Si](C)(C)C(C)(C)C]

Using ethyl (R)-1-(2-((tert-butyldimethylsilyl)oxy)propyl)-5-(trifluoromethyl)-1H-pyrazole-4-carboxylate (0.3 mmol) and 4-methylpyrimidine: The residue was purified by prep. TLC on silica gel (eluent: petroleum ether/ethyl acetate 3:1) to give 1-{1-[(2R)-2-[(tert-butyldimethylsilyl)oxy]propyl]-5-(trifluoromethyl)-1H-pyrazol-4-yl}-2-(pyrimidin-4-yl)ethan-1-one (74%).

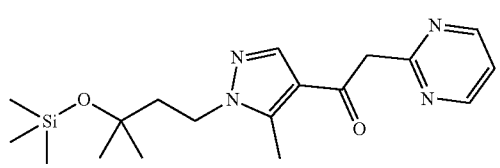 [SMILES: Cc1c(C(=O)Cc2ncccn2)cnn1CCC(C)(C)O[Si](C)(C)C]

Using ethyl 5-methyl-1-{3-methyl-3-[(trimethylsilyl)oxy]butyl}-1H-pyrazole-4-carboxylate (0.9 mmol) and 2-methylpyrimidine: The residue was purified by prep. TLC on silica gel (eluent: petroleum ether/ethyl acetate 1:1) to give 1-(5-methyl-1-{3-methyl-3-[(trimethylsilyl)oxy]butyl}-1H-pyrazol-4-yl)-2-(pyrimidin-2-yl)ethan-1-one as yellowish oil (31%).

Result of LC/MS [M+H]$^+$: 361.1;

$^1$H NMR (CDCl$_3$): δ0.11 (9H, s, 3xCH$_3$), 1.26 (6H, 2, 2xCH$_3$), 1.95-1.80 (2H, m, CH$_2$), 2.55 (3H, s, CH$_3$), 4.24-4.09 (2H, m, CH$_2$), 4.43 (2H, s, CH$_2$), 7.16 (1H, t, CH-arom.), 7.90 (1H, s, CH-arom.), 8.70 (2H, d, 2xCH-arom.).

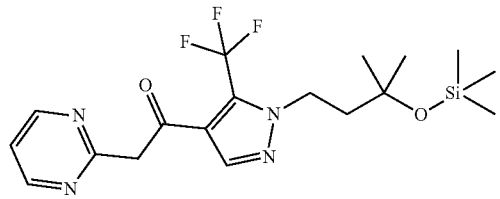 [SMILES: CC(C)(CCn1ncc(C(=O)Cc2ncccn2)c1C(F)(F)F)O[Si](C)(C)C]

Using ethyl 1-{3-methyl-3-[(trimethylsilyl)oxy]butyl}-5-(trifluoromethyl)-1H-pyrazole-4-carboxylate (0.33 mmol) and 2-methylpyrimidine: The residue was purified by prep. TLC on silica gel (eluent: petroleum ether/ethyl acetate 1:1) to give crude 1-(1-{3-methyl-3-[(trimethylsilyl)oxy]butyl}-5-(trifluoromethyl)-1H-pyrazol-4-yl)-2-(pyrimidin-2-yl)ethan-1-one as orange oil (quant.).

Result of LC/MS [M+H]$^+$: 415.4;

$^1$H NMR (CDCl$_3$): δ0.14 (9H, s, 3xCH$_3$), 1.31 (6H, s, 2xCH$_3$), 2.09-1.93 (2H, m, CH$_2$), 4.47-4.39 (2H, m, CH$_2$), 4.49 (2H, s, CH$_2$), 7.00 (1H, t, CH-arom.), 7.76 (1H, s, CH-arom.), 8.71 (2H, d, 2xCH-arom.).

Synthesis of 3-(pyrazol-4-yl)-3-oxopropanoates

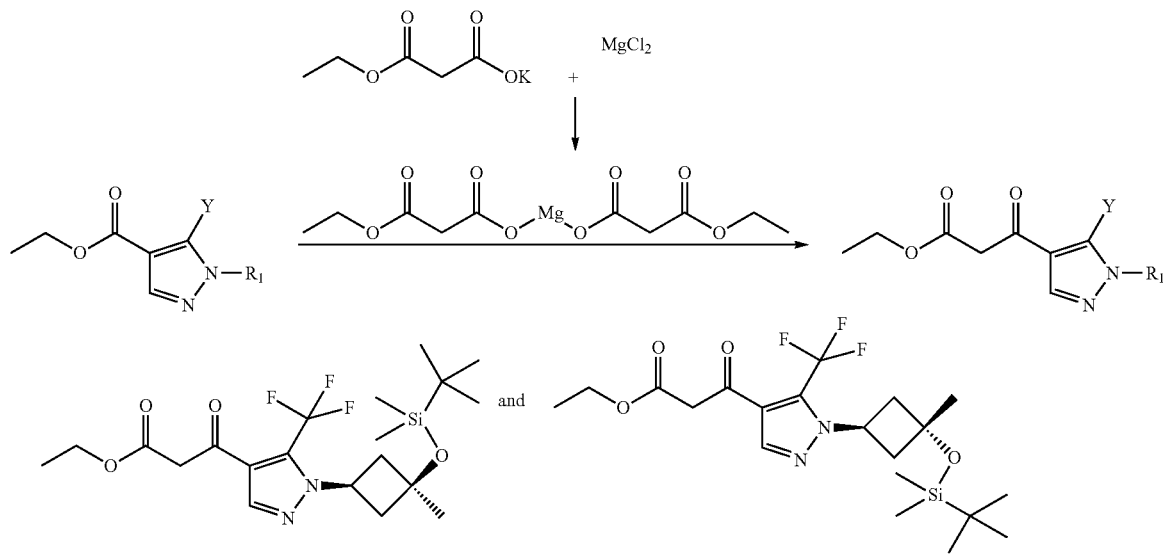

ethyl 3-(1-{3-[(tert-butyldimethylsily)oxy]-3-methylcyclobutyl}-5-(trifluoromethyl)-1H-pyrazol-4-yl)-3-oxopropanoate, Syn- and Anti-Configuration, was Synthesized from ethyl 1-(3-((tert-butyldimethylsilyl)oxy)-3-methylcyclobutyl)-5-(trifluoromethyl)-1H-pyrazole-4-carboxylate (Syn/Anti Mixture)

1.) To a solution of ethyl 1-(3-((tert-butyldimethylsilyl)oxy)-3-methylcyclobutyl)-5-(trifluoromethyl)-1H-pyrazole-4-carboxylate (syn/anti mixture) (1.84 mmol) in THF (3 ml) was added aq. NaOH (1 M, 4 mL) and the mixture was stirred at room temperature for 72 h. The mixture was poured into 5% aq. citric acid, which was extracted with $CH_2Cl_2$. Combined organic layers were dried over $MgSO_4$ and concentrated to dryness. Separation of diastereomers was not possible at this stage, thus the crude brown oil 1-{3-[(tert-butyldimethylsilyl)oxy]-3-methylcyclobutyl}-5-(trifluoromethyl)-1H-pyrazole-4-carboxylic acid (94%) was used for further conversions.
Result of LC/MS [M+H]$^+$: 379.1;

2.) A solution of crude 1-{3-[(tert-butyldimethylsilyl)oxy]-3-methylcyclobutyl}-5-(trifluoromethyl)-1H-pyrazole-4-carboxylic acid (1.73 mmol) and 1,1'-carbonyldiimidazole (1.5 eq.; CDI) in THF (Sure/Seal, 7 mL) was stirred at room temperature for 18 h to form an activated carboxylic acid derivative. 1-[(3-ethoxy-3-oxopropanoyl)oxy]magnesio 3-ethyl propanedioate (1.2 eq., synthesis described below) was added and the solution was stirred at 55° C. for 2 h. The mixture was diluted with ethyl acetate and washed with water. The aqueous layer was extracted with ethyl acetate, and combined organic layers were dried over $MgSO_4$ and concentrated to dryness. Purification and diastereomer separation was accomplished via column chromatography on silica gel (eluent: petroleum ether/$CH_2Cl_2$/ethyl acetate 8:2:1). Syn- and anti-isomers (relative configuration within cyclobutanol unit) of ethyl 3-(1-{3-[(tert-butyldimethylsilyl)oxy]-3-methylcyclobutyl}-5-(trifluoromethyl)-1H-pyrazol-4-yl)-3-oxopropanoate were obtained as yellow oils (each 29-36%).

Syn-Configuration:
Result of LC/MS [M+H]$^+$: 449.4;
$^1$H-NMR (syn-Keto-Isomer) (CDCl$_3$, J [Hz]: δ=7.92 (s, 1H pyrazole-H), 4.62-4.48 (m, 1H, CH), 4.20 (q, 2H, 3J=7.1, OCH$_2$CH$_3$), 3.80 (s, 2H, CH$_2$), 2.92-2.86 (m, 2H, CH$_2$), 2.61-2.54 (m, 2H, CH$_2$), 1.45 (s, 3H, CH$_3$), 1.26 (t, 3H, 3J=7.1, OCH$_2$CH$_3$), 0.89 (s, 9H, C(CH$_3$)$_3$), 0.11 (s, 6H, CH$_3$).

Anti-Configuration:
Result of LC/MS [M+H]$^+$: 449.3;
$^1$H-NMR (anti-Keto-Isomer) (CDCl$_3$, J [Hz]): δ=7.90 (s, 1H pyrazole-H), 5.21-5.08 (m, 1H, CH), 4.20 (q, 2H, 3J=7.1, OCH$_2$CH$_3$), 3.80 (s, 2H, CH$_2$), 2.75-2.56 (m, 4H, CH$_2$), 1.46 (s, 3H, CH$_3$), 1.26 (t, 3H, 3J=7.1, OCH$_2$CH$_3$), 0.91 (s, 9H, C(CH$_3$)$_3$), 0.12 (s, 6H, CH$_3$).

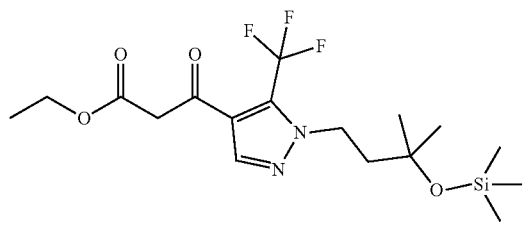 [SMILES: CCOC(=O)CC(=O)c1cnn(CCC(C)(C)O[Si](C)(C)C)c1C(F)(F)F]

ethyl 3-(1-{3-methyl-3-[(trimethylsilyl)oxy]butyl}-5-(trifluoromethyl)-1H-pyrazol-4-yl)-3-oxopropanoate Crude 1-{3-methyl-3-[(trimethylsilyl)oxy]butyl}-5-(trifluoromethyl)-1H-pyrazole-4-carboxylic acid (0.96 mmol; synthesis described above within section "General O-silylation procedures") was treated with CDI and 1-[(3-ethoxy-3-oxopropanoyl)oxy]magnesio 3-ethyl propanedioate according to the procedure described above to give the title compound as orange oil (crude, quant.; partial O-desilylation occurred).

Result of LC/MS [M+H]+: 409.1.

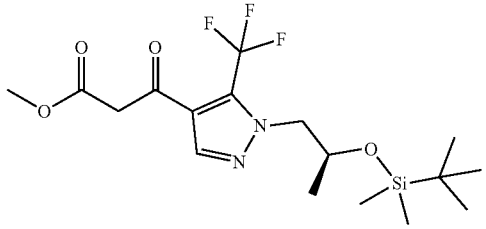 [SMILES: COC(=O)CC(=O)c1cnn(C[C@H](C)O[Si](C)(C)C(C)(C)C)c1C(F)(F)F]

methyl 3-{1-[(2S)-2-[(tert-butyldimethylsilyl)oxy]propyl]-5-(trifluoromethyl)-1H-pyrazol-4-yl}-3-oxopropanoate Ethyl (S)-1-(2-((tert-butyldimethylsilyl)oxy)propyl)-5-(trifluoromethyl)-1H-pyrazole-4-carboxylate (0.8 mmol) was first saponified to give the acid, which was next treated with CDI and 1-[(3-methoxy-3-oxopropanoyl)oxy]magnesio 3-methyl propanedioate according to the procedures described above to give crude title compound (quant.).

Synthesis of [4(3-ethoxy-3-oxopropanoyl)oxy]magnesio 3-ethyl propanedioate according to *J. Am. Soc. Chem.* 2011, 133, 326: To a solution of 2.00 g (11.8 mmol) ethyl malonate potassium salt in 10 ml water were added 1.19 mg (5.88 mmol) MgCl₂x6H₂O and the solution was stirred at room temperature for 30 min 60 ml of iPrOH were added to precipitate potassium chloride. The suspension was stirred for 1 h at room temperature followed by filtration and washing with iPrOH (2×5 ml). The filtrate was evaporated to dryness to yield 1-[(3-ethoxy-3-oxopropanoyl)oxy]magnesio 3-ethyl propanedioate as a white solid (2.00 g). 1-[(3-methoxy-3-oxopropanoyl)oxy]magnesio 3-methyl propanedioate was synthesized accordingly.

Cycloaddition Reaction

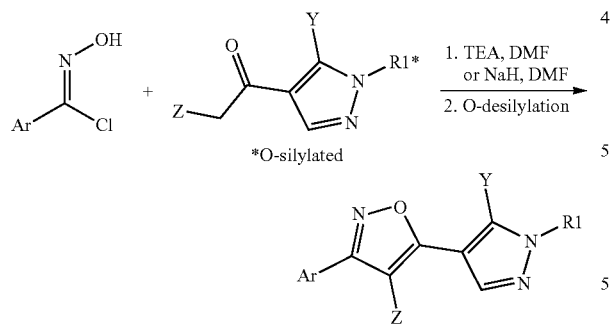

Step 1: To a stirring solution of the respective pyrazol-4-yl-2-(heteroaryl)ethan-1-one or alkyl 3-(pyrazol-4-yl)-3-oxopropanoate (1.0 eq.) and triethylamine (TEA; 4.0 eq.) in DMF (Sure/Seal; 5 mL/mmol) was added the appropriately substituted N-hydroxybenzimidoyl chloride (3.0 eq.). The mixture was stirred at indicated temperature for 18 h. The reaction was poured into water and extracted with EtOAc. Combined organic layers were washed with brine, dried over anhydrous Na₂SO₄, and concentrated under reduced pressure. Upon purification as described specifically below for each product, O-desilylation was conducted.

Step 2: A solution of purified silyl-protected product (1.0 eq.) in HCl/MeOH (3.0 M; 15 mL/mmol) was stirred at room temperature for 3 h. The pH was adjusted to around 8 by adding aq. NaOH (1.0 M), and the mixture was extracted with EtOAc. Combined organic layers were washed with brine, dried over anhydrous Na₂SO₄, concentrated under reduced pressure.

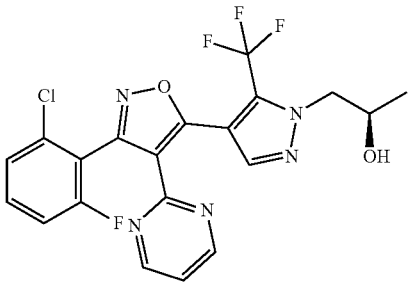 [SMILES: C[C@@H](O)Cn1ncc(-c2onc(-c3c(F)cccc3Cl)c2-c2ncccn2)c1C(F)(F)F]

Example 97: (R)-1-(4-(3-(2-chloro-6-fluorophenyl)-4-(pyrimidin-2-yl)isoxazol-5-yl)-5-(trifluoromethyl)-1H-pyrazol-1-yl)propan-2-ol Step 1: (R)-1-(1-(2-((tert-butyldimethylsilyl)oxy)propyl)-5-(trifluoromethyl)-1H-pyrazol-4-yl)-2-(pyrimidin-2-yl)ethan-1-one (4.0 mmol) and 2-chloro-6-fluoro-N-hydroxybenzimidoyl chloride; the reaction was conducted at room temperature; the residue was purified by column chromatography on silica gel (eluent: petroleum ether/ethyl acetate 6:1) to give (R)-5-(1-(2-((tert-butyldimethylsilyl)oxy)propyl)-5-(trifluoromethyl)-1H-pyrazol-4-yl)-3-(2-chloro-6-fluorophenyl)-4-(pyrimidin-2-yl)isoxazole as a yellow oil (24%);

Result of LC/MS [M+H]+: 582.0;

Step 2, general cycloaddition procedure: Mixture after step 2 was purified by column chromatography on silica gel (eluent: petroleum ether/ethyl acetate 2:1) to give the title compound (54%).

Result of LC/MS [M+H]+: 467.7;

¹H NMR (CDCl₃): δ1.32 (3H, d, CH₃), 4.24 (1H, dd, CH), 4.52-4.32 (2H, m, CH₂), 7.05 (1H, t, CH-arom.), 7.10 (1H, td, CH-arom.), 7.29 (1H, t, CH-arom.), 7.44-7.34 (1H, m, CH-arom.), 8.03 (1H, s, CH-arom.), 8.48 (2H, d, 2xCH-arom.).

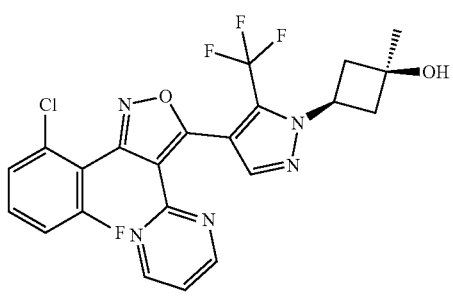 [SMILES: C[C@]1(O)C[C@@H](n2ncc(-c3onc(-c4c(F)cccc4Cl)c3-c3ncccn3)c2C(F)(F)F)C1]

Example 98: 3-(4-(3-(2-chloro-6-fluorophenyl)-4-(pyrimidin-2-yl)isoxazol-5-yl)-5-(trifluoromethyl)-1H-pyrazol-1-yl)-1-methylcyclobutanol (Syn-Configuration)

Step 1: 1-(1-(3-((tert-butyldimethylsilyl)oxy)-3-methylcyclobutyl)-5-(trifluoromethyl)-1H-pyrazol-4-yl)-2-(pyrimidin-2-yl)ethanone (syn-configuration) (0.11 mmol) and 2-chloro-6-fluoro-N-hydroxybenzimidoyl chloride; the reaction was conducted at 50° C.; the residue was purified by prep. TLC on silica gel (eluent: petroleum ether/ethyl acetate 3:1) to give 5-(1-(3-((tert-butyldimethylsilyl)oxy)-3-methylcyclobutyl)-5-(trifluoromethyl)-1H-pyrazol-4-yl)-3-(2-chloro-6-fluorophenyl)-4-(pyrimidin-2-yl)isoxazole (syn-configuration) as yellow oil (75%);

Result of LC/MS [M+H]$^+$: 608;

Step 2, general cycloaddition procedure: Mixture after step 2 was purified by prep. TLC on silica gel (eluent: petroleum ether/ethyl acetate 1:1) to give the title compound as a colorless solid (12%).

Result of LC/MS [M+H]$^+$: 494.2;

$^1$H NMR (CDCl$_3$): δ1.58 (3H, s, CH$_3$), 2.94-2.68 (4H, m, 2xCH$_2$), 4.78-4.65 (1H, m, CH), 7.04 (1H, t, CH-arom.), 7.10 (1H, td, CH-arom.), 7.31-7.28 (1H, m, CH-arom.), 7.44-7.32 (1H, m, CH-arom.), 7.61 (1H, s, CH-arom.), 8.47 (1H, s, CH-arom.), 8.49 (1H, s, CH-arom.).

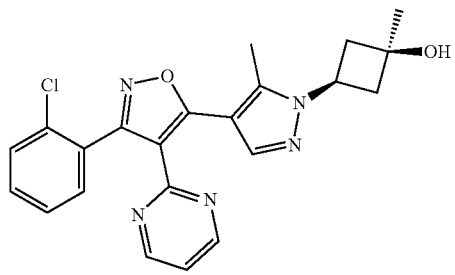 [SMILES: Cc1c(-c2onc(-c3ccccc3Cl)c2-c2ncccn2)cnn1[C@H]1C[C@@](C)(O)C1]

Example 99: 3-(4-(3-(2-chlorophenyl)-4-(pyrimidin-2-yl)isoxazol-5-yl)-5-methyl-1H-pyrazol-1-yl)-1-methylcyclobutan-1-ol (Syn-Configuration)

Alternative Step 1:

To a solution of 1-(1-(3-((tert-butyldimethylsilyl)oxy)-3-methylcyclobutyl)-5-methyl-1H-pyrazol-4-yl)-2-(pyrimidin-2-yl)ethan-1-one (syn-configuration) (0.09 mmol) in DMF (3 mL) was added NaH (5.0 eq.) at 0° C. Ice bath was removed and the mixture was stirred at room temperature for 20 min. Then 2-chloro-N-hydroxybenzimidoyl chloride (3.0 eq.) was added, and the mixture was stirred at 60° C. for 3 h. The reaction was quenched with saturated aq. NH$_4$Cl, and extracted with EtOAc. The organic layers were washed with brine, dried over anhydrous Na$_2$SO$_4$ and concentrated. The residue was purified by preparative TLC (eluent: petroleum ether/ethyl acetate 2:1) to give 5-(1-(3-((tert-butyldimethylsilyl)oxy)-3-methylcyclobutyl)-5-methyl-1H-pyrazol-4-yl)-3-(2-chlorophenyl)-4-(pyrimidin-2-yl)isoxazole (syn-configuration) (41%);

Result of LC/MS [M+H]$^+$: 536.5;

$^1$H NMR (CDCl$_3$): δ−0.08 (6H, s, 2x CH$_3$), 0.88 (9H, s, tBu), 1.45 (3H, s, CH$_3$), 2.52 (2H, m, CH$_2$), 2.56 (3H, s, CH$_3$), 2.78 (2H, m, CH$_2$), 4.25 (1H, m, CH), 7.37 (4H, m, CH-arom.), 7.86 (1H, s, CH-arom.), 8.60 (1H, d, CH-arom.), 8.78 (1H, d, CH-arom.), 8.82 (1H, d, CH-arom.), Step 2, general cycloaddition procedure: Mixture after step 2 was purified by prep. TLC on silica gel (eluent: petroleum ether/ethyl acetate 1:5) to give the title compound as a colorless solid (32%).

Result of LC/MS [M+H]$^+$: 422.3;

$^1$H NMR (CDCl$_3$): δ1.47 (3H, s, CH$_3$), 2.55 (3H, s, CH$_3$), 2.79-2.66 (4H, m, 2xCH$_2$), 4.55 (1H, quint, CH), 7.11 (1H, t, CH-arom.), 7.43-7.32 (3H, m, 3xCH-arom.), 7.64-7.57 (1H, m, CH-arom.), 8.18 (1H, s, CH-arom.), 8.62 (2H, d, 2xCH).

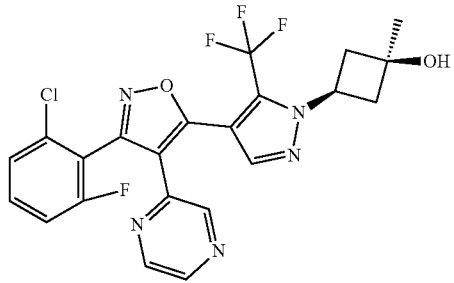 [SMILES: C[C@]1(O)C[C@@H](n2ncc(-c3onc(-c4c(F)cccc4Cl)c3-c3cnccn3)c2C(F)(F)F)C1]

Example 100: 3-{4-[3-(2-chloro-6-fluorophenyl)-4-(pyrazin-2-yl)-1,2-oxazol-5-yl]-5-(trifluoromethyl)-1H-pyrazol-1-yl}-1-methylcyclobutan-1-ol (Syn-Configuration)

Step 1: 1-(1-{3-[(tert-butyldimethylsilyl)oxy]-3-methylcyclobutyl}-5-(trifluoromethyl)-1H-pyrazol-4-yl)-2-(pyrazin-2-yl)ethan-1-one (syn-configuration) (0.11 mmol) and 2-chloro-6-fluoro-N-hydroxybenzimidoyl chloride; the reaction was conducted at 50° C.; the residue was purified by prep. TLC on silica gel (eluent: petroleum ether/ethyl acetate 3:1) to give 2-[3-(2-chloro-6-fluorophenyl)-5-{1-[3-[(tert-butyldimethylsilyl)oxy]-3-methylcyclobutyl]-5-(trifluoromethyl)-1H-pyrazol-4-yl}-1,2-oxazol-4-yl]pyrazine (syn-configuration) (75%);

Step 2, general cycloaddition procedure: Mixture after step 2 was purified by prep. TLC on silica gel (eluent: petroleum ether/ethyl acetate 1:5) to give the title compound (49%).

Result of LC/MS [M+H]$^+$: 494.3;

$^1$H NMR (CDCl$_3$): δ1.48 (3H, s, CH$_3$), 2.94-2.67 (4H, m, 2xCH$_2$), 4.68 (1H, quint, CH), 7.12 (1H, td, CH-arom.), 7.30 (1H, d, CH-arom.), 7.49-7.36 (1H, m, CH-arom.), 7.94 (1H, s, CH-arom.), 8.26 (1H, br, CH-arom.), 8.49-8.34 (2H, m, 2xCH-arom.).

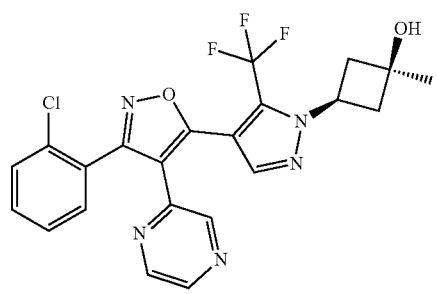 [SMILES: C[C@]1(O)C[C@@H](n2ncc(-c3onc(-c4ccccc4Cl)c3-c3cnccn3)c2C(F)(F)F)C1]

Example 101: 3-{4-[3-(2-chlorophenyl)-4-(pyrazin-2-yl)-1,2-oxazol-5-yl]-5-(trifluoromethyl)-1H-pyrazol-1-yl}-1-methylcyclobutan-1-ol (Syn-Configuration)

Step 1: 1-(1-{3-[(tert-butyldimethylsilyl)oxy]-3-methylcyclobutyl}-5-(trifluoromethyl)-1H-pyrazol-4-yl)-2-(pyrazin-2-yl)ethan-1-one (syn-configuration) (0.22 mmol) and 2-chloro-N-hydroxybenzimidoyl chloride; the reaction was conducted at 50° C.; the residue was purified by prep. TLC on silica gel (eluent: petroleum ether/ethyl acetate 3:1) to give 2-[3-(2-chlorophenyl)-5-{1-[3-[(tert-butyldimethylsilyl)oxy]-3-methylcyclobutyl}-5-(trifluoromethyl)-1H-pyrazol-4-yl]-1,2-oxazol-4-yl}pyrazine (syn-configuration) (20%);

Step 2, general cycloaddition procedure: Mixture after step 2 was purified by prep. TLC on silica gel (eluent: petroleum ether/ethyl acetate 1:5) to give the title compound (15%).

Result of LC/MS [M+H]$^+$: 476.2;

$^1$H NMR (CDCl$_3$): δ1.44 (3H, s, CH$_3$), 2.81-2.64 (4H, m, 2xCH$_2$), 4.63 (1H, quint, CH), 7.54-7.45 (1H, m, CH-arom.), 7.66-7.54 (2H, m, 2xCH-arom.), 7.70 (1H, s, CH-arom.), 7.98 (1H, d, CH-arom.), 8.50 (1H, s, CH-arom.), 9.10 (1H, s, CH-arom.).

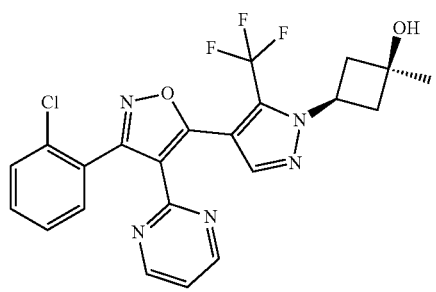 [SMILES: C[C@]1(O)C[C@@H](n2ncc(-c3onc(-c4ccccc4Cl)c3-c3ncccn3)c2C(F)(F)F)C1]

Example 102: 3-{4-[3-(2-chlorophenyl)-4-(pyrimidin-2-yl)-1,2-oxazol-5-yl]-5-(trifluoromethyl)-1H-pyrazol-1-yl}-1-methylcyclobutan-1-ol (Syn-Configuration)

Step 1: 1-(1-(3-((tert-butyldimethylsilyl)oxy)-3-methylcyclobutyl)-5-(trifluoromethyl)-1H-pyrazol-4-yl)-2-(pyrimidin-2-yl)ethanone (syn-configuration) (0.33 mmol) and 2-chloro-N-hydroxybenzimidoyl chloride; the reaction was conducted at 50° C.; the residue was purified by prep. TLC on silica gel (eluent: petroleum ether/ethyl acetate 3:1) to give 2-[3-(2-chlorophenyl)-5-{1-[3-[(tert-butyldimethylsilyl)oxy]-3-methylcyclobutyl}-5-(trifluoromethyl)-1H-pyrazol-4-yl]-1,2-oxazol-4-yl]pyrimidine (syn-configuration) (27%);

Step 2, general cycloaddition procedure: Mixture after step 2 was purified by prep. TLC on silica gel (eluent: petroleum ether/ethyl acetate 1:5) to give the title compound (8%).

Result of LC/MS [M+H]$^+$: 476.2;

$^1$H NMR (CDCl$_3$): δ1.48 (3H, s, CH$_3$), 2.92-2.70 (4H, m, CH$_2$), 4.70 (1H, quint, CH), 7.08 (1H, t, CH-arom.), 7.45-7.34 (3H, m, 3xCH-arom.), 7.67-7.58 (1H, m, CH-arom.), 8.08 (1H, s, CH-arom.), 8.54 (2H, d, 2xCH-arom.).

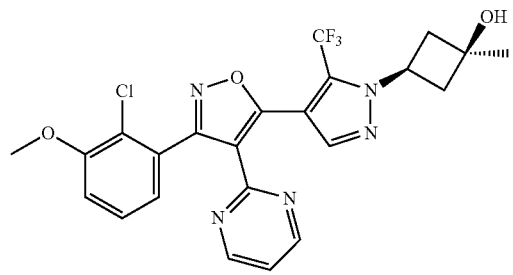

Example 103: 3-{4-[3-(2-chloro-3-methoxyphenyl)-4-(pyrimidin-2-yl)-1,2-oxazol-5-yl]-5-(trifluoromethyl)-1H-pyrazol-1-yl}-1-methylcyclobutan-1-ol (Syn-Configuration)

Step 1: 1-(1-(3-((tert-butyldimethylsilyl)oxy)-3-methylcyclobutyl)-5-(trifluoromethyl)-1H-pyrazol-4-yl)-2-(pyrimidin-2-yl)ethanone (syn-configuration) (0.38 mmol) and 2-chloro-3-methoxy-N-hydroxybenzimidoyl chloride; reaction was conducted at 65° C.; the residue was purified by prep. TLC on silica gel (eluent: petroleum ether/ethyl acetate 7:3 and again 4:1) to give 2-[3-(2-chloro-3-methoxyphenyl)-5-{1-[3-[(tert-butyldimethylsilyl)oxy]-3-methylcyclobutyl]-5-(trifluoromethyl)-1H-pyrazol-4-yl}-1,2-oxazol-4-yl]pyrimidine (syn-configuration) as an orange oil (14%);

Result of LC/MS [M+H]$^+$: 620.1;

$^1$H NMR (CDCl$_3$): δ0.13 (6H, s, 2xCH$_3$), 0.91 (9H, s, 3xCH$_3$), 1.27 (3H, s, CH$_3$), 2.69-2.51 (2H, m, CH$_2$), 2.84-2.70 (2H, m, CH$_2$), 3.89 (3H, s, OCH$_3$), 7.42-7.01 (4H, m, 4xCH-arom.), 8.03 (1H, s, CH-arom.), 8.52 (2H, d, 2xCH-arom.).

Alternative Step 2: A solution of purified silyl-protected product (1.0 eq., 0.06 mmol) in THF (Sure/Seal, 0.5 mL) was treated with tetrabutylammonium fluoride (1 M in THF; 1.1 eq.) at room temperature for 2 h. Solvent was removed under reduced pressure and title product was obtained from preparative TLC on silica gel (eluent: petroleum ether/ethyl acetate 3:2 and again 3:2) as pale yellow oil (16%).

Result of LC/MS [M+H]$^+$: 506.0;

$^1$H NMR (CDCl$_3$): δ1.48 (3H, s, CH$_3$), 2.91-2.70 (4H, m, 2xCH$_2$), 3.91 (3H, s, OCH$_3$), 4.70 (1H, quint, CH), 7.10-7.03 (2H, m, 2xCH-arom.), 7.26-7.22 (1H, m, CH-arom.), 7.37 (1H, t, CH-arom.), 8.08 (1H, s, CH-arom.), 8.52 (2H, d, 2xCH-arom.).

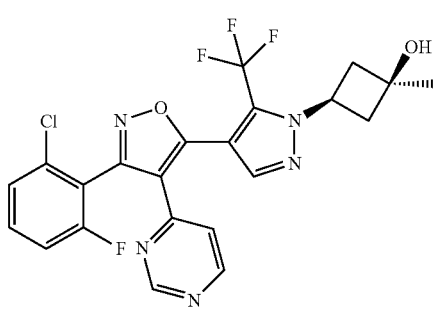

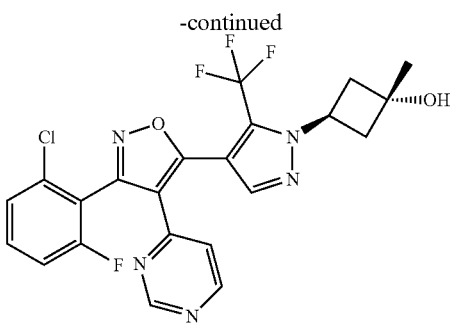

Example 104 and 105

3-{4-[3-(2-chloro-6-fluorophenyl)-4-(pyrimidin-4-yl)-1,2-oxazol-5-yl]-5-(trifluoromethyl)-1H-pyrazol-1-yl}-1-methylcyclobutan-1-ol, Syn-Configuration and Anti-Configuration Step 1: 1-(1-{3-[(tert-butyldimethylsilyl)oxy]-3-methylcyclobutyl}-5-(trifluoromethyl)-1H-pyrazol-4-yl)-2-(pyrimidin-4-yl)ethan-1-one (syn and anti-configuration, respectively) (0.17 mmol each) and 2-chloro-6-fluoro-N-hydroxybenzimidoyl chloride; the reaction was conducted at 60° C.; crude 4-[3-(2-chloro-6-fluorophenyl)-5-{1-[3-[(tert-butyldimethylsilyl)oxy]-3-methylcyclobutyl]-5-(trifluoromethyl)-1H-pyrazol-4-yl}-1,2-oxazol-4-yl]pyrimidine (syn and anti-configuration, respectively) (quant.) were directly used in step 2;

Step 2, general cycloaddition procedure: Mixture after step 2 was purified by prep. TLC on silica gel (eluent: petroleum ether/ethyl acetate 1:5) to give the title compounds:

Example 104, syn-configuration (9%)

Result of LC/MS [M+H]⁺: 493.9;

$^1$H NMR (CDCl$_3$): δ1.50 (3H, s, CH$_3$), 2.97-2.71 (4H, m, 2xCH$_2$), 4.70 (1H, quint, CH), 6.92 (1H, d, CH-arom.), 7.15 (1H, td, CH-arom.), 7.34 (1H, d, CH-arom.), 7.52-7.41 (1H, m, CH-arom.), 7.98 (1H, s, CH-arom.), 8.56 (1H, br, CH-arom.), 9.04 (1H, s, CH-arom.).

Example 105, anti-configuration (11%)

Result of LC/MS [M+H]⁺: 494.0;

$^1$H NMR (CDCl$_3$): δ1.56 (3H, s, CH$_3$), 2.74-2.60 (2H, m, CH$_2$), 2.91-2.80 (2H, m, CH$_2$), 5.25 (1H, quint, CH), 6.98 (1H, d, CH-arom.), 7.16 (1H, t, CH-arom.), 7.34 (1H, d, CH-arom.), 7.53-7.42 (1H, m, CH-arom.), 7.94 (1H, s, CH-arom.), 8.56 (1H, d, CH-arom.), 9.04 (1H, s, CH-arom.).

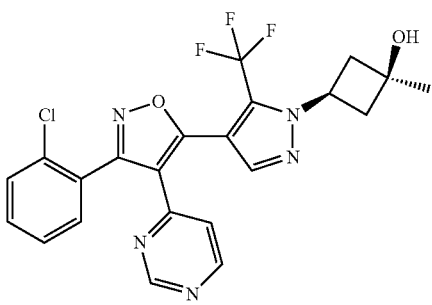 [SMILES: C[C@]1(O)C[C@@H](n2ncc(-c3onc(-c4ccccc4Cl)c3-c3ccncn3)c2C(F)(F)F)C1]

Example 106

3-{4-[3-(2-chlorophenyl)-4-(pyrimidin-4-yl)-1,2-oxazol-5-yl]-5-(trifluoromethyl)-1H-pyrazol-1-yl}-1-methylcyclobutan-1-ol (Syn-Configuration)

Step 1: 1-(1-{3-[(tert-butyldimethylsilyl)oxy]-3-methylcyclobutyl}-5-(trifluoromethyl)-1H-pyrazol-4-yl)-2-(pyrimidin-4-yl)ethan-1-one (syn-configuration) (0.18 mmol) and 2-chloro-N-hydroxybenzimidoyl chloride; the reaction was conducted at 50° C.; the residue was purified by prep. TLC on silica gel (eluent: petroleum ether/ethyl acetate 3:1) to give 4-[3-(2-chlorophenyl)-5-{1-[3-[(tert-butyldimethylsilyl)oxy]-3-methylcyclobutyl]-5-(trifluoromethyl)-1H-pyrazol-4-yl}-1,2-oxazol-4-yl]pyrimidine (syn-configuration) (48%);

Step 2, general cycloaddition procedure: Mixture after step 2 was purified by prep. TLC on silica gel (eluent: petroleum ether/ethyl acetate 1:5) to give the title compound (20%).

Result of LC/MS [M+H]⁺: 476.2;

$^1$H NMR (CDCl$_3$): δ1.50 (3H, s, CH$_3$), 2.97-2.72 (4H, m, 2xCH$_2$), 4.70 (1H, quint, CH), 6.97-6.81 (1H, m, CH-arom.), 7.56-7.40 (3H, m, 3xCH-arom.), 7.60 (1H, d, CH-arom.), 8.00 (1H, s, CH-arom.), 8.54 (1H, br, CH-arom.), 9.07 (1H, s, CH-arom.).

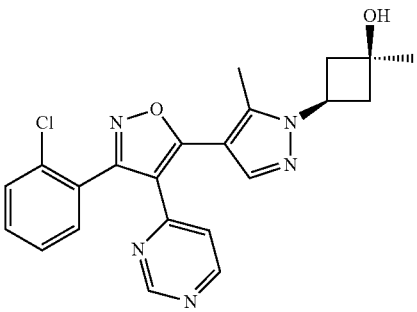 [SMILES: Cc1c(-c2onc(-c3ccccc3Cl)c2-c2ccncn2)cnn1[C@H]1C[C@@](C)(O)C1]

Example 107

3-{4-[3-(2-chlorophenyl)-4-(pyrimidin-4-yl)-1,2-oxazol-5-yl]-5-methyl-1H-pyrazol-1-yl}-1-methylcyclobutan-1-ol (Syn-Configuration)

Step 1: 1-(1-{3-[(tert-butyldimethylsilyl)oxy]-3-methylcyclobutyl}-5-methyl-1H-pyrazol-4-yl)-2-(pyrimidin-4-yl)ethan-1-one (syn-configuration) (0.13 mmol) and 2-chloro-N-hydroxybenzimidoyl chloride; the reaction was conducted at 50° C.; the residue was purified by prep. TLC on silica gel (eluent: petroleum ether/ethyl acetate 3:1) to give 4-[3-(2-chlorophenyl)-5-{5-methyl-1-[3-[(tert-butyldimethylsilyl)oxy]-3-methylcyclobutyl]-1H-pyrazol-4-yl}-1,2-oxazol-4-yl]pyrimidine (syn-configuration) (60%);

Step 2, general cycloaddition procedure: Mixture after step 2 was purified by prep. TLC on silica gel (eluent: petroleum ether/ethyl acetate 1:5) to give the title compound (25%).

Result of LC/MS [M+H]⁺: 422.3;

$^1$H NMR (CDCl$_3$): δ1.47 (3H, s, CH$_3$), 2.49 (3H, s, CH$_3$), 2.80-2.65 (4H, m, CH$_2$), 3.51 (1H, br, OH), 4.51 (1H, quint, CH), 6.95 (1H, dd, CH-arom.), 7.49-7.36 (3H, m, 3xCH-arom.), 7.60-7.49 (1H, m, CH-arom.), 7.97 (1H, s, CH-arom.), 8.54 (1H, d, CH-arom.), 9.16 (1H, d, CH-arom.).

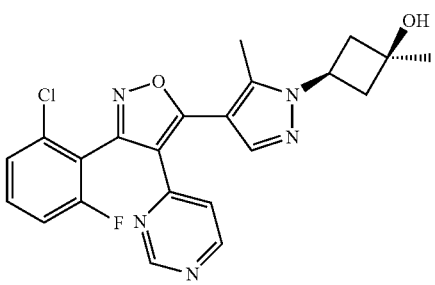 [SMILES: Cc1c(-c2onc(-c3c(F)cccc3Cl)c2-c2ccncn2)cnn1[C@H]1C[C@@](C)(O)C1]

Example 108

3-{4-[3-(2-chloro-6-fluorophenyl)-4-(pyrimidin-4-yl)-1,2-oxazol-5-yl]-5-methyl-1H-pyrazol-1-yl}-1-methylcyclobutan-1-ol (Syn-Configuration)

Step 1: 1-(1-{3-[(tert-butyldimethylsilyl)oxy]-3-methylcyclobutyl}-5-methyl-1H-pyrazol-4-yl)-2-(pyrimidin-4-yl)ethan-1-one (syn-configuration) (0.12 mmol) and 2-chloro-6-fluoro-N-hydroxybenzimidoyl chloride; the reaction was conducted at 50° C.; the residue was purified by prep. TLC on silica gel (eluent: petroleum ether/ethyl acetate 3:1) to give 4-[3-(2-chloro-6-fluorophenyl)-5-{5-methyl-1-[3-[(tert-butyldimethylsilyl)oxy]-3-methylcyclobutyl]-1H-pyrazol-4-yl}-1,2-oxazol-4-yl]pyrimidine (syn-configuration) (72%);

Step 2, general cycloaddition procedure: Mixture after step 2 was purified by prep. TLC on silica gel (eluent: petroleum ether/ethyl acetate 1:5) to give the title compound (13%).

Result of LC/MS [M+H]⁺: 440.3;

¹H NMR (CDCl₃): δ1.47 (3H, s, CH₃), 2.49 (3H, s, CH₃), 2.81-2.66 (4H, m, CH₂), 3.46 (1H, br, OH), 4.52 (1H, quint, CH), 7.05 (1H, dd, CH-arom.), 7.11 (1H, td, CH-arom.), 7.30 (1H, dt, CH-arom.), 7.47-7.37 (1H, m, CH), 7.93 (1H, s, CH-arom.), 8.57 (1H, d, CH-arom.), 9.12 (1H, d, CH-arom.).

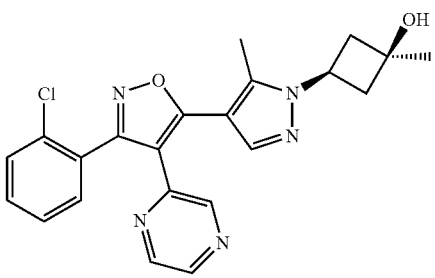 [SMILES: Cc1c(-c2onc(-c3ccccc3Cl)c2-c2cnccn2)cnn1[C@H]1C[C@@](C)(O)C1]

Example 109

3-{4-[3-(2-chlorophenyl)-4-(pyrazin-2-yl)-1,2-oxazol-5-yl]-5-methyl-1H-pyrazol-1-yl}-1-methylcyclobutan-1-ol (Syn-Configuration)

Step 1: 1-(1-{3-[(tert-butyldimethylsilyl)oxy]-3-methylcyclobutyl}-5-methyl-1H-pyrazol-4-yl)-2-(pyrazin-2-yl)ethan-1-one (syn-configuration) (0.47 mmol) and 2-chloro-N-hydroxybenzimidoyl chloride; the reaction was conducted at 50° C.; the residue was purified by prep. TLC on silica gel (eluent: petroleum ether/ethyl acetate 3:1) to give 2-[3-(2-chlorophenyl)-5-{5-methyl-1-[3-[(tert-butyldimethylsilyl)oxy]-3-methylcyclobutyl]-1H-pyrazol-4-yl}-1,2-oxazol-4-yl]pyrazine (syn-configuration) (25%);

Step 2, general cycloaddition procedure: Mixture after step 2 was purified by prep. TLC on silica gel (eluent: petroleum ether/ethyl acetate 1:5) to give the title compound (32%).

Result of LC/MS [M+H]⁺: 422.3;

¹H NMR (CDCl₃): δ1.46 (3H, s, CH₃), 2.49 (3H, s, CH₃), 2.81-2.61 (4H, m, CH₂), 3.51 (1H, br, OH), 4.50 (1H, quint, CH), 7.45-7.33 (3H, m, 3xCH-arom.), 7.62-7.51 (1H, m, CH-arom.), 7.81 (1H, d, CH-arom.), 8.28 (1H, s, CH-arom.), 8.43 (1H, d, CH-arom.), 8.55 (1H, t, CH-arom.).

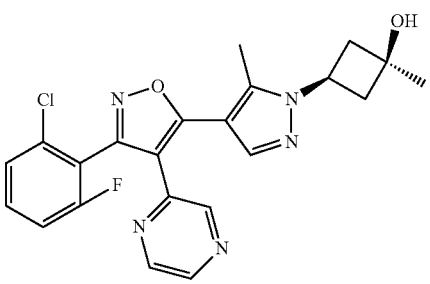 [SMILES: Cc1c(-c2onc(-c3c(F)cccc3Cl)c2-c2cnccn2)cnn1[C@H]1C[C@@](C)(O)C1]

Example 110

3-{4-[3-(2-chloro-6-fluorophenyl)-4-(pyrazin-2-yl)-1,2-oxazol-5-yl]-5-methyl-1H-pyrazol-1-yl}-1-methylcyclobutan-1-ol (Syn-Configuration)

Step 1: 1-(1-{3-[(tert-butyldimethylsilyl)oxy]-3-methylcyclobutyl}-5-methyl-1H-pyrazol-4-yl)-2-(pyrazin-2-yl)ethan-1-one (syn-configuration) (0.15 mmol) and 2-chloro-6-fluoro-N-hydroxybenzimidoyl chloride; the reaction was conducted at 50° C.; the residue was purified by prep. TLC on silica gel (eluent: petroleum ether/ethyl acetate 3:1) to give 2-[3-(2-chloro-6-fluorophenyl)-5-{5-methyl-1-[3-[(tert-butyldimethylsilyl)oxy]-3-methylcyclobutyl]-1H-pyrazol-4-yl}-1,2-oxazol-4-yl]pyrazine (syn-configuration) (19%);

Step 2, general cycloaddition procedure: Mixture after step 2 was purified by prep. TLC on silica gel (eluent: petroleum ether/ethyl acetate 1:5) to give the title compound (13%).

Result of LC/MS [M+H]⁺: 440.3;

¹H NMR (CDCl₃): δ1.46 (3H, s, CH₃), 2.51 (3H, s, CH₃), 2.82-2.68 (4H, m, CH₂), 4.52 (1H, quint, CH), 7.10 (1H, td, CH-arom.), 7.30-7.27 (1H, m, CH-arom.), 7.45-7.34 (1H, m, CH-arom.), 7.88 (1H, s, CH-arom.), 8.36 (1H, s, CH-arom.), 8.44 (1H, s, CH-arom.), 8.55 (1H, s, CH-arom.).

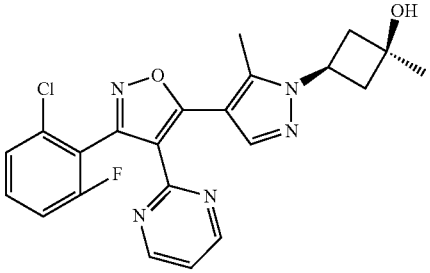 [SMILES: Cc1c(-c2onc(-c3c(F)cccc3Cl)c2-c2ncccn2)cnn1[C@H]1C[C@@](C)(O)C1]

Example 111

3-{4-[3-(2-chloro-6-fluorophenyl)-4-(pyrimidin-2-yl)-1,2-oxazol-5-yl]-5-methyl-1H-pyrazol-1-yl}-1-methylcyclobutan-1-ol (Syn-Configuration)

Step 1: 1-(1-(3-((tert-butyldimethylsilyl)oxy)-3-methylcyclobutyl)-5-methyl-1H-pyrazol-4-yl)-2-(pyrimidin-2-yl)ethan-1-one (syn-configuration) (0.15 mmol) and 2-chloro-6-fluoro-N-hydroxybenzimidoyl chloride; the reaction was conducted at 50° C.; the residue was purified by prep. TLC on silica gel (eluent: petroleum ether/ethyl acetate 3:1) to give 2-[3-(2-chloro-6-fluorophenyl)-5-{5-methyl-1-[3-[(tert-butyldimethylsilyl)oxy]-3-methylcyclobutyl]-1H-pyrazol-4-yl]-1,2-oxazol-4-yl}pyrimidine (syn-configuration) (36%);

Result of LC/MS [M+H]+: 554.2;

Step 2, general cycloaddition procedure: Mixture after step 2 was purified by prep. TLC on silica gel (eluent: petroleum ether/ethyl acetate 1:5) to give the title compound (21%).

Result of LC/MS [M+H]+: 440.3;

1NMR (CDCl3): δ1.47 (3H, s, CH3), 2.62 (3H, s, CH3), 3.01-2.70 (4H, m, CH2), 4.58 (1H, quint, CH), 7.16-7.04 (2H, m, 2xCH-arom.), 7.32-7.20 (1H, m, CH-arom.), 7.43-7.32 (1H, m, CH-arom.), 8.47 (1H, br, CH-arom.), 8.59 (2H, d, 2xCH-arom.).

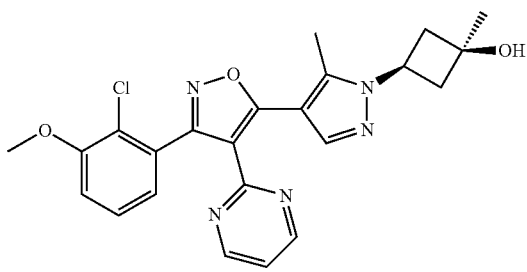 [SMILES: COc1cccc(-c2noc(-c3cnn([C@H]4C[C@@](C)(O)C4)c3C)c2-c2ncccn2)c1Cl]

Example 112

3-{4-[3-(2-chloro-3-methoxyphenyl)-4-(pyrimidin-2-yl)-1,2-oxazol-5-yl]-5-methyl-1H-pyrazol-1-yl}-1-methylcyclobutan-1-ol (Syn-Configuration)

Alternative Step 1 as described for Example 99 (reaction with NaH): 1-(1-(3-((tert-butyldimethylsilyl)oxy)-3-methylcyclobutyl)-5-methyl-1H-pyrazol-4-yl)-2-(pyrimidin-2-yl)ethan-1-one (syn-configuration) (0.25 mmol) and 2-chloro-3-methoxy-N-hydroxybenzimidoyl chloride; 2-[3-(2-chloro-3-methoxyphenyl)-5-{5-methyl-1-[3-[(tert-butyldimethylsilyl)oxy]-3-methylcyclobutyl]-1H-pyrazol-4-yl]-1,2-oxazol-4-yl]pyrimidine (syn-configuration) (36%) was used in next step as crude material without purification by chromatography on silica gel;

Result of LC/MS [M+H]+: 566.5.

Alternative Step 2 as described for Example 103 (O-desilylation using TBAF): The residue was purified by column chromatography on silica gel (eluent: CH2Cl2/MeOH/NH3 100:10:1 and again with eluent: petroleum ether/ethyl acetate 4:1) to give the title compound (17%).

Result of LC/MS [M+H]+: 452.4;

1H NMR (CDCl3): δ1.45 (3H, s, CH3), 2.52 (3H, s, CH3), 2.72 (4H, d, 2xCH2), 3.89 (3H, s, OCH3), 4.50 (1H, quint, CH), 7.03 (1H, dd, CH-arom.), 7.08 (1H, t, CH-arom.), 7.22 (1H, dd, CH-arom.), 7.34 (1H, t, CH-arom.), 8.11 (1H, s, CH-arom.), 8.59 (2H, d, CH-arom.).

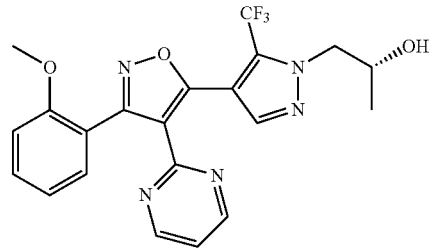 [SMILES: COc1ccccc1-c1noc(-c2cnn(C[C@@H](C)O)c2C(F)(F)F)c1-c1ncccn1]

Example 113

(2R)-1-{4-[3-(2-methoxyphenyl)-4-(pyrimidin-2-yl)-1,2-oxazol-5-yl]-5-(trifluoromethyl)-1H-pyrazol-1-yl}propan-2-ol Alternative Step 1 as described for Example 99 (reaction with NaH): (R)-1-(1-(2-((tert-butyldimethylsilyl)oxy)propyl)-5-(trifluoromethyl)-1H-pyrazol-4-yl)-2-(pyrimidin-2-yl)ethan-1-one (1.0 mmol) and 2-methoxy-N-hydroxybenzimidoyl chloride; the residue was purified by prep. TLC on silica gel (eluent: petroleum ether/ethyl acetate 3:1) to give 2-(5-{1-[(2R)-2-1[(tert-butyldimethylsilyl)oxy]propyl]-5-(trifluoromethyl)-1H-pyrazol-4-yl}-3-(2-methoxyphenyl)-1,2-oxazol-4-yl)pyrimidine (34%);

Step 2, general cycloaddition procedure: Mixture after step 2 was purified by prep. TLC on silica gel (eluent: petroleum ether/ethyl acetate 1:5) to give the title compound (86%).

Result of LC/MS [M+H]+: 445.9;

1H NMR (CDCl3): δ1.30 (3H, d, CH3), 3.29 (3H, s, OCH3), 4.19 (1H, dd, CH), 4.46-4.26 (2H, m, CH2), 6.81 (1H, d, CH-arom.), 7.15-7.05 (2H, m, 2xCH-arom.), 7.43 (1H, td, CH-arom.), 7.69 (1H, dd, CH-arom.), 8.05 (1H, s, CH-arom.), 8.60 (2H, d, 2xCH-arom.).

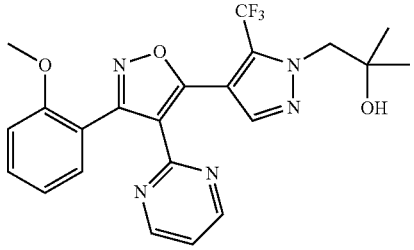 [SMILES: COc1ccccc1-c1noc(-c2cnn(CC(C)(C)O)c2C(F)(F)F)c1-c1ncccn1]

Example 114

1-{4-[3-(2-methoxyphenyl)-4-(pyrimidin-2-yl)-1,2-oxazol-5-yl]-5-(trifluoromethyl)-1H-pyrazol-1-yl}-2-methylpropan-2-ol To a stirred solution of Example 113 (0.25 mmol) in CH2Cl2 (1.5 mL) was added Dess-Martin periodinane (3.5 eq.). The reaction mixture was stirred at room temperature for 18 h. The reaction mixture was quenched by adding aq. Na2S2O3, and extracted with CH2Cl2. Combined organic layers were washed with saturated. aq. NaHCO₃ and brine, dried over anhydrous Na₂SO₄, and concentrated under reduced pressure. The residue was purified by column chromatography on silica gel (eluent: petroleum ether/ethyl acetate 3:1) to give 1-{4-[3-(2-methoxyphenyl)-4-(pyrimidin-2-yl)-1,2-oxazol-5-yl]-5-(trifluoromethyl)-1H-pyrazol-1-yl}propan-2-one as a colorless solid (61%).

Result of LC/MS [M+H]⁺: 443.8;

¹H NMR (CDCl₃): δ2.18 (3H, s, CH₃), 3.29 (3H, s, OCH₃), 5.11 (2H, s, CH₂), 6.81 (1H, d, CH-arom.), 7.14-7.09 (2H, m, 2xCH-arom.), 7.48-7.39 (1H, m, CH-arom.), 7.69 (1H, dd, CH-arom.), 8.12 (1H, s, CH-arom.), 8.61 (2H, d, 2xCH-arom.).

To a solution of this propanone derivative (0.15 mmol) in THF (3 mL) was added dropwise MeMgBr (1 M in THF; 10 eq.) at 0° C. under N₂. The reaction mixture was stirred at room temperature for 18 h. The reaction was quenched by adding saturated aq. NH₄Cl and extracted with CH₂Cl₂. Combined organic layers were washed with brine, dried over anhydrous Na₂SO₄, and concentrated under reduced pressure. The residue was purified by column chromatography on silica gel (eluent: petroleum ether/ethyl acetate 5:1) to give the title compound as a colorless solid (10%).

Result of LC/MS [M+H]⁺: 459.8;

¹H NMR (CDCl₃): δ1.23 (6H, d, 2xCH₃), 3.30 (3H, s, OCH₃), 4.26 (2H, s, CH₂), 6.82 (1H, d, CH-arom.), 7.15-7.05 (2H, m, 2xCH-arom.), 7.44 (1H, td, CH-arom.), 7.68 (1H, dd, CH-arom.), 8.06 (1H, s, CH-arom.), 8.58 (2H, d, 2xCH-arom.).

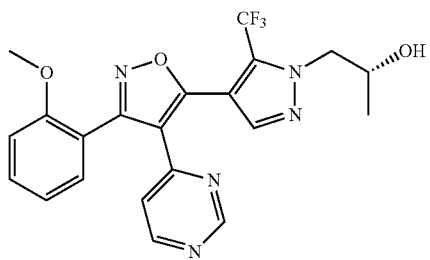 [SMILES: COc1ccccc1-c1noc(-c2cnn(C[C@@H](C)O)c2C(F)(F)F)c1-c1ccncn1]

Example 115

(2R)-1-{4-[3-(2-methoxyphenyl)-4-(pyrimidin-4-yl)-1,2-oxazol-5-yl]-5-(trifluoromethyl)-1H-pyrazol-1-yl}propan-2-ol Alternative Step 1 as described for Example 99 (reaction with NaH): (R)-1-(1-(2-((tert-butyldimethylsilyl)oxy)propyl)-5-(trifluoromethyl)-1H-pyrazol-4-yl)-2-(pyrimidin-4-yl)ethan-1-one (1.6 mmol) and 2-methoxy-N-hydroxybenzimidoyl chloride; the residue was purified by prep. TLC on silica gel (eluent: petroleum ether/ethyl acetate 3:1) to give 4-(5-{1-[(2R)-2-[(tert-butyldimethylsilyl)oxy]propyl}-5-(trifluoromethyl)-1H-pyrazol-4-yl]-3-(2-methoxyphenyl)-1,2-oxazol-4-yl)pyrimidine (55%);

Step 2, general cycloaddition procedure: Mixture after step 2 was purified by prep. TLC on silica gel (eluent: petroleum ether/ethyl acetate 1:5) to give the title compound (88%).

Result of LC/MS [M+H]⁺: 446.0;

¹H NMR (CDCl₃): δ1.30 (3H, d, CH₃), 3.38 (3H, s, OCH₃), 4.21 (1H, dd, CH), 4.45-4.27 (2H, m, CH₂), 6.89 (1H, d, CH-arom.), 6.95 (1H, d, CH-arom.), 7.13 (1H, td, CH-arom.), 7.50 (1H, td, CH-arom.), 7.62 (1H, dd, CH-arom.), 7.99 (1H, s, CH-arom.), 8.53 (1H, br, CH-arom.), 9.10 (1H, s, CH-arom.).

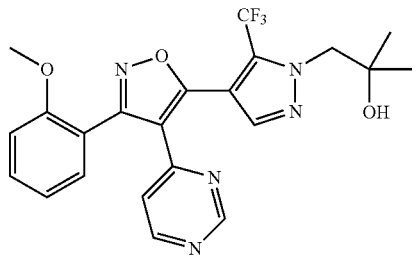 [SMILES: COc1ccccc1-c1noc(-c2cnn(CC(C)(C)O)c2C(F)(F)F)c1-c1ccncn1]

Example 116

1-{4-[3-(2-methoxyphenyl)-4-(pyrimidin-4-yl)-1,2-oxazol-5-yl]-5-(trifluoromethyl)-1H-pyrazol-1-yl}-2-methylpropan-2-ol 2-Propanol derivative Example 115 (0.25 mmol) was converted into the corresponding propanone and then into the corresponding 2-methyl-2-propanol according to the procedures described for Example 114. Oxidation to 1-{1-[3-(2-methoxyphenyl)-4-(pyrimidin-4-yl)-1,2-oxazol-5-yl]-5-(trifluoromethyl)-1H-pyrazol-1-yl}propan-2-one was achieved with 83% yield;

Result of LC/MS [M+H]⁺: 443.8;

¹H NMR (CDCl₃): δ1.26 (6H, s, 2*CH₃), 2.24 (3H, s, CH₃), 2.95 (1H, s, OH), 3.42 (3H, s, CH₃), 5.17 (2H, s, CH₂), 6.92 (1H, d, CH-arom.), 7.08 (1H, d, CH-arom.), 7.15 (1H, t, CH-arom.), 7.53 (1H, t, CH-arom.), 7.63 (1H, d, CH-arom.), 8.03 (1H, s, CH-arom.), 8.55 (1H, d, CH-arom.), 9.14 (1H, s, CH-arom.);

Grignard treatment provided the title compound in 10% yield.

Result of LC/MS [M+H]⁺: 459.9;

¹H NMR (CDCl₃): δ1.24 (6H, s, 2xCH₃), 3.42 (3H, s, OCH₃), 4.28 (2H, s, CH₂), 6.92 (1H, d, CH-arom.), 7.01 (1H, d, CH-arom.), 7.15 (1H, td, CH-arom.), 7.53 (1H, td, CH-arom.), 7.62 (1H, dd, CH-arom.), 8.01 (1H, s, CH-arom.), 8.55 (1H, d, CH-arom.), 9.08 (1H, s, CH-arom.).

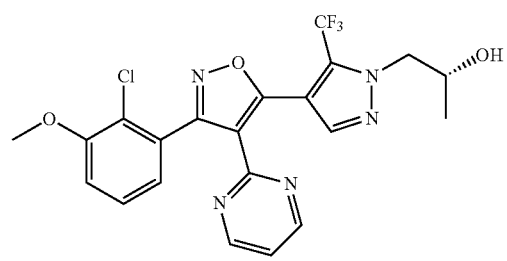 [SMILES: COc1cccc(-c2noc(-c3cnn(C[C@@H](C)O)c3C(F)(F)F)c2-c2ncccn2)c1Cl]

Example 117

(2R)-1-{4-[3-(2-chloro-3-methoxyphenyl)-4-(pyrimidin-2-yl)-1,2-oxazol-5-yl]-5-(trifluoromethyl)-1H-pyrazol-1-yl}propan-2-ol Alternative Step 1 as described for Example 99 (reaction with NaH): (R)-1-(1-(2-((tert-butyldimethylsilyl)oxy)propyl)-5-(trifluoromethyl)-1H-pyrazol-4-yl)-2-(pyrimidin-2-yl)ethan-1-one (3.0 mmol) and 2-chloro-3-methoxy-N-hydroxybenzimidoyl chloride; the residue was purified by prep. TLC on silica gel (eluent: petroleum ether/ethyl acetate 3:1) to give 2-(5-{1-[(2R)-2-[(tert-butyldimethylsilyl)oxy]propyl]-5-(trifluoromethyl)-1H-pyrazol-4-yl}-3-(2-chloro-3-methoxyphenyl)-1,2-oxazol-4-yl)pyrimidine (83%);

Step 2, general cycloaddition procedure: Mixture after step 2 was purified by prep. TLC on silica gel (eluent: petroleum ether/ethyl acetate 1:5) to give the title compound (77%).

Result of LC/MS [M+H]$^+$: 479.8;

$^1$H NMR (CDCl$_3$): δ1.30 (3H, d, CH$_3$), 3.85 (3H, s, OCH$_3$), 4.21 (1H, dd, CH), 4.44-4.27 (2H, m, CH$_2$), 6.97-6.89 (2H, m, 2xCH-arom.), 7.09 (1H, t, CH-arom.), 7.57-7.52 (1H, m, CH-arom.), 8.04 (1H, s, CH-arom.), 8.55 (1H, s, CH-arom.).

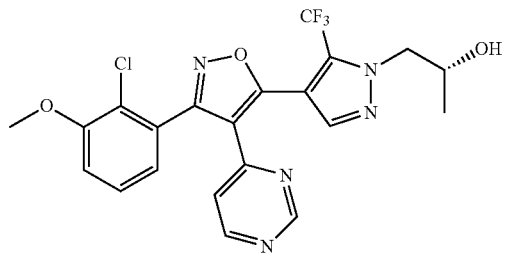

Example 119

(2R)-1-{4-[3-(2-chloro-3-methoxyphenyl)-4-(pyrimidin-4-yl)-1,2-oxazol-5-yl]-5-(trifluoromethyl)-1H-pyrazol-1-yl}propan-2-ol Step 1: (R)-1-(1-(2-((tert-butyldimethylsilypoxy)propyl)-5-(trifluoromethyl)-1H-pyrazol-4-yl)-2-(pyrimidin-4-yl)ethan-1-one (2.0 mmol) and 2-chloro-3-methoxy-N-hydroxybenzimidoyl chloride; THF was used instead of DMF; the reaction was conducted at 50° C.; crude 4-(5-{1-[(2R)-2-[(tert-butyldimethylsilyl)oxy]propyl]-5-(trifluoromethyl)-1H-pyrazol-4-yl}-3-(2-chloro-3-methoxyphenyl)-1,2-oxazol-4-yl)pyrimidine (quant.) was directly used for O-desilylation;

Step 2, general cycloaddition procedure: Mixture after step 2 was purified by prep. TLC on silica gel (eluent: petroleum ether/ethyl acetate 1:5) to give the title compound (83%).

Result of LC/MS [M+H]$^+$: 479.8;

$^1$H NMR (CDCl$_3$): δ1.32 (3H, d, CH$_3$), 3.88 (3H, s, OCH$_3$), 4.23 (1H, dd, CH), 4.49-4.29 (2H, m, CH$_2$), 6.86 (1H, d, CH-arom.), 7.04-6.93 (2H, m, CH-arom.), 7.49 (1H, d, CH-arom.), 8.00 (1H, s, CH-arom.), 8.52 (1H, br, CH-arom.), 9.06 (1H, s, CH-arom.).

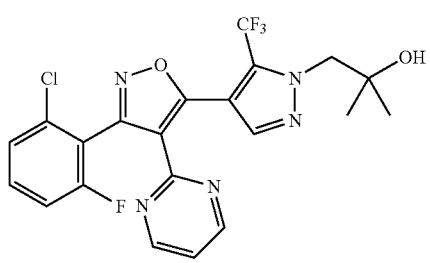 [SMILES: CC(C)(O)Cn1ncc(-c2onc(-c3c(F)cccc3Cl)c2-c2ncccn2)c1C(F)(F)F]

Example 118

1-{4-[3-(2-chloro-6-fluorophenyl)-4-(pyrimidin-2-yl)-1,2-oxazol-5-yl]-5-(trifluoromethyl)-1H-pyrazol-1-yl}-2-methylpropan-2-ol 2-Propanol derivative Example 97 (1.6 mmol) was converted into the corresponding propanone and then into the corresponding 2-methyl-2-propanol according to the procedures described for Example 114. Oxidation to 1-(4-(3-(2-chloro-6-fluorophenyl)-4-(pyrimidin-2-yl)isoxazol-5-yl)-5-(trifluoromethyl)-1H-pyrazol-1-yl)propan-2-one was achieved with 67% yield;

Result of LC/MS [M+H]$^+$: 465.7;

$^1$H NMR (CDCl$_3$): δ2.20 (3H, s, CH$_3$), 5.14 (2H, s, CH$_2$), 7.15-7.02 (2H, m, CH-arom.), 7.31-7.27 (1H, m, CH-arom.), 7.45-7.33 (1H, m, CH-arom.), 8.12 (1H, s, CH-arom.), 8.49 (2H, d, 2xCH-arom.).

Grignard treatment provided the title compound in 50% yield.

Result of LC/MS [M+H]$^+$: 481.8;

$^1$H NMR (CDCl$_3$): δ1.25 (6H, s, 2xCH$_3$), 4.30 (2H, s, CH$_2$), 7.09-7.00 (1H, m, CH-arom.), 7.15-7.09 (1H, m, CH-arom.), 7.31-7.24 (1H, m, CH-arom.), 7.44-7.34 (1H, m, CH-arom.), 8.04 (1H, br, CH-arom.), 8.48-8.42 (2H, m, 2xCH-arom.).

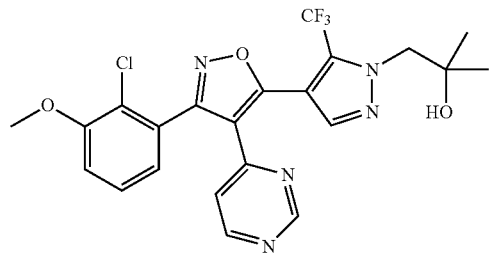 [SMILES: COc1cccc(-c2noc(-c3cnn(CC(C)(C)O)c3C(F)(F)F)c2-c2ccncn2)c1Cl]

Example 120

1-{4-[3-(2-chloro-3-methoxyphenyl)-4-(pyrimidin-4-yl)-1,2-oxazol-5-yl]-5-(trifluoromethyl)-1H-pyrazol-1-yl}-2-methylpropan-2-ol 2-Propanol derivative Example 119 (0.25 mmol) was converted into the corresponding propanone and then into the corresponding 2-methyl-2-propanol according to the procedures described for Example 114. Oxidation to 1-{4-[3-(2-chloro-3-methoxyphenyl)-4-(pyrimidin-4-yl)-1,2-oxazol-5-yl]-5-(trifluoromethyl)-1H-pyrazol-1-yl}propan- 2-one was achieved with 76% yield, Grignard treatment provided the title compound in 16% yield.

Result of LC/MS [M+H]⁺: 494.2;

¹H NMR (CDCl₃): δ1.25 (6H, s, 2xCH₃), 3.88 (3H, s, OCH₃), 4.29 (2H, s, CH₂), 6.85 (1H, d, CH-arom.), 7.03-6.95 (2H, m, 2xCH-arom.), 7.49 (1H, d, CH-arom.), 8.01 (1H, s, CH-arom.), 8.52 (1H, d, CH-arom.), 9.02 (1H, s, CH-arom.).

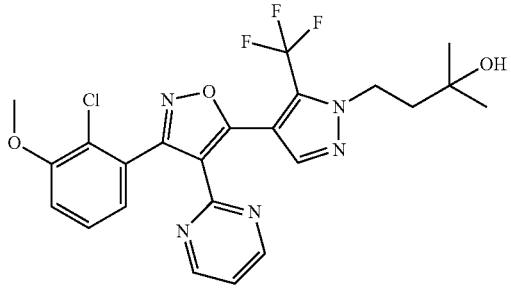 [SMILES: COc1cccc(-c2noc(-c3cnn(CCC(C)(C)O)c3C(F)(F)F)c2-c2ncccn2)c1Cl]

Example 121

4-{4-[3-(2-chloro-3-methoxyphenyl)-4-(pyrimidin-2-yl)-1,2-oxazol-5-yl]-5-(trifluoromethyl)-1H-pyrazol-1-yl}-2-methylbutan-2-ol Alternative Step 1 as described for Example 99 (reaction with NaH): 1-(1-{3-methyl-3-[(trimethylsilyl)oxy]butyl}-5-(trifluoromethyl)-1H-pyrazol-4-yl)-2-(pyrimidin-2-yl)ethan-1-one (0.6 mmol) and 2-chloro-3-methoxy-N-hydroxybenzimidoyl chloride; reaction time: 20 h, reaction conditions led to simultaneous O-desilylation; the residue was purified by prep. TLC on silica gel (eluent: petroleum ether/ethyl acetate 3:1) to give the title compound as yellow oil (11%).

Result of LC/MS [M+H]⁺: 508.3;

¹H NMR (CDCl₃): δ1.31 (6H, s, 2xCH₃), 2.19-2.10 (2H, m, CH₂), 3.91 (3H, s, OCH₃), 4.56-4.44 (2H, m, CH₂), 7.09-7.02 (2H, m, 2xCH-arom.), 7.37 (1H, t, CH-arom.), 8.02 (1H, s, CH-arom.), 8.52 (2H, d, 2xCH-arom.).

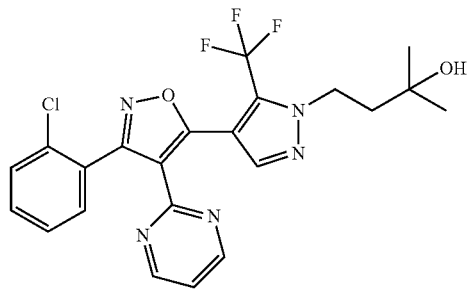 [SMILES: CC(C)(O)CCn1ncc(-c2onc(-c3ccccc3Cl)c2-c2ncccn2)c1C(F)(F)F]

Example 122

4-{4-[3-(2-chlorophenyl)-4-(pyrimidin-2-yl)-1,2-oxazol-5-yl]-5-(trifluoromethyl)-1H-pyrazol-1-yl}-2-methylbutan-2-ol Alternative Step 1 as described for Example 99 (reaction with NaH): 1-(1-{3-methyl-3-[(trimethylsilyl)oxy]butyl}-5-(trifluoromethyl)-1H-pyrazol-4-yl)-2-(pyrimidin-2-yl)ethan-1-one (0.41 mmol) and 2-chloro-N-hydroxybenzimidoyl chloride; reaction time: 20 h, reaction conditions led to simultaneous O-desilylation; the residue was purified by prep. TLC on silica gel (eluent: CH₂Cl₂/MeOH 95:5 and again with eluent: petroleum ether/ethyl acetate 1:1) to give the title compound as pale yellow oil (9%).

Result of LC/MS [M+H]⁺: 478.4;

¹H NMR (CDCl₃): δ1.32 (6H, s, 2xCH₃), 2.18-2.09 (2H, m, CH₂), 4.55-4.46 (2H, m, CH₂), 7.07 (1H, t, CH-arom.), 7.43-7.36 (3H, m, 3xCH-arom.), 7.66-7.59 (1H, m, CH-arom.), 8.01 (1H, s, CH-arom.), 8.52 (2H, d, 2xCH-arom.).

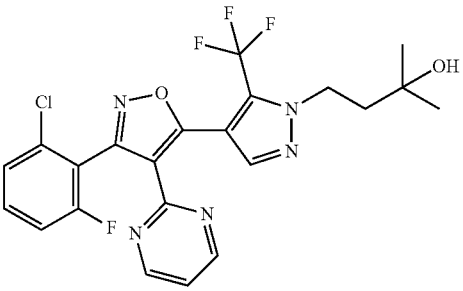 [SMILES: CC(C)(O)CCn1ncc(-c2onc(-c3c(F)cccc3Cl)c2-c2ncccn2)c1C(F)(F)F]

Example 123

4-{4-[3-(2-chloro-6-fluorophenyl)-4-(pyrimidin-2-yl)-1,2-oxazol-5-yl]-5-(trifluoromethyl)-1H-pyrazol-1-yl}-2-methylbutan-2-ol Alternative Step 1 as described for Example 99 (reaction with NaH): 1-(1-{3-methyl-3-[(trimethylsilyl)oxy]butyl}-5-(trifluoromethyl)-1H-pyrazol-4-yl)-2-(pyrimidin-2-yl)ethan-1-one (0.41 mmol) and 2-chloro-6-fluoro-N-hydroxybenzimidoyl chloride; reaction time: 18 h, reaction conditions led to simultaneous O-desilylation; the residue was purified by prep. TLC on silica gel (eluent: CH₂Cl₂/MeOH 95:5 and again with eluent: CH₂Cl₂/MeOH 95:5) to give the title compound as colorless oil (27%).

Result of LC/MS [M+H]⁺: 496.0;

¹H NMR (CDCl₃): δ1.33 (6H, s, 2xCH₃), 2.21-2.11 (2H, m, CH₂), 4.57-4.47 (2H, m, CH₂), 7.04 (1H, t, CH-arom.), 7.10 (1H, td, CH-arom.), 7.30-7.26 (1H, m, CH-arom.), 7.44-7.33 (1H, m, CH-arom.), 8.00 (1H, s, CH-arom.), 8.48 (2H, d, 2xCH-arom.).

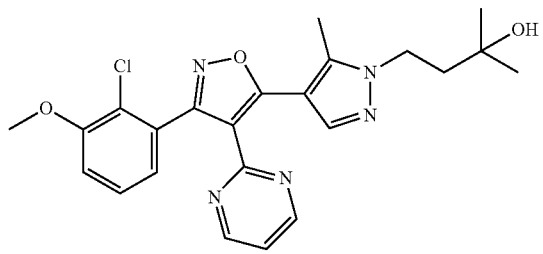 [SMILES: COc1cccc(-c2noc(-c3cnn(CCC(C)(C)O)c3C)c2-c2ncccn2)c1Cl]

Example 124

4-{4-[3-(2-chloro-3-methoxyphenyl)-4-(pyrimidin-2-yl)-1,2-oxazol-5-yl]-5-methyl-1H-pyrazol-1-yl}-2-methylbutan-2-ol Alternative Step 1 as described for Example 99 (reaction with NaH): 1-(5-methyl-1-{3-methyl-3-[(trimethylsilyl)

oxy]butyl}-1H-pyrazol-4-yl)-2-(pyrimidin-2-yl)ethan-1-one (0.16 mmol) and 2-chloro-3-methoxy-N-hydroxybenzimidoyl chloride; reaction time: 3 h, reaction conditions led to simultaneous O-desilylation; the residue was purified by flash column chromatography on silica gel (eluent: CH$_2$Cl$_2$/MeOH 95:5) to give the title compound as a yellowish solid (24%).

Result of LC/MS [M+H]$^+$: 454.0;

$^1$H NMR (CDCl$_3$): δ1.28 (6H, s, 2xCH$_3$), 2.07-1.98 (2H, m, CH$_2$), 2.56 (3H, s, CH$_3$), 3.89 (3H, s, OCH$_3$), 4.34-4.22 (2H, m, CH$_2$), 7.03 (1H, dd, CH-arom.), 7.08 (1H, t, CH-arom.), 7.22 (1H, dd, CH-arom.), 7.34 (1H, t, CH-arom.), 8.08 (1H, s, CH-arom.), 8.59 (2H, d, 2xCH-arom.).

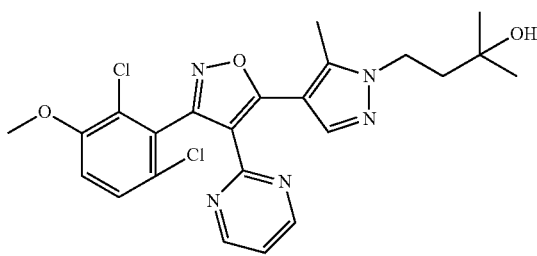 [SMILES: COc1ccc(Cl)c(-c2noc(-c3cnn(CCC(C)(C)O)c3C)c2-c2ncccn2)c1Cl]

Example 125

4-{4-[3-(2,6-dichloro-3-methoxyphenyl)-4-(pyrimidin-2-yl)-1,2-oxazol-5-yl]-5-methyl-1H-pyrazol-1-yl}-2-methylbutan-2-ol Alternative Step 1 as described for Example 99 (reaction with NaH): 1-(5-methyl-1-{3-methyl-3-[(trimethylsilyl)oxy]butyl}-1H-pyrazol-4-yl)-2-(pyrimidin-2-yl)ethan-1-one (0.04 mmol) and 2,6-dichloro-3-methoxy-N-hydroxybenzimidoyl chloride; reaction time: 3 h, reaction conditions led to simultaneous O-desilylation; the residue was purified by flash column chromatography on silica gel (eluent: CH$_2$Cl$_2$/MeOH 95:5) to give the title compound as a reddish oil (15%).

Result of LC/MS [M+H]$^+$: 488.0;

$^1$H NMR (CDCl$_3$): δ1.30 (6H, s, 2xCH$_3$), 2.08-2.00 (2H, m, CH$_2$), 2.62 (3H, s, CH$_3$), 3.93 (3H, s, OCH$_3$), 4.37-4.24 (2H, m, CH$_2$), 6.96 (1H, d, CH-arom.), 7.04 (1H, t, CH-arom.), 7.33 (1H, d, CH-arom.), 8.25 (1H, s, CH-arom.), 8.55 (2H, d, 2xCH-arom.).

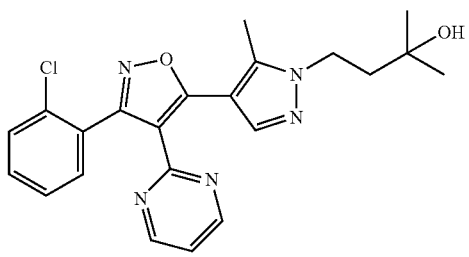 [SMILES: Cc1c(-c2onc(-c3ccccc3Cl)c2-c2ncccn2)cnn1CCC(C)(C)O]

Example 126

4-[4-[3-(2-chlorophenyl)-4-(pyrimidin-2-yl)-1,2-oxazol-5-yl]-5-methyl-1H-pyrazol-1-yl]-2-methylbutan-2-ol Alternative Step 1 as described for Example 99 (reaction with NaH): 1-(5-methyl-1-{3-methyl-3-[(trimethylsilyl)- oxy]butyl}-1H-pyrazol-4-yl)-2-(pyrimidin-2-yl)ethan-1-one (0.1 mmol) and 2-chloro-N-hydroxybenzimidoyl chloride; reaction time: 1.5 h, reaction conditions led to simultaneous O-desilylation; the residue was purified by prep. TLC on silica gel (eluent: CH$_2$Cl$_2$/MeOH 95:5 and again eluent: CH$_2$Cl$_2$/MeOH 95:5) to give the title compound (12%).

Result of LC/MS [M+H]$^+$: 424.0;

$^1$H NMR (CDCl$_3$): δ1.30 (6H, s, 2xCH$_3$), 2.08-2.00 (2H, m, CH$_2$), 2.58 (3H, s, CH$_3$), 4.33-4.26 (2H, m, CH$_2$), 7.10 (1H, t, 2xCH-arom.), 7.42-7.31 (3H, m, 3xCH-arom.), 7.65-7.56 (1H, m, CH-arom.), 8.11 (1H, s, CH-arom.), 8.60 (2H, d, 2xCH-arom.).

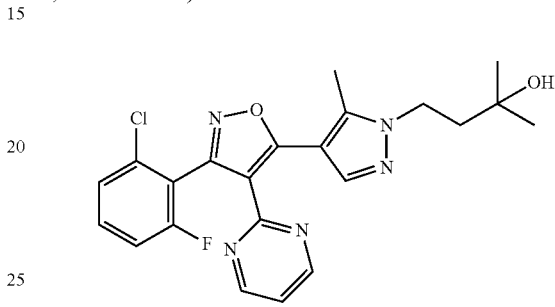

Example 127

4-{4-[3-(2-chloro-6-fluorophenyl)-4-(pyrimidin-2-yl)-1,2-oxazol-5-yl]-5-methyl-1H-pyrazol-1-yl}-2-methylbutan-2-ol Alternative Step 1 as described for Example 99 (reaction with NaH): 1-(5-methyl-1-{3-methyl-3-[(trimethylsilyl)oxy]butyl}-1H-pyrazol-4-yl)-2-(pyrimidin-2-yl)ethan-1-one (0.1 mmol) and 2-chloro-6-fluoro-N-hydroxybenzimidoyl chloride; reaction time: 1.5 h, reaction conditions led to simultaneous O-desilylation; the residue was purified by flash column chromatography on silica gel (eluent: CH$_2$Cl$_2$/MeOH 95:5) to give the title compound as an orange oil (30%).

Result of LC/MS [M+H]$^+$: 442.0;

$^1$H NMR (CDCl$_3$): δ1.30 (6H, s, 2xCH$_3$), 2.04 (2H, t, CH$_2$), 2.60 (3H, s, CH$_3$), 4.30 (2H, t, CH$_2$), 7.14-7.02 (2H, m, 2xCH-arom.), 7.25-7.19 (1H, m, CH-arom.), 7.41-7.30 (1H, m, CH-arom.), 8.22 (1H, s, CH-arom.), 8.56 (2H, d, 2xCH-arom.).

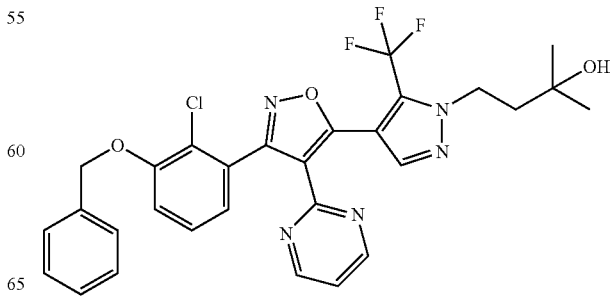

Example 128

4-(4-{3-[3-(benzyloxy)-2-chlorophenyl]-4-(pyrimidin-2-yl)-1,2-oxazol-5-yl}-5-(trifluoromethyl)-1H-pyrazol-1-yl)-2-methylbutan-2-ol

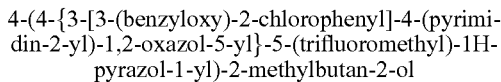

Alternative Step 1 as described for Example 99 (reaction with NaH): 1-(1-{3-methyl-3-[(trimethylsilyl)oxy]butyl}-5-(trifluoromethyl)-1H-pyrazol-4-yl)-2-(pyrimidin-2-yl)ethan-1-one (2.5 mmol) and 3-(benzyloxy)-2-chloro-N-hydroxybenzimidoyl chloride; reaction time: 3 h, reaction conditions led to simultaneous O-desilylation; the residue was purified by flash column chromatography on silica gel (eluent: $CH_2Cl_2$/MeOH 95:5) to give the title compound as an orange oil (12%).

Result of LC/MS [M+H]$^+$: 584.1;

$^1$H NMR (CDCl$_3$): δ1.25 (6H, s, 2xCH$_3$), 2.15-2.02 (2H, m, CH$_2$), 4.51-4.38 (2H, m, CH$_2$), 5.11 (2H, s, OCH$_2$), 7.07-6.97 (2H, m, 2xCH-arom.), 7.42-7.16 (7H, m, 7xCH-arom.), 7.96 (1H, s, CH-arom.), 8.45 (2H, d, 2xCH-arom.).

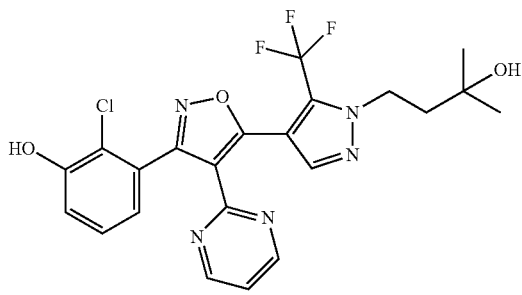 [SMILES: CC(C)(O)CCn1ncc(-c2onc(-c3cccc(O)c3Cl)c2-c2ncccn2)c1C(F)(F)F]

Example 129

2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol Benzyloxy derivative Example 128 (0.9 mmol) was dissolved in isopropanol/ethyl acetate (1:1; 6 ml) and Pd/C (10%; 0.3 eq.) was added. The atmosphere within the flask was replaced with hydrogen and the mixture was stirred at room temperature for 18 h. Pd/C was filtered off over celite, the filtrate was concentrated to dryness under reduced pressure and then in vacuo to give the title compound as pale brownish solid (83%).

Result of LC/MS [M+H]$^+$: 494.0;

$^1$H NMR (CDCl$_3$): δ1.66 (6H, s, 2xCH$_3$), 2.54-2.44 (2H, m, CH$_2$), 4.90-4.81 (2H, m, CH$_2$), 7.41 (1H, t, CH-arom.), 7.55-7.45 (2H, m, 2xCH-arom.), 7.64 (1H, q, CH-arom.), 8.40-8.32 (2H, m, CH-arom. and OH), 8.87 (2H, d, 2xCH-arom.).

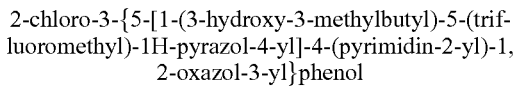

2-chloro-3-{5-[1-(3-hydroxy-3-methylbutyl)-5-methyl-1H-pyrazol-4-yl]-4-(pyrimidin-2-yl)-1,2-oxazol-3-yl}phenol Alternative Step 1 as described for Example 99 (reaction with NaH): 1-(5-methyl-1-{3-methyl-3-[(trimethylsilyl)oxy]butyl}-1H-pyrazol-4-yl)-2-(pyrimidin-2-yl)ethan-1-one (0.75 mmol) and 3-(benzyloxy)-2-chloro-N-hydroxybenzimidoyl chloride; reaction time: 1.5 h, reaction conditions led to simultaneous O-desilylation; the residue was purified by flash column chromatography on silica gel (eluent: $CH_2Cl_2$/MeOH 95:5) to give 4-(4-{3-[3-(benzyloxy)-2-chlorophenyl]-4-(pyrimidin-2-yl)-1,2-oxazol-5-yl}-5-methyl-1H-pyrazol-1-yl)-2-methylbutan-2-ol in 22% yield;

Result of LC/MS [M+H]$^+$: 530.1;

$^1$H NMR (CDCl$_3$): δ1.46 (6H, s, 2x CH$_3$), 2.21 (2H, m, CH$_2$), 2.74 (3H, s, CH$_3$), 4.46 (2H, m, CH$_2$), 5.33 (2H, s, CH$_2$), 7.23 (1H, d, CH-arom.), 7.38-7.62 (8H, m, CH-arom.), 8.27 (1H, s, CH-arom.), 8.76 (2H, d, CH-arom.).

Benzyloxy derivative was O-debenzylated following the protocol described for Example 129, providing the title compound as pale yellowish solid (crude 96%).

Result of LC/MS [M+H]$^+$: 440.0;

$^1$H NMR (CDCl$_3$): δ1.29 (6H, s, 2x CH$_3$), 2.35 (2H, m, CH$_2$), 2.58 (3H, s, CH$_3$), 4.28 (2H, m, CH$_2$), 5.33 (2H, s, CH$_2$), 7.06-7.17 (4H, m, CH-arom.), 8.09 (1H, s, CH-arom.), 8.62 (2H, d, CH-arom.).

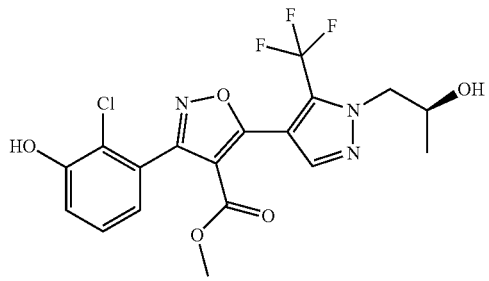 [SMILES: COC(=O)c1c(-c2cccc(O)c2Cl)noc1-c1cnn(C[C@H](C)O)c1C(F)(F)F]

methyl (S)-3-(2-chloro-3-hydroxyphenyl)-5-(1-(2-hydroxypropyl)-5-(trifluoromethyl)-1H-pyrazol-4-yl)isoxazole-4-carboxylate Alternative Step 1 as described for Example 99 (reaction with NaH): methyl 3-{1-[(2S)-2-[(tert-butyldimethylsilyl)oxy]propyl]-5-(trifluoromethyl)-1H-pyrazol-4-yl}-3-oxopropanoate (1.5 mmol) and 3-(benzyloxy)-2-chloro-N-hydroxybenzimidoyl chloride; reaction time: 1.5 h; the residue was purified by flash column chromatography on silica gel (eluent: $CH_2Cl_2$/MeOH 95:5) to give methyl 3-[3-(benzyloxy)-2-chlorophenyl]-5-{1-[(2S)-2-[(tert-butyldimethylsilyl)oxy]propyl]-5-methyl-1H-pyrazol-4-yl}-1,2-oxazole-4-carboxylate in 27% yield.

Benzyloxy derivative was O-debenzylated following the protocol described for Example 129, providing the title compound as pale yellowish solid (crude 96%).

The title compound was synthesized by final O-desilylation according to the alternative step 2 described above in Example 103 (using TBAF) (15%): The residue was purified by prep. TLC on silica gel (eluent: $CH_2Cl_2$/MeOH 95:5).

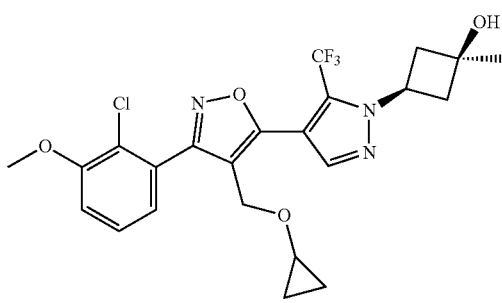

Example 130

3-(4-(3-(2-chloro-3-methoxyphenyl)-4-(cyclopropoxymethyl)isoxazol-5-yl)-5-(trifluoromethyl)-1H-pyrazol-1-yl)-1-methylcyclobutan-1-ol (Syn-Configuration)

Step 1: ethyl 3-(1-{3-[(tert-butyldimethylsilyl)oxy]-3-methylcyclobutyl}-5-(trifluoromethyl)-1H-pyrazol-4-yl)-3-oxopropanoate (syn-configuration) (0.25 mmol) and 2-chloro-3-methoxy-N-hydroxybenzimidoyl chloride; the reaction was conducted at 65° C.; the residue was purified by flash column chromatography on silica gel (eluent: petroleum ether/ethyl acetate 9:1) to give ethyl 3-(2-chloro-3-methoxyphenyl)-5-{1-[3-[(tert-butyldimethylsilyl)oxy]-3-methylcyclobutyl]-5-(trifluoromethyl)-1H-pyrazol-4-yl}-1,2-oxazole-4-carboxylate (syn-configuration) (72%);

Result of LC/MS [M+H]$^+$: 614.2;

$^1$H NMR (CDCl$_3$): δ0.13 (6H, s, 2xCH$_3$), 0.91 (9H, s, 3xCH$_3$), 0.99 (3H, t, CH$_3$), 1.26 (3H, s, CH$_3$), 2.68-2.54 (2H, m, CH$_2$), 3.03-2.91 (2H, m, CH$_2$), 3.95 (3H, s, OCH$_3$), 4.08 (2H, q, OCH$_2$), 4.56 (1H, quint, CH), 7.14-7.05 (2H, m, 2xCH-arom.), 7.34 (1H, t, CH-arom.), 7.96 (1H, s, CH-arom.).

Step 2: Conversion of the ethyl ester group into a cyclopropoxymethyl unit was achieved according to the general procedures for the synthesis of 4-alkoxymethyl isoxazoles described above:

LiAlH$_4$ reduction of ethyl 3-(2-chloro-3-methoxyphenyl)-5-{1-[3-[(tert-butyldimethylsilyl)oxy]-3-methylcyclobutyl]-5-(trifluoromethyl)-1H-pyrazol-4-yl}-1,2-oxazole-4-carboxylate (syn-configuration) (0.18 mmol) to give [5-(1-{3-[(tert-butyldimethylsilyl)oxy]-3-methylcyclobutyl}-5-(trifluoromethyl)-1H-pyrazol-4-yl)-3-(2-chloro-3-methoxyphenyl)-1,2-oxazol-4-yl]methanol (syn-configuration) as a pale yellow oil (quant.).

Result of LC/MS [M+H]$^+$: 572.1;

$^1$H NMR (CDCl$_3$): δ0.13 (6H, s, 2x CH$_3$), 0.92 (9H, s, tBu), 1.48 (3H, s, CH$_3$), 1.72 (1H, s, OH), 1.85 (2H, m, CH$_2$), 3.88 (2H, s, CH$_2$), 3.96 (3H, s, CH$_3$), 4.42 (2H, s, CH$_2$), 4.56 (1H, s, CH), 7.09 (2H, m, CH-arom.), 7.36 (1H, t, CH-arom.), 8.94 (1H, s, CH-arom.).

Synthesis of bromomethyl-isoxazole according to method A (Et$_2$O, 20 min) to give 4-(bromomethyl)-5-(1-{3-[(tert-butyldimethylsilyl)oxy]-3-methylcyclobutyl}-5-(trifluoromethyl)-1H-pyrazol-4-yl)-3-(2-chloro-3-methoxyphenyl)-1,2-oxazole (syn-configuration) as yellow oil (quant.)

Result of LC/MS [M+H]$^+$: 634.0;

Synthesis of 4-cyclopropoxymethyl-isoxazole according to method C (using cyclopropanol) to give 5-(1-{3-[(tert-butyldimethylsilypoxy]-3-methylcyclobutyl}-5-(trifluoromethyl)-1H-pyrazol-4-yl)-3-(2-chloro-3-methoxyphenyl)-4-(cyclopropoxymethyl)-1,2-oxazole (syn-configuration) as a pale yellow oil (35%).

Result of LC/MS [M+H]$^+$: 612.2;

$^1$H NMR (CDCl$_3$): δ0.13 (6H, s, 2xCH$_3$), 0.35-0.24 (4H, m, 2xCH$_2$), 0.91 (9H, s, 3xCH$_3$), 1.48 (3H, s, CH$_3$), 2.68-2.56 (2H, m, CH$_2$), 3.03-2.88 (2H, m, CH$_2$), 3.16-3.05 (1H, m, CH), 3.97 (3H, s, OCH$_3$), 4.28 (2H, s, OCH$_2$), 4.57 (1H, quint, CH), 7.39-6.82 (3H, m, 3xCH-arom.), 7.86 (1H, s, CH-arom.).

Step 3: the title compound was synthesized by final O-desilylation according to the alternative step 2 described above in Example 103 (using TBAF): The residue was purified by prep. TLC on silica gel (eluent: CH$_2$Cl$_2$/MeOH 95:5 and again with eluent: petroleum ether/ethyl acetate 4:1) to give the title compound as orange oil (12%).

Result of LC/MS [M+H]$^+$: 498.0;

$^1$H NMR (CDCl$_3$): δ0.30 (4H, m, 2x CH$_2$), 1.50 (3H, s, CH$_3$), 2.80 (4H, m, 2x CH$_2$), 3.11 (1H, m, CH), 3.97 (3H, s, CH$_3$), 4.27 (2H, s, CH$_2$), 4.72 (1H, quint., CH), 7.08 (2H, d, CH-arom.), 7.34 (1H, t, CH-arom.), 7.89 (1H, s, CH-arom.).

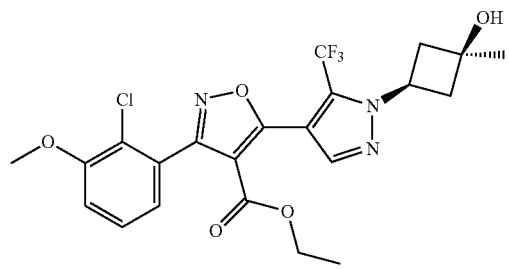

Example 131: ethyl 3-(2-chloro-3-methoxyphenyl)-5-{1-[3-hydroxy-3-methylcyclobutyl]-5-(trifluoromethyl)-1H-pyrazol-4-yl}-1,2-oxazole-4-carboxylate (Syn-Configuration)

Intermediate after step 1, Example 130, ethyl 3-(2-chloro-3-methoxyphenyl)-5-{1-[3-[(tert-butyldimethylsilyl)oxy]-3-methylcyclobutyl]-5-(trifluoromethyl)-1H-pyrazol-4-yl}-1,2-oxazole-4-carboxylate (syn-configuration), was O-desilylated according to the alternative step 2 described above in Example 103 (using TBAF): The residue was purified by prep. TLC on silica gel (eluent: CH$_2$Cl$_2$/MeOH 95:5) to give the title compound as orange oil (72%).

Result of LC/MS [M+H]$^+$: 500.0;

$^1$H NMR (CDCl$_3$): δ0.99 (3H, t, CH$_3$), 1.49 (3H, s, CH$_3$), 2.81 (4H, m, 2x CH$_2$), 2.95 (3H, s, CH$_3$), 4.08 (2H, q, CH$_2$), 4.72 (1H, m, CH), 7.09 (2H, m, CH-arom.), 7.35 (1H, t, CH-arom.), 8.00 (1H, s, CH-arom).

Example 132: ethyl 3-(2-chloro-3-methoxyphenyl)-5-[1-(3-hydroxy-3-methylbutyl)-5-(trifluoromethyl)-1H-pyrazol-4-yl]-1,2-oxazole-4-carboxylate

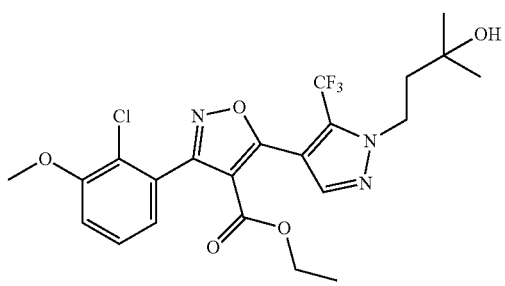 [SMILES: CCOC(=O)c1c(-c2cccc(OC)c2Cl)noc1-c1cnn(CCC(C)(C)O)c1C(F)(F)F]

Step 1: ethyl 3-(1-{3-methyl-3-[(trimethylsilyl)oxy]butyl}-5-(trifluoromethyl)-1H-pyrazol-4-yl)-3-oxopropanoate (0.80 mmol) and 2-chloro-3-methoxy-N-hydroxybenzimidoyl chloride; the reaction was conducted at 65° C.; reaction conditions led to simultaneous O-desilylation; the residue was purified by prep. TLC on silica gel (eluent: CH$_2$Cl$_2$/MeOH 95:5) to give the title compound as an orange oil (19%);

Result of LC/MS [M+H]$^+$: 502.0;

$^1$H NMR (CDCl$_3$): δ1.00 (3H, t, CH$_3$), 1.32 (6H, s, 2x CH3), 2.14 (2H, m, CH$_2$), 3.95 (3H, s, CH$_3$), 4.08 (2H, q, CH$_2$), 4.52 (2H, m, CH$_2$), 7.09 (2H, m, CH-arom.), 7.34 (1H, t, CH-arom.), 7.97 (1H, s, CH-arom.).

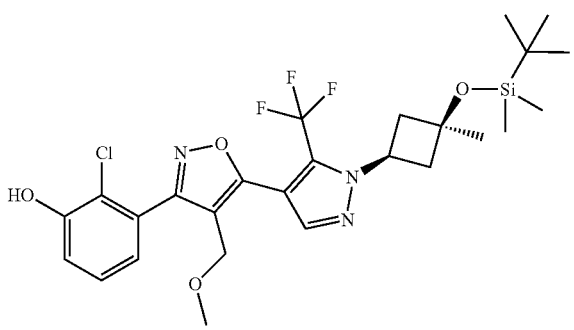 [SMILES: COCc1c(-c2cccc(O)c2Cl)noc1-c1cnn([C@H]2C[C@@](C)(O[Si](C)(C)C(C)(C)C)C2)c1C(F)(F)F]

Building Block for the Synthesis of Examples 150 and 151

2-chloro-3-[4-(methoxymethyl)-5-{1-[3-[(tert-butyldimethylsilyl)oxy]-3-methylcyclobutyl]-5-(trifluoromethyl)-1H-pyrazol-4-yl}-1,2-oxazol-3-yl]phenol (Syn-Configuration)

Step 1: ethyl 3-(1-{3-[(tert-butyldimethylsilyl)oxy]-3-methylcyclobutyl}-5-(trifluoromethyl)-1H-pyrazol-4-yl)-3-oxopropanoate (syn-configuration) (0.18 mmol) and 3-(benzyloxy)-2-chloro-N-hydroxybenzimidoyl chloride; the reaction was conducted at 65° C.; the residue was purified by flash column chromatography on silica gel (eluent: CH$_2$Cl$_2$/MeOH 100:1) to give ethyl 3-[3-(benzyloxy)-2-chlorophenyl]-5-{1-[3-[(tert-butyldimethylsilyl)oxy]-3-methylcyclobutyl]-5-(trifluoromethyl)-1H-pyrazol-4-yl}-1,2-oxazole-4-carboxylate (syn-configuration) as a colorless oil (64%);

Result of LC/MS [M+H]$^+$: 690.4;

$^1$H-NMR (CDCl$_3$, J [Hz]): δ=7.97 (s, 1H pyrazole-H), 7.49-7.29 (m, 6H, benzyl-H), 7.11 (d, 2H, $^3$J=7.9, benzyl-H), 5.22 (s, 2H, CH$_2$), 4.62-4.51 (m, 1H, CH), 4.08 (q, 2H, $^3$J=7.1, OCH$_2$CH$_3$), 3.01-2.94 (m, 2H, CH$_2$), 2.64-2.58 (m, 2H, CH$_2$), 1.48 (s, 3H, CH$_3$), 0.98 (t, 3H, $^3$J=7.1, OCH$_2$CH$_3$), 0.92 (s, 9H, C(CH$_3$)$_3$), 0.13 (s, 6H, CH$_3$).

Step 2: Conversion of the ethyl ester group into a methoxymethyl unit was achieved according to the general procedures for the synthesis of 4-alkoxymethyl isoxazoles described above:

LiAlH$_4$ reduction of ethyl 3-[3-(benzyloxy)-2-chlorophenyl]-5-{1-[3-[(tert-butyldimethylsilyl)oxy]-3-methylcyclobutyl]-5-(trifluoromethyl)-1H-pyrazol-4-yl}-1,2-oxazole-4-carboxylate (syn-configuration) (0.12 mmol) to give {3-[3-(benzyloxy)-2-chlorophenyl]-5-{1-[3-[(tert-butyldimethylsilyl)oxy]-3-methylcyclobutyl]-5-(trifluoromethyl)-1H-pyrazol-4-yl}-1,2-oxazol-4-yl}methanol (syn-configuration) as a colorless oil (83%).

Result of LC/MS [M+H]$^+$: 648.4;

Synthesis of methoxymethyl-isoxazole according to method A (MeI) to give 3-[3-(benzyloxy)-2-chlorophenyl]-4-(methoxymethyl)-5-{1-[3-[(tert-butyldimethylsilyl)oxy]-3-methylcyclobutyl]-5-(trifluoromethyl)-1H-pyrazol-4-yl}-1,2-oxazole (syn-configuration) as colorless oil (32%)

Result of LC/MS [M+H]$^+$: 662.5;

$^1$H-NMR (CDCl$_3$, J [Hz]): δ=7.88 (s, 1H pyrazole-H), 7.50-7.32 (m, 6H, benzyl-H), 7.11 (d, 2H, $^3$J=8.0, benzyl-H), 5.22 (s, 2H, CH$_2$), 4.63-4.52 (m, 1H, CH), 4.21 (s, 2H, CH$_2$), 3.15 (s, 3H, OCH$_3$), 3.00-2.93 (m, 2H, CH$_2$), 2.65-2.59 (m, 2H, CH$_2$), 1.49 (s, 3H, CH$_3$), 0.92 (s, 9H, C(CH$_3$)$_3$), 0.14 (s, 6H, CH$_3$).

Step 3: the title compound was synthesized by final O-debenzylation according to following the protocol described for Example 129, providing the title compound as colorless oil after purification by flash column chromatography on silica gel (eluent: petroleum ether/ethyl acetate 7:3) (51%);

Result of LC/MS [M+H]$^+$: 572.1.

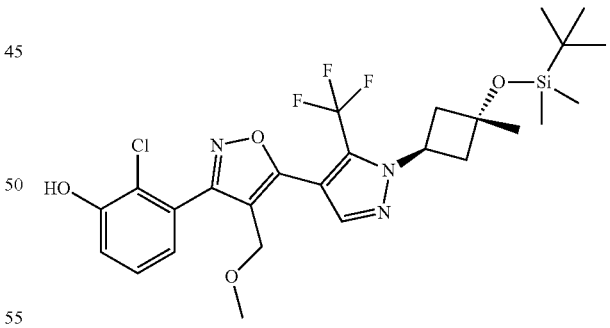

Building Block for the Synthesis of Examples 152 and 153

2-chloro-3-[4-(methoxymethyl)-5-{1-[3-[(tert-butyldimethylsilyl)oxy]-3-methylcyclobutyl]-5-(trifluoromethyl)-1H-pyrazol-4-yl}-1,2-oxazol-3-yl]phenol (Anti-Configuration)

Step 1: ethyl 3-(1-{3-[(tert-butyldimethylsilyl)oxy]-3-methylcyclobutyl}-5-(trifluoromethyl)-1H-pyrazol-4-yl)-3- oxopropanoate (anti-configuration) (0.28 mmol) and 3-(benzyloxy)-2-chloro-N-hydroxybenzimidoyl chloride; the reaction was conducted at 60° C.; the residue was purified by flash column chromatography on silica gel (eluent: CH$_2$Cl$_2$/MeOH 100:1) to give ethyl 3-[3-(benzyloxy)-2-chlorophenyl]-5-{1-[3-[(tert-butyldimethylsilyl)oxy]-3-methylcyclobutyl]-5-(trifluoromethyl)-1H-pyrazol-4-yl}-1,2-oxazole-4-carboxylate (anti-configuration) as a colorless oil (83%);

Result of LC/MS [M+H]$^+$: 690.4;

$^1$H-NMR (CDCl$_3$, J [Hz]): δ=7.96 (s, 1H pyrazole-H), 7.49-7.29 (m, 6H, benzyl-H), 7.11 (d, 2H, $^3$J=8.2, benzyl-H), 5.22-5.17 (m, 3H, CH, CH$_2$), 4.08 (q, 2H, $^3$J=7.1, OCH$_2$CH$_3$), 2.81-2.74 (m, 2H, CH$_2$), 2.68-2.61 (m, 2H, CH$_2$), 1.52 (s, 3H, CH$_3$), 0.99 (t, 3H, $^3$J=7.1, OCH$_2$CH$_3$), 0.93 (s, 9H, C(CH$_3$)$_3$), 0.14 (s, 6H, CH$_3$).

Step 2: Conversion of the ethyl ester group into a methoxymethyl unit was achieved according to the general procedures for the synthesis of 4-alkoxymethyl isoxazoles described above:

LiAlH$_4$ reduction of ethyl 3-[3-(benzyloxy)-2-chlorophenyl]-5-{1-[3-[(tert-butyldimethylsilyl)oxy]-3-methylcyclobutyl]-5-(trifluoromethyl)-1H-pyrazol-4-yl}-1,2-oxazole-4-carboxylate (syn-configuration) (0.23 mmol) to give {3-[3-(benzyloxy)-2-chlorophenyl]-5-{1-[3-[(tert-butyldimethylsilyl)oxy]-3-methylcyclobutyl]-5-(trifluoromethyl)-1H-pyrazol-4-yl}-1,2-oxazol-4-yl}methanol (anti-configuration) as a greyish oil (73%).

Result of LC/MS [M+H]$^+$: 648.4;

Synthesis of methoxymethyl-isoxazole according to method A (MeI) to give 3-[3-(benzyloxy)-2-chlorophenyl]-4-(methoxymethyl)-5-{1-[3-[(tert-butyldimethylsilyl)oxy]-3-methylcyclobutyl]-5-(trifluoromethyl)-1H-pyrazol-4-yl}-1,2-oxazole (anti-configuration) as colorless oil (37%)

Result of LC/MS [M+H]$^+$: 662.3;

$^1$H NMR (CDCl$_3$): δ0.14 (6H, s, 2xCH$_3$), 0.93 (9H, s, 3xCH$_3$), 1.51 (3H, s, CH$_3$), 2.84-2.53 (4H, m, 2xCH$_2$), 3.15 (3H, s, OCH$_3$), 4.20 (2H, s, OCH$_2$), 5.22 (2H, s, OCH$_2$), 7.18-7.07 (2H, d, 2xCH-arom.), 7.55-7.28 (6H, 6xCH-arom.), 7.87 (1H, s, CH-arom.).

Step 3: the title compound was synthesized by final O-debenzylation following the protocol described for Example 129, providing the title compound as colorless oil after purification by prep. TLC on silica gel (eluent: petroleum ether/ethyl acetate 7:3) (56%).

Result of LC/MS [M+H]$^+$: 572.4.

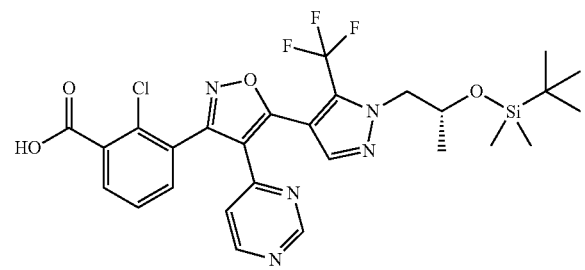 [SMILES: C[C@H](Cn1ncc(-c2onc(-c3cccc(C(=O)O)c3Cl)c2-c2ccncn2)c1C(F)(F)F)O[Si](C)(C)C(C)(C)C]

Building Block for the Synthesis of Examples 154 to 160

3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-chlorobenzoic acid Step 1: 1-{1-[(2R)-2-[(tert-butyldimethylsilyl)oxy]propyl]-5-(trifluoromethyl)-1H-pyrazol-4-yl}-2-(pyrimidin-4-yl)ethan-1-one (1.0 mmol) and methyl 2-chloro-3-(chloro(hydroxyimino)methyl)benzoate; the reaction was conducted at 60° C.; the residue was purified by flash column chromatography on silica gel (eluent: CH$_2$Cl$_2$/MeOH 100:1) to give methyl 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-chlorobenzoate (43%);

Step 2: ester group was saponified in ethanol (8 mL/mmol) and aq. NaOH (2.0 M; 8 mL/mmol) and heating to 60° C. for 1 h. and then acidified by addition of aq. HCl (1.0 M). The resulting suspension was partitioned between CH$_2$Cl$_2$ and water, combined organic layers were dried over MgSO$_4$, the solvent was removed under reduced pressure to give the crude carboxylic acid, which was used as such in further conversions.

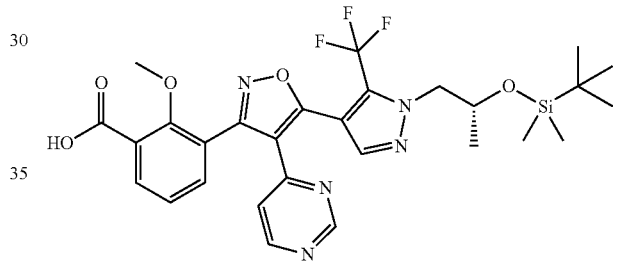

Building Block for the Synthesis of Examples 161 to 165

3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-methoxybenzoic acid Step 1: 1-{1-[(2R)-2-[(tert-butyldimethylsilyl)oxy]propyl]-5-(trifluoromethyl)-1H-pyrazol-4-yl}-2-(pyrimidin-4-yl)ethan-1-one (1.0 mmol) and methyl 3-(chloro(hydroxyimino)methyl)-2-methoxybenzoate; the reaction was conducted at 60° C.; the residue was purified by flash column chromatography on silica gel (eluent: CH$_2$Cl$_2$/MeOH 100:1) to give methyl 3-(5-{1-[R2R]-2-[(tert-butyldimethylsilyl)oxy]propyl]-5-(trifluoromethyl)-1H-pyrazol-4-yl}-4-(pyrimidin-4-yl)-1,2-oxazol-3-yl)-2-methoxybenzoate (37%);

Step 2: ester group was saponified in ethanol (8 mL/mmol) and aq. NaOH (2.0 M; 8 mL/mmol) and heating to 60° C. for 1 h. and then acidified by addition of aq. HCl (1.0 M). The resulting suspension was partitioned between CH$_2$Cl$_2$ and water, combined organic layers were dried over MgSO$_4$, the solvent was removed under reduced pressure to give the crude carboxylic acid, which was used as such in further conversions.

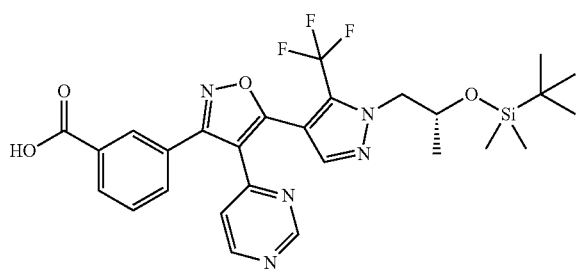 [SMILES: C[C@H](Cn1ncc(-c2onc(-c3cccc(C(=O)O)c3)c2-c2ccncn2)c1C(F)(F)F)O[Si](C)(C)C(C)(C)C]

Building Block for the Synthesis of Examples 166 and 167

3-(5-{1-[(2R)-2-[(tert-butyldimethylsilypoxy]propyl]-5-(trifluoromethyl)-1H-pyrazol-4-yl}-4-(pyrimidin-4-yl)-1,2-oxazol-3-yl)-benzoic acid Step 1: 1-{1-[(2R)-2-[(tert-butyldimethylsilypoxy]propyl]-5-(trifluoromethyl)-1H-pyrazol-4-yl}-2-(pyrimidin-4-yl)ethan-1-one (1.0 mmol) and methyl 3-(chloro(hydroxyimino)methyl)benzoate; the reaction was conducted at 60° C.; the residue was purified by flash column chromatography on silica gel (eluent: CH₂Cl₂/MeOH 100:1) to give methyl 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-benzoate (41%);

Step 2: ester group was saponified in ethanol (8 mL/mmol) and aq. NaOH (2.0 M; 8 mL/mmol) and heating to 60° C. for 1 h and then acidified by addition of aq. HCl (1.0 M). The resulting suspension was partitioned between CH₂Cl₂ and water, combined organic layers were dried over MgSO₄, the solvent was removed under reduced pressure to give the crude carboxylic acid, which was used as such in further conversions.

General Procedure for Aminoalkylation of Phenolic Groups

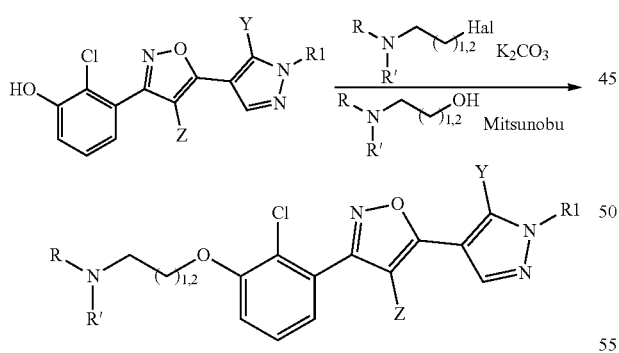

A) The respective phenol derivative (1.0 eq.) was dissolved in DMF (15 mL/mmol) and K₂CO₃ (3.5 eq.) was added, followed by the respective aminoalkyl halogenid (2.0 eq.). The mixture was stirred at indicated temperature for 18 h and then diluted with CH₂Cl₂ and extracted with water and brine. The organic phase was dried over MgSO₄, filtered and concentrated under reduced pressure. Crude product was purified via prep. TLC on silica gel (eluent: CH₂Cl₂/MeOH 95:5).
B) Mitsunobu reaction: The respective phenol derivative (1.0 eq.), PPh₃ (1.5 eq.) and the respective alcohol (1.5 eq.) were dissolved in THF (15 mL/mmol), and the mixture was cooled to 0° C. Diisopropyl azodicarboxylate (DIAD; 1.5 eq.) was added and the mixture was stirred at 0° C. for 30 min at room temperature for the indicated time, and then diluted with CH₂Cl₂ and extracted with water and brine. The organic phase was dried over MgSO₄, filtered and concentrated under reduced pressure. Crude product was purified via prep. TLC on silica gel (eluent: CH₂Cl₂/MeOH 95:5).

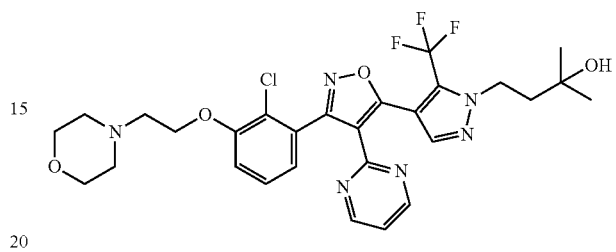

Example 133: 4-[4-(3-{2-chloro-3-[2-(morpholin-4-yl)ethoxy]phenyl}-4-(pyrimidin-2-yl)-1,2-oxazol-5-yl)-5-(trifluoromethyl)-1H-pyrazol-1-yl]-2-methylbutan-2-ol 2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol (Example 129) (0.09 mmol) and N-(2-chloroethyl)morpholine hydrochloride were used in method A, reaction temperature 50° C., to give title compound as an orange oil (14%).
Result of LC/MS [M+H]⁺: 607.5;
¹H NMR (CDCl₃): δ1.32 (6H, s, 2xCH₃), 2.19-2.09 (2H, m, CH₂), 2.68-2.57 (4H, m, 2xCH₂), 2.90-2.79 (2H, m, CH₂), 3.78-3.65 (4H, m, 2xCH₂), 4.24-4.16 (2H, m, CH₂), 4.56-4.44 (2H, m, CH₂), 7.09-7.03 (2H, m, 2xCH-arom.), 7.25-7.21 (1H, m, CH-arom.), 7.34 (1H, t, CH-arom.), 8.01 (1H, s, CH-arom.), 8.52 (2H, d, 2xCH-arom.).

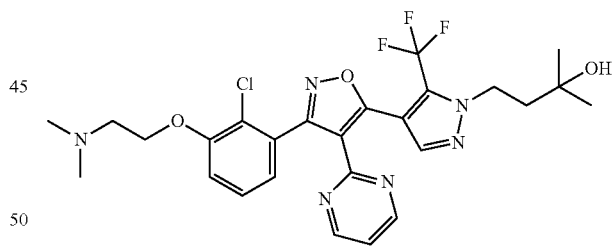 [SMILES: CC(C)(O)CCn1ncc(-c2onc(-c3cccc(OCCN4CCOCC4)c3Cl)c2-c2ncccn2)c1C(F)(F)F]

Example 134: 4-[4-(3-{2-chloro-3-[2-(dimethylamino)ethoxy]phenyl}-4-(pyrimidin-2-yl)-1,2-oxazol-5-yl)-5-(trifluoromethyl)-1H-pyrazol-1-yl]-2-methylbutan-2-ol 2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol (Example 129) (0.09 mmol) and 2-chloro-N,N-dimethylethylamine were used in method A, reaction temperature 50° C., to give title compound as a brownish oil (8%).
Result of LC/MS [M+H]⁺: 565.5;
¹H NMR (CDCl₃): δ1.32 (6H, s, 2xCH₃), 2.19-2.09 (2H, m, CH₂), 2.37 (6H, s, 2xCH₃), 2.82 (2H, t, CH₂), 4.18 (2H, t, CH$_2$), 4.56-4.45 (2H, m, CH$_2$), 7.09-7.03 (2H, m, 2xCH-arom.), 7.25-7.21 (1H, m, CH-arom.), 7.34 (1H, t, CH-arom.), 8.01 (1H, s, CH-arom.), 8.52 (2H, d, 2xCH-arom.).

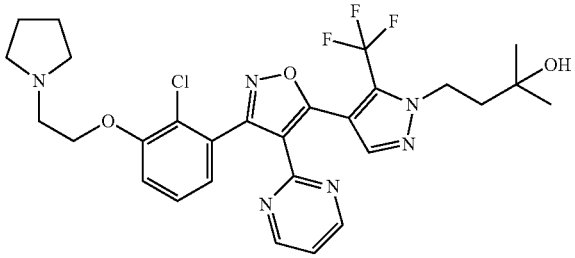 [SMILES: CC(C)(O)CCn1ncc(-c2onc(-c3cccc(OCCN4CCCC4)c3Cl)c2-c2ncccn2)c1C(F)(F)F]

Example 135: 4-[4-(3-{2-chloro-3-[2-(pyrrolidin-1-yl)ethoxy]phenyl}-4-(pyrimidin-2-yl)-1,2-oxazol-5-yl)-5-(trifluoromethyl)-1H-pyrazol-1-yl]-2-methylbutan-2-ol 2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol (Example 129) (0.09 mmol) and 1-(2-chloroethyl)pyrrolidine were used in method A, reaction temperature 50° C., to give title compound as a brownish oil (5%).

Result of LC/MS [M+H]$^+$: 591.5;

$^1$H NMR (CDCl$_3$): δ1.32 (6H, s, 2xCH$_3$), 1.96-1.88 (6H, m, 3xCH$_2$), 2.18-2.10 (2H, m, CH$_2$), 3.01-2.89 (2H, m, CH$_2$), 3.22-3.12 (2H, m, CH$_2$), 4.39-4.29 (2H, m, CH$_2$), 4.54-4.46 (2H, m, CH$_2$), 7.09-7.03 (2H, m, 2xCH-arom.), 7.25-7.21 (1H, m, CH-arom.), 7.35 (1H, t, CH-arom.), 8.00 (1H, s, CH-arom.), 8.52 (2H, d, 2xCH-arom.).

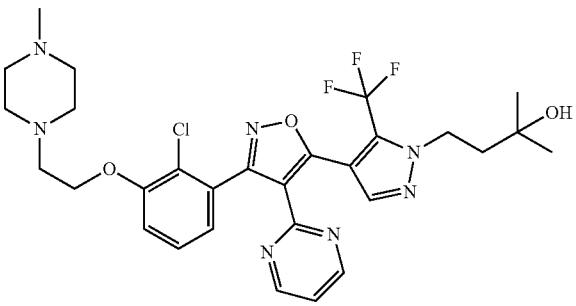 [SMILES: CN1CCN(CCOc2cccc(-c3noc(-c4cnn(CCC(C)(C)O)c4C(F)(F)F)c3-c3ncccn3)c2Cl)CC1]

Example 136: 4-[4-(3-{2-chloro-3-[2-(4-methylpiperazin-1-yl)ethoxy]phenyl}-4-(pyrimidin-2-yl)-1,2-oxazol-5-yl)-5-(trifluoromethyl)-1H-pyrazol-1-yl]-2-methylbutan-2-ol 2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol (Example 129) (0.09 mmol) and 1-(2-chloroethyl)-4-methylpiperazine were used in method A, reaction temperature 100° C., to give title compound as a brownish oil (6%).

Result of LC/MS [M+H]$^+$: 620.5;

$^1$H NMR (CDCl$_3$): δ1.31 (6H, s, 2xCH$_3$), 2.19-2.08 (2H, m, CH$_2$), 2.31 (3H, s, CH$_3$), 2.55-2.45 (4H, m, 2xCH$_2$), 2.70-2.64 (4H, m, 2xCH$_2$), 2.85 (2H, t, CH$_2$), 4.18 (2H, t, CH$_2$), 4.55-4.46 (2H, m, CH$_2$), 7.09-7.03 (2H, m, 2xCH-arom.), 7.25-7.21 (1H, m, CH-arom.), 7.33 (1H, t, CH-arom.), 8.01 (1H, s, CH-arom.), 8.51 (2H, d, 2xCH-arom.).

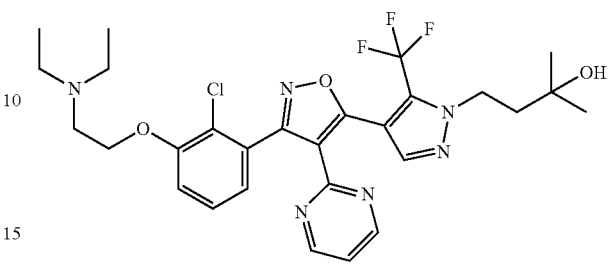

Example 137: 4-[4-(3-{2-chloro-3-[2-(diethylamino)ethoxy]phenyl}-4-(pyrimidin-2-yl)-1,2-oxazol-5-yl)-5-(trifluoromethyl)-1H-pyrazol-1-yl]-2-methylbutan-2-ol 2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol (Example 129) (0.09 mmol) and 2-chloro-N,N-diethylethylamine were used in method A, reaction temperature 50° C., to give title compound as an orange oil (13%).

Result of LC/MS [M+H]$^+$: 593.5;

$^1$H NMR (CDCl$_3$): δ1.38-1.29 (12H, m, 4xCH$_3$), 2.19-2.08 (2H, m, CH$_2$), 3.20-3.07 (4H, m, 2xCH$_2$), 3.41-3.33 (2H, m, CH$_2$), 4.59-4.46 (4H, m, 2xCH$_2$), 7.11-7.04 (2H, m, 2xCH-arom.), 7.26-7.21 (1H, m, CH-arom.), 7.36 (1H, t, CH-arom.), 8.00 (1H, s, CH-arom.), 8.53 (2H, d, 2xCH-arom.).

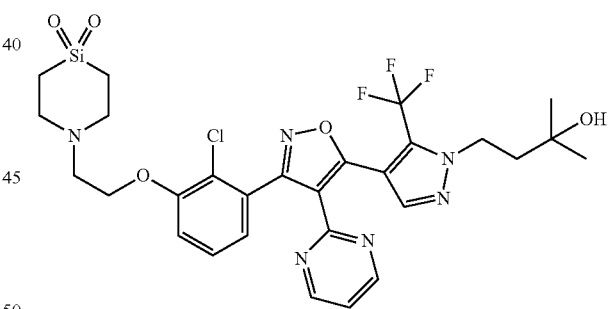

Example 138: 4-[2-(2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenoxy)ethyl]-thiomorpholine-1,1-dione 2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol (Example 129) (0.06 mmol) and 4-(2-hydroxyethyl)thiomorpholin-1,1-dione were used in method B (18 h); additional purification by a second prep. TLC (eluent: petroleum ether/ethyl acetate 3:7) yielded the title compound as greyish oil (6%).

Result of LC/MS [M+H]$^+$: 655.4;

$^1$H NMR (CDCl$_3$): δ1.32 (6H, s, 2xCH$_3$), 2.19-2.10 (2H, m, CH$_2$), 3.11-2.99 (6H, m, 3xCH$_2$), 3.27-3.15 (4H, m,

2xCH₂), 4.23-4.14 (2H, m, CH₂), 4.56-4.45 (2H, m, CH₂), 7.11-7.00 (2H, m, 2xCH-arom.), 7.29-7.26 (1H, m, CH-arom.), 7.36 (1H, t, CH-arom.), 8.01 (1H, s, CH-arom.), 8.53 (2H, d, 2xCH-arom.).

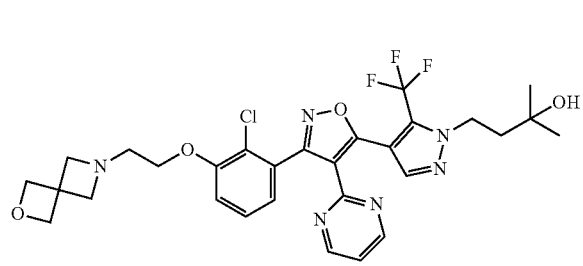 [SMILES: CC(C)(O)CCn1ncc(-c2onc(-c3cccc(OCCN4CC5(COC5)C4)c3Cl)c2-c2ncccn2)c1C(F)(F)F]

Example 139: 4-(4-{3-[2-chloro-3-(2-{2-oxa-6-azaspiro[3.3]heptan-6-yl}ethoxy)phenyl]-4-(pyrimidin-2-yl)-1,2-oxazol-5-yl}-5-(trifluoromethyl)-1H-pyrazol-1-yl)-2-methylbutan-2-ol 2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol (Example 129) (0.08 mmol) and 6-(2-chloroethyl)-2-oxa-6-azaspiro[3.3]heptane were used in method A, reaction temperature 70° C., to give title compound as a brownish oil (15%).

Result of LC/MS [M+H]⁺: 619.5;

¹H NMR (CDCl₃): δ1.32 (6H, s, 2xCH₃), 2.18-2.11 (2H, m, CH₂), 2.83 (2H, t, CH₂), 3.52 (4H, s, 2xCH₂), 4.06 (2H, t, CH₂), 4.55-4.47 (2H, m, CH₂), 4.71 (4H, s, 2xCH₂), 7.00 (1H, dd, CH-arom.), 7.07 (1H, t, CH-arom.), 7.23 (1H, dd, CH-arom.), 7.33 (1H, t, CH-arom.), 8.01 (1H, s, CH-arom.), 8.52 (2H, d, 2xCH-arom.).

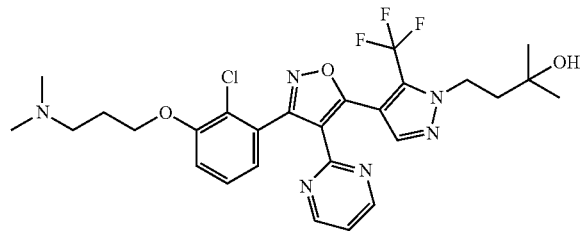 [SMILES: CN(C)CCCOc1cccc(-c2noc(-c3cnn(CCC(C)(C)O)c3C(F)(F)F)c2-c2ncccn2)c1Cl]

Example 140: 4-[4-(3-{2-chloro-3-[3-(dimethylamino)propoxy]phenyl}-4-(pyrimidin-2-yl)-1,2-oxazol-5-yl)-5-(trifluoromethyl)-1H-pyrazol-1-yl]-2-methylbutan-2-ol 2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol (Example 129) (0.2 mmol) and 3-dimethylamino-1-propyl chloride were used in method A, reaction temperature 60° C., to give title compound as yellow oil (49%).

Result of LC/MS [M+H]⁺: 578.9;

¹H NMR (CDCl₃): δ1.31 (6H, s, 2xCH₃), 2.07-1.95 (2H, m, CH₂), 2.18-2.08 (2H, m, CH₂), 2.27 (6H, s, 2xCH₃), 2.51 (2H, t, CH₂), 4.11 (2H, t, CH₂), 4.56-4.44 (2H, m, CH₂), 7.10-7.02 (2H, m, 2xCH-arom.), 7.22 (1H, dd, CH-arom.), 7.33 (1H, t, CH-arom.), 8.01 (1H, s, CH-arom.), 8.52 (2H, d, 2xCH-arom.).

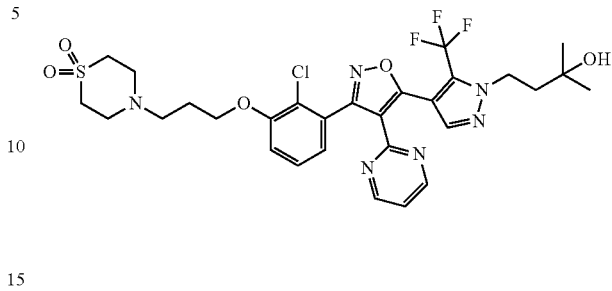

Example 141: 4-[3-(2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenoxy)propyl]-thiomorpholine-1,1-dione 2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol (Example 129) (0.06 mmol) and 4-(3-hydroxypropyl)thiomorpholin-1,1-dione were used in method B (2 h); title compound was obtained as yellow solid (6%).

Result of LC/MS [M+H]⁺: 669.2

¹H NMR (CDCl₃): δ1.32 (6H, s, 2xCH₃), 2.02-1.94 (2H, m, CH₂), 2.18-2.10 (2H, m, CH₂), 2.72 (2H, t, CH₂), 3.05-2.98 (8H, m, 4xCH₂), 4.12 (2H, t, CH₂), 4.54-4.47 (2H, m, CH₂), 7.10-7.02 (2H, m, 2xCH-arom.), 7.26-7.21 (1H, m, CH-arom.), 7.35 (1H, t, CH-arom.), 8.01 (1H, s, CH-arom.), 8.52 (2H, d, 2xCH-arom.).

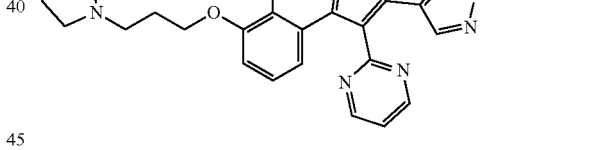

Example 142: 4-[4-(3-{2-chloro-3-[3-(pyrrolidin-1-yl)propoxy]phenyl}-4-(pyrimidin-2-yl)-1,2-oxazol-5-yl)-5-(trifluoromethyl)-1H-pyrazol-1-yl]-2-methylbutan-2-ol 2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol (Example 129) (0.2 mmol) and 1-(3-chloropropyl)pyrrolidine were used in method A, reaction temperature 60° C., second prep. TLC (eluent: CHCl₃/MeOH/aq. NH₃ 80:9:1 to give title compound as yellow oil (9%).

Result of LC/MS [M+H]⁺: 605.1;

¹H NMR (CDCl₃): δ1.33 (6H, s, 2xCH₃), 2.12-2.05 (4H, m, 2xCH₂), 2.21-2.12 (2H, m, CH₂), 2.47-2.33 (2H, m, CH₂), 3.30-3.09 (6H, m, 3xCH₂), 4.30-4.11 (2H, m, CH₂), 4.58-4.46 (2H, m, CH₂), 7.10-6.96 (3H, m, 3xCH-arom.), 7.34 (1H, d, CH-arom.), 8.00 (1H, s, CH-arom.), 8.47 (2H, d, 2xCH-arom.).

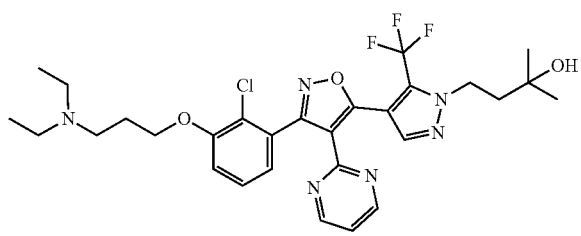 [SMILES: CCN(CC)CCCOc1cccc(-c2noc(-c3cnn(CCC(C)(C)O)c3C(F)(F)F)c2-c2ncccn2)c1Cl]

Example 143: 4-[4-(3-{2-chloro-3-[3-(diethylamino) propoxy]phenyl}-4-(pyrimidin-2-yl)-1,2-oxazol-5-yl)-5-(trifluoromethyl)-1H-pyrazol-1-yl]-2-methylbutan-2-ol 2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol (Example 129) (0.2 mmol) and 3-diethylamino-1-propanol were used in method B (1.5 h); title compound was obtained as yellow solid (22%).
Result of LC/MS [M+H]⁺: 607.2;
¹H NMR (CDCl₃): δ1.09 (6H, t, 2xCH₃), 1.31 (6H, s, 2xCH₃), 2.09-2.00 (2H, m, CH₂), 2.19-2.09 (2H, m, CH₂), 2.72-2.60 (2H, m, CH₂), 2.84-2.72 (2H, m, CH₂), 4.12 (2H, t, CH₂), 4.56-4.45 (2H, m, CH₂), 7.09-7.02 (2H, m, 2xCH-arom.), 7.23 (1H, dd, CH-arom.), 7.33 (1H, t, CH-arom.), 8.00 (1H, s, CH-arom.), 8.52 (2H, d, 2xCH-arom.).

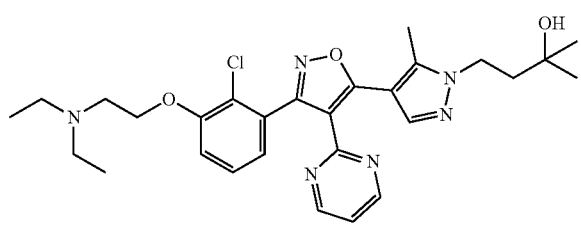 [SMILES: CCN(CC)CCOc1cccc(-c2noc(-c3cnn(CCC(C)(C)O)c3C)c2-c2ncccn2)c1Cl]

Example 144: 4-[4-(3-{2-chloro-3-[2-(diethylamino) ethoxy]phenyl}-4-(pyrimidin-2-yl)-1,2-oxazol-5-yl)-5-methyl-1H-pyrazol-1-yl]-2-methylbutan-2-ol 2-chloro-3-{5-[1-(3-hydroxy-3-methylbutyl)-5-methyl-1H-pyrazol-4-yl]-4-(pyrimidin-2-yl)-1,2-oxazol-3-yl}phenol (0.08 mmol) and 2-chloro-N,N-diethylethylamine were used in method A, reaction temperature 50° C., to give title compound in 21% yield.
Result of LC/MS [M+H]⁺: 539.1;
¹H NMR (CDCl₃): δ1.08 (6H, t, 2xCH₃), 1.28 (6H, s, 2xCH₃), 2.08-1.97 (2H, m, CH₂), 2.56 (3H, s, CH₃), 2.70 (4H, q, 2xCH₂), 2.96 (2H, t, CH₂), 4.17 (2H, t, CH₂), 4.34-4.24 (2H, m, CH₂), 7.03 (1H, dd, CH-arom.), 7.08 (1H, t, CH-arom.), 7.20 (1H, dd, CH-arom.), 7.31 (1H, t, CH-arom.), 8.08 (1H, s, CH-arom.), 8.60 (2H, d, 2xCH-arom.).

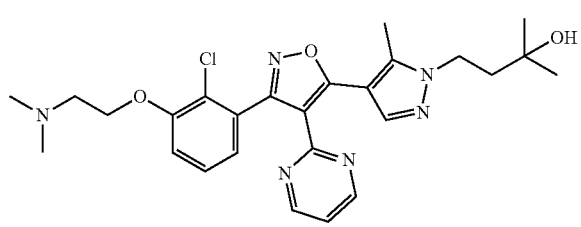 [SMILES: Cc1c(-c2onc(-c3cccc(OCCN(C)C)c3Cl)c2-c2ncccn2)cnn1CCC(C)(C)O]

Example 145: 4-[4-(3-{2-chloro-3-[2-(dimethylamino)ethoxy]phenyl}-4-(pyrimidin-2-yl)-1,2-oxazol-5-yl)-5-methyl-1H-pyrazol-1-yl]-2-methylbutan-2-ol 2-chloro-3-{5-[1-(3-hydroxy-3-methylbutyl)-5-methyl-1H-pyrazol-4-yl]-4-(pyrimidin-2-yl)-1,2-oxazol-3-yl}phenol (0.16 mmol) and 2-chloro-N,N-dimethylethylamine were used in method A, reaction temperature 50° C., to give title compound as pale yellow oil (11%).
Result of LC/MS [M+H]⁺: 511.1;
¹H NMR (CDCl₃): δ1.29 (6H, s, 2xCH₃), 2.08-1.98 (2H, m, CH₂), 2.37 (6H, s, 2xCH₃), 2.57 (3H, s, CH₃), 2.81 (2H, t, CH₂), 4.16 (2H, t, CH₂), 4.33-4.24 (2H, m, CH₂), 7.12-7.00 (2H, m, 2xCH-arom.), 7.22 (1H, dd, CH-arom.), 7.32 (1H, t, CH-arom.), 8.07 (1H, s, CH-arom.), 8.60 (2H, d, 2xCH-arom.).

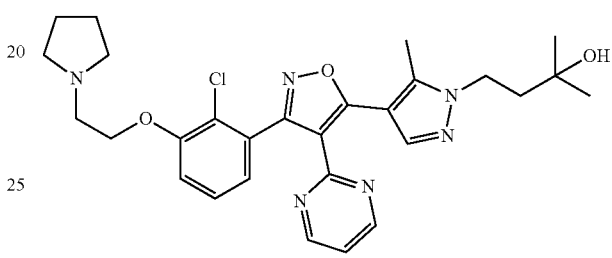

Example 146

4-[4-(3-{2-chloro-3-[2-(pyrrolidin-1-yl)ethoxy]phenyl}-4-(pyrimidin-2-yl)-1,2-oxazol-5-yl)-5-methyl-1H-pyrazol-1-yl]-2-methylbutan-2-ol 2-chloro-3-{5-[1-(3-hydroxy-3-methylbutyl)-5-methyl-1H-pyrazol-4-yl]-4-(pyrimidin-2-yl)-1,2-oxazol-3-yl}phenol (0.16 mmol) and 1-(2-chloroethyl)pyrrolidine were used in method A, reaction temperature 50° C. to give title compound upon second prep. TLC (eluent: CH₂Cl₂/MeOH 9:1) as pale yellow oil (8%).
Result of LC/MS [M+H]⁺: 537.1;
¹H NMR (CDCl₃): δ1.29 (6H, s, 2xCH₃), 1.86-1.76 (4H, m, 2xCH₂), 2.07-1.99 (2H, m, CH₂), 2.57 (3H, s, CH₃), 2.75-2.66 (4H, m, 2xCH₂), 2.98 (2H, t, CH₂), 4.21 (2H, t, CH₂), 4.33-4.25 (2H, m, CH₂), 7.04 (1H, dd, CH-arom.), 7.08 (1H, t, CH-arom.), 7.21 (1H, dd, CH-arom.), 7.32 (1H, t, CH-arom.), 8.08 (1H, s, CH-arom.), 8.60 (2H, d, 2xCH-arom.).

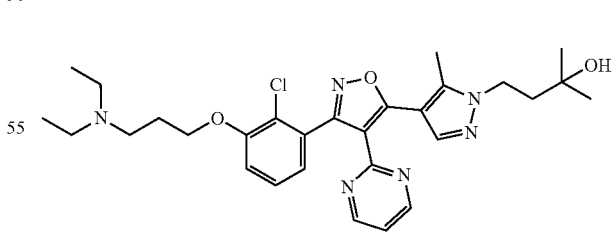

Example 147: 4-[4-(3-{2-chloro-3-[3-(diethylamino) propoxy]phenyl}-4-(pyrimidin-2-yl)-1,2-oxazol-5-yl)-5-methyl-1H-pyrazol-1-yl]-2-methylbutan-2-ol 2-chloro-3-{5-[1-(3-hydroxy-3-methylbutyl)-5-methyl-1H-pyrazol-4-yl]-4-(pyrimidin-2-yl)-1,2-oxazol-3- yl}phenol (0.08 mmol) and 3-diethylamino-1-propanol were used in method B (1.5 h); title compound was obtained as a pale yellow oil (22%).

Result of LC/MS [M+H]⁺: 553.2;

¹H NMR (CDCl₃): δ1.13 (6H, t, 2xCH₃), 1.29 (6H, s, 2xCH₃), 2.07-1.98 (2H, m, CH₂), 2.16-2.07 (2H, m, CH₂), 2.57 (3H, s, CH₃), 2.73 (4H, q, 2xCH₂), 2.82 (2H, t, CH₂), 4.11 (2H, t, CH₂), 4.32-4.23 (2H, m, CH₂), 7.02 (1H, dd, 2xCH-arom.), 7.09 (1H, t, CH-arom.), 7.20 (1H, dd, CH-arom.), 7.31 (1H, t, CH-arom.), 8.08 (1H, s, CH-arom.), 8.60 (2H, d, 2xCH-arom.).

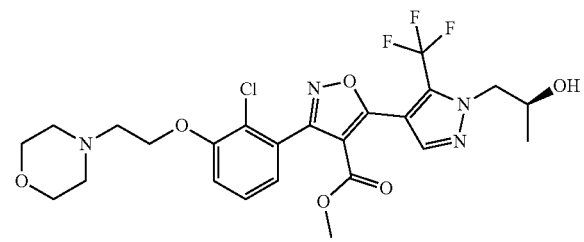 [SMILES: COC(=O)c1c(-c2cccc(OCCN3CCOCC3)c2Cl)noc1-c1cnn(C[C@H](C)O)c1C(F)(F)F]

Example 148: methyl 3-{2-chloro-3-[2-(morpholin-4-yl)ethoxy]phenyl}-5-{1-[(2S)-2-hydroxypropyl]-5-(trifluoromethyl)-1H-pyrazol-4-yl}-1,2-oxazole-4-carboxylate methyl (S)-3-(2-chloro-3-hydroxyphenyl)-5-(1-(2-hydroxypropyl)-5-(trifluoromethyl)-1H-pyrazol-4-yl)isoxazole-4-carboxylate (0.06 mmol) and N-(2-chloroethyl)morpholine hydrochloride were used in method A, reaction temperature 50° C., to give title compound (24%).

Result of LC/MS [M+H]⁺: 559.3;

¹H NMR (CDCl₃): δ1.32 (3H, d, CH₃), 2.69 (4H, br, 2xCH₂), 2.93 (2H, t, CH₂), 3.63 (3H, s, OCH₃), 3.76 (4H, t, 2xCH₂), 4.30-4.19 (3H, m, CH and CH₂), 4.46-4.30 (2H, m, CH₂), 7.14-7.06 (2H, m, 2xCH-arom.), 7.33 (1H, t, CH-arom.), 7.99 (1H, s, CH-arom.).

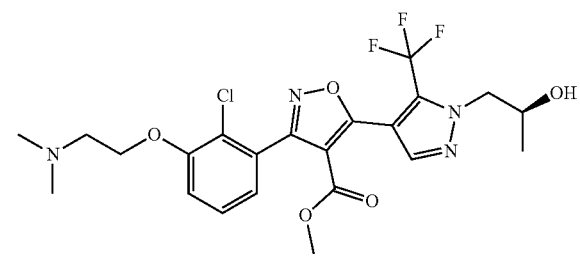 [SMILES: COC(=O)c1c(-c2cccc(OCCN(C)C)c2Cl)noc1-c1cnn(C[C@H](C)O)c1C(F)(F)F]

Example 149: methyl 3-{2-chloro-3-[2-(dimethylamino)ethoxy]phenyl}-5-{1-[(2S)-2-hydroxypropyl]-5-(trifluoromethyl)-1H-pyrazol-4-yl}-1,2-oxazole-4-carboxylate methyl (S)-3-(2-chloro-3-hydroxyphenyl)-5-(1-(2-hydroxypropyl)-5-(trifluoromethyl)-1H-pyrazol-4-yl)isoxazole-4-carboxylate (0.06 mmol) and 2-chloro-N,N-dimethylethylamine were used in method A, reaction temperature 50° C., to give title compound (19%).

Result of LC/MS [M+H]⁺: 517.3;

¹H NMR (CDCl₃): δ1.32 (3H, d, CH₃), 2.92 (6H, s, 2xCH₃), 3.48 (2H, t, CH₂), 3.63 (3H, s, OCH₃), 4.24 (1H, dd, CH), 4.47-4.31 (2H, m, CH₂), 4.60 (2H, t, CH₂), 7.19-7.11 (2H, m, 2xCH-arom.), 7.38 (1H, t, CH-arom.), 7.99 (1H, s, CH-arom.).

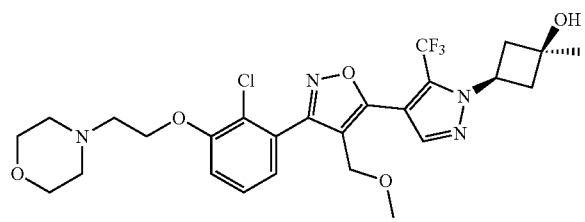 [SMILES: COCc1c(-c2cccc(OCCN3CCOCC3)c2Cl)noc1-c1cnn([C@H]2C[C@@](C)(O)C2)c1C(F)(F)F]

Example 150: 3-[4-(3-{2-chloro-3-[2-(morpholin-4-yl)ethoxy]phenyl}-4-(methoxymethyl)-1,2-oxazol-5-yl)-5-(trifluoromethyl)-1H-pyrazol-1-yl]-1-methyl-cyclobutan-1-ol (Syn-Configuration)

2-chloro-3-[4-(methoxymethyl)-5-{1-[3-[(tert-butyldimethylsilyl)oxy]-3-methylcyclobutyl]-5-(trifluoromethyl)-1H-pyrazol-4-yl}-1,2-oxazol-3-yl]phenol (syn-configuration) (0.03 mmol) and N-(2-chloroethyl)morpholine hydrochloride were used in method A, reaction temperature 50° C.; upon standard workup, crude material was taken up in THF (0.5 mL) and treated with TBAF (1 M in THF; 1.1 eq.) at room temperature for 2 h. The solvent was removed under reduced pressure and the title compound was isolated from prep. TLC (eluent: CH₂Cl₂(MeOH/aq. NH₃ 100:10:1) as pale yellow oil (56%).

Result of LC/MS [M+H]⁺: 571.4;

¹H-NMR (CDCl₃, J [Hz]): δ=7.90 (s, 1H pyrazole-H), 7.35-7.29 (m, 1H, benzyl-H), 7.11-7.06 (m, 2H, benzyl-H), 4.77-4.67 (m, 1H, CH), 4.25-4.19 (m, 4H, CH₂, RCH₂OCH₃), 3.75-3.72 (m, 4H, morpholino-H), 3.15 (s, 3H, RCH₂OCH₃), 2.91-2.72 (m, 6H, 3 x CH₂), 2.66-2.63 (m, 4H, morpholino-H), 1.49 (s, 3H CH₃).

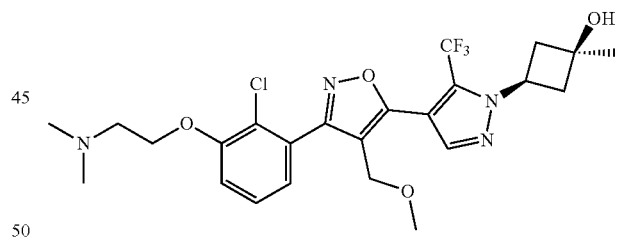

Example 151

3-[4-(3-{2-chloro-3-[2-(dimethylamino)ethoxy]phenyl}-4-(methoxymethyl)-1,2-oxazol-5-yl)-5-(trifluoromethyl)-1H-pyrazol-1-yl]-1-methylcyclobutan-1-ol (Syn-Configuration)

2-chloro-3-[4-(methoxymethyl)-5-{1-[3-[(tert-butyldimethylsilyl)oxy]-3-methylcyclobutyl]-5-(trifluoromethyl)-1H-pyrazol-4-yl}-1,2-oxazol-3-yl]phenol (syn-configuration) (0.03 mmol) and 2-chloro-N,N-dimethylethylamine were used in method A, reaction temperature 45° C.; upon standard workup, crude material was taken up in THF (0.5 mL) and treated with TBAF (1 M in THF; 1.1 eq.) at room temperature for 3.5 h. The solvent was removed under reduced pressure and the title compound was isolated from prep. TLC (eluent: CH$_2$Cl$_2$(MeOH/aq. NH$_3$ 100:10:1) as colorless oil (48%).

Result of LC/MS [M+H]$^+$: 529.50;

$^1$H-NMR (CDCl$_3$, J [Hz]): δ=7.91 (s, 1H pyrazole-H), 7.35-7.29 (m, 1H, benzyl-H), 7.11-7.06 (m, 2H, benzyl-H), 4.77-4.67 (m, 1H, CH), 4.22-4.18 (m, 4H, CH$_2$, RCH$_2$OCH$_3$), 3.15 (s, 3H, RCH$_2$OCH$_3$), 2.88-2.72 (m, 6H, 3 x CH$_2$), 2.39 (s, 6H, N(CH$_3$)$_2$), 1.49 (s, 3H CH$_3$).

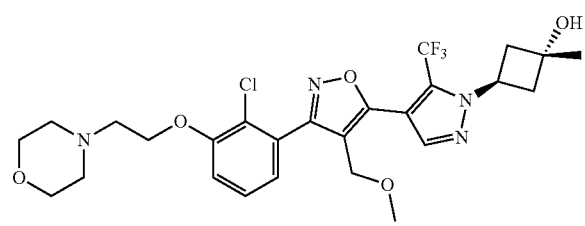 [SMILES: COCc1c(-c2cccc(OCCN3CCOCC3)c2Cl)noc1-c1cnn([C@H]2C[C@](C)(O)C2)c1C(F)(F)F]

Example 152: 3-[4-(3-{2-chloro-3-[2-(morpholin-4-yl)ethoxy]phenyl}-4-(methoxymethyl)-1,2-oxazol-5-yl)-5-(trifluoromethyl)-1H-pyrazol-1-yl]-1-methyl-cyclobutan-1-ol (Anti-Configuration)

2-chloro-3-[4-(methoxymethyl)-5-{1-[3-[(tert-butyldimethylsilyl)oxy]-3-methylcyclobutyl]-5-(trifluoromethyl)-1H-pyrazol-4-yl}-1,2-oxazol-3-yl]phenol (anti-configuration) (0.02 mmol) and N-(2-chloroethyl)morpholine hydrochloride were used in method A, reaction temperature 50° C.; upon standard workup, crude material was taken up in THF (0.5 mL) and treated with TBAF (1 M in THF; 1.1 eq.) at room temperature for 4.5 h. The solvent was removed under reduced pressure and the title compound was isolated from prep. TLC (eluent: CH$_2$Cl$_2$(MeOH/aq. NH$_3$ 100:10:1) as pale yellow oil (60%).

Result of LC/MS [M+H]$^+$: 571.3;

$^1$H-NMR (CDCl$_3$, J [Hz]): δ=7.87 (s, 1H pyrazole-H), 7.35-7.29 (m, 1H, benzyl-H), 7.12-7.06 (m, 2H, benzyl-H), 5.32-5.21 (m, 1H, CH), 4.25-4.19 (m, 4H, CH$_2$, RCH$_2$OCH$_3$), 3.75-3.72 (m, 4H, morpholino-H), 3.15 (s, 3H, RCH$_2$OCH$_3$), 2.91-2.80 (m, 4H, 2 x CH$_2$), 2.68-2.61 (m, 6H, CH$_2$, morpholino-H), 1.55 (s, 3H CH$_3$).

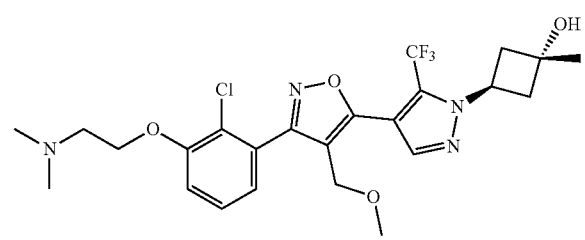

Example 153: 3-[4-(3-{2-chloro-3-[2-(dimethylamino)ethoxy]phenyl}-4-(methoxymethyl)-1,2-oxazol-5-yl)-5-(trifluoromethyl)-1H-pyrazol-1-yl]-1-methylcyclobutan-1-ol (Anti-Configuration)

2-chloro-3-[4-(methoxymethyl)-5-{1-[3-[(tert-butyldimethylsilyl)oxy]-3-methylcyclobutyl]-5-(trifluoromethyl)-1H-pyrazol-4-yl}-1,2-oxazol-3-yl]phenol (anti-configuration) (0.03 mmol) and 2-chloro-N,N-dimethylethylamine were used in method A, reaction temperature 50° C.; upon standard workup, crude material was taken up in THF (0.5 mL) and treated with TBAF (1 M in THF; 1.1 eq.) at room temperature for 3.5 h. The solvent was removed under reduced pressure and the title compound was isolated from prep. TLC (eluent: CH$_2$Cl$_2$/MeOH/aq. NH$_3$ 100:10:1) as pale yellow oil (87%).

Result of LC/MS [M+H]$^+$: 529.30;

$^1$H-NMR (CDCl$_3$, J [Hz]): δ=7.87 (s, 1H pyrazole-H), 7.35-7.29 (m, 1H, benzyl-H), 7.11-7.06 (m, 2H, benzyl-H), 5.31-5.21 (m, 1H, CH), 4.23-4.19 (m, 4H, CH$_2$, RCH$_2$OCH$_3$), 3.15 (s, 3H, RCH$_2$OCH$_3$), 2.87-2.80 (m, 2H, CH$_2$), 2.68-2.60 (m, 2H, CH$_2$), 2.40 (s, 6H, N(CH$_3$)$_2$), 1.55 (s, 3H, CH$_3$).

General Procedure for the Synthesis of isoxazol-3-yl-benzamides

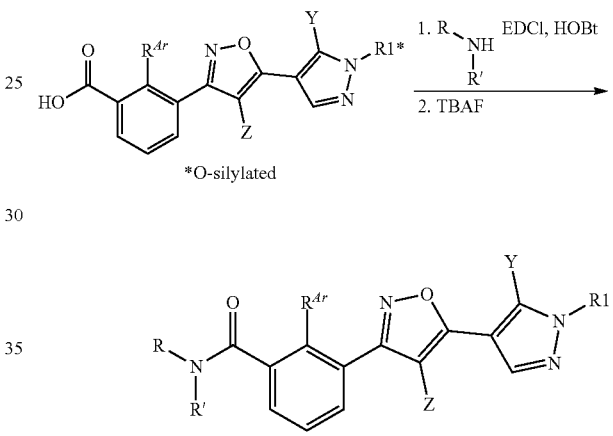

*O-silylated

Either 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-chlorobenzoic acid (Examples 154 to 160), 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-methoxybenzoic acid (Examples 161 to 165), or 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-benzoic acid (Examples 166 and 167) (0.15 mmol), the respective amine (1.8 eq.), 1-hydroxybenzotriazole (1.5 eq.) and 1-(3-dimethylaminopropyl)-3-ethylcarbodiimide hydrochloride (EDCI; 1.7 eq.) were dissolved in 1 mL dry DMF. N-Methylmorpholine (10. eq.) was added and the mixture was stirred at room temperature for 18 h. The mixture was partitioned between saturated aq. NH$_4$Cl-solution and CH$_2$Cl$_2$, combined organic layers were washed with water and brine and dried over MgSO$_4$, filtrated and concentrated under reduced pressure. Product purification was achieved by prep. TLC on silica gel (eluent: petroleum ether/ethyl acetate 1:1; if required, second prep. TLC, diluent: CH$_2$Cl$_2$/MeOH 98:2).

Final O-desilylation of benzamides was achieved in THF (0.5 mL) with TBAF (1 M in THF; 1.1 eq.) at room temperature for 3.5 h. The solvent was removed under

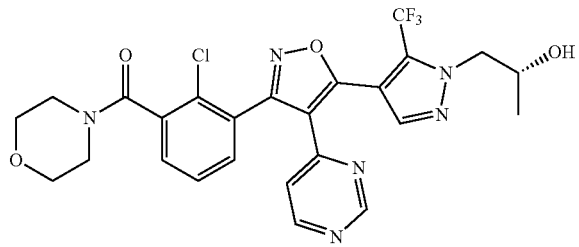 [SMILES: C[C@@H](O)Cn1ncc(-c2onc(-c3cccc(C(=O)N4CCOCC4)c3Cl)c2-c2ccncn2)c1C(F)(F)F]

Example 154: (R)-(2-chloro-3-(5-(1-(2-hydroxypropyl)-5-(trifluoromethyl)-1H-pyrazol-4-yl)-4-(pyrimidin-4-yl)isoxazol-3-yl)phenyl) (morpholino)methanone From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-chlorobenzoic acid and morpholine in 23% yield over two steps.

Result of LC/MS [M+H]$^+$: 562.9;

$^1$H NMR (CDCl$_3$): δ1.32 (3H, d, CH$_3$), 3.19 (2H, t, CH$_2$), 3.58 (2H, t, CH$_2$), 3.91-3.66 (4H, m, 2xCH$_2$), 4.23 (1H, dd, CH), 4.47-4.30 (2H, m, CH$_2$), 6.90 (1H, br, CH-arom.), 7.57-7.45 (2H, m, 2xCH-arom.), 7.64 (1H, dd, CH-arom.), 7.97 (1H, s, CH-arom.), 8.55 (1H, br, CH-arom.), 9.06 (1H, br, CH-arom.).

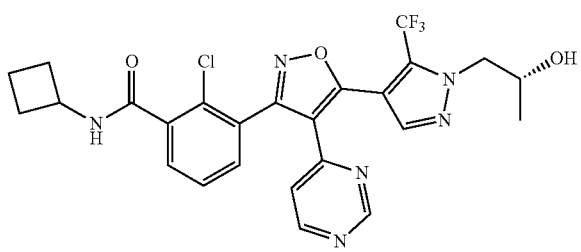 [SMILES: C[C@@H](O)Cn1ncc(-c2onc(-c3cccc(C(=O)NC4CCC4)c3Cl)c2-c2ccncn2)c1C(F)(F)F]

Example 155: (R)-2-chloro-N-cyclobutyl-3-(5-(1-(2-hydroxypropyl)-5-(trifluoromethyl)-1H-pyrazol-4-yl)-4-(pyrimidin-4-yl)isoxazol-3-yl)benzamide From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-chlorobenzoic acid and cyclobutylamine in 14% yield over two steps.

Result of LC/MS [M+H]$^+$: 546.9;

$^1$H NMR (CDCl$_3$): δ1.32 (3H, d, CH$_3$), 2.60-1.70 (6H, m, 3xCH$_2$), 4.24 (1H, dd, CH), 4.50-4.31 (2H, m, CH$_2$), 4.58 (1H, quint, CH), 6.19 (1H, br, NH), 6.94 (1H, s, CH-arom.), 7.50 (1H, t, CH-arom.), 7.61 (1H, d, CH-arom.), 7.78 (1H, d, CH-arom.), 7.98 (1H, s, CH-arom.), 8.61 (1H, br, CH-arom.), 9.07 (1H, s, CH-arom.).

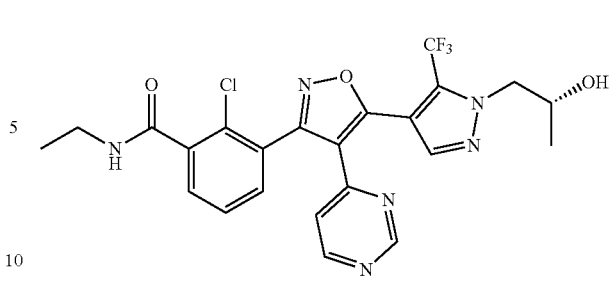

Example 156: (R)-2-chloro-N-ethyl-3-(5-(1-(2-hydroxypropyl)-5-(trifluoromethyl)-1H-pyrazol-4-yl)-4-(pyrimidin-4-yl)isoxazol-3-yl)benzamide From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-chlorobenzoic acid and ethylamine (2 M in THF) in 8% yield over two steps.

Result of LC/MS [M+H]$^+$: 520.9;

$^1$H NMR (CDCl$_3$): δ1.25 (3H, q, CH$_3$), 1.32 (3H, d, CH$_3$), 3.56-3.42 (2H, m, CH$_2$), 4.24 (1H, dd, CH), 4.48-4.31 (2H, m, CH$_2$), 6.00 (1H, br, N—H), 6.91 (1H, br, CH-arom.), 7.51 (1H, t, CH-arom.), 7.61 (1H, d, CH-arom.), 7.78 (1H, d, CH-arom.), 7.98 (1H, s, CH-arom.), 8.60 (1H, br, CH-arom.), 9.06 (1H, s, CH-arom.).

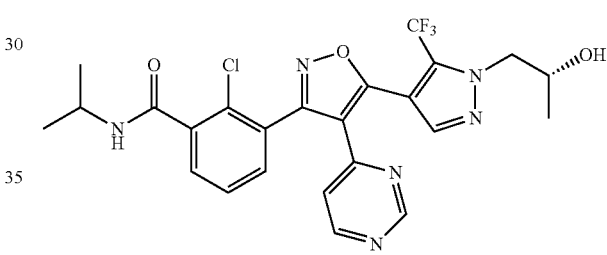

Example 157: (R)-2-chloro-3-(5-(1-(2-hydroxypropyl)-5-(trifluoromethyl)-1H-pyrazol-4-yl)-4-(pyrimidin-4-yl)isoxazol-3-yl)-N-isopropylbenzamide From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-chlorobenzoic acid and isopropylamine in 12% yield over two steps.

Result of LC/MS [M+H]$^+$: 534.9;

$^1$H NMR (CDCl$_3$): δ1.26 (6H, d, 2xCH$_3$), 1.32 (3H, d, CH$_3$), 4.48-4.18 (4H, m, 2xCH and CH$_2$), 5.84 (1H, d, N—H), 6.96 (1H, s, CH-arom.), 7.50 (1H, t, CH-arom.), 7.60 (1H, d, CH-arom.), 7.76 (1H, d, CH-arom.), 7.98 (1H, s, CH-arom.), 8.62 (1H, br, CH-arom.), 9.07 (1H, s, CH-arom.).

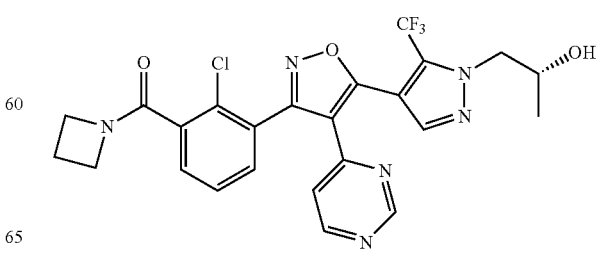

Example 158: (R)-(azetidin-1-yl)(2-chloro-3-(5-(1-(2-hydroxypropyl)-5-(trifluoromethyl)-1H-pyrazol-4-yl)-4-(pyrimidin-4-yl)isoxazol-3-yl)phenyl)methanone From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-chlorobenzoic acid and azetidine in 19% yield over two steps.

Result of LC/MS [M+H]⁺: 532.9;

¹H NMR (CDCl₃): δ1.32 (3H, d, CH₃), 2.43-2.24 (2H, m, CH₂), 4.00-3.83 (2H, m, CH₂), 4.49-4.14 (5H, m, CH and 2xCH₂), 7.03 (1H, d, CH-arom.), 7.59-7.47 (2H, m, 2xCH-arom.), 7.63 (1H, dd, CH-arom.), 7.97 (1H, s, CH-arom.), 8.63 (1H, br, CH-arom.), 9.08 (1H, s, CH-arom.).

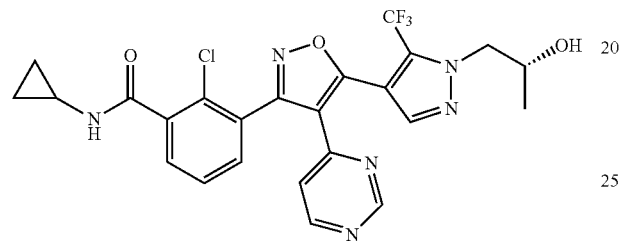

Example 159: (R)-2-chloro-N-cyclopropyl-3-(5-(1-(2-hydroxypropyl)-5-(trifluoromethyl)-1H-pyrazol-4-yl)-4-(pyrimidin-4-yl)isoxazol-3-yl)benzamide From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-chlorobenzoic acid and cyclopropylamine in 6% yield over two steps.

Result of LC/MS [M+H]⁺: 532.9;

¹H NMR (CDCl₃): δ0.68 (2H, m, CH₂), 0.91-0.85 (2H, m, CH₂), 1.32 (3H, d, CH₃), 2.98-2.84 (1H, m, CH), 4.46-4.18 (3H, m, CH and CH₂), 6.17 (1H, br, NH), 6.91 (1H, br, CH-arom.), 7.56-7.46 (1H, m, CH-arom.), 7.64-7.57 (1H, m, CH-arom.), 7.77 (1H, dd, CH-arom.), 7.97 (1H, s, CH-arom.), 8.60 (1H, br, CH-arom.), 9.06 (1H, s, CH-arom.).

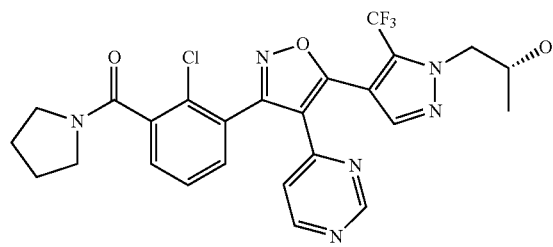

Example 160: (R)-(2-chloro-3-(5-(1-(2-hydroxypropyl)-5-(trifluoromethyl)-1H-pyrazol-4-yl)-4-(pyrimidin-4-yl)isoxazol-3-yl)phenyl)(pyrrolidin-1-yl)methanone From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-chlorobenzoic acid and pyrrolidine in 23% yield over two steps.

Result of LC/MS [M+H]⁺: 547.0;

¹H NMR (CDCl₃): δ1.31 (3H, d, CH₃), 2.02-1.81 (4H, m, 2xCH₂), 3.13 (2H, t, CH₂), 3.62 (2H, t, CH₂), 4.23 (1H, dd, CH), 4.46-4.29 (2H, m, CH₂), 6.90 (1H, d, CH-arom.), 7.55-7.44 (2H, m, 2xCH-arom.), 7.65-7.55 (1H, m, CH-arom.), 7.96 (1H, s, CH-arom.), 8.56 (1H, br, CH-arom.), 9.03 (1H, s, CH-arom.).

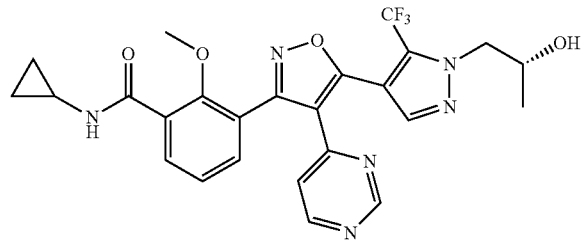 [SMILES: COc1c(C(=O)NC2CC2)cccc1-c1noc(-c2cnn(C[C@@H](C)O)c2C(F)(F)F)c1-c1ccncn1]

Example 161: (R)—N-cyclopropyl-3-(5-(1-(2-hydroxypropyl)-5-(trifluoromethyl)-1H-pyrazol-4-yl)-4-(pyrimidin-4-yl)isoxazol-3-yl)-2-methoxybenzamide From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-methoxybenzoic acid and cyclopropylamine in 9% yield over two steps.

Result of LC/MS [M+H]⁺: 529.0;

¹H NMR (CDCl₃): δ0.61-0.49 (2H, m, CH₂), 0.94-0.80 (2H, m, CH₂), 1.33 (3H, d, CH₃), 3.06-2.78 (1H, m, CH), 3.53 (3H, s, OCH₃), 4.25 (1H, dd, CH), 4.48-4.32 (2H, m, CH₂), 7.08 (1H, d, CH-arom.), 7.50-7.36 (2H, m, 2xCH-arom.), 7.67 (1H, dd, CH-arom.), 7.94 (1H, s, CH-arom.), 8.29 (1H, dd, CH-arom.), 8.66 (1H, d, CH-arom.), 9.14 (1H, s, CH-arom.).

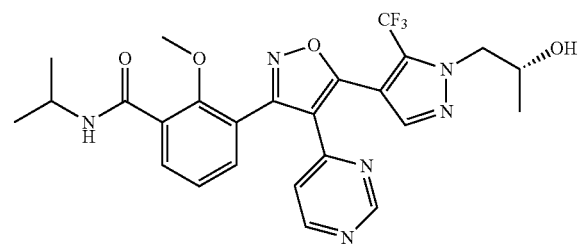 [SMILES: COc1c(C(=O)NC(C)C)cccc1-c1noc(-c2cnn(C[C@@H](C)O)c2C(F)(F)F)c1-c1ccncn1]

Example 162: (R)-3-(5-(1-(2-hydroxypropyl)-5-(trifluoromethyl)-1H-pyrazol-4-yl)-4-(pyrimidin-4-yl)isoxazol-3-yl)-N-isopropyl-2-methoxybenzamide From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-methoxybenzoic acid and isopropylamine in 18% yield over two steps.

Result of LC/MS [M+H]⁺: 531.0;

¹H NMR (CDCl₃): δ1.22 (6H, d, 2xCH₃), 1.33 (3H, d, CH₃), 3.57 (3H, s, OCH₃), 4.48-4.17 (4H, m, 2xCH and CH₂), 7.08 (1H, br, NH), 7.21-7.11 (1H, m, CH-arom.), 7.42 (1H, t, CH-arom.), 7.64 (1H, dd, CH-arom.), 7.95 (1H, s, CH-arom.), 8.27 (1H, dd, CH-arom.), 8.64 (1H, s, CH-arom.), 9.14 (1H, s, CH-arom.).

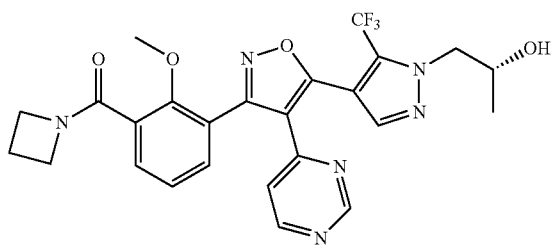 [SMILES: COc1c(C(=O)N2CCC2)cccc1-c1noc(-c2cnn(C[C@@H](C)O)c2C(F)(F)F)c1-c1ccncn1]

Example 163: (R)-(azetidin-1-yl)(3-(5-(1-(2-hydroxypropyl)-5-(trifluoromethyl)-1H-pyrazol-4-yl)-4-(pyrimidin-4-yl)isoxazol-3-yl)-2-methoxyphenyl)methanone From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-methoxybenzoic acid and azetidine in 15% yield over two steps.

Result of LC/MS [M+H]$^+$: 529.0;

$^1$H NMR (CDCl$_3$): δ1.33 (3H, d, CH$_3$), 2.40-2.19 (2H, m, CH$_2$), 3.51 (3H, s, OCH$_3$), 4.18-3.70 (4H, m, 2xCH$_2$), 4.48-4.18 (3H, m, CH and CH$_2$), 7.14 (1H, d, CH-arom.), 7.33 (1H, t, CH-arom.), 7.58 (1H, dd, CH-arom.), 7.66 (1H, dd, CH-arom.), 7.95 (1H, s, CH-arom.), 8.63 (1H, br, CH-arom.), 9.13 (1H, s, CH-arom.).

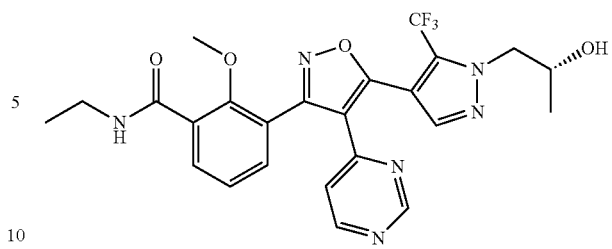

Example 165: (R)—N-ethyl-3-(5-(1-(2-hydroxypropyl)-5-(trifluoromethyl)-1H-pyrazol-4-yl)-4-(pyrimidin-4-yl)isoxazol-3-yl)-2-methoxybenzamide From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-methoxybenzoic acid and ethylamine (2 M in THF) in 4% yield over two steps.

Result of LC/MS [M+H]$^+$: 517.0;

$^1$H NMR (CDCl$_3$): δ1.18 (3H, t, CH$_3$), 1.32 (3H, d, CH$_3$), 3.52-3.38 (2H, m, CH$_2$), 3.55 (3H, s, OCH$_3$), 4.24 (1H, dd, CH), 4.47-4.30 (2H, m, CH$_2$), 6.90 (1H, br, NH), 7.47-7.30 (2H, m, 2xCH-arom.), 7.64 (1H, dd, CH-arom.), 7.94 (1H, s, CH-arom.), 8.26 (1H, dd, CH-arom.), 8.56 (1H, br, CH-arom.), 9.08 (1H, s, CH-arom.).

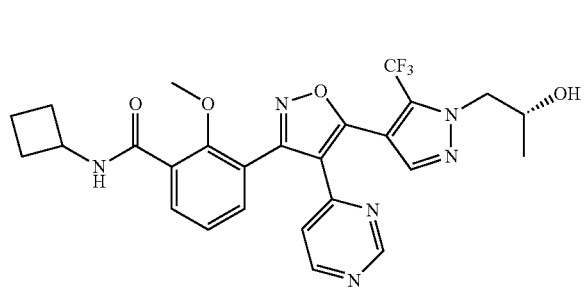 [SMILES: COc1c(C(=O)NC2CCC2)cccc1-c1noc(-c2cnn(C[C@@H](C)O)c2C(F)(F)F)c1-c1ccncn1]

Example 164: (R)—N-cyclobutyl-3-(5-(1-(2-hydroxypropyl)-5-(trifluoromethyl)-1H-pyrazol-4-yl)-4-(pyrimidin-4-yl)isoxazol-3-yl)-2-methoxybenzamide From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-2-methoxybenzoic acid and cyclobutylamine in 11% yield over two steps.

Result of LC/MS [M+H]$^+$: 543.0;

$^1$H NMR (CDCl$_3$): δ1.32 (3H, d, CH$_3$), 1.92-1.68 (4H, m, 2xCH$_2$), 2.47-2.26 (2H, m, CH$_2$), 3.58 (3H, s, OCH$_3$), 4.24 (1H, dd, CH), 4.46-4.30 (2H, m, CH$_2$), 4.64-4.49 (1H, m, CH$_2$), 6.93 (1H, br, NH), 7.38 (1H, t, CH-arom.), 7.51 (1H, d, CH-arom.), 7.62 (1H, dd, CH-arom.), 7.95 (1H, s, CH-arom.), 8.24 (1H, dd, CH-arom.), 8.58 (1H, br, CH-arom.), 9.10 (1H, s, CH-arom.).

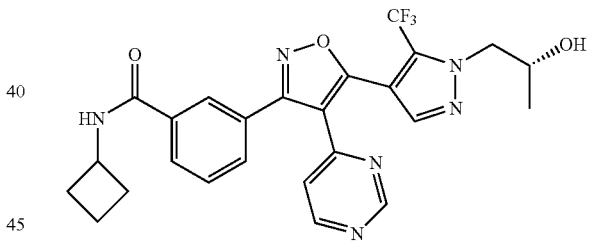

Example 166: (R)—N-cyclobutyl-3-(5-(1-(2-hydroxypropyl)-5-(trifluoromethyl)-1H-pyrazol-4-yl)-4-(pyrimidin-4-yl)isoxazol-3-yl)benzamide From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-benzoic acid and cyclobutylamine in 16% yield over two steps.

Result of LC/MS [M+H]$^+$: 513.0;

$^1$H NMR (CDCl$_3$): δ1.31 (3H, d, CH$_3$), 1.88-1.71 (2H, m, CH$_2$), 2.07-1.88 (2H, m, CH$_2$), 2.54-2.36 (2H, m, CH$_2$), 3.22 (1H, d, CH), 4.22 (1H, dd, CH), 4.47-4.29 (2H, m, CH$_2$), 4.68-4.49 (1H, m, CH), 6.23 (1H, d, N—H), 6.97 (1H, dd, CH-arom.), 7.60-7.43 (2H, m, 2xCH-arom.), 8.02-7.88 (3H, m, 3xCH-arom.), 8.59 (1H, d, CH-arom.), 9.18 (1H, d, CH-arom.).

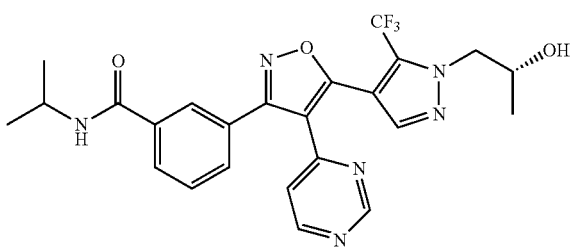 [SMILES: CC(C)NC(=O)c1cccc(-c2noc(-c3cnn(C[C@@H](C)O)c3C(F)(F)F)c2-c2ccncn2)c1]

Example 167: (R)-3-(5-(1-(2-hydroxypropyl)-5-(trifluoromethyl)-1H-pyrazol-4-yl)-4-(pyrimidin-4-yl)isoxazol-3-yl)-N-isopropylbenzamide From 3-(5-{1-[(2R)-2-[(tert-butyldimethylsilyl)oxy]propyl]-5-(trifluoromethyl)-1H-pyrazol-4-yl}-4-(pyrimidin-4-yl)-1,2-oxazol-3-yl)-benzoic acid and isopropylamine in 8% yield over two steps.

Result of LC/MS [M+H]$^+$: 501.0;

$^1$H NMR (CDCl$_3$): δ1.27 (6H, d, 2xCH$_3$), 1.31 (3H, d, CH$_3$), 3.22 (1H, br, OH), 4.58-4.07 (4H, m, 2xCH and CH$_2$), 5.91 (1H, d, N—H), 6.97 (1H, dd, CH-arom.), 7.57-7.45 (2H, m, 2xCH-arom.), 7.99-7.88 (3H, m, 3xCH-arom.), 8.59 (1H, d, CH-arom.), 9.18 (1H, d, CH-arom.).

b) Biological Tests

Cytokine Assay: Analysis of Proliferation of and Cytokine Production by Human PBMC Stimulated with PHA Peripheral blood mononuclear cells (PBMC) from healthy human donors were purified using Accuspin™ System-Histopaque-1077 (Sigma) according to the protocol recommended by the manufacturer. Purified PBMC were then washed twice with phosphate-buffered saline (PBS) and resuspended in RPMI1640 culture medium supplemented with 10% dialyzed heat inactivated fetal calf serum, 1.5 mM L-glutamine, 100 U penicillin/ml, and 100 mg streptomycin/ml (all from PAN Biotech, Aidenbach, Germany). For stimulation, PBMC were seeded at 1×10$^5$ cells/well, activated with 2 μg/ml phytohaemagglutinin (PHA, Sigma) and incubated with the test compounds for 48 hours. IL-17A, IL-17F and INF-γ were then determined in the culture supernatant using a Luminex BioPlex system, following the manufacturer's instructions (BioRad, Munich, Germany). For screening, compounds were used at 10, 1, 0.1 and 0.01 μM. To determine the IC$_{50}$, compounds were titrated semi-logarithmically.

Cell proliferation was analyzed using the BrdU based cell proliferation ELISA from Roche (Mannheim, Germany) according to the manufacturer's instructions.

Cytokines were determined in the aforementioned culture supernatant using the following methods: IL-17A was measured using the human homodimer IL-17A ELISA Ready Set Go Kit from eBioscience (Frankfurt, Germany); IL-17F using the human IL-17F ELI-Pair from Hölzel DiagnosticaGmBH (Köln, Germany); and IFN-γ using the OptEIA human IFN-g ELISA from BD Bioscience (Heidelberg, Germany), all following the manufacturer's instructions.

c) Aqueous Solubility

Aqueous solubility was tested in 50 mM phosphate buffer (pH 4.0, 6.0, 7.4 and 9.0 were tested, the below values were obtained with pH 7.4) and determined with a HPLC/DAD system using a gradient program (see below) and a reversed phase system. To achieve this, the samples (final volume 500 μl, 200 μM compound concentration) were incubated for 24 hours at 23° C. under continuous shaking at 1400 rpm (Thermomixer, Eppendorf) in aqueous phosphate buffers (pH 4.0, 6.0, 7.4 and 9.0) with a final DMSO concentration of 1%. To separate the undissolved compound from the solution, the samples were centrifuged (30 min 18000 g at 23° C.). Supernatants were measured via HPLC equipped with a UV detector and concentrations were calculated according to signals of a standard curve. The standard curve was prepared by diluting a stock solution of each compound (c=0.1 mg/ml; received by adding 10 μl of 20 mM compound in DMSO to 914 μl MeCN) in a certain amount of MeCN to cover a range of 0.1 to 200 μg/ml. Examples for dilution are given in the table below.

| Concentration [μg/ml] | Stocksolution [μl] | solvent MeCN [μl] |
|---|---|---|
| 0.1 | 1 | 999 |
| 0.5 | 5 | 995 |
| 1 | 10 | 990 |
| 2 | 20 | 980 |
| 5 | 50 | 950 |
| 10 | 100 | 900 |

The following equipment was used:
HPLC/PDA: Dionex Rapid Separation LC-System UltiMate 3000
HPLC-Pump: HPG-3400 no 8007268
Autosampler: WPS-3000SL no 8007769
Column Oven: TCC-3200 no 8006790
Detector: PDA-3000 no 08011269
Column: dependent on the test compound
Software: Chromeleon 6.80 SP3 Build 2345 (128616) no 36452
Excel 2000/2007
Glassware: pasteur-pipettes
Vials: glass vial (2 ml) with gasket (Dionex)
Analytical balance: Sartorius LE225D-OCE (accuracy: 0.01 mg)
Miscellaneous: Rainin GPS Tips, Rainin pipet lite, Minishaker
HPLC-Parameters:
Mobile phase A: dependent on the test compound, e.g. water with 0.1% formic acid
Mobile phase B: dependent on the test compound, e.g. acetonitrile
Injection volume: 5 μl
Column temperature: dependent on the test compound, e.g. 30° C.
Autosampler temperature: ambient temperature
Sample loop: 25 μl
PDA detection wavelength: dependent on the test compound, Data collection rate 5 Hz
Chrom.-stop-time: dependent on the test compound, e.g. 3.4 min
Program HPLC: dependent on the test compound
As an example, the following gradient was used for the measurement of a specific compound:

| Time [min] | A [%] | B [%] | Flow [ml/min] |
|---|---|---|---|
| 0.0 | 80 | 20 | 1.7 |
| 0.4 | 80 | 20 | 1.7 |
| 2.2 | 5 | 95 | 1.7 |
| 2.7 | 5 | 95 | 1.7 |

-continued

| Time [min] | A [%] | B [%] | Flow [ml/min] |
|---|---|---|---|
| 2.8 | 80 | 20 | 1.7 |
| 3.4 | 80 | 20 | 1.7 | d) Microsomal Stability

Metabolic stability of compounds of the present invention was determined by incubation with human liver microsomes and subsequent determination of residual amount of the respective compound ("parent compound") by HPLC-MS/MS.

In order to achieve this, in a final reaction volume of 1000 μl, each compound was incubated at a final concentration of 1 μM with 0.5 mg/ml human liver microsomes (HLM Pool 50 Donors, 20 mg/ml, BD Gentest, #452156, LotNr 88114) in 0.1 M Potassium phosphate buffer at pH 7.4, with a cofactor in form of a NADPH regenerating system (Promega, #V9510) according to the manufacturers' specifications. The final DMSO concentration in each sample was 0.4%. The incubation was performed at 37° C. under shaking conditions (Thermomixer, 1400 rpm) for different time intervals up to 60 min. To stop the reaction, for each time point 200 μl of the reaction were taken out and 200 μl ice-cold acetonitrile was added. Then, the samples were centrifuged (4° C., 14000*g for 15 min). The supernatant was analyzed for residual parent compound concentration and scanned for metabolites using HPLC-MS/MS. By using optimized MS methods for each compound, the peak area under curve for the compound specific signal is determined. The change of the peak areas over the assay time of 60 min resemble the remaining parent compound in % of T0. By these points, a balancing line was set. The half-time, as well as the clearance, can then be calculated on the basis of the slope.

Equipment: Waters Xevo™ TQ MS, Agilent 1200 HPLC, CTC-PAL Autosampler (temperature 8° C.)

TABLE 1

Exemplary compounds of formula (I) of the present invention include the following:

| Ex. | Name | IL-17A Inhib. | IL-17F Inhib. | IFN-gamma Inhib. | aq. solub. | $t_{1/2}$ hLM |
|---|---|---|---|---|---|---|
| 1 | 1-{4-[3-(2-chloro-6-fluorophenyl)-4-(1,3-thiazol-2-yl)-1,2-oxazol-5-yl]-5-(trifluoromethyl)-1H-pyrazol-1-yl}-2-methylpropan-2-ol | ++ | ++ | +++ | +++ | +++ |
| 2 | 1-({4-[3-(2-chloro-6-fluorophenyl)-4-(1,3-thiazol-2-yl)-1,2-oxazol-5-yl]-5-(trifluoromethyl)-1H-pyrazol-1-yl}methyl)cyclopropan-1-ol | +++ | ++ | +++ | ++ | + |
| 3 | 4-{4-[3-(2-chloro-6-fluorophenyl)-4-(1,3-thiazol-2-yl)-1,2-oxazol-5-yl]-5-(trifluoromethyl)-1H-pyrazol-1-yl}-2-methylbutan-2-ol | +++ | +++ | +++ | n.t. | +++ |
| 4 | (2R)-1-{4-[3-(2-chloro-6-fluorophenyl)-4-(1,3-thiazol-2-yl)-1,2-oxazol-5-yl]-5-(trifluoromethyl)-1H-pyrazol-1-yl}propan-2-ol | +++ | +++ | +++ | n.t. | + |
| 5 | (2S)-1-{4-[3-(2-chloro-6-fluorophenyl)-4-(1,3-thiazol-2-yl)-1,2-oxazol-5-yl]-5-(trifluoromethyl)-1H-pyrazol-1-yl}propan-2-ol | +++ | ++ | +++ | n.t. | ++ |
| 6 | 1-{4-[3-(2-chloro-6-fluorophenyl)-4-(1,3-thiazol-2-yl)-1,2-oxazol-5-yl]-5-(trifluoromethyl)-1H-pyrazol-1-yl}butan-2-ol (rac) | +++ | +++ | +++ | n.t. | + |
| 7 | 3-{4-[3-(2-chloro-6-fluorophenyl)-4-(1,3-thiazol-2-yl)-1,2-oxazol-5-yl]-5-(trifluoromethyl)-1H-pyrazol-1-yl}-1,1,1-trifluoropropan-2-ol (rac) | +++ | +++ | +++ | n.t. | + |
| 8 | ethyl 3-(2-chloro-6-fluorophenyl)-5-[1-(2-hydroxy-2-methylpropyl)-5-(trifluoromethyl)-1H-pyrazol-4-yl]-1,2-oxazole-4-carboxylate | +++ | ++ | +++ | ++ | +++ |
| 9 | ethyl 3-(2-chloro-6-fluorophenyl)-5-[1-(3-hydroxy-3-methylbutyl)-5-(trifluoromethyl)-1H-pyrazol-4-yl]-1,2-oxazole-4-carboxylate | +++ | +++ | +++ | ++ | ++ |
| 10 | ethyl 3-(2-chloro-6-fluorophenyl)-5-{1-[(1R,3S)-3-hydroxy-3-methylcyclobutyl]-5-(trifluoromethyl)-1H-pyrazol-4-yl}-1,2-oxazole-4-carboxylate (syn) | +++ | +++ | +++ | ++ | +++ |
| 11 | ethyl 3-(2-chloro-6-fluorophenyl)-5-{1-[(1S,3R)-3-hydroxy-3-methylcyclobutyl]-5-(trifluoromethyl)-1H-pyrazol-4-yl}-1,2-oxazole-4-carboxylate (anti) | +++ | +++ | +++ | n.t. | n.t. |

TABLE 1-continued

Exemplary compounds of formula (I) of the present invention include the following:

| Ex. | Name | IL-17A Inhib. | IL-17F Inhib. | IFN-gamma Inhib. | aq. solub. | $t_{1/2}$ hLM |
|---|---|---|---|---|---|---|
| 12 | ethyl 3-(2-chloro-6-fluorophenyl)-5-{1-[(2R)-2-hydroxypropyl]-5-(trifluoromethyl)-1H-pyrazol-4-yl}-1,2-oxazole-4-carboxylate | +++ | +++ | +++ | +++ | + |
| 13 | ethyl 3-(2-chloro-6-fluorophenyl)-5-{1-[(2S)-2-hydroxypropyl]-5-(trifluoromethyl)-1H-pyrazol-4-yl}-1,2-oxazole-4-carboxylate | +++ | +++ | +++ | +++ | ++ |
| 14 | ethyl 3-(2-chloro-6-fluorophenyl)-5-[1-(2-hydroxybutyl)-5-(trifluoromethyl)-1H-pyrazol-4-yl]-1,2-oxazole-4-carboxylate (rac) | +++ | +++ | +++ | ++ | + |
| 15 | ethyl 3-(2-chloro-6-fluorophenyl)-5-[1-(3,3,3-trifluoro-2-hydroxypropyl)-5-(trifluoromethyl)-1H-pyrazol-4-yl]-1,2-oxazole-4-carboxylate (rac) | +++ | +++ | +++ | ++ | 0 |
| 16 | ethyl 3-(2-chloro-6-fluorophenyl)-5-{1-[(2R)-3,3,3-trifluoro-2-hydroxypropyl]-5-(trifluoromethyl)-1H-pyrazol-4-yl}-1,2-oxazole-4-carboxylate | +++ | +++ | +++ | n.t. | 0 |
| 17 | methyl 3-(2-chlorophenyl)-5-{5-methyl-1-[(1S,3R)-3-hydroxy-3-methylcyclobutyl]-1H-pyrazol-4-yl}-1,2-oxazole-4-carboxylate (anti) | + | + | + | n.t. | n.t. |
| 18 | methyl 3-(2-chlorophenyl)-5-{5-methyl-1-[(1R,3S)-3-hydroxy-3-methylcyclobutyl]-1H-pyrazol-4-yl}-1,2-oxazole-4-carboxylate (syn) | ++ | +++ | +++ | n.t. | +++ |
| 19 | methyl 3-(2-chlorophenyl)-5-[1-(3-hydroxy-3-methylbutyl)-5-methyl-1H-pyrazol-4-yl]-1,2-oxazole-4-carboxylate | +++ | ++ | +++ | n.t. | +++ |
| 20 | methyl 3-(2-chloro-6-fluorophenyl)-5-[1-(3-hydroxy-3-methylbutyl)-5-methyl-1H-pyrazol-4-yl]-1,2-oxazole-4-carboxylate | +++ | +++ | +++ | +++ | +++ |
| 21 | methyl 5-{1-[(2R)-2-hydroxypropyl]-5-(trifluoromethyl)-1H-pyrazol-4-yl}-3-(2-methoxypyridin-3-yl)-1,2-oxazole-4-carboxylate | + | + | + | n.t. | n.t. |
| 22 | methyl 3-(2-chlorophenyl)-5-{1-[(2S)-2-hydroxypropyl]-5-(trifluoromethyl)-1H-pyrazol-4-yl}-1,2-oxazole-4-carboxylate | ++ | ++ | +++ | n.t. | n.t. |
| 23 | methyl 3-(2-chloro-6-fluorophenyl)-5-{1-[(2S)-2-hydroxypropyl]-5-(trifluoromethyl)-1H-pyrazol-4-yl}-1,2-oxazole-4-carboxylate | ++ | ++ | +++ | n.t. | + |
| 24 | methyl 3-(2-chlorophenyl)-5-{1-[(2S)-2-hydroxypropyl]-5-methyl-1H-pyrazol-4-yl}-1,2-oxazole-4-carboxylate | + | ++ | ++ | n.t. | n.t. |
| 25 | methyl 3-(2-chloro-3-methoxyphenyl)-5-[1-(3-hydroxy-3-methylbutyl)-5-methyl-1H-pyrazol-4-yl]-1,2-oxazole-4-carboxylate | +++ | +++ | +++ | n.t. | +++ |
| 26 | methyl 3-(2-chloro-6-fluorophenyl)-5-{1-[(1S,3R)-3-hydroxy-3-methylcyclobutyl]-5-(trifluoromethyl)-1H-pyrazol-4-yl}-1,2-oxazole-4-carboxylate (anti) | + | + | + | + | ++ |
| 27 | methyl 3-(2-chloro-6-fluorophenyl)-5-{1-[(1R,3S)-3-hydroxy-3-methylcyclobutyl]-5-(trifluoromethyl)-1H-pyrazol-4-yl}-1,2-oxazole-4-carboxylate (syn) | +++ | +++ | +++ | ++ | ++ |
| 28 | methyl 3-(2-chloro-6-fluorophenyl)-5-[1-(3-hydroxycyclobutyl)-5-(trifluoromethyl)-1H-pyrazol-4-yl]-1,2-oxazole-4-carboxylate | + | + | + | n.t. | n.t. |

TABLE 1-continued

Exemplary compounds of formula (I) of the present invention include the following:

| Ex. | Name | IL-17A Inhib. | IL-17F Inhib. | IFN-gamma Inhib. | aq. solub. | $t_{1/2}$ hLM |
|---|---|---|---|---|---|---|
| 29 | methyl 3-(2-chlorophenyl)-5-{1-[(1S,3S)-3-hydroxy-3-(methoxymethyl)cyclobutyl]-5-(trifluoromethyl)-1H-pyrazol-4-yl}-1,2-oxazole-4-carboxylate (syn) | + | + | ++ | n.t. | n.t. |
| 30 | 1-{4-[3-(2-chloro-6-fluorophenyl)-4-(5-methyl-1,3,4-oxadiazol-2-yl)-1,2-oxazol-5-yl]-5-(trifluoromethyl)-1H-pyrazol-1-yl}-2-methylpropan-2-ol | ++ | + | + | n.t. | n.t. |
| 31 | 1-{4-[3-(2-chloro-6-fluorophenyl)-4-(1,3-thiazol-2-yl)-1,2-oxazol-5-yl]-5-(trifluoromethyl)-1H-pyrazol-1-yl}(2-²H)propan-2-ol (rac) | +++ | +++ | +++ | 0 | ++ |
| 32 | ethyl 3-(2-chloro-6-fluorophenyl)-5-{1-[2-hydroxy(2-²H)propyl]-5-(trifluoromethyl)-1H-pyrazol-4-yl}-1,2-oxazole-4-carboxylate (rac) | +++ | +++ | +++ | +++ | ++ |
| 33 | methyl 3-(2-chloro-6-fluorophenyl)-5-{1-[2-hydroxy(2-²H)propyl]-5-(trifluoromethyl)-1H-pyrazol-4-yl}-1,2-oxazole-4-carboxylate (rac) | +++ | +++ | +++ | +++ | +++ |
| 34 | 1-[3-(2-chloro-6-fluorophenyl)-5-[1-(2-hydroxy-2-methylpropyl)-5-(trifluoromethyl)-1H-pyrazol-4-yl]-1,2-oxazol-4-yl]ethan-1-one | + | + | + | n.t. | n.t. |
| 35 | 1-[3-(2-chloro-6-fluorophenyl)-5-{1-[(2R)-2-hydroxypropyl]-5-(trifluoromethyl)-1H-pyrazol-4-yl}-1,2-oxazol-4-yl]ethan-1-one | ++ | ++ | ++ | +++ | ++ |
| 36 | 1-[3-(2-chloro-6-fluorophenyl)-5-[1-(2-hydroxy-2-methylpropyl)-5-(trifluoromethyl)-1H-pyrazol-4-yl]-1,2-oxazol-4-yl]-2-cyclobutylethan-1-one | + | ++ | ++ | n.t. | n.t. |
| 37 | 1-[3-(2-chloro-6-fluorophenyl)-5-[1-(2-hydroxy-2-methylpropyl)-5-(trifluoromethyl)-1H-pyrazol-4-yl]-1,2-oxazol-4-yl]pent-4-en-1-one | ++ | ++ | ++ | n.t. | n.t. |
| 38 | 2-[3-(2-chloro-6-fluorophenyl)-5-[1-(2-hydroxy-2-methylpropyl)-5-(trifluoromethyl)-1H-pyrazol-4-yl]-1,2-oxazol-4-yl]-1-cyclopropylhex-5-en-2-ol (rac) | + | 0 | 0 | n.t. | n.t. |
| 39 | 1-[3-(2-chloro-6-fluorophenyl)-5-[1-(2-hydroxy-2-methylpropyl)-5-(trifluoromethyl)-1H-pyrazol-4-yl]-1,2-oxazol-4-yl]-2-methoxyethan-1-one | + | 0 | + | n.t. | n.t. |
| 40 | 1-[3-(2-chloro-6-fluorophenyl)-5-{1-[(2R)-2-hydroxypropyl]-5-(trifluoromethyl)-1H-pyrazol-4-yl}-1,2-oxazol-4-yl]-2-methoxyethan-1-one | + | + | + | n.t. | n.t. |
| 41 | 3-(2-chloro-6-fluorophenyl)-N-cyclopentyl-5-[1-(2-hydroxy-2-methylpropyl)-5-(trifluoromethyl)-1H-pyrazol-4-yl]-1,2-oxazole-4-carboxamide | 0 | 0 | 0 | n.t. | n.t. |
| 42 | 3-(2-chloro-6-fluorophenyl)-N-cyclopropyl-5-[1-(2-hydroxy-2-methylpropyl)-5-(trifluoromethyl)-1H-pyrazol-4-yl]-1,2-oxazole-4-carboxamide | 0 | 0 | 0 | n.t. | n.t. |
| 43 | 3-(2-chloro-6-fluorophenyl)-N-cyclobutyl-5-[1-(2-hydroxy-2-methylpropyl)-5-(trifluoromethyl)-1H-pyrazol-4-yl]-1,2-oxazole-4-carboxamide | + | + | + | n.t. | n.t. |
| 44 | 3-(2-chloro-6-fluorophenyl)-N-cyclopentyl-5-{1-[(2R)-2-hydroxypropyl]-5-(trifluoromethyl)-1H-pyrazol-4-yl}-1,2-oxazole-4-carboxamide | ++ | + | ++ | +++ | 0 |

TABLE 1-continued

Exemplary compounds of formula (I) of the present invention include the following:

| Ex. | Name | IL-17A Inhib. | IL-17F Inhib. | IFN-gamma Inhib. | aq. solub. | $t_{1/2}$ hLM |
|---|---|---|---|---|---|---|
| 45 | 3-(2-chloro-6-fluorophenyl)-N-cyclopropyl-5-{1-[(2R)-2-hydroxypropyl]-5-(trifluoromethyl)-1H-pyrazol-4-yl}-1,2-oxazole-4-carboxamide | + | + | + | n.t. | n.t. |
| 46 | 3-(2-chloro-6-fluorophenyl)-N-cyclobutyl-5-{1-[(2R)-2-hydroxypropyl]-5-(trifluoromethyl)-1H-pyrazol-4-yl}-1,2-oxazole-4-carboxamide | + | ++ | ++ | n.t. | n.t. |
| 47 | oxetan-3-yl 3-(2-chlorophenyl)-5-{1-[(2S)-2-hydroxypropyl]-5-methyl-1H-pyrazol-4-yl}-1,2-oxazole-4-carboxylate | ++ | ++ | ++ | n.t. | n.t. |
| 48 | cyclopropyl 3-(2-chlorophenyl)-5-{1-[(1S,3R)-3-hydroxy-3-methylcyclobutyl]-5-(trifluoromethyl)-1H-pyrazol-4-yl}-1,2-oxazole-4-carboxylate (anti) | + | + | + | n.t. | n.t. |
| 49 | cyclopropyl 3-(2-chlorophenyl)-5-{1-[(1R,3S)-3-hydroxy-3-methylcyclobutyl]-5-(trifluoromethyl)-1H-pyrazol-4-yl}-1,2-oxazole-4-carboxylate (syn) | +++ | +++ | +++ | + | +++ |
| 50 | cyclopropyl 3-(2-chloro-6-fluorophenyl)-5-{1-[(1S,3R)-3-hydroxy-3-methylcyclobutyl]-5-(trifluoromethyl)-1H-pyrazol-4-yl}-1,2-oxazole-4-carboxylate (anti) | ++ | +++ | +++ | n.t. | n.t. |
| 51 | cyclopropyl 3-(2-chloro-6-fluorophenyl)-5-{1-[(1R,3S)-3-hydroxy-3-methylcyclobutyl]-5-(trifluoromethyl)-1H-pyrazol-4-yl}-1,2-oxazole-4-carboxylate (syn) | ++ | +++ | +++ | ++ | ++ |
| 52 | oxetan-3-yl 3-(2-chlorophenyl)-5-{1-[(1R,3S)-3-hydroxy-3-methylcyclobutyl]-5-methyl-1H-pyrazol-4-yl}-1,2-oxazole-4-carboxylate (syn) | ++ | ++ | ++ | n.t. | n.t. |
| 53 | cyclopropyl 3-(2-chlorophenyl)-5-{5-methyl-1-[(1R,3S)-3-hydroxy-3-methylcyclobutyl]-1H-pyrazol-4-yl}-1,2-oxazole-4-carboxylate (syn) | +++ | +++ | +++ | n.t. | +++ |
| 54 | cyclopropyl 3-(2-chlorophenyl)-5-{5-methyl-1-[(1S,3R)-3-hydroxy-3-methylcyclobutyl]-1H-pyrazol-4-yl}-1,2-oxazole-4-carboxylate (anti) | + | + | ++ | n.t. | n.t. |
| 55 | cyclopropyl 3-(2-chloro-6-fluorophenyl)-5-[1-(2-hydroxy-2-methylpropyl)-5-(trifluoromethyl)-1H-pyrazol-4-yl]-1,2-oxazole-4-carboxylate | +++ | +++ | +++ | n.t. | ++ |
| 56 | cyclobutyl 3-(2-chloro-6-fluorophenyl)-5-[1-(2-hydroxy-2-methylpropyl)-5-(trifluoromethyl)-1H-pyrazol-4-yl]-1,2-oxazole-4-carboxylate | +++ | +++ | +++ | + | 0 |
| 57 | oxetan-3-yl 3-(2-chloro-6-fluorophenyl)-5-[1-(2-hydroxy-2-methylpropyl)-5-(trifluoromethyl)-1H-pyrazol-4-yl]-1,2-oxazole-4-carboxylate | + | ++ | ++ | n.t. | n.t. |
| 58 | oxetan-3-yl 3-(2-chloro-6-fluorophenyl)-5-{1-[(2R)-2-hydroxypropyl]-5-(trifluoromethyl)-1H-pyrazol-4-yl}-1,2-oxazole-4-carboxylate | ++ | +++ | +++ | n.t. | ++ |
| 59 | cyclopropyl 3-(2-chloro-6-fluorophenyl)-5-{1-[(2S)-2-hydroxypropyl]-5-(trifluoromethyl)-1H-pyrazol-4-yl}-1,2-oxazole-4-carboxylate | +++ | +++ | +++ | +++ | + |

TABLE 1-continued

Exemplary compounds of formula (I) of the present invention include the following:

| Ex. | Name | IL-17A Inhib. | IL-17F Inhib. | IFN-gamma Inhib. | aq. solub. | $t_{1/2}$ hLM |
|---|---|---|---|---|---|---|
| 60 | oxetan-3-yl 3-(2-chloro-6-fluorophenyl)-5-{1-[(2S)-2-hydroxypropyl]-5-(trifluoromethyl)-1H-pyrazol-4-yl}-1,2-oxazole-4-carboxylate | ++ | ++ | ++ | +++ | + |
| 61 | cyclopropyl 3-(2-chloro-6-fluorophenyl)-5-{5-methyl-1-[(1R,3S)-3-hydroxy-3-methylcyclobutyl]-1H-pyrazol-4-yl}-1,2-oxazole-4-carboxylate (syn) | +++ | +++ | +++ | n.t. | ++ |
| 62 | cyclopropyl 3-(2-chloro-6-fluorophenyl)-5-{5-methyl-1-[(1S,3R)-3-hydroxy-3-methylcyclobutyl]-1H-pyrazol-4-yl}-1,2-oxazole-4-carboxylate (anti) | +++ | +++ | +++ | n.t. | n.t. |
| 63 | 1-{4-[3-(2-chloro-6-fluorophenyl)-4-(hydroxymethyl)-1,2-oxazol-5-yl]-5-(trifluoromethyl)-1H-pyrazol-1-yl}-2-methylpropan-2-ol | 0 | 0 | 0 | n.t. | n.t. |
| 64 | (1R,3S)-3-{4-[3-(2-chlorophenyl)-4-(hydroxymethyl)-1,2-oxazol-5-yl]-5-(trifluoromethyl)-1H-pyrazol-1-yl}-1-methylcyclobutan-1-ol (syn) | 0 | 0 | + | n.t. | n.t. |
| 65 | 1-{4-[3-(2-chloro-6-fluorophenyl)-4-(methoxymethyl)-1,2-oxazol-5-yl]-5-(trifluoromethyl)-1H-pyrazol-1-yl}-2-methylpropan-2-ol | + | + | + | +++ | n.t. |
| 66 | (2R)-1-{4-[3-(2-chloro-6-fluorophenyl)-4-(methoxymethyl)-1,2-oxazol-5-yl]-5-(trifluoromethyl)-1H-pyrazol-1-yl}propan-2-ol | ++ | ++ | +++ | +++ | n.t. |
| 67 | 4-{4-[3-(2-chloro-6-fluorophenyl)-4-(methoxymethyl)-1,2-oxazol-5-yl]-5-(trifluoromethyl)-1H-pyrazol-1-yl}-2-methylbutan-2-ol | ++ | ++ | +++ | +++ | +++ |
| 68 | (2S)-1-{4-[3-(2-chloro-6-fluorophenyl)-4-(methoxymethyl)-1,2-oxazol-5-yl]-5-(trifluoromethyl)-1H-pyrazol-1-yl}propan-2-ol | + | + | ++ | n.t. | n.t. |
| 69 | (1R,3S)-3-{4-[3-(2-chloro-6-fluorophenyl)-4-(methoxymethyl)-1,2-oxazol-5-yl]-5-(trifluoromethyl)-1H-pyrazol-1-yl}-1-methylcyclobutan-1-ol (syn) | ++ | ++ | +++ | n.t. | +++ |
| 70 | (1R,3S)-3-{4-[3-(2-chloro-6-fluorophenyl)-4-(methoxymethyl)-1,2-oxazol-5-yl]-5-methyl-1H-pyrazol-1-yl}-1-methylcyclobutan-1-ol (syn) | | + | + | n.t. | n.t. |
| 71 | (1S,3R)-3-{4-[3-(2-chloro-6-fluorophenyl)-4-(methoxymethyl)-1,2-oxazol-5-yl]-5-methyl-1H-pyrazol-1-yl}-1-methylcyclobutan-1-ol (anti) | | + | + | n.t. | n.t. |
| 72 | (1R,3S)-3-{4-[3-(2-chlorophenyl)-4-(methoxymethyl)-1,2-oxazol-5-yl]-5-methyl-1H-pyrazol-1-yl}-1-methylcyclobutan-1-ol (syn) | ++ | ++ | +++ | n.t. | n.t. |
| 73 | (1S,3R)-3-{4-[3-(2-chlorophenyl)-4-(methoxymethyl)-1,2-oxazol-5-yl]-5-methyl-1H-pyrazol-1-yl}-1-methylcyclobutan-1-ol (anti) | + | + | + | n.t. | n.t. |
| 74 | (1R,3S)-3-{4-[3-(2-chlorophenyl)-4-(methoxymethyl)-1,2-oxazol-5-yl]-5-(trifluoromethyl)-1H-pyrazol-1-yl}-1-methylcyclobutan-1-ol (syn) | ++ | ++ | ++ | n.t. | n.t. |
| 75 | (2S)-1-{4-[3-(2-chlorophenyl)-4-[(2-methoxyethoxy)methyl]-1,2-oxazol-5-yl]-5-(trifluoromethyl)-1H-pyrazol-1-yl}propan-2-ol | + | + | + | n.t. | n.t. |
| 76 | (2R)-1-{4-[3-(2-chloro-6-fluorophenyl)-4-(ethoxymethyl)-1,2-oxazol-5-yl]-5-(trifluoromethyl)-1H-pyrazol-1-yl}propan-2-ol | ++ | ++ | +++ | +++ | + |
| 77 | 4-{4-[3-(2-chloro-6-fluorophenyl)-4-(cyclopropoxymethyl)-1,2-oxazol-5- | +++ | +++ | +++ | ++ | +++ |

TABLE 1-continued

Exemplary compounds of formula (I) of the present invention include the following:

| Ex. | Name | IL-17A Inhib. | IL-17F Inhib. | IFN-gamma Inhib. | aq. solub. | $t_{1/2}$ hLM |
|---|---|---|---|---|---|---|
|  | yl]-5-(trifluoromethyl)-1H-pyrazol-1-yl}-2-methylbutan-2-ol |  |  |  |  |  |
| 78 | 4-{4-[3-(2-chlorophenyl)-4-(cyclopropoxymethyl)-1,2-oxazol-5-yl]-5-(trifluoromethyl)-1H-pyrazol-1-yl}-2-methylbutan-2-ol | ++ | +++ | +++ | +++ | ++ |
| 79 | 4-{4-[3-(2-chlorophenyl)-4-(cyclopropoxymethyl)-1,2-oxazol-5-yl]-5-methyl-1H-pyrazol-1-yl}-2-methylbutan-2-ol | ++ | ++ | +++ | n.t. | n.t. |
| 80 | (1R,3S)-3-{4-[3-(2-chlorophenyl)-4-(cyclopropoxymethyl)-1,2-oxazol-5-yl]-5-methyl-1H-pyrazol-1-yl}-1-methylcyclobutan-1-ol (syn) |  |  |  | n.t. | n.t. |
| 81 | (1S,3R)-3-{4-[3-(2-chlorophenyl)-4-(cyclopropoxymethyl)-1,2-oxazol-5-yl]-5-methyl-1H-pyrazol-1-yl}-1-methylcyclobutan-1-ol (anti) | + | + | ++ | n.t. | n.t. |
| 82 | 4-{4-[3-(2-chloro-6-fluorophenyl)-4-(cyclopropoxymethyl)-1,2-oxazol-5-yl]-5-methyl-1H-pyrazol-1-yl}-2-methylbutan-2-ol | +++ | +++ | +++ | +++ | +++ |
| 83 | (1R,3S)-3-{4-[3-(2-chloro-6-fluorophenyl)-4-(cyclopropoxymethyl)-1,2-oxazol-5-yl]-5-methyl-1H-pyrazol-1-yl}-1-methylcyclobutan-1-ol (syn) | +++ | +++ | +++ | + | ++ |
| 84 | (1S,3R)-3-{4-[3-(2-chloro-6-fluorophenyl)-4-(cyclopropoxymethyl)-1,2-oxazol-5-yl]-5-methyl-1H-pyrazol-1-yl}-1-methylcyclobutan-1-ol (anti) | ++ | ++ | ++ | n.t. | n.t. |
| 85 | (2R)-1-{4-[3-(2-chloro-6-fluorophenyl)-4-(cyclopropoxymethyl)-1,2-oxazol-5-yl]-5-(trifluoromethyl)-1H-pyrazol-1-yl}propan-2-ol | +++ | +++ | +++ | n.t. | + |
| 86 | (1R,3S)-3-{4-[3-(2-chloro-6-fluorophenyl)-4-(cyclopropoxymethyl)-1,2-oxazol-5-yl]-5-(trifluoromethyl)-1H-pyrazol-1-yl}-1-methylcyclobutan-1-ol (syn) | +++ | +++ | +++ | n.t. | +++ |
| 87 | (1R,3S)-3-{4-[3-(2-chlorophenyl)-4-(cyclopropoxymethyl)-1,2-oxazol-5-yl]-5-(trifluoromethyl)-1H-pyrazol-1-yl}-1-methylcyclobutan-1-ol (syn) | ++ | +++ | +++ | +++ | +++ |
| 88 | (2S)-1-{4-[3-(2-chlorophenyl)-4-[(oxetan-3-yloxy)methyl]-1,2-oxazol-5-yl]-5-(trifluoromethyl)-1H-pyrazol-1-yl}propan-2-ol | 0 | + | + | n.t. | n.t. |
| 89 | (2R)-1-{4-[3-(2-chloro-6-fluorophenyl)-4-[(propan-2-yloxy)methyl]-1,2-oxazol-5-yl]-5-(trifluoromethyl)-1H-pyrazol-1-yl}propan-2-ol | +++ | +++ | +++ | +++ | 0 |
| 90 | (2R)-1-{4-[3-(2-chloro-6-fluorophenyl)-4-(cyclobutoxymethyl)-1,2-oxazol-5-yl]-5-(trifluoromethyl)-1H-pyrazol-1-yl}propan-2-ol | +++ | +++ | +++ | +++ | 0 |
| 91 | 4-{4-[3-(2-chloro-3-methoxyphenyl)-4-(cyclopropoxymethyl)-1,2-oxazol-5-yl]-5-(trifluoromethyl)-1H-pyrazol-1-yl}-2-methylbutan-2-ol | +++ | +++ | +++ | n.t. | n.t. |
| 92 | (1R,3S)-3-[4-(3-{2-chloro-3-[2-(morpholin-4-yl)ethoxy]phenyl}-4-(cyclopropoxymethyl)-1,2-oxazol-5-yl]-5-(trifluoromethyl)-1H-pyrazol-1-yl]-1-methylcyclobutan-1-ol (syn) | +++ | +++ | +++ | n.t. | 0 |
| 93 | methyl 5-[1-(2-hydroxy-2-methylpropyl)-5-(trifluoromethyl)-1H-pyrazol-4-yl]-3-(2-hydroxypyridin-3-yl)-1,2-oxazole-4-carboxylate | + | ++ | ++ | n.t. | n.t. |
| 94 | (2R)-1-{4-[3-(2-chloro-6-fluorophenyl)-1,2-oxazol-5-yl]-5- | 0 | 0 | + | n.t. | n.t. |

TABLE 1-continued

Exemplary compounds of formula (I) of the present invention include the following:

| Ex. | Name | IL-17A Inhib. | IL-17F Inhib. | IFN-gamma Inhib. | aq. solub. | $t_{1/2}$ hLM |
|---|---|---|---|---|---|---|
|  | (trifluoromethyl)-1H-pyrazol-1-yl}propan-2-ol |  |  |  |  |  |
| 95 | 1-{4-[3-(2-chloro-6-fluorophenyl)-4-(methoxymethyl)-1,2-oxazol-5-yl]-5-(trifluoromethyl)-1H-pyrazol-1-yl}(2-2H)propan-2-ol (rac) | ++ | ++ | ++ | +++ | +++ |
| 96 | (2S)-1-{4-[3-(2-chlorophenyl)-4-(oxolan-2-yl)-1,2-oxazol-5-yl]-5-(trifluoromethyl)-1H-pyrazol-1-yl}propan-2-ol | + | + | ++ | n.t. | n.t. |
| 97 | (2R)-1-{4-[3-(2-chloro-6-fluorophenyl)-4-(pyrimidin-2-yl)-1,2-oxazol-5-yl]-5-(trifluoromethyl)-1H-pyrazol-1-yl}propan-2-ol | +++ | +++ | +++ | n.t. | ++ |
| 98 | (1R,3S)-3-{4-[3-(2-chloro-6-fluorophenyl)-4-(pyrimidin-2-yl)-1,2-oxazol-5-yl]-5-(trifluoromethyl)-1H-pyrazol-1-yl}-1-methylcyclobutan-1-ol (syn) | +++ | +++ | +++ | n.t. | +++ |
| 99 | (1R,3S)-3-{4-[3-(2-chlorophenyl)-4-(pyrimidin-2-yl)-1,2-oxazol-5-yl]-5-methyl-1H-pyrazol-1-yl}-1-methylcyclobutan-1-ol (syn) | ++ | +++ | +++ | +++ | +++ |
| 100 | (1R,3S)-3-{4-[3-(2-chloro-6-fluorophenyl)-4-(pyrazin-2-yl)-1,2-oxazol-5-yl]-5-(trifluoromethyl)-1H-pyrazol-1-yl}-1-methylcyclobutan-1-ol (syn) | ++ | +++ | +++ | n.t. | +++ |
| 101 | (1R,3S)-3-{4-[3-(2-chlorophenyl)-4-(pyrazin-2-yl)-1,2-oxazol-5-yl]-5-(trifluoromethyl)-1H-pyrazol-1-yl}-1-methylcyclobutan-1-ol (syn) | + | 0 | 0 | + | +++ |
| 102 | (1R,3S)-3-{4-[3-(2-chlorophenyl)-4-(pyrimidin-2-yl)-1,2-oxazol-5-yl]-5-(trifluoromethyl)-1H-pyrazol-1-yl}-1-methylcyclobutan-1-ol (syn) | +++ | +++ | +++ | +++ | +++ |
| 103 | (1R,3S)-3-{4-[3-(2-chloro-3-methoxyphenyl)-4-(pyrimidin-2-yl)-1,2-oxazol-5-yl]-5-(trifluoromethyl)-1H-pyrazol-1-yl}-1-methylcyclobutan-1-ol (syn) | +++ | +++ | +++ | n.t. | +++ |
| 104 | (1R,3S)-3-{4-[3-(2-chloro-6-fluorophenyl)-4-(pyrimidin-4-yl)-1,2-oxazol-5-yl]-5-(trifluoromethyl)-1H-pyrazol-1-yl}-1-methylcyclobutan-1-ol (syn) | +++ | +++ | +++ | + | +++ |
| 105 | (1S,3R)-3-{4-[3-(2-chloro-6-fluorophenyl)-4-(pyrimidin-4-yl)-1,2-oxazol-5-yl]-5-(trifluoromethyl)-1H-pyrazol-1-yl}-1-methylcyclobutan-1-ol (anti) | + | ++ | ++ | n.t. | n.t. |
| 106 | (1R,3S)-3-{4-[3-(2-chlorophenyl)-4-(pyrimidin-4-yl)-1,2-oxazol-5-yl]-5-(trifluoromethyl)-1H-pyrazol-1-yl}-1-methylcyclobutan-1-ol (syn) | +++ | +++ | +++ | +++ | +++ |
| 107 | (1R,3S)-3-{4-[3-(2-chlorophenyl)-4-(pyrimidin-4-yl)-1,2-oxazol-5-yl]-5-methyl-1H-pyrazol-1-yl}-1-methylcyclobutan-1-ol (syn) | ++ | ++ | +++ | n.t. | n.t. |
| 108 | (1R,3S)-3-{4-[3-(2-chloro-6-fluorophenyl)-4-(pyrimidin-4-yl)-1,2-oxazol-5-yl]-5-methyl-1H-pyrazol-1-yl}-1-methylcyclobutan-1-ol (syn) | ++ | ++ | ++ | n.t. | n.t. |
| 109 | (1R,3S)-3-{4-[3-(2-chlorophenyl)-4-(pyrazin-2-yl)-1,2-oxazol-5-yl]-5-methyl-1H-pyrazol-1-yl}-1-methylcyclobutan-1-ol (syn) | + | + | ++ | n.t. | n.t. |
| 110 | (1R,3S)-3-{4-[3-(2-chloro-6-fluorophenyl)-4-(pyrazin-2-yl)-1,2-oxazol-5-yl]-5-methyl-1H-pyrazol-1-yl}-1-methylcyclobutan-1-ol (syn) | ++ | ++ | ++ | +++ | +++ |

TABLE 1-continued

Exemplary compounds of formula (I) of the present invention include the following:

| Ex. | Name | IL-17A Inhib. | IL-17F Inhib. | IFN-gamma Inhib. | aq. solub. | $t_{1/2}$ hLM |
|---|---|---|---|---|---|---|
| 111 | (1R,3S)-3-{4-[3-(2-chloro-6-fluorophenyl)-4-(pyrimidin-2-yl)-1,2-oxazol-5-yl]-5-methyl-1H-pyrazol-1-yl}-1-methylcyclobutan-1-ol (syn) | +++ | +++ | +++ | +++ | +++ |
| 112 | (1R,3S)-3-{4-[3-(2-chloro-3-methoxyphenyl)-4-(pyrimidin-2-yl)-1,2-oxazol-5-yl]-5-methyl-1H-pyrazol-1-yl}-1-methylcyclobutan-1-ol (syn) | +++ | +++ | +++ | +++ | +++ |
| 113 | (2R)-1-{4-[3-(2-methoxyphenyl)-4-(pyrimidin-2-yl)-1,2-oxazol-5-yl]-5-(trifluoromethyl)-1H-pyrazol-1-yl}propan-2-ol | + | ++ | + | n.t. | n.t. |
| 114 | 1-{4-[3-(2-methoxyphenyl)-4-(pyrimidin-2-yl)-1,2-oxazol-5-yl]-5-(trifluoromethyl)-1H-pyrazol-1-yl}-2-methylpropan-2-ol | 0 | 0 | + | n.t. | n.t. |
| 115 | (2R)-1-{4-[3-(2-methoxyphenyl)-4-(pyrimidin-4-yl)-1,2-oxazol-5-yl]-5-(trifluoromethyl)-1H-pyrazol-1-yl}propan-2-ol | + | + | ++ | n.t. | n.t. |
| 116 | 1-{4-[3-(2-methoxyphenyl)-4-(pyrimidin-4-yl)-1,2-oxazol-5-yl]-5-(trifluoromethyl)-1H-pyrazol-1-yl}-2-methylpropan-2-ol | 0 | 0 | + | n.t. | n.t. |
| 117 | (2R)-1-{4-[3-(2-chloro-3-methoxyphenyl)-4-(pyrimidin-2-yl)-1,2-oxazol-5-yl]-5-(trifluoromethyl)-1H-pyrazol-1-yl}propan-2-ol | + | + | ++ | n.t. | n.t. |
| 118 | 1-{4-[3-(2-chloro-6-fluorophenyl)-4-(pyrimidin-2-yl)-1,2-oxazol-5-yl]-5-(trifluoromethyl)-1H-pyrazol-1-yl}-2-methylpropan-2-ol | +++ | +++ | +++ | n.t. | +++ |
| 119 | (2R)-1-{4-[3-(2-chloro-3-methoxyphenyl)-4-(pyrimidin-4-yl)-1,2-oxazol-5-yl]-5-(trifluoromethyl)-1H-pyrazol-1-yl}propan-2-ol | + | + | ++ | n.t. | n.t. |
| 120 | 1-{4-[3-(2-chloro-3-methoxyphenyl)-4-(pyrimidin-4-yl)-1,2-oxazol-5-yl]-5-(trifluoromethyl)-1H-pyrazol-1-yl}-2-methylpropan-2-ol | + | 0 | + | n.t. | n.t. |
| 121 | 4-{4-[3-(2-chloro-3-methoxyphenyl)-4-(pyrimidin-2-yl)-1,2-oxazol-5-yl]-5-(trifluoromethyl)-1H-pyrazol-1-yl}-2-methylbutan-2-ol | +++ | ++ | +++ | n.t. | +++ |
| 122 | 4-{4-[3-(2-chlorophenyl)-4-(pyrimidin-2-yl)-1,2-oxazol-5-yl]-5-(trifluoromethyl)-1H-pyrazol-1-yl}-2-methylbutan-2-ol | +++ | +++ | +++ | n.t. | n.t. |
| 123 | 4-{4-[3-(2-chloro-6-fluorophenyl)-4-(pyrimidin-2-yl)-1,2-oxazol-5-yl]-5-(trifluoromethyl)-1H-pyrazol-1-yl}-2-methylbutan-2-ol | +++ | +++ | +++ | +++ | +++ |
| 124 | 4-{4-[3-(2-chloro-3-methoxyphenyl)-4-(pyrimidin-2-yl)-1,2-oxazol-5-yl]-5-methyl-1H-pyrazol-1-yl}-2-methylbutan-2-ol | +++ | +++ | +++ | n.t. | +++ |
| 125 | 4-{4-[3-(2,6-dichloro-3-methoxyphenyl)-4-(pyrimidin-2-yl)-1,2-oxazol-5-yl]-5-methyl-1H-pyrazol-1-yl}-2-methylbutan-2-ol | ++ | +++ | +++ | n.t. | +++ |
| 126 | 4-{4-[3-(2-chlorophenyl)-4-(pyrimidin-2-yl)-1,2-oxazol-5-yl]-5-methyl-1H-pyrazol-1-yl}-2-methylbutan-2-ol | ++ | ++ | ++ | +++ | +++ |
| 127 | 4-{4-[3-(2-chloro-6-fluorophenyl)-4-(pyrimidin-2-yl)-1,2-oxazol-5-yl]-5-methyl-1H-pyrazol-1-yl}-2-methylbutan-2-ol | ++ | ++ | +++ | n.t. | +++ |
| 128 | 4-(4-{3-[3-(benzyloxy)-2-chlorophenyl]-4-(pyrimidin-2-yl)-1,2-oxazol-5-yl}-5-(trifluoromethyl)-1H-pyrazol-1-yl)-2-methylbutan-2-ol | +++ | +++ | 0 | 0 | 0 |
| 129 | 2-chloro-3-{5-[1-(3-hydroxy-3-methylbutyl)-5-(trifluoromethyl)-1H- | ++ | ++ | + | n.t. | n.t. |

TABLE 1-continued

Exemplary compounds of formula (I) of the present invention include the following:

| Ex. | Name | IL-17A Inhib. | IL-17F Inhib. | IFN-gamma Inhib. | aq. solub. | $t_{1/2}$ hLM |
|---|---|---|---|---|---|---|
| | pyrazol-4-yl]-4-(pyrimidin-2-yl)-1,2-oxazol-3-yl}phenol | | | | | |
| 130 | (1R,3S)-3-{4-[3-(2-chloro-3-methoxyphenyl)-4-(cyclopropoxymethyl)-1,2-oxazol-5-yl]-5-(trifluoromethyl)-1H-pyrazol-1-yl}-1-methylcyclobutan-1-ol (syn) | +++ | +++ | +++ | ++ | ++ |
| 131 | ethyl 3-(2-chloro-3-methoxyphenyl)-5-{1-[(1R,3S)-3-hydroxy-3-methylcyclobutyl]-5-(trifluoromethyl)-1H-pyrazol-4-yl}-1,2-oxazole-4-carboxylate (syn) | +++ | +++ | +++ | +++ | +++ |
| 132 | ethyl 3-(2-chloro-3-methoxyphenyl)-5-[1-(3-hydroxy-3-methylbutyl)-5-(trifluoromethyl)-1H-pyrazol-4-yl]-1,2-oxazole-4-carboxylate | +++ | +++ | +++ | ++ | ++ |
| 133 | 4-[4-(3-{2-chloro-3-[2-(morpholin-4-yl)ethoxy]phenyl}-4-(pyrimidin-2-yl)-1,2-oxazol-5-yl)-5-(trifluoromethyl)-1H-pyrazol-1-yl]-2-methylbutan-2-ol | +++ | +++ | +++ | n.t. | 0 |
| 134 | 4-[4-(3-{2-chloro-3-[2-(dimethylamino)ethoxy]phenyl}-4-(pyrimidin-2-yl)-1,2-oxazol-5-yl)-5-(trifluoromethyl)-1H-pyrazol-1-yl]-2-methylbutan-2-ol | +++ | ++ | ++ | n.t. | +++ |
| 135 | 4-[4-(3-{2-chloro-3-[2-(pyrrolidin-1-yl)ethoxy]phenyl}-4-(pyrimidin-2-yl)-1,2-oxazol-5-yl)-5-(trifluoromethyl)-1H-pyrazol-1-yl]-2-methylbutan-2-ol | ++ | ++ | +++ | n.t. | ++ |
| 136 | 4-[4-(3-{2-chloro-3-[2-(4-methylpiperazin-1-yl)ethoxy]phenyl}-4-(pyrimidin-2-yl)-1,2-oxazol-5-yl)-5-(trifluoromethyl)-1H-pyrazol-1-yl]-2-methylbutan-2-ol | ++ | ++ | ++ | n.t. | n.t. |
| 137 | 4-[4-(3-{2-chloro-3-[2-(diethylamino)ethoxy]phenyl}-4-(pyrimidin-2-yl)-1,2-oxazol-5-yl)-5-(trifluoromethyl)-1H-pyrazol-1-yl]-2-methylbutan-2-ol | ++ | ++ | ++ | n.t. | + |
| 138 | 4-[2-(2-chloro-3-{4-[1-(3-hydroxy-3-methylbutyl)-5-(trifluoromethyl)-1H-pyrazol-4-yl]-4-(pyrimidin-2-yl)-1,2-oxazol-3-yl}phenoxy)ethyl]-1lambda6-thiomorpholine-1,1-dione | +++ | +++ | ++ | n.t. | 0 |
| 139 | 4-(4-{3-[2-chloro-3-(2-{2-oxa-6-azaspiro[3.3]heptan-6-yl}ethoxy)phenyl]-4-(pyrimidin-2-yl)-1,2-oxazol-5-yl}-5-(trifluoromethyl)-1H-pyrazol-1-yl)-2-methylbutan-2-ol | +++ | +++ | ++ | n.t. | + |
| 140 | 4-[4-(3-{2-chloro-3-[3-(dimethylamino)propoxy]phenyl}-4-(pyrimidin-2-yl)-1,2-oxazol-5-yl)-5-(trifluoromethyl)-1H-pyrazol-1-yl]-2-methylbutan-2-ol | ++ | ++ | ++ | n.t. | n.t. |
| 141 | 4-[3-(2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenoxy)propyl]-1lambda6-thiomorpholine-1,1-dione | +++ | +++ | +++ | n.t. | 0 |
| 142 | 4-[4-(3-{-chloro-3-[3-(pyrrolidin-1-yl)propoxy]phenyl}-4-(pyrimidin-2-yl)-1,2-oxazol-5-yl)-5-(trifluoromethyl)-1H-pyrazol-1-yl]-2-methylbutan-2-ol | ++ | ++ | ++ | n.t. | n.t. |
| 143 | 4-[4-(3-{2-chloro-3-[3-(diethylamino)propoxy]phenyl}-4-(pyrimidin-2-yl)-1,2-oxazol-5-yl)-5-(trifluoromethyl)-1H-pyrazol-1-yl]-2-methylbutan-2-ol | +++ | +++ | +++ | n.t. | n.t. |
| 144 | 4-[4-(3-{2-chloro-3-[2-(diethylamino)ethoxy]phenyl}-4-(pyrimidin-2-yl)-1,2-oxazol-5-yl)-5-methyl-1H-pyrazol-1-yl]-2-methylbutan-2-ol | + | + | ++ | +++ | n.t. |

TABLE 1-continued

Exemplary compounds of formula (I) of the present invention include the following:

| Ex. | Name | IL-17A Inhib. | IL-17F Inhib. | IFN-gamma Inhib. | aq. solub. | $t_{1/2}$ hLM |
|---|---|---|---|---|---|---|
| 145 | 4-[4-(3-{2-chloro-3-[2-(dimethylamino)ethoxy]phenyl}-4-(pyrimidin-2-yl)-1,2-oxazol-5-yl)-5-methyl-1H-pyrazol-1-yl]-2-methylbutan-2-ol | + | + | ++ | n.t. | +++ |
| 146 | 4-[4-(3-{2-chloro-3-[2-(pyrrolidin-1-yl)ethoxy]phenyl}-4-(pyrimidin-2-yl)-1,2-oxazol-5-yl)-5-methyl-1H-pyrazol-1-yl]-2-methylbutan-2-ol | ++ | + | ++ | n.t. | +++ |
| 147 | 4-[4-(3-{2-chloro-3-[3-(diethylamino)propoxy]phenyl}-4-(pyrimidin-2-yl)-1,2-oxazol-5-yl)-5-methyl-1H-pyrazol-1-yl]-2-methylbutan-2-ol | + | + | ++ | +++ | +++ |
| 148 | methyl 3-{2-chloro-3-[2-(morpholin-4-yl)ethoxy]phenyl}-5-{1-[(2S)-2-hydroxypropyl]-5-(trifluoromethyl)-1H-pyrazol-4-yl}-1,2-oxazole-4-carboxylate | +++ | +++ | +++ | n.t. | 0 |
| 149 | methyl 3-{2-chloro-3-[2-(dimethylamino)ethoxy]phenyl}-5-{1-[(2S)-2-hydroxypropyl]-5-(trifluoromethyl)-1H-pyrazol-4-yl}-1,2-oxazole-4-carboxylate | ++ | + | ++ | n.t. | n.t. |
| 150 | (1R,3S)-3-[4-(3-{2-chloro-3-[2-(morpholin-4-yl)ethoxy]phenyl}-4-(methoxymethyl)-1,2-oxazol-5-yl)-5-(trifluoromethyl)-1H-pyrazol-1-yl]-1-methylcyclobutan-1-ol (syn) | +++ | +++ | +++ | n.t. | 0 |
| 151 | (1R,3S)-3-[4-(3-{2-chloro-3-[2-(dimethylamino)ethoxy]phenyl}-4-(methoxymethyl)-1,2-oxazol-5-yl)-5-(trifluoromethyl)-1H-pyrazol-1-yl]-1-methylcyclobutan-1-ol (syn) | ++ | ++ | ++ | n.t. | +++ |
| 152 | (1S,3R)-3-[4-(3-{2-chloro-3-[2-(morpholin-4-yl)ethoxy]phenyl}-4-(methoxymethyl)-1,2-oxazol-5-yl)-5-(trifluoromethyl)-1H-pyrazol-1-yl]-1-methylcyclobutan-1-ol (anti) | ++ | ++ | ++ | n.t. | 0 |
| 153 | (1S,3R)-3-[4-(3-{2-chloro-3-[2-(dimethylamino)ethoxy]phenyl}-4-(methoxymethyl)-1,2-oxazol-5-yl)-5-(trifluoromethyl)-1H-pyrazol-1-yl]-1-methylcyclobutan-1-ol (anti) | 0 | + | + | n.t. | +++ |
| 154 | (2R)-1-(4-{3-[2-chloro-3-(morpholine-4-carbonyl)phenyl]-4-(pyrimidin-4-yl)-1,2-oxazol-5-yl}-5-(trifluoromethyl)-1H-pyrazol-1-yl)propan-2-ol | + | 0 | ++ | n.t. | n.t. |
| 155 | 2-chloro-N-cyclobutyl-3-(5-{1-[(2R)-2-hydroxypropyl]-5-(trifluoromethyl)-1H-pyrazol-4-yl}-4-(pyrimidin-4-yl)-1,2-oxazol-3-yl)benzamide | ++ | ++ | ++ | n.t. | n.t. |
| 156 | 2-chloro-N-ethyl-3-(5-{1-[(2R)-2-hydroxypropyl]-5-(trifluoromethyl)-1H-pyrazol-4-yl}-4-(pyrimidin-4-yl)-1,2-oxazol-3-yl)benzamide | 0 | 0 | + | n.t. | n.t. |
| 157 | 2-chloro-3-(5-{1-[(2R)-2-hydroxypropyl]-5-(trifluoromethyl)-1H-pyrazol-4-yl}-4-(pyrimidin-4-yl)-1,2-oxazol-3-yl)-N-(propan-2-yl)benzamide | + | + | ++ | n.t. | n.t. |
| 158 | (2R)-1-(4-{3-[3-(azetidine-1-carbonyl)-2-chlorophenyl]-4-(pyrimidin-4-yl)-1,2-oxazol-5-yl}-5-(trifluoromethyl)-1H-pyrazol-1-yl)propan-2-ol | ++ | ++ | ++ | n.t. | n.t. |
| 159 | 2-chloro-N-cyclopropyl-3-(5-{1-[(2R)-2-hydroxypropyl]-5-(trifluoromethyl)-1H-pyrazol-4-yl}-4-(pyrimidin-4-yl)-1,2-oxazol-3-yl)benzamide | + | + | ++ | n.t. | n.t. |
| 160 | (2R)-1-(4-{3-[2-chloro-3-(pyrrolidine-1-carbonyl)phenyl]-4-(pyrimidin-4-yl)-1,2-oxazol-5-yl}-5-(trifluoromethyl)-1H-pyrazol-1-yl)propan-2-ol | +++ | +++ | +++ | +++ | + |

TABLE 1-continued

Exemplary compounds of formula (I) of the present invention include the following:

| Ex. | Name | IL-17A Inhib. | IL-17F Inhib. | IFN-gamma Inhib. | aq. solub. | $t_{1/2}$ hLM |
|---|---|---|---|---|---|---|
| 161 | N-cyclopropyl-3-(5-{1-[(2R)-2-hydroxypropyl]-5-(trifluoromethyl)-1H-pyrazol-4-yl}-4-(pyrimidin-4-yl)-1,2-oxazol-3-yl)-2-methoxybenzamide | 0 | 0 | + | n.t. | n.t. |
| 162 | 3-(5-{1-[(2R)-2-hydroxypropyl]-5-(trifluoromethyl)-1H-pyrazol-4-yl}-4-(pyrimidin-4-yl)-1,2-oxazol-3-yl)-2-methoxy-N-(propan-2-yl)benzamide | + | 0 | ++ | n.t. | n.t. |
| 163 | (2R)-1-(4-{3-[3-(azetidine-1-carbonyl)-2-methoxyphenyl]-4-(pyrimidin-4-yl)-1,2-oxazol-5-yl}-5-(trifluoromethyl)-1H-pyrazol-1-yl)propan-2-ol | 0 | 0 | + | n.t. | n.t. |
| 164 | N-cyclobutyl-3-(5-{1-[(2R)-2-hydroxypropyl]-5-(trifluoromethyl)-1H-pyrazol-4-yl}-4-(pyrimidin-4-yl)-1,2-oxazol-3-yl)-2-methoxybenzamide | + | + | + | n.t. | n.t. |
| 165 | N-ethyl-3-(5-{1-[(2R)-2-hydroxypropyl]-5-(trifluoromethyl)-1H-pyrazol-4-yl}-4-(pyrimidin-4-yl)-1,2-oxazol-3-yl)-2-methoxybenzamide | + | 0 | + | n.t. | n.t. |
| 166 | N-cyclobutyl-3-(5-{1-[(2R)-2-hydroxypropyl]-5-(trifluoromethyl)-1H-pyrazol-4-yl}-4-(pyrimidin-4-yl)-1,2-oxazol-3-yl)benzamide | + | 0 | + | n.t. | n.t. |
| 167 | 3-(5-{1-[(2R)-2-hydroxypropyl]-5-(trifluoromethyl)-1H-pyrazol-4-yl}-4-(pyrimidin-4-yl)-1,2-oxazol-3-yl)-N-(propan-2-yl)benzamide | 0 | 0 | + | n.t. | n.t. |

The $IC_{50}$ values for the cytokines are determined with the Cytokine Assay as described herein: +++: <50 nM; ++: 50 nM to <500 nM; +: 500 nM to <5 μM; 0: ≥5 μM.
The values for aqueous solubility are determined with the method described herein: 0: <1 μM; +: 1-2.99 μM; ++: 3-9.99 μM, +++: >10 μM, n.t.: not tested
The $t_{1/2}$ values for microsomal stability are determined with the method described herein: 0: 2-9.99 min; +: 10-39.99 min, ++: 40-100 min, +++: >100 min, n.t.: not tested

The invention claimed is:
1. A compound of formula (I) or a pharmaceutically acceptable salt or solvate thereof,

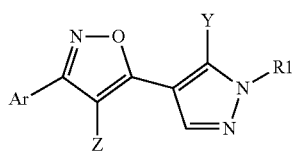

formula (I)

wherein
Ar is selected from the group consisting of phenyl and heteroaryl, each of which is optionally substituted by one or more independently selected substituents $R^{Ar}$;
$R^{Ar}$
is selected from the group consisting of halogen, —OH, —CN, alkoxy, haloalkoxy, alkyl, haloalkyl, mono- or dialkylamino-alkyl, mono- or di-alkylamino-alkoxy, —COOR', —CONHR', —CO—R', —SO$_2$NHR', —NH—CO—R', —NO$_2$, —NH—SO$_2$—R', —SO$_2$—R', benzyloxy, —CO-heterocyclyl, —CO-cycloalkyl, —CONH-cycloalkyl, —CONH— heterocyclyl, —O-alkyl-heterocyclyl, —O-alkyl-cycloalkyl, (2-oxa-6-azaspiro[3.3]hept-6-yl)-C$_{1-4}$-alkoxy, amino, aralkyl, cycloalkyl, heterocyclyl, phenyl and heteroaryl, wherein each of said alkoxy, aralkyl, alkyl, cycloalkyl, heterocyclyl, phenyl and heteroaryl groups is optionally substituted be one or more substituents independently selected from alkyl, haloalkyl, halogen and OH, and wherein R' is independently selected from the group consisting of independently represents H, OH, alkyl and haloalkyl;
Z is selected from the group consisting of H, halogen, —CO—R$^Z$, —CH$_2$—O—R$^Z$, —CO—CH$_2$—R$^Z$, —CO—CH$_2$—O—R$^Z$, —COOR$^Z$, —NHCO—R$^Z$, —CO—NHR$^Z$, —N(R$^Z$)$_2$, —CN, —NHCOOR$^Z$, —SO$_2$—R$^Z$, —SO$_2$NHR$^Z$, -alkyl-O—R$^Z$, -alkyl-O-alkyl-O—R$^Z$, amino, alkyl, phenyl, heteroaryl, heterocyclyl and cycloalkyl, wherein each of said alkyl, phenyl, heteroaryl, heterocyclyl and cycloalkyl groups is optionally substituted be one or more substituents independently selected from the group consisting of halogen, alkyl, alkoxy, haloalkyl, —COO-alkyl, OH and cycloalkyl;
$R^Z$ is selected from the group consisting of H, halogen, —OH, alkyl, haloalkyl, cycloalkyl, heterocyclyl, heterocyclyl, phenyl and heteroaryl,
Y is H, halogen, haloalkyl, alkyl or an alkylester;
R1 is a group of the structure

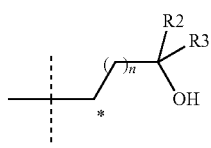

wherein n is 0 or 1; and

R2 and R3 are methyl, or taken together form a cyclopropyl group and X is H or methyl;

or R2 is methyl and R3 forms a methylene bridge to the carbon atom marked * and X is H or methyl;

or R2 and R3 are methyl, or taken together form a cyclopropyl group and X forms an ethylene bridge to the carbon atom marked *.

2. The compound of formula (I) according to claim 1 or a pharmaceutically acceptable salt or solvate thereof, wherein Ar is selected from the group consisting of phenyl, and heteroaryl, each of which is optionally substituted by one or more independently selected substituents $R^{Ar}$;

$R^{Ar}$ is selected from the group consisting of halogen, —OH, —CN, alkoxy, haloalkoxy, alkyl, haloalkyl, mono- or dialkylamino-alkyl, mono- or di-alkylamino-alkoxy, —COOR', —CONHR', —CO—R', —SO$_2$NHR', —NH—CO—R', —NO$_2$, —NH—SO$_2$—R', —SO$_2$—R', benzyloxy, —CO-heterocyclyl, —CO-cycloalkyl, —CONH-cycloalkyl, —CONH— heterocyclyl, —O-alkyl-heterocyclyl, —O-alkyl-cycloalkyl, (2-oxa-6-azaspiro[3.3]hept-6-yl)-C$_{1-4}$-alkoxy, amino, aralkyl, cycloalkyl, heterocyclyl, phenyl and heteroaryl, wherein each of said alkoxy, aralkyl, alkyl, cycloalkyl, heterocyclyl, phenyl and heteroaryl groups is optionally substituted be one or more substituents independently selected from alkyl, haloalkyl, halogen and OH, and wherein R' is independently selected from the group consisting of independently represents H, OH, alkyl and haloalkyl;

Z is selected from the group consisting of H, halogen, —CO—$R^Z$, —CH$_2$—O—$R^Z$, —CO—CH$_2$—$R^Z$, —CO—CH$_2$—O—$R^Z$, —COOR$^Z$, —NHCO—$R^Z$, —CO—NHR$^Z$, —N(R$^Z$)$_2$, —CN, —NHCO$_2$R$^Z$, —SO$_2$—R$^Z$, —SO$_2$NHR$^Z$, -alkyl-O—R$^Z$, -alkyl-O-alkyl-O—R$^Z$, amino, alkyl, phenyl, heteroaryl, heterocyclyl and cycloalkyl, wherein each of said alkyl, phenyl, heteroaryl, heterocyclyl and cycloalkyl groups is optionally substituted be one or more substituents independently selected from the group consisting of halogen, alkyl, alkoxy, haloalkyl, —COO-alkyl, OH and cycloalkyl;

$R^Z$ is selected from the group consisting of H, halogen, —OH, alkyl, haloalkyl, cycloalkyl, heterocyclyl, heterocyclyl, phenyl and heteroaryl, Y is H, halogen, haloalkyl, alkyl or an alkylester;

R1 is a group of the structure wherein n is 0 or 1;

R2 is H, deuterium or methyl;

R3 is methyl, trifluoromethyl, ethyl, or taken with R2 together forms a cyclopropyl group;

or n is 1, R2 is H, deuterium or methyl and R3 forms a methylene bridge to the carbon atom marked *.

3. The compound of formula (I) according to claim 1 or a pharmaceutically acceptable salt or solvate thereof, wherein Ar is selected from the group consisting of phenyl and 5- or 6-membered heteroaryl, each of which is optionally substituted by one or more substituents $R^{Ar}$;

$R^{Ar}$ is selected from the group consisting of halogen, OH, CN, C$_{1-4}$-alkyl, C$_{1-4}$-haloalkyl, —NH$_2$, acetamido, —COO—C$_{1-4}$-alkyl, C$_{1-4}$-alkoxy, and (mono- or di-C$_{1-4}$-alkyl-amino)-C$_{1-4}$-alkoxy, more particularly halogen, C$_{1-4}$-alkoxy, and (mono- or di-C$_{1-4}$-alkyl-amino)-C$_{1-4}$-alkoxy, benzyloxy, —CO—N(R$^N$)$_2$ wherein one $R^N$ is H and the other is C$_{1-3}$-alkyl, C$_{3-4}$cycloalkyl or both $R^N$ taken together with the N to which they are attached form an azetane, pyrrolidine or morpholine ring, —CONR$^N$ wherein one $R^N$ is H and the other is isopropyl or cyclobutyl or both $R^N$ taken together with the N to which they are attached form a pyrrolidine, morpholine, 1,1-dioxothiomorpholine, 4-methyl-piperazin, or 2-oxa-6-azaspiro[3.3]heptane ring;

Z is selected from the group consisting of H, halogen, —CO—C$_{1-4}$-alkyl, —CO—CH$_2$—C$_{1-4}$-alkoxy, —CO—CH$_2$—O—C$_{3-5}$-cycloalkyl, —CO-heterocyclyl, —CH$_2$—OH, —CH$_2$—O—C$_{1-4}$-alkyl, —CH$_2$—O—C$_{3-5}$-cycloalkyl, —NH$_2$, —NH—COO—C$_{1-4}$alkyl, —CN, —COO—C$_{1-4}$alkyl, —CONH—C$_{1-4}$alkyl, —CONH-arylalkyl, —CONH-cycloalkyl, —CON(C$_{1-4}$alkyl)$_2$, —CON(C$_{1-4}$alkyl)-O—C$_{1-4}$alkyl, —CO—CH$_2$-cycloalkyl, COO-heterocyclyl, —COO— cycloalkyl, cycloalkylmethyl, alken-1-one, alkyloxyalkyl, —C$_{1-2}$-alkyl-O—C$_{1-2}$-alkyl-O—C$_{1-4}$-alkyl, cycloalkylmethyl-alken-1-ol, heteroaryl, phenyl, or heterocyclyl, wherein said phenyl, and heterocyclyl is optionally substituted by one or more substituents independently selected from the group comprising halogen, alkyl, alkoxy, haloalkyl, —COO-alkyl, OH and cycloalkyl;

Y is selected from the group consisting of H, alkyl, haloalkyl, and alkylester;

R1 is a group of the structure wherein n is 0;

R2 is H, deuterium or methyl;

R3 is methyl, trifluoromethyl, ethyl, or taken with R2 together forms a cyclopropyl group;

or n is 1;

R2 is H, deuterium or methyl;

R3 is methyl or trifluoromethyl or forms a methylene bridge to the carbon atom marked *.

4. The compound according to claim 1 or a pharmaceutically acceptable salt or solvate thereof, wherein Ar is selected from the group consisting of phenyl and pyridyl, each of which is optionally substituted by one or more substituents $R^{Ar}$;

$R^{Ar}$ is selected from the group consisting of halogen, OH, —O—C$_{1-3}$-alkyl, —O—C$_{1-3}$-haloalkyl, C$_{1-4}$-alkyl, $C_{1-4}$-haloalkyl, (mono- or dimethylamino)-$C_{1-3}$-alkyl and (mono- or dimethylamino)-$C_{1-2}$-alkoxy;

Z is selected from the group consisting of COO—$C_{1-3}$-alkyl, —CO—$CH_2$—O—$C_{1-2}$-alkyl, 5- or 6-membered heteroaryl, phenyl, —COO—$C_{3-6}$-cycloalkyl, —COO—$C_{3-6}$-heterocyclyl, —CON—$C_{3-6}$-cycloalkyl, —CON—$C_{3-6}$-heterocyclyl, —CO—$CH_2$—$C_{3-6}$-cycloalkyl, —$CH_2$—O—$C_{3-6}$-cycloalkyl, —CO—$C_{1-4}$-alkyl, —$C_{1-2}$-alkyl-O—$C_{1-2}$-alkyl, —$C_{1-2}$-alkyl-O—$C_{1-2}$-alkyl-O—$C_{1-2}$-alkyl and —C(OH)($C_{1-4}$-alkyl)($CH_2$—$C_{3-6}$-cycloalkyl), wherein said heteroaryl, phenyl, heterocyclyl, cycloalkyl and alkyl is optionally substituted with one or more substituents independently selected from the group consisting of methyl, halogen, $CF_3$, OMe and OH;

Y is selected from the group consisting of $CF_3$ and Me;

R1 is selected from the group consisting of 3-hydroxy-3-methylbutyl, 2-hydroxy-2-methylpropyl, 3-hydroxy-3-methyl-cyclobutyl, 2-hydroxypropyl, 2-hydroxybutyl, 3-hydroxy-cyclobutyl, 2-hydroxy-3,3,3-trifluoropropyl, 2-hydroxy-2-deutero-propyl, and 1-hydroxy-cyclopropylmethyl.

5. The compound according to claim 1 or a pharmaceutically acceptable salt or solvate thereof, wherein Ar is selected from the group consisting of phenyl optionally substituted by one or more substituents $R^{Ar}$;

$R^{Ar}$ is selected from the group consisting of halogen, —O—$C_{1-3}$-alkyl, —O—$C_{1-3}$-haloalkyl, $C_{1-4}$-alkyl, $C_{1-4}$-haloalkyl and (dimethylamino)-$C_{1-2}$-alkoxy;

Z is selected from the group consisting of H, COO—$C_{1-3}$-alkyl, pyrimidyl, pyrazinyl, thiazolyl, oxazolyl, isoxazolyl, isothiazolyl imidazolyl, oxadiazolyl, thiadiazolyl, thiophenyl, furan, tetrahydrofuran, cyclopropoxymethyl, cyclohexoxymethyl, cyclopentoxymethyl, —COO-cyclopropyl, —COO-cyclobutyl, —COO-cyclopentyl, —COO-cyclohexyl, pent-4-en-1-one, hydroxymethyl, methoxymethyl, ethoxymethyl, isopropoxymethyl, cyclobutoxymethyl, methoxyethyl, acetyl, methoxyacetyl, —CO—$CH_2$-cyclobutyl, —CO—$CH_2$-cyclopropyl, —CO—$CH_2$-cyclopentyl, —CO—$CH_2$-cyclohexyl, —COO-oxetan, 1-cyclopropylmethyl-pent-4-en-1-ol, -methoxy-ethoxy-methyl, —CONH-cyclopropyl, —CONH-cyclobutyl, —CONH— cyclopentyl, and —CONH-cyclohexyl, wherein said pyrimidyl, pyrazinyl, thiazolyl, oxazolyl, isoxazolyl, isothiazolyl imidazolyl, oxadiazolyl, thiadiazolyl, thiophenyl, tetrahydrofuran and furan is optionally substituted with one or more substituents independently selected from the group consisting of methyl, halogen, $CF_3$, OMe and OH;

Y is selected from the group consisting of $CF_3$ and Me;

R1 is selected from the group consisting of 3-hydroxy-3-methylbutyl, 2-hydroxy-2-methylpropyl, 3-hydroxy-3-methyl-cyclobutyl, 2-hydroxypropyl, 2-hydroxybutyl, 3-hydroxy-cyclobutyl, 2-hydroxy-3,3,3-trifluoropropyl, 2-hydroxy-2-deutero-propyl, and 1-hydroxy-cyclopropylmethyl.

6. The compound according to claim 1 or a pharmaceutically acceptable salt or solvate thereof, wherein Ar is phenyl which is optionally substituted by one or more substituents $R^{Ar}$;

Ra is selected from the group consisting of Cl, —OMe, F and 2-(dimethylamino)-ethoxy;

Z is selected from the group consisting of —COOMe, —COOEt, pyrimidin-2-yl, thiazol-2-yl, cyclopropoxymethyl, —COO-cyclopropyl, —COO-cyclobutyl, pent-4-en-1-one, pyrimidin-4-yl, methoxymethyl, pyrazin-2-yl, —CO—$CH_2$-cyclobutyl, COO-oxetan, 5-methyl-isoxazol-2-yl, 1-cyclopropylmethyl-pent-4-en-1-ol, —CONH-cyclopentyl;

Y is selected from the group consisting of $CF_3$ and Me;

R1 is selected from the group consisting of 3-hydroxy-3-methylbutyl, 3-hydroxy-3-methyl-cyclobutyl, 2-hydroxypropyl, 2-hydroxybutyl, 3-hydroxy-cyclobutyl, 2-hydroxy-3,3,3-trifluoropropyl, 2-hydroxy-2-deutero-propyl, and 1-hydroxy-cyclopropylmethyl.

7. The compound according to claim 1, wherein the compound is selected from the group consisting of 1-{4-[3-(2-chloro-6-fluorophenyl)-4-(1,3-thiazol-2-yl)-1,2-oxazol-5-yl]-5-(trifluoromethyl)-1H-pyrazol-1-yl}-2-methylpropan-2-ol 1-({4-[3-(2-chloro-6-fluorophenyl)-4-(1,3-thiazol-2-yl)-1,2-oxazol-5-yl]-5-(trifluoromethyl)-1H-pyrazol-1-yl}methyl)cyclopropan-1-ol 4-{4-[3-(2-chloro-6-fluorophenyl)-4-(1,3-thiazol-2-yl)-1,2-oxazol-5-yl]-5-(trifluoromethyl)-1H-pyrazol-1-yl}-2-methylbutan-2-ol (2R)-1-{4-[3-(2-chloro-6-fluorophenyl)-4-(1,3-thiazol-2-yl)-1,2-oxazol-5-yl]-5-(trifluoromethyl)-1H-pyrazol-1-yl}propan-2-ol (2S)-1-{4-[3-(2-chloro-6-fluorophenyl)-4-(1,3-thiazol-2-yl)-1,2-oxazol-5-yl]-5-(trifluoromethyl)-1H-pyrazol-1-yl}propan-2-ol 1-{4-[3-(2-chloro-6-fluorophenyl)-4-(1,3-thiazol-2-yl)-1,2-oxazol-5-yl]-5-(trifluoromethyl)-1H-pyrazol-1-yl}butan-2-ol (rac)

3-{4-[3-(2-chloro-6-fluorophenyl)-4-(1,3-thiazol-2-yl)-1,2-oxazol-5-yl]-5-(trifluoromethyl)-1H-pyrazol-1-yl}-1,1,1-trifluoropropan-2-ol (rac)

ethyl 3-(2-chloro-6-fluorophenyl)-5-[1-(2-hydroxy-2-methylpropyl)-5-(trifluoromethyl)-1H-pyrazol-4-yl]-1,2-oxazole-4-carboxylate ethyl 3-(2-chloro-6-fluorophenyl)-5-[1-(3-hydroxy-3-methylbutyl)-5-(trifluoromethyl)-1H-pyrazol-4-yl]-1,2-oxazole-4-carboxylate ethyl 3-(2-chloro-6-fluorophenyl)-5-{1-[(1R,3S)-3-hydroxy-3-methylcyclobutyl]-5-(trifluoromethyl)-1H-pyrazol-4-yl}-1,2-oxazole-4-carboxylate (syn)

ethyl 3-(2-chloro-6-fluorophenyl)-5-{1-[(1S,3R)-3-hydroxy-3-methylcyclobutyl]-5-(trifluoromethyl)-1H-pyrazol-4-yl}-1,2-oxazole-4-carboxylate (anti)

ethyl 3-(2-chloro-6-fluorophenyl)-5-{1-[(2R)-2-hydroxypropyl]-5-(trifluoromethyl)-1H-pyrazol-4-yl}-1,2-oxazole-4-carboxylate ethyl 3-(2-chloro-6-fluorophenyl)-5-{1-[(2S)-2-hydroxypropyl]-5-(trifluoromethyl)-1H-pyrazol-4-yl}-1,2-oxazole-4-carboxylate ethyl 3-(2-chloro-6-fluorophenyl)-5-[1-(2-hydroxybutyl)-5-(trifluoromethyl)-1H-pyrazol-4-yl]-1,2-oxazole-4-carboxylate (rac)

ethyl 3-(2-chloro-6-fluorophenyl)-5-[1-(3,3,3-trifluoro-2-hydroxypropyl)-5-(trifluoromethyl)-1H-pyrazol-4-yl]-1,2-oxazole-4-carboxylate (rac)

ethyl 3-(2-chloro-6-fluorophenyl)-5-{1-[(2R)-3,3,3-trifluoro-2-hydroxypropyl]-5-(trifluoromethyl)-1H-pyrazol-4-yl}-1,2-oxazole-4-carboxylate methyl 3-(2-chlorophenyl)-5-{5-methyl-1-[(1S,3R)-3-hydroxy-3-methylcyclobutyl]-1H-pyrazol-4-yl}-1,2-oxazole-4-carboxylate (anti)

methyl 3-(2-chlorophenyl)-5-{5-methyl-1-[(1R,3S)-3-hydroxy-3-methylcyclobutyl]-1H-pyrazol-4-yl}-1,2-oxazole-4-carboxylate (syn)

methyl 3-(2-chlorophenyl)-5-[1-(3-hydroxy-3-methylbutyl)-5-methyl-1H-pyrazol-4-yl]-1,2-oxazole-4-carboxylate
methyl 3-(2-chloro-6-fluorophenyl)-5-[1-(3-hydroxy-3-methylbutyl)-5-methyl-1H-pyrazol-4-yl]-1,2-oxazole-4-carboxylate
methyl 5-{1-[(2R)-2-hydroxypropyl]-5-(trifluoromethyl)-1H-pyrazol-4-yl}-3-(2-methoxypyridin-3-yl)-1,2-oxazole-4-carboxylate
methyl 3-(2-chlorophenyl)-5-{1-[(2S)-2-hydroxypropyl]-5-(trifluoromethyl)-1H-pyrazol-4-yl}-1,2-oxazole-4-carboxylate
methyl 3-(2-chloro-6-fluorophenyl)-5-{1-[(2S)-2-hydroxypropyl]-5-(trifluoromethyl)-1H-pyrazol-4-yl}-1,2-oxazole-4-carboxylate
methyl 3-(2-chlorophenyl)-5-{1-[(2S)-2-hydroxypropyl]-5-methyl-1H-pyrazol-4-yl}-1,2-oxazole-4-carboxylate
methyl 3-(2-chloro-3-methoxyphenyl)-5-[1-(3-hydroxy-3-methylbutyl)-5-methyl-1H-pyrazol-4-yl]-1,2-oxazole-4-carboxylate
methyl 3-(2-chloro-6-fluorophenyl)-5-{1-[(1S,3R)-3-hydroxy-3-methylcyclobutyl]-5-(trifluoromethyl)-1H-pyrazol-4-yl}-1,2-oxazole-4-carboxylate (anti)
methyl 3-(2-chloro-6-fluorophenyl)-5-{1-[(1R,3S)-3-hydroxy-3-methylcyclobutyl]-5-(trifluoromethyl)-1H-pyrazol-4-yl}-1,2-oxazole-4-carboxylate (syn)
methyl 3-(2-chloro-6-fluorophenyl)-5-[1-(3-hydroxycyclobutyl)-5-(trifluoromethyl)-1H-pyrazol-4-yl]-1,2-oxazole-4-carboxylate
methyl 3-(2-chlorophenyl)-5-{1-[(1S,3S)-3-hydroxy-3-(methoxymethyl)cyclobutyl]-5-(trifluoromethyl)-1H-pyrazol-4-yl}-1,2-oxazole-4-carboxylate (syn)
1-{4-[3-(2-chloro-6-fluorophenyl)-4-(5-methyl-1,3,4-oxadiazol-2-yl)-1,2-oxazol-5-yl]-5-(trifluoromethyl)-1H-pyrazol-1-yl}-2-methylpropan-2-ol
1-{4-[3-(2-chloro-6-fluorophenyl)-4-(1,3-thiazol-2-yl)-1,2-oxazol-5-yl]-5-(trifluoromethyl)-1H-pyrazol-1-yl}(2-$^{2}$H)propan-2-ol (rac)
ethyl 3-(2-chloro-6-fluorophenyl)-5-{1-[2-hydroxy(2-$^{2}$H)propyl]-5-(trifluoromethyl)-1H-pyrazol-4-yl}-1,2-oxazole-4-carboxylate (rac)
methyl 3-(2-chloro-6-fluorophenyl)-5-{1-[2-hydroxy(2-$^{2}$H)propyl]-5-(trifluoromethyl)-1H-pyrazol-4-yl}-1,2-oxazole-4-carboxylate (rac)
1-[3-(2-chloro-6-fluorophenyl)-5-[1-(2-hydroxy-2-methylpropyl)-5-(trifluoromethyl)-1H-pyrazol-4-yl]-1,2-oxazol-4-yl]ethan-1-one
1-[3-(2-chloro-6-fluorophenyl)-5-{1-[(2R)-2-hydroxypropyl]-5-(trifluoromethyl)-1H-pyrazol-4-yl}-1,2-oxazol-4-yl]ethan-1-one
1-[3-(2-chloro-6-fluorophenyl)-5-[1-(2-hydroxy-2-methylpropyl)-5-(trifluoromethyl)-1H-pyrazol-4-yl]-1,2-oxazol-4-yl]-2-cyclobutylethan-1-one
1-[3-(2-chloro-6-fluorophenyl)-5-[1-(2-hydroxy-2-methylpropyl)-5-(trifluoromethyl)-1H-pyrazol-4-yl]-1,2-oxazol-4-yl]pent-4-en-1-one
2-[3-(2-chloro-6-fluorophenyl)-5-[1-(2-hydroxy-2-methylpropyl)-5-(trifluoromethyl)-1H-pyrazol-4-yl]-1,2-oxazol-4-yl]-1-cyclopropylhex-5-en-2-ol (rac)
1-[3-(2-chloro-6-fluorophenyl)-5-[1-(2-hydroxy-2-methylpropyl)-5-(trifluoromethyl)-1H-pyrazol-4-yl]-1,2-oxazol-4-yl]-2-methoxyethan-1-one
1-[3-(2-chloro-6-fluorophenyl)-5-{1-[(2R)-2-hydroxypropyl]-5-(trifluoromethyl)-1H-pyrazol-4-yl}-1,2-oxazol-4-yl]-2-methoxyethan-1-one
3-(2-chloro-6-fluorophenyl)-N-cyclopentyl-5-[1-(2-hydroxy-2-methylpropyl)-5-(trifluoromethyl)-1H-pyrazol-4-yl]-1,2-oxazole-4-carboxamide
3-(2-chloro-6-fluorophenyl)-N-cyclopropyl-5-[1-(2-hydroxy-2-methylpropyl)-5-(trifluoromethyl)-1H-pyrazol-4-yl]-1,2-oxazole-4-carboxamide
3-(2-chloro-6-fluorophenyl)-N-cyclobutyl-5-[1-(2-hydroxy-2-methylpropyl)-5-(trifluoromethyl)-1H-pyrazol-4-yl]-1,2-oxazole-4-carboxamide
3-(2-chloro-6-fluorophenyl)-N-cyclopentyl-5-{1-[(2R)-2-hydroxypropyl]-5-(trifluoromethyl)-1H-pyrazol-4-yl}-1,2-oxazole-4-carboxamide
3-(2-chloro-6-fluorophenyl)-N-cyclopropyl-5-{1-[(2R)-2-hydroxypropyl]-5-(trifluoromethyl)-1H-pyrazol-4-yl}-1,2-oxazole-4-carboxamide
3-(2-chloro-6-fluorophenyl)-N-cyclobutyl-5-{1-[(2R)-2-hydroxypropyl]-5-(trifluoromethyl)-1H-pyrazol-4-yl}-1,2-oxazole-4-carboxamide
oxetan-3-yl 3-(2-chlorophenyl)-5-{1-[(2S)-2-hydroxypropyl]-5-methyl-1H-pyrazol-4-yl}-1,2-oxazole-4-carboxylate
cyclopropyl 3-(2-chlorophenyl)-5-{1-[(1S,3R)-3-hydroxy-3-methylcyclobutyl]-5-(trifluoromethyl)-1H-pyrazol-4-yl}-1,2-oxazole-4-carboxylate (anti)
cyclopropyl 3-(2-chlorophenyl)-5-{1-[(1R,3S)-3-hydroxy-3-methylcyclobutyl]-5-(trifluoromethyl)-1H-pyrazol-4-yl}-1,2-oxazole-4-carboxylate (syn)
cyclopropyl 3-(2-chloro-6-fluorophenyl)-5-{1-[(1S,3R)-3-hydroxy-3-methylcyclobutyl]-5-(trifluoromethyl)-1H-pyrazol-4-yl}-1,2-oxazole-4-carboxylate (anti)
cyclopropyl 3-(2-chloro-6-fluorophenyl)-5-{1-[(1R,3S)-3-hydroxy-3-methylcyclobutyl]-5-(trifluoromethyl)-1H-pyrazol-4-yl}-1,2-oxazole-4-carboxylate (syn)
oxetan-3-yl 3-(2-chlorophenyl)-5-{1-[(1R,3S)-3-hydroxy-3-methylcyclobutyl]-5-methyl-1H-pyrazol-4-yl}-1,2-oxazole-4-carboxylate (syn)
cyclopropyl 3-(2-chlorophenyl)-5-{5-methyl-1-[(1R,3S)-3-hydroxy-3-methylcyclobutyl]-1H-pyrazol-4-yl}-1,2-oxazole-4-carboxylate (syn)
cyclopropyl 3-(2-chlorophenyl)-5-{5-methyl-1-[(1S,3R)-3-hydroxy-3-methylcyclobutyl]-1H-pyrazol-4-yl}-1,2-oxazole-4-carboxylate (anti)
cyclopropyl 3-(2-chloro-6-fluorophenyl)-5-[1-(2-hydroxy-2-methylpropyl)-5-(trifluoromethyl)-1H-pyrazol-4-yl]-1,2-oxazole-4-carboxylate
cyclobutyl 3-(2-chloro-6-fluorophenyl)-5-[1-(2-hydroxy-2-methylpropyl)-5-(trifluoromethyl)-1H-pyrazol-4-yl]-1,2-oxazole-4-carboxylate
oxetan-3-yl 3-(2-chloro-6-fluorophenyl)-5-[1-(2-hydroxy-2-methylpropyl)-5-(trifluoromethyl)-1H-pyrazol-4-yl]-1,2-oxazole-4-carboxylate
oxetan-3-yl 3-(2-chloro-6-fluorophenyl)-5-{1-[(2R)-2-hydroxypropyl]-5-(trifluoromethyl)-1H-pyrazol-4-yl}-1,2-oxazole-4-carboxylate
cyclopropyl 3-(2-chloro-6-fluorophenyl)-5-{1-[(2S)-2-hydroxypropyl]-5-(trifluoromethyl)-1H-pyrazol-4-yl}-1,2-oxazole-4-carboxylate
oxetan-3-yl 3-(2-chloro-6-fluorophenyl)-5-{1-[(2S)-2-hydroxypropyl]-5-(trifluoromethyl)-1H-pyrazol-4-yl}-1,2-oxazole-4-carboxylate
cyclopropyl 3-(2-chloro-6-fluorophenyl)-5-{5-methyl-1-[(1R,3S)-3-hydroxy-3-methylcyclobutyl]-1H-pyrazol-4-yl}-1,2-oxazole-4-carboxylate (syn)
cyclopropyl 3-(2-chloro-6-fluorophenyl)-5-{5-methyl-1-[(1S,3R)-3-hydroxy-3-methylcyclobutyl]-1H-pyrazol-4-yl}-1,2-oxazole-4-carboxylate (anti)

1-{4-[3-(2-chloro-6-fluorophenyl)-4-(hydroxymethyl)-1,2-oxazol-5-yl]-5-(trifluoromethyl)-1H-pyrazol-1-yl}-2-methylpropan-2-ol (1R,3S)-3-{4-[3-(2-chloro-6-fluorophenyl)-4-(hydroxymethyl)-1,2-oxazol-5-yl]-5-(trifluoromethyl)-1H-pyrazol-1-yl}-1-methylcyclobutan-1-ol (syn)

1-{4-[3-(2-chloro-6-fluorophenyl)-4-(methoxymethyl)-1,2-oxazol-5-yl]-5-(trifluoromethyl)-1H-pyrazol-1-yl}-2-methylpropan-2-ol (2R)-1-{4-[3-(2-chloro-6-fluorophenyl)-4-(methoxymethyl)-1,2-oxazol-5-yl]-5-(trifluoromethyl)-1H-pyrazol-1-yl}propan-2-ol 4-{4-[3-(2-chloro-6-fluorophenyl)-4-(methoxymethyl)-1,2-oxazol-5-yl]-5-(trifluoromethyl)-1H-pyrazol-1-yl}-2-methylbutan-2-ol (2S)-1-{4-[3-(2-chloro-6-fluorophenyl)-4-(methoxymethyl)-1,2-oxazol-5-yl]-5-(trifluoromethyl)-1H-pyrazol-1-yl}propan-2-ol (1R,3S)-3-{4-[3-(2-chloro-6-fluorophenyl)-4-(methoxymethyl)-1,2-oxazol-5-yl]-5-(trifluoromethyl)-1H-pyrazol-1-yl}-1-methylcyclobutan-1-ol (syn)

(1R,3S)-3-{4-[3-(2-chloro-6-fluorophenyl)-4-(methoxymethyl)-1,2-oxazol-5-yl]-5-methyl-1H-pyrazol-1-yl}-1-methylcyclobutan-1-ol (syn)

(1S,3R)-3-{4-[3-(2-chloro-6-fluorophenyl)-4-(methoxymethyl)-1,2-oxazol-5-yl]-5-methyl-1H-pyrazol-1-yl}-1-methylcyclobutan-1-ol (anti)

(1R,3S)-3-{4-[3-(2-chlorophenyl)-4-(methoxymethyl)-1,2-oxazol-5-yl]-5-methyl-1H-pyrazol-1-yl}-1-methylcyclobutan-1-ol (syn)

(1S,3R)-3-{4-[3-(2-chlorophenyl)-4-(methoxymethyl)-1,2-oxazol-5-yl]-5-methyl-1H-pyrazol-1-yl}-1-methylcyclobutan-1-ol (anti)

(1R,3S)-3-{4-[3-(2-chlorophenyl)-4-(methoxymethyl)-1,2-oxazol-5-yl]-5-(trifluoromethyl)-1H-pyrazol-1-yl}-1-methylcyclobutan-1-ol (syn)

(2S)-1-{4-[3-(2-chlorophenyl)-4-[(2-methoxyethoxy)methyl]-1,2-oxazol-5-yl]-5-(trifluoromethyl)-1H-pyrazol-1-yl}propan-2-ol (2R)-1-{4-[3-(2-chloro-6-fluorophenyl)-4-(ethoxymethyl)-1,2-oxazol-5-yl]-5-(trifluoromethyl)-1H-pyrazol-1-yl}propan-2-ol 4-{4-[3-(2-chloro-6-fluorophenyl)-4-(cyclopropoxymethyl)-1,2-oxazol-5-yl]-5-(trifluoromethyl)-1H-pyrazol-1-yl}-2-methylbutan-2-ol 4-{4-[3-(2-chlorophenyl)-4-(cyclopropoxymethyl)-1,2-oxazol-5-yl]-5-(trifluoromethyl)-1H-pyrazol-1-yl}-2-methylbutan-2-ol 4-{4-[3-(2-chlorophenyl)-4-(cyclopropoxymethyl)-1,2-oxazol-5-yl]-5-methyl-1H-pyrazol-1-yl}-2-methylbutan-2-ol (1R,3S)-3-{4-[3-(2-chlorophenyl)-4-(cyclopropoxymethyl)-1,2-oxazol-5-yl]-5-methyl-1H-pyrazol-1-yl}-1-methylcyclobutan-1-ol (syn)

(1S,3R)-3-{4-[3-(2-chlorophenyl)-4-(cyclopropoxymethyl)-1,2-oxazol-5-yl]-5-methyl-1H-pyrazol-1-yl}-1-methylcyclobutan-1-ol (anti)

4-{4-[3-(2-chloro-6-fluorophenyl)-4-(cyclopropoxymethyl)-1,2-oxazol-5-yl]-5-methyl-1H-pyrazol-1-yl}-2-methylbutan-2-ol (1R,3S)-3-{4-[3-(2-chloro-6-fluorophenyl)-4-(cyclopropoxymethyl)-1,2-oxazol-5-yl]-5-methyl-1H-pyrazol-1-yl}-1-methylcyclobutan-1-ol (syn)

(1S,3R)-3-{4-[3-(2-chloro-6-fluorophenyl)-4-(cyclopropoxymethyl)-1,2-oxazol-5-yl]-5-methyl-1H-pyrazol-1-yl}-1-methylcyclobutan-1-ol (anti)

(2R)-1-{4-[3-(2-chloro-6-fluorophenyl)-4-(cyclopropoxymethyl)-1,2-oxazol-5-yl]-5-(trifluoromethyl)-1H-pyrazol-1-yl}propan-2-ol (1R,3S)-3-{4-[3-(2-chloro-6-fluorophenyl)-4-(cyclopropoxymethyl)-1,2-oxazol-5-yl]-5-(trifluoromethyl)-1H-pyrazol-1-yl}-1-methylcyclobutan-1-ol (syn)

(1R,3S)-3-{4-[3-(2-chlorophenyl)-4-(cyclopropoxymethyl)-1,2-oxazol-5-yl]-5-(trifluoromethyl)-1H-pyrazol-1-yl}-1-methylcyclobutan-1-ol (syn)

(2S)-1-{4-[3-(2-chlorophenyl)-4-[(oxetan-3-yloxy)methyl]-1,2-oxazol-5-yl]-5-(trifluoromethyl)-1H-pyrazol-1-yl}propan-2-ol (2R)-1-{4-[3-(2-chloro-6-fluorophenyl)-4-[(propan-2-yloxy)methyl]-1,2-oxazol-5-yl]-5-(trifluoromethyl)-1H-pyrazol-1-yl}propan-2-ol (2R)-1-{4-[3-(2-chloro-6-fluorophenyl)-4-(cyclobutoxymethyl)-1,2-oxazol-5-yl]-5-(trifluoromethyl)-1H-pyrazol-1-yl}propan-2-ol 4-{4-[3-(2-chloro-3-methoxyphenyl)-4-(cyclopropoxymethyl)-1,2-oxazol-5-yl]-5-(trifluoromethyl)-1H-pyrazol-1-yl}-2-methylbutan-2-ol (1R,3S)-3-[4-(3-{2-chloro-3-[2-(morpholin-4-yl)ethoxy]phenyl}-4-(cyclopropoxymethyl)-1,2-oxazol-5-yl)-5-(trifluoromethyl)-1H-pyrazol-1-yl]-1-methylcyclobutan-1-ol (syn)

methyl 5-[1-(2-hydroxy-2-methylpropyl)-5-(trifluoromethyl)-1H-pyrazol-4-yl]-3-(2-hydroxypyridin-3-yl)-1,2-oxazole-4-carboxylate (2R)-1-{4-[3-(2-chloro-6-fluorophenyl)-1,2-oxazol-5-yl]-5-(trifluoromethyl)-1H-pyrazol-1-yl}propan-2-ol 1-{4-[3-(2-chloro-6-fluorophenyl)-4-(methoxymethyl)-1,2-oxazol-5-yl]-5-(trifluoromethyl)-1H-pyrazol-1-yl}(2-2H)propan-2-ol (rac)

(2S)-1-{4-[3-(2-chlorophenyl)-4-(oxolan-2-yl)-1,2-oxazol-5-yl]-5-(trifluoromethyl)-1H-pyrazol-1-yl}propan-2-ol (2R)-1-{4-[3-(2-chloro-6-fluorophenyl)-4-(pyrimidin-2-yl)-1,2-oxazol-5-yl]-5-(trifluoromethyl)-1H-pyrazol-1-yl}propan-2-ol (1R,3S)-3-{4-[3-(2-chloro-6-fluorophenyl)-4-(pyrimidin-2-yl)-1,2-oxazol-5-yl]-5-(trifluoromethyl)-1H-pyrazol-1-yl}-1-methylcyclobutan-1-ol (syn)

(1R,3S)-3-{4-[3-(2-chlorophenyl)-4-(pyrimidin-2-yl)-1,2-oxazol-5-yl]-5-methyl-1H-pyrazol-1-yl}-1-methylcyclobutan-1-ol (syn)

(1R,3S)-3-{4-[3-(2-chloro-6-fluorophenyl)-4-(pyrazin-2-yl)-1,2-oxazol-5-yl]-5-(trifluoromethyl)-1H-pyrazol-1-yl}-1-methylcyclobutan-1-ol (syn)

(1R,3S)-3-{4-[3-(2-chlorophenyl)-4-(pyrazin-2-yl)-1,2-oxazol-5-yl]-5-(trifluoromethyl)-1H-pyrazol-1-yl}-1-methylcyclobutan-1-ol (syn)

(1R,3S)-3-{4-[3-(2-chlorophenyl)-4-(pyrimidin-2-yl)-1,2-oxazol-5-yl]-5-(trifluoromethyl)-1H-pyrazol-1-yl}-1-methylcyclobutan-1-ol (syn)

(1R,3S)-3-{4-[3-(2-chloro-3-methoxyphenyl)-4-(pyrimidin-2-yl)-1,2-oxazol-5-yl]-5-(trifluoromethyl)-1H-pyrazol-1-yl}-1-methylcyclobutan-1-ol (syn)

(1R,3S)-3-{4-[3-(2-chloro-6-fluorophenyl)-4-(pyrimidin-4-yl)-1,2-oxazol-5-yl]-5-(trifluoromethyl)-1H-pyrazol-1-yl}-1-methylcyclobutan-1-ol (syn)

(1S,3R)-3-{4-[3-(2-chloro-6-fluorophenyl)-4-(pyrimidin-4-yl)-1,2-oxazol-5-yl]-5-(trifluoromethyl)-1H-pyrazol-1-yl}-1-methylcyclobutan-1-ol (anti)

(1R,3S)-3-{4-[3-(2-chlorophenyl)-4-(pyrimidin-4-yl)-1,2-oxazol-5-yl]-5-(trifluoromethyl)-1H-pyrazol-1-yl}-1-methylcyclobutan-1-ol (syn)

(1R,3S)-3-{4-[3-(2-chlorophenyl)-4-(pyrimidin-4-yl)-1,2-oxazol-5-yl]-5-methyl-1H-pyrazol-1-yl}-1-methylcyclobutan-1-ol (syn)
(1R,3S)-3-{4-[3-(2-chloro-6-fluorophenyl)-4-(pyrimidin-4-yl)-1,2-oxazol-5-yl]-5-methyl-1H-pyrazol-1-yl}-1-methylcyclobutan-1-ol (syn)
(1R,3S)-3-{4-[3-(2-chlorophenyl)-4-(pyrazin-2-yl)-1,2-oxazol-5-yl]-5-methyl-1H-pyrazol-1-yl}-1-methylcyclobutan-1-ol (syn)
(1R,3S)-3-{4-[3-(2-chloro-6-fluorophenyl)-4-(pyrazin-2-yl)-1,2-oxazol-5-yl]-5-methyl-1H-pyrazol-1-yl}-1-methylcyclobutan-1-ol (syn)
(1R,3S)-3-{4-[3-(2-chloro-6-fluorophenyl)-4-(pyrimidin-2-yl)-1,2-oxazol-5-yl]-5-methyl-1H-pyrazol-1-yl}-1-methylcyclobutan-1-ol (syn)
(1R,3S)-3-{4-[3-(2-chloro-3-methoxyphenyl)-4-(pyrimidin-2-yl)-1,2-oxazol-5-yl]-5-methyl-1H-pyrazol-1-yl}-1-methylcyclobutan-1-ol (syn)
(2R)-1-{4-[3-(2-methoxyphenyl)-4-(pyrimidin-2-yl)-1,2-oxazol-5-yl]-5-(trifluoromethyl)-1H-pyrazol-1-yl}propan-2-ol
1-{4-[3-(2-methoxyphenyl)-4-(pyrimidin-2-yl)-1,2-oxazol-5-yl]-5-(trifluoromethyl)-1H-pyrazol-1-yl}-2-methylpropan-2-ol
(2R)-1-{4-[3-(2-methoxyphenyl)-4-(pyrimidin-4-yl)-1,2-oxazol-5-yl]-5-(trifluoromethyl)-1H-pyrazol-1-yl}propan-2-ol
1-{4-[3-(2-methoxyphenyl)-4-(pyrimidin-4-yl)-1,2-oxazol-5-yl]-5-(trifluoromethyl)-1H-pyrazol-1-yl}-2-methylpropan-2-ol
(2R)-1-{4-[3-(2-chloro-3-methoxyphenyl)-4-(pyrimidin-2-yl)-1,2-oxazol-5-yl]-5-(trifluoromethyl)-1H-pyrazol-1-yl}propan-2-ol
1-{4-[3-(2-chloro-6-fluorophenyl)-4-(pyrimidin-2-yl)-1,2-oxazol-5-yl]-5-(trifluoromethyl)-1H-pyrazol-1-yl}-2-methylpropan-2-ol
(2R)-1-{4-[3-(2-chloro-3-methoxyphenyl)-4-(pyrimidin-4-yl)-1,2-oxazol-5-yl]-5-(trifluoromethyl)-1H-pyrazol-1-yl}propan-2-ol
1-{4-[3-(2-chloro-3-methoxyphenyl)-4-(pyrimidin-4-yl)-1,2-oxazol-5-yl]-5-(trifluoromethyl)-1H-pyrazol-1-yl}-2-methylpropan-2-ol
4-{4-[3-(2-chloro-3-methoxyphenyl)-4-(pyrimidin-2-yl)-1,2-oxazol-5-yl]-5-(trifluoromethyl)-1H-pyrazol-1-yl}-2-methylbutan-2-ol
4-{4-[3-(2-chlorophenyl)-4-(pyrimidin-2-yl)-1,2-oxazol-5-yl]-5-(trifluoromethyl)-1H-pyrazol-1-yl}-2-methylbutan-2-ol
4-{4-[3-(2-chloro-6-fluorophenyl)-4-(pyrimidin-2-yl)-1,2-oxazol-5-yl]-5-(trifluoromethyl)-1H-pyrazol-1-yl}-2-methylbutan-2-ol
4-{4-[3-(2-chloro-3-methoxyphenyl)-4-(pyrimidin-2-yl)-1,2-oxazol-5-yl]-5-methyl-1H-pyrazol-1-yl}-2-methylbutan-2-ol
4-{4-[3-(2,6-dichloro-3-methoxyphenyl)-4-(pyrimidin-2-yl)-1,2-oxazol-5-yl]-5-methyl-1H-pyrazol-1-yl}-2-methylbutan-2-ol
4-{4-[3-(2-chlorophenyl)-4-(pyrimidin-2-yl)-1,2-oxazol-5-yl]-5-methyl-1H-pyrazol-1-yl}-2-methylbutan-2-ol
4-{4-[3-(2-chloro-6-fluorophenyl)-4-(pyrimidin-2-yl)-1,2-oxazol-5-yl]-5-methyl-1H-pyrazol-1-yl}-2-methylbutan-2-ol
4-(4-{3-[3-(benzyloxy)-2-chlorophenyl]-4-(pyrimidin-2-yl)-1,2-oxazol-5-yl}-5-(trifluoromethyl)-1H-pyrazol-1-yl)-2-methylbutan-2-ol
2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenol
(1R,3S)-3-{4-[3-(2-chloro-3-methoxyphenyl)-4-(cyclopropoxymethyl)-1,2-oxazol-5-yl]-5-(trifluoromethyl)-1H-pyrazol-1-yl}-1-methylcyclobutan-1-ol (syn)
ethyl 3-(2-chloro-3-methoxyphenyl)-5-{1-[(1R,3S)-3-hydroxy-3-methylcyclobutyl]-5-(trifluoromethyl)-1H-pyrazol-4-yl}-1,2-oxazole-4-carboxylate (syn)
ethyl 3-(2-chloro-3-methoxyphenyl)-5-[1-(3-hydroxy-3-methylbutyl)-5-(trifluoromethyl)-1H-pyrazol-4-yl]-1,2-oxazole-4-carboxylate
4-[4-(3-{2-chloro-3-[2-(morpholin-4-yl)ethoxy]phenyl}-4-(pyrimidin-2-yl)-1,2-oxazol-5-yl)-5-(trifluoromethyl)-1H-pyrazol-1-yl]-2-methylbutan-2-ol
4-[4-(3-{2-chloro-3-[2-(dimethylamino)ethoxy]phenyl}-4-(pyrimidin-2-yl)-1,2-oxazol-5-yl)-5-(trifluoromethyl)-1H-pyrazol-1-yl]-2-methylbutan-2-ol
4-[4-(3-{2-chloro-3-[2-(pyrrolidin-1-yl)ethoxy]phenyl}-4-(pyrimidin-2-yl)-1,2-oxazol-5-yl)-5-(trifluoromethyl)-1H-pyrazol-1-yl]-2-methylbutan-2-ol
4-[4-(3-{2-chloro-3-[2-(4-methylpiperazin-1-yl)ethoxy]phenyl}-4-(pyrimidin-2-yl)-1,2-oxazol-5-yl)-5-(trifluoromethyl)-1H-pyrazol-1-yl]-2-methylbutan-2-ol
4-[4-(3-{2-chloro-3-[2-(diethylamino)ethoxy]phenyl}-4-(pyrimidin-2-yl)-1,2-oxazol-5-yl)-5-(trifluoromethyl)-1H-pyrazol-1-yl]-2-methylbutan-2-ol
4-[2-(2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenoxy)ethyl]-1lambda6-thiomorpholine-1,1-dione
4-(4-{3-[2-chloro-3-(2-{2-oxa-6-azaspiro[3.3]heptan-6-yl}ethoxy)phenyl]-4-(pyrimidin-2-yl)-1,2-oxazol-5-yl}-5-(trifluoromethyl)-1H-pyrazol-1-yl)-2-methylbutan-2-ol
4-[4-(3-{2-chloro-3-[3-(dimethylamino)propoxy]phenyl}-4-(pyrimidin-2-yl)-1,2-oxazol-5-yl)-5-(trifluoromethyl)-1H-pyrazol-1-yl]-2-methylbutan-2-ol
4-[3-(2-chloro-3-{5-[1-(3-hydroxy-3-methylbutyl)-5-(trifluoromethyl)-1H-pyrazol-4-yl]-4-(pyrimidin-2-yl)-1,2-oxazol-3-yl}phenoxy)propyl]-1lambda6-thiomorpholine-1,1-dione
4-[4-(3-{2-chloro-3-[3-(pyrrolidin-1-yl)propoxy]phenyl}-4-(pyrimidin-2-yl)-1,2-oxazol-5-yl)-5-(trifluoromethyl)-1H-pyrazol-1-yl]-2-methylbutan-2-ol
4-[4-(3-{2-chloro-3-[3-(diethylamino)propoxy]phenyl}-4-(pyrimidin-2-yl)-1,2-oxazol-5-yl)-5-(trifluoromethyl)-1H-pyrazol-1-yl]-2-methylbutan-2-ol
4-[4-(3-{2-chloro-3-[2-(diethylamino)ethoxy]phenyl}-4-(pyrimidin-2-yl)-1,2-oxazol-5-yl)-5-methyl-1H-pyrazol-1-yl]-2-methylbutan-2-ol
4-[4-(3-{2-chloro-3-[2-(dimethylamino)ethoxy]phenyl}-4-(pyrimidin-2-yl)-1,2-oxazol-5-yl)-5-methyl-1H-pyrazol-1-yl]-2-methylbutan-2-ol
4-[4-(3-{2-chloro-3-[2-(pyrrolidin-1-yl)ethoxy]phenyl}-4-(pyrimidin-2-yl)-1,2-oxazol-5-yl)-5-methyl-1H-pyrazol-1-yl]-2-methylbutan-2-ol
4-[4-(3-{2-chloro-3-[3-(diethylamino)propoxy]phenyl}-4-(pyrimidin-2-yl)-1,2-oxazol-5-yl)-5-methyl-1H-pyrazol-1-yl]-2-methylbutan-2-ol
methyl 3-{2-chloro-3-[2-(morpholin-4-yl)ethoxy]phenyl}-5-{1-[(2S)-2-hydroxypropyl]-5-(trifluoromethyl)-1H-pyrazol-4-yl}-1,2-oxazole-4-carboxylate
methyl 3-{2-chloro-3-[2-(dimethylamino)ethoxy]phenyl}-5-{1-[(2S)-2-hydroxypropyl]-5-(trifluoromethyl)-1H-pyrazol-4-yl}-1,2-oxazole-4-carboxylate (1R,3S)-3-[4-(3-{2-chloro-3-[2-(morpholin-4-yl)ethoxy]phenyl}-4-(methoxymethyl)-1,2-oxazol-5-yl)-5-(trifluoromethyl)-1H-pyrazol-1-yl]-1-methylcyclobutan-1-ol (syn)

(1R,3S)-3-[4-(3-{2-chloro-3-[2-(dimethylamino)ethoxy]phenyl}-4-(methoxymethyl)-1,2-oxazol-5-yl)-5-(trifluoromethyl)-1H-pyrazol-1-yl]-1-methylcyclobutan-1-ol (syn)

(1S,3R)-3-[4-(3-{2-chloro-3-[2-(morpholin-4-yl)ethoxy]phenyl}-4-(methoxymethyl)-1,2-oxazol-5-yl)-5-(trifluoromethyl)-1H-pyrazol-1-yl]-1-methylcyclobutan-1-ol (anti)

(1S,3R)-3-[4-(3-{2-chloro-3-[2-(dimethylamino)ethoxy]phenyl}-4-(methoxymethyl)-1,2-oxazol-5-yl)-5-(trifluoromethyl)-1H-pyrazol-1-yl]-1-methylcyclobutan-1-ol (anti)

(2R)-1-(4-{3-[2-chloro-3-(morpholine-4-carbonyl)phenyl]-4-(pyrimidin-4-yl)-1,2-oxazol-5-yl}-5-(trifluoromethyl)-1H-pyrazol-1-yl)propan-2-ol 2-chloro-N-cyclobutyl-3-(5-{1-[(2R)-2-hydroxypropyl]-5-(trifluoromethyl)-1H-pyrazol-4-yl}-4-(pyrimidin-4-yl)-1,2-oxazol-3-yl)benzamide 2-chloro-N-ethyl-3-(5-{1-[(2R)-2-hydroxypropyl]-5-(trifluoromethyl)-1H-pyrazol-4-yl}-4-(pyrimidin-4-yl)-1,2-oxazol-3-yl)benzamide 2-chloro-3-(5-{1-[(2R)-2-hydroxypropyl]-5-(trifluoromethyl)-1H-pyrazol-4-yl}-4-(pyrimidin-4-yl)-1,2-oxazol-3-yl)-N-(propan-2-yl)benzamide (2R)-1-(4-{3-[3-(azetidine-1-carbonyl)-2-chlorophenyl]-4-(pyrimidin-4-yl)-1,2-oxazol-5-yl}-5-(trifluoromethyl)-1H-pyrazol-1-yl)propan-2-ol 2-chloro-N-cyclopropyl-3-(5-{1-[(2R)-2-hydroxypropyl]-5-(trifluoromethyl)-1H-pyrazol-4-yl}-4-(pyrimidin-4-yl)-1,2-oxazol-3-yl)benzamide (2R)-1-(4-{3-[2-chloro-3-(pyrrolidine-1-carbonyl)phenyl]-4-(pyrimidin-4-yl)-1,2-oxazol-5-yl}-5-(trifluoromethyl)-1H-pyrazol-1-yl)propan-2-ol N-cyclopropyl-3-(5-{1-[(2R)-2-hydroxypropyl]-5-(trifluoromethyl)-1H-pyrazol-4-yl}-4-(pyrimidin-4-yl)-1,2-oxazol-3-yl)-2-methoxybenzamide 3-(5-{1-[(2R)-2-hydroxypropyl]-5-(trifluoromethyl)-1H-pyrazol-4-yl}-4-(pyrimidin-4-yl)-1,2-oxazol-3-yl)-2-methoxy-N-(propan-2-yl)benzamide (2R)-1-(4-{3-[3-(azetidine-1-carbonyl)-2-methoxyphenyl]-4-(pyrimidin-4-yl)-1,2-oxazol-5-yl}-5-(trifluoromethyl)-1H-pyrazol-1-yl)propan-2-ol N-cyclobutyl-3-(5-{1-[(2R)-2-hydroxypropyl]-5-(trifluoromethyl)-1H-pyrazol-4-yl}-4-(pyrimidin-4-yl)-1,2-oxazol-3-yl)-2-methoxybenzamide N-ethyl-3-(5-{1-[(2R)-2-hydroxypropyl]-5-(trifluoromethyl)-1H-pyrazol-4-yl}-4-(pyrimidin-4-yl)-1,2-oxazol-3-yl)-2-methoxybenzamide N-cyclobutyl-3-(5-{1-[(2R)-2-hydroxypropyl]-5-(trifluoromethyl)-1H-pyrazol-4-yl}-4-(pyrimidin-4-yl)-1,2-oxazol-3-yl)benzamide 3-(5-{1-[(2R)-2-hydroxypropyl]-5-(trifluoromethyl)-1H-pyrazol-4-yl}-4-(pyrimidin-4-yl)-1,2-oxazol-3-yl)-N-(propan-2-yl)benzamide.

8. A medicament comprising a compound according to claim 1 and a pharmaceutically acceptable carrier.

9. A method of treating a disease or medical condition comprising administering an effective amount of a compound according to claim 1 to a subject in need thereof wherein said disease or medical condition is selected from the group consisting of psoriasis, psoriatic arthritis, autoimmune thyroiditis, Grave's disease, rheumatoid arthritis, vitiligo, Crohn's disease, ulcerative colitis, inflammatory bowel disease, ankylosing spondylitis, diabetes type I, multiple sclerosis, celiac disease, systemic lupus erythematosus, uveitis, Behcet disease, atopic dermatitis, Lichen planus, Sjögren's syndrome, spinal disc herniation, acne, Graft-versus-Host-Reaction, Host-versus-Graft-Reaction, AIH (Autoimmunhepatitis), PBC (peripheral biliary cholangitis), PSC (primary scleroting cholangitis), obesity, Lupus nephritis, Autoimmune Thyroid Disorders including Graves Disease and Hashimoto's Disease, Autoimmune Uveitis, Colitis, IMQ Psoriasis, Juvenile Idiopathic Arthritis, Myasthenia Gravis, Systemic Sclerosis, diabetis melitus and osteoarthritis.

10. A method for preparing a medicament for the treatment of a disease or medical condition in which the inhibition of interleukin-17 (IL-17) and/or Interferon-γ (INF-γ) is beneficial, comprising including a compound of claim 1 in said medicament.

11. A method of claim 10 wherein the disease or medical condition is selected from the group consisting of psoriasis, psoriatic arthritis, autoimmune thyroiditis, Grave's disease, rheumatoid arthritis, vitiligo, Crohn's disease, ulcerative colitis, inflammatory bowel disease, ankylosing spondylitis, diabetes type I, multiple sclerosis, celiac disease, systemic lupus erythematosus, uveitis, Behcet disease, atopic dermatitis, Lichen planus, Sjögren's syndrome, spinal disc herniation, acne, Graft-versus-Host-Reaction, Host-versus-Graft-Reaction, AIH (Autoimmunhepatitis), PBC (peripheral biliary cholangitis), PSC (primary scleroting cholangitis), obesity, Lupus nephritis, Autoimmune Thyroid Disorders including Graves Disease and Hashimoto's Disease, Autoimmune Uveitis, Colitis, IMQ Psoriasis, Juvenile Idiopathic Arthritis, Myasthenia Gravis, Systemic Sclerosis, diabetes mellitus and osteoarthritis.

* * * * *